United States Patent
Stewart et al.

(10) Patent No.: US 12,404,522 B2
(45) Date of Patent: Sep. 2, 2025

(54) DISRUPTING THE LINC COMPLEX FOR TREATING LAMINOPATHY

(71) Applicant: Agency for Science, Technology and Research, Singapore (SG)

(72) Inventors: Colin Lawson Stewart, Singapore (SG); Jinfen Chai, Singapore (SG); Yin Loon Lee, Singapore (SG); Brian Edmund Burke, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 756 days.

(21) Appl. No.: 16/962,877

(22) PCT Filed: Jan. 18, 2019

(86) PCT No.: PCT/SG2019/050033
§ 371 (c)(1),
(2) Date: Jul. 17, 2020

(87) PCT Pub. No.: WO2019/143300
PCT Pub. Date: Jul. 25, 2019

(65) Prior Publication Data
US 2020/0347408 A1    Nov. 5, 2020

Related U.S. Application Data

(63) Continuation-in-part of application No. PCT/SG19/50033, filed on Jan. 18, 2019.

(30) Foreign Application Priority Data

Jan. 19, 2018 (SG) .......................... 10201800530Q

(51) Int. Cl.
C12N 15/86 (2006.01)
A61P 9/00 (2006.01)
C12N 7/00 (2006.01)
G01N 33/50 (2006.01)

(52) U.S. Cl.
CPC ................ *C12N 15/86* (2013.01); *A61P 9/00* (2018.01); *C12N 7/00* (2013.01); *G01N 33/502* (2013.01); *C12N 2750/14143* (2013.01)

(58) Field of Classification Search
CPC . C12N 15/86; C12N 2750/14143; A61P 9/00; A01K 2217/075; A01K 2267/0375
See application file for complete search history.

(56) References Cited

U.S. PATENT DOCUMENTS

2018/0169040 A1    6/2018    Wilcox et al.

FOREIGN PATENT DOCUMENTS

WO    WO-2013/158046 A1    10/2013
WO    WO-2018/138478 A1    8/2018

OTHER PUBLICATIONS

Stewart CL et. al., Mouse models of the laminopathies. Exp Cell Res. Jun. 10, 2007;313(10):2144-56. doi: 10.1016/j.yexcr.2007.03.026. Epub Mar. 31, 2007. PMID: 17493612; PMCID: PMC1949387 (Year: 2007).*

Turgay Y, Ungricht R, Rothballer A, Kiss A, Csucs G, Horvath P, Kutay U. A classical NLS and the SUN domain contribute to the targeting of SUN2 to the inner nuclear membrane. EMBO J. Jul. 21, 2010;29(14):2262-75. doi: 10.1038/emboj.2010.119. Epub Jun. 15, 2010. PMID: 20551905; PMCID: PMC2910269. (Year: 2010).*

Crisp M, Liu Q, Roux K, Rattner JB, Shanahan C, Burke B, Stahl PD, Hodzic D. Coupling of the nucleus and cytoplasm: role of the LINC complex. J Cell Biol. Jan. 2, 2006;172(1):41-53. doi: 10.1083/jcb.200509124. Epub Dec. 27, 2005. PMID: 16380439; PMCID: PMC2063530. (Year: 2006).*

Li, P., Stumpf, M., Müller, R. et al. The function of the inner nuclear envelope protein SUN1 in mRNA export is regulated by phosphorylation. Sci Rep 7, 9157 (2017). https://doi.org/10.1038/s41598-017-08837-7) (Year: 2017).*

Werfel S et. al. Rapid and highly efficient inducible cardiac gene knockout in adult mice using AAV-mediated expression of Cre recombinase. Cardiovasc Res. Oct. 1, 2014;104(1):15-23. doi: 10.1093/cvr/cvu174. Epub Jul. 31, 2014. PMID: 25082846. (Year: 2014).*

Kapp K, Schrempf S, Lemberg MK, et al. Post-Targeting Functions of Signal Peptides. In: Madame Curie Bioscience Database [Internet]. Austin (TX): Landes Bioscience; 2000-2013. Available from: https://www.ncbi.nlm.nih.gov/books/NBK6322/?report=classic) (Year: 2013).*

Chen CY et al.. Accumulation of the inner nuclear envelope protein Sun1 is pathogenic in progeric and dystrophic laminopathies. Cell. Apr. 27, 2012;149(3):565-77. doi: 10.1016/j.cell.2012.01.059. PMID: 22541428; PMCID: PMC3340584 (Year: 2012).*

Razafsky D. et al. Validation of a Mouse Model to Disrupt LINC Complexes in a Cell-specific Manner. J Vis Exp. Dec. 10, 2015;(106): e53318. doi: 10.3791/53318. PMID: 26710083; PMCID: PMC4692791 (Year: 2015).*

(Continued)

*Primary Examiner* — Maria G Leavitt
*Assistant Examiner* — Vyoma Shubham Tiwari
(74) *Attorney, Agent, or Firm* — Wolf, Greenfield & Sacks, P.C.

(57) ABSTRACT

The present invention relates to use of expression vectors and other compounds in methods to disrupt the LInker of Nucleoskeleton and Cytoskeleton (LINC) complex, uncoupling the nucleus from its linkage to the cytoskeleton, resulting in amelioration of diseases caused by one or more Lmna mutations, so-called laminopathies. More particularly, the invention relates to the expression of dominant negative SUN domain protein and/or dominant negative KASH domain protein to disrupt, for example, the LINC complex in cardiomyocytes for suppressing disease progression in dilated cardiomyopathy (DCM).

13 Claims, 55 Drawing Sheets

Specification includes a Sequence Listing.

(56) References Cited

OTHER PUBLICATIONS

Lombardi ML, et. al. The interaction between nesprins and sun proteins at the nuclear envelope is critical for force transmission between the nucleus and cytoskeleton. J Biol Chem. Jul. 29, 2011;286(30):26743-53. doi: 10.1074/jbc.M111.233700. Epub Jun. 7, 2011. PMID: 21652697; PMCID: PMC3143636 (Year: 2011).*
Li, P. et al. The function of the inner nuclear envelope protein SUN1 in mRNA export is regulated by phosphorylation. Sci Rep 7, 9157 (2017). https://doi.org/10.1038/s41598-017-08837-7 (Year: 2017).*
Smith H et al. Construction and use of signal sequence selection vectors in *Escherichia coli* and Bacillus subtilis. J Bacteriol. Jul. 1987;169(7):3321-8. doi: 10.1128/jb.169.7.3321-3328.1987. PMID: 3110136; PMCID: PMC212386 (Year: 1987).*
Hu L. et al. The Coiled-Coil and Nucleotide Binding Domains of Brown Planthopper Resistance14 Function in Signaling and Resistance against Planthopper in Rice. Plant Cell. Dec. 2017;29(12):3157-3185. doi: 10.1105/tpc.17.00263. Epub Nov. 1, 2017. PMID: 29093216; PMCID: PMC5757267 (Year: 2017).*
Werfel et. al. Rapid and highly efficient inducible cardiac gene knockout in adult mice using AAV-mediated expression of Cre recombinase. Cardiovasc Res. Oct. 1, 2014;104(1):15-23. doi: 10.1093/cvr/cvu174. Epub Jul. 31, 2014. PMID: 25082846. (Year: 2014).*
Mohammed Hakim Jafferali et al. MCLIP, an effective method to detect interactions of transmembrane proteins of the nuclear envelope in live cells, Biochimica et Biophysica Acta (BBA)—Biomembranes, vol. 1838, Issue 10, 2014, pp. 2399-2403, https://doi.org/10.1016/j.bbamem.2014.06.008 (Year: 2014).*
Chai R. The Importance of Proper Neuromuscular Innervation in Muscle Maintenance, Ageing, and Disease, University of Western Australia, Oct. 17, 2013 (Year: 2013).*
Prasad KM. et al. Robust cardiomyocyte-specific gene expression following systemic injection of AAV: in vivo gene delivery follows a Poisson distribution. Gene Ther. Jan. 2011;18(1):43-52. doi: 10.1038/gt.2010.105. Epub Aug. 12, 2010. PMID: 20703310; PMCID: PMC2988989 (Year: 2010).*
Prasad, KM. et al. Robust cardiomyocyte-specific gene expression following systemic injection of AAV: in vivo gene delivery follows a Poisson distribution. Gene Ther 18, 43-52 (2011) (Year: 2011).*
Chen, C-Y., et al., Accumulation of the Inner Nuclear Envelope Protein Sun1 Is Pathogenic in Progeric and Dystrophic Laminopathies, Cell, 149:565-577 (2012).
Crisp, M. et al., Coupling of the nucleus and cytoplasm: role of the LINC complex, Jrnl. Cell. Biol. 172(1):41-53 (2006).
International Search Report for PCT/SG2019/050033, 4 pages (mailed Apr. 17, 2019).
Kim, P. et al., Disrupting the LINC Complex in Smooth Muscle Cells Reduces Aortic Disease in a Mouse Model of HGPS, Sci. Transl. Med., 10(460):1-28 (2018).
Lombardi, M. L. et al., The Interaction between Nesprins and Sun Proteins at the Nuclear Envelope Is Critical for Force Transmission between the Nucleus and Cytoskeleton, Jrnl. Biol. Chem., 286(30):26743-26753 (2011).
Razafsky, D. and Hodzic, D., Temporal and Tissue-Specific Disruption Of LINC Complexes In Vivo, Genesis, 52(4):359-365 (2014).
Wang, X. et al., Lamin A/C Cardiomyopathies: Current Understanding and Novel Treatment Strategies, Curr. Treat Opt. Cardio. Med., 19(21):1-15 (2017).
Worman, H. J. and Bonne, G., "Laminopathies:" a wide spectrum of human diseases, Exp. Cell. Res., 313(10):2121-2133 (2007).
Written Opinion for PCT/SG2019/050033, 9 pages (mailed Apr. 17, 2019).
Zhou, C. et al., Novel nesprin-1 mutations associated with dilated cardiomyopathy cause nuclear envelope disruption and defects in myogenesis, Hum. Mol. Gen., 26(12):2258-2276 (2017).
Banerjee, I. et al., Targeted Ablation of Nesprin 1 and Nesprin 2 from Murine Myocardium Results in Cardiomyopathy, Altered Nuclear Morphology in Inhibition of the Biomechanical Gene Response, PLOS Genetics, 10(2):1-14 (2014).

Chang, W. et al., Linker of nucleoskeleton and cytoskeleton (LINC) complex-mediated actin-dependent nuclear positioning orients centrosomes in migrating myoblasts, Nucleus, 6:77-88 (2015).
Chi, Y. et al., Reversal of laminopathies: the curious case of SUN1, Nucleus, 3(5):418-421 (2012).
Grady, M. R. et al., Syne proteins anchor muscle nuclei at the neuromuscular junction, PNAS, 102(12): 4359-4364 (2005).
Haque, F. et al., SUN1 Interacts with Nuclear Lamin A and Cytoplasmic Nesprins To Provide a Physical Connection between the Nuclear Lamina and the Cytoskeleton, Mol. and Cell. Bio., 26(10):3738-3751 (2006).
Haskell, G. T. et al., Whole Exome Sequencing Identifies Truncating Variants in Nuclear Envelope Genes in Patients With Cardiovascular Disease, Circ Cardiovasc Genet, 1-11 (2017).
Hatch, E. M. and Hetzer, M. W., Nuclear envelope rupture is induced by actin-based nucleus confinement, Jrnl. of Cell Bio., 215:27-36 (2016).
Horn, H. F. et al., A mammalian KASH domain protein coupling meiotic chromosomes to the cytoskeleton, Jrnl. of Cell Bio., 202(7):1023-1039 (2013).
Janin, A. and Gache, V., Nesprins and Lamins in Health and Diseases of Cardiac and Skeletal Muscles, Frontiers in Physiology, 9(1277):1-12 (2018).
Kandert, S. et al., Nesprin-2 giant safeguards nuclear envelope architecture in LMNA S143F progeria cells, Hum. Mol. Gene., 16(23): 2944-2959 (2007).
Kim, Y., et al., Mouse B-Type Lamins Are Required for Proper Organogenesis But Not by Embryonic Stem Cells, Science, 334(6063):1706-1710 (2011).
Lei, K. et al., SUN1 and SUN2 play critical but partially redundant roles in anchoring nuclei in skeletal muscle cells in mice, PNAS, 106(25):10207-10212 (2009).
Li, P. et al., Contribution of SUN1 Mutations to the Pathomechanism in Muscular Dystrophies, Human Mutation, 35(4):452-461 (2014).
Libotte, T. et al., Lamin A/C-dependent Localization of Nesprin-2, a Giant Scaffolder at the Nuclear Envelope, Mol. Bio. of the Cell, 16:3411-3424 (2005).
Lv, X. et al., SUN2 exerts tumor suppressor functions by suppressing the Warburg effect in lung cancer, Scientific Reports, 1-12 (2015).
Meinke, P. et al., Muscular Dystrophy-Associated SUN1 and SUN2 Variants Disrupt Nuclear-Cytoskeletal Connections and Myonuclear Organization, PLOS Genetics, 10(9):1-18 (2014).
Morimoto, A. et al., A conserved KASH domain protein associates with telomeres, SUN1, and dynactin during mammalian meiosis, Jrnl. of Cell Bio., 198(2):165-172 (2012).
Ostlund, C. et al., Dynamics and molecular interactions of linker of nucleoskeleton and cytoskeleton (LINC) complex proteins, Jrnl. of Cell Sci., 122(22):4099-4108 (2009).
Padmakumar, V.C. et al., The inner nuclear membrane protein Sun1 mediates the anchorage of Nesprin-2 to the nuclear envelope, Jrnl. of Cell Sci., 118(15):3419-3430 (2005).
Puckelwartz, M. J. et al., Nesprin-1 mutations in human and murine cardiomyopathy, J. Mol. Cell Cardiol., 48(4):600-608 (2010).
Razafsky, D. et al., LINC Complexes Mediate the Positioning of Cone Photoreceptor Nuclei in Mouse Retina, PLOS One, 7(10): e47180 (2012).
Roux, K. J. et al., Nesprin 4 is an outer nuclear membrane protein that can induce kinesin-mediated cell polarization, PNAS, 106(7):2194-2199 (2009).
Starr, D. A. and Han, M., Role of ANC-1 in Tethering Nuclei to the Actin Cytoskeleton, Science, 298:406-409 (2002).
Starr, D. A., Laminopathies: Too Much SUN Is a Bad Thing, Cuurent Biology, 22(17): R678-R679 (2012).
Stewart-Hutchinson, P. J. et al., Structural requirements for the assembly of LINC complexes and their function in cellular mechanical stiffness, Exp. Cell Res., 314(8):1892-1905 (2008).
Stroud, M. J., Linker of nucleoskeleton and cytoskeleton complex proteins in cardiomyopathy, Biophysical Reviews, 10:1033-1051 (2018).
Sullivan, T. et al., Loss of A-type Lamin Expression Compromises Nuclear Envelope Integrity Leading to Muscular Dystrophy, Jrnl. of Cell Bio., 147(5):913-919 (1999).

(56) References Cited

OTHER PUBLICATIONS

Swiech, L. et al., In vivo interrogation of gene function in the mammalian brain using CRISPR-Cas9, Nat. Biotech., 33:102-106 (2015).
Wang, W. et al., Structural insights into SUN-KASH complexes across the nuclear envelope, Cell Research, 22:1440-1452 (2012).
Zhang, X et al., Syne-1 and Syne-2 play crucial roles in myonuclear anchorage and motor neuron innervation, Development, 134:901-908 (2007).
Zhen, Y. et al., NUANCE, a giant protein connecting the nucleus and actin cytoskeleton, Jrnl. of Cell Sci., 115:3207-3222 (2002).
Jahed et al., "A Molecular Model for LINC Complex Regulation: Activation of SUN2 for KASH Binding", Molecular Biology of the Cell, vol. 29, No. 16, Aug. 8, 2018, pp. 2012-2023.
Ketema et al., "Requirements for the Localization of Nesprin-3 at the Nuclear Envelope and its Interaction with Plectin", Journal of Cell Science, vol. 120, No. 19, Oct. 1, 2007, pp. 3384-3394.
Nie et al., "Coiled-Coil Domains of SUN Proteins as Intrinsic Dynamic Regulators", Structure, vol. 24, No. 1, Jan. 5, 2016, pp. 80-91.
Sosa et al., "LINC Complexes Form by Binding of Three KASH Peptides to the Interfaces of Trimeric SUN Proteins", Cell, vol. 149, No. 5, May 25, 2012, pp. 1035-1047.
Haque et al., "Mammalian SUN Protein Interaction Networks at the Inner Nuclear Membrane and Their Role in Laminopathy Disease Processes", Journal of Biological Chemistry, vol. 285, No. 5, Jan. 29, 2010, pp. 3487-3498.
Stroud, et al., "Linker of Nucleoskeleton and Cytoskeleton Complex Proteins in Cardiac Structure, Function, and Disease", Circulation Research, vol. 114, Issue 3, Jan. 31, 2014, pp. 538-548.

\* cited by examiner

Fig. 3
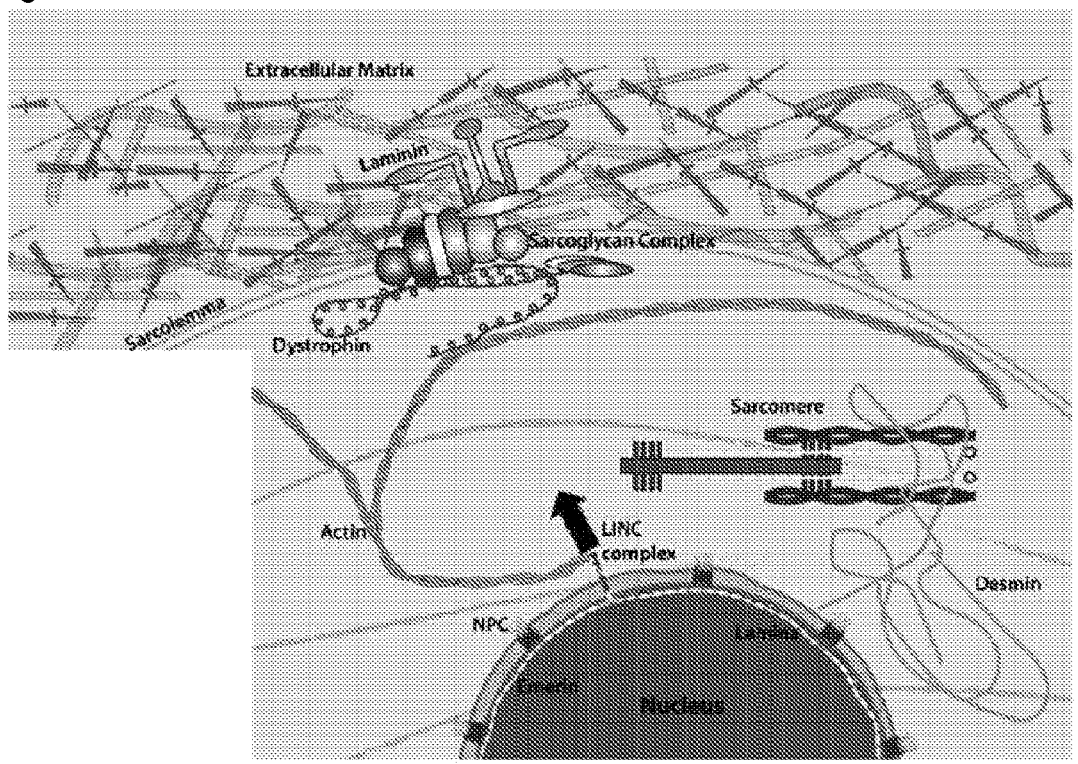
Fig. 4
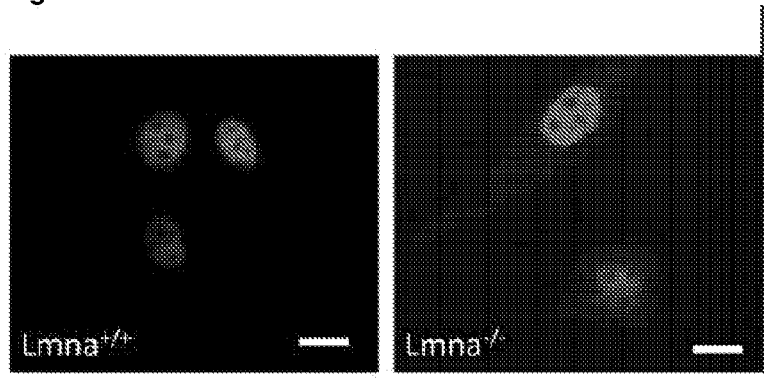
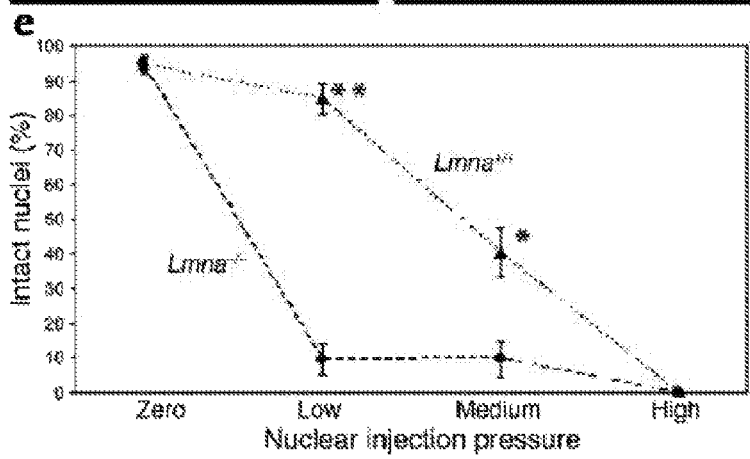

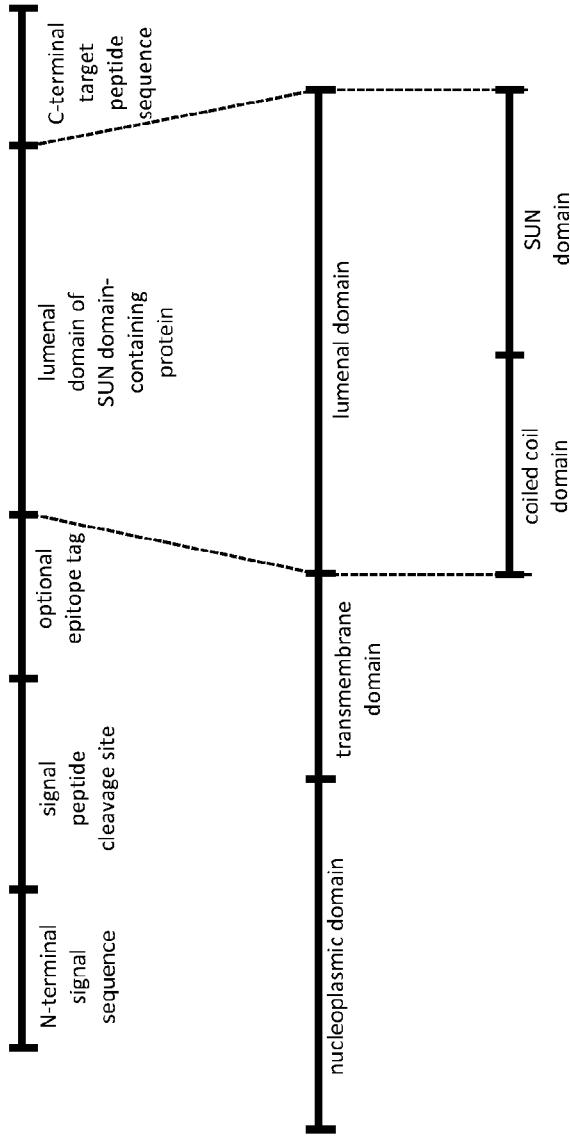

Fig. 29A (continued)
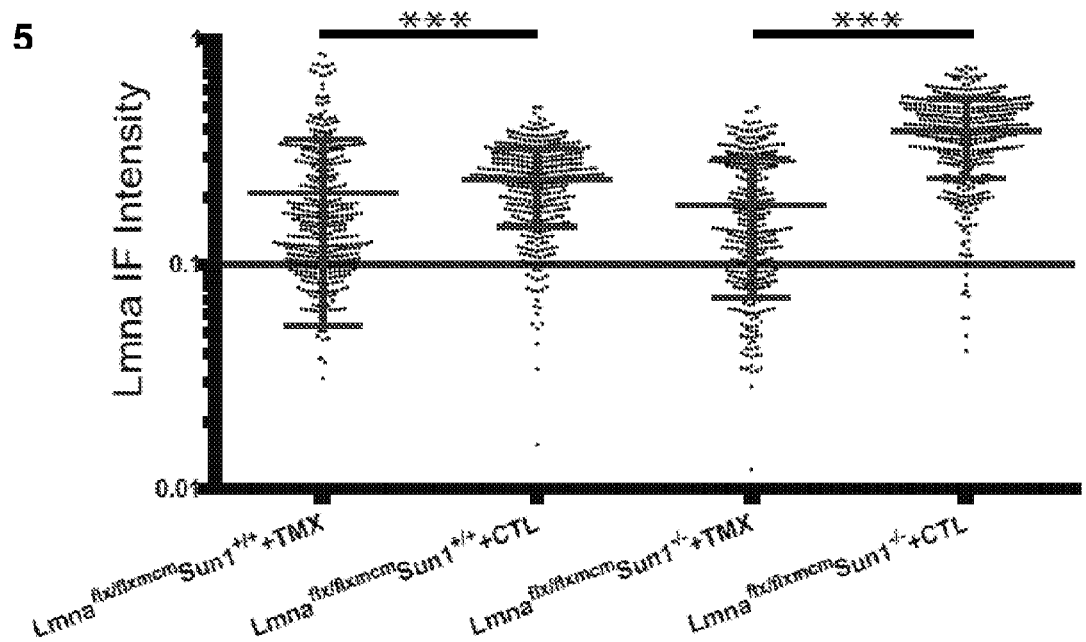
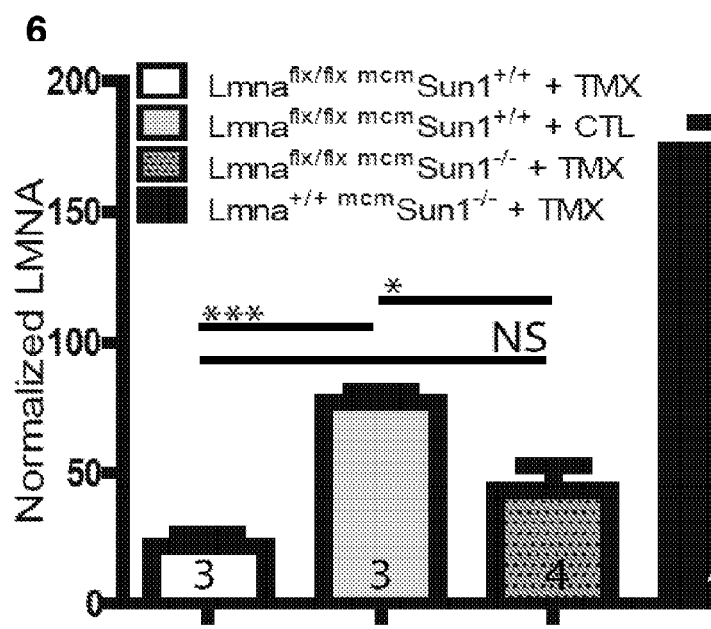

Fig. 31E (i)
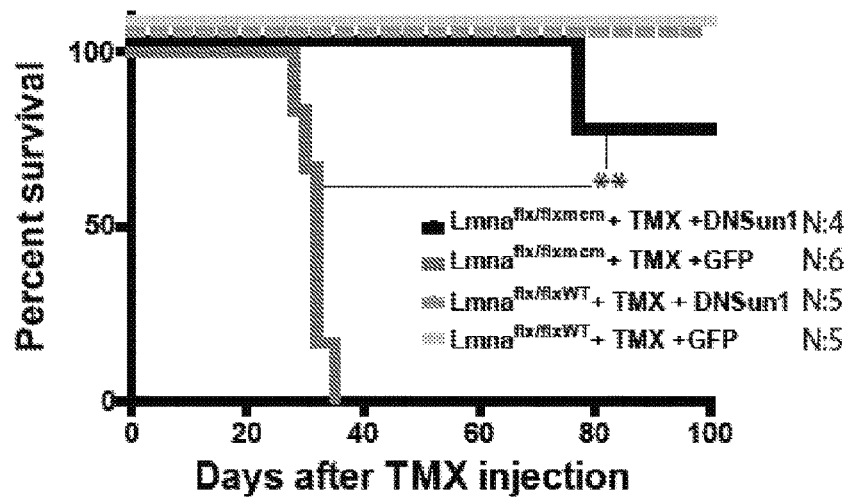
Fig. 31E (ii)
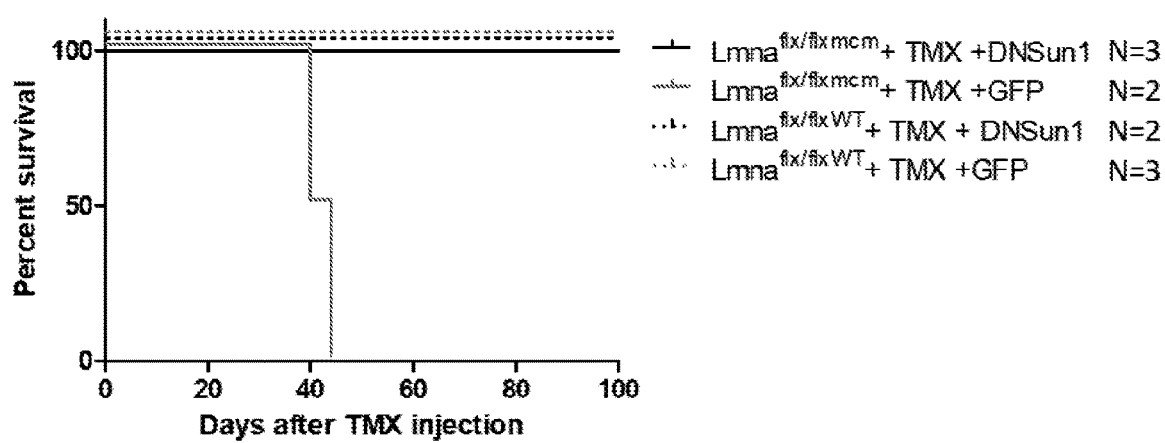

Fig. 40A

```
SEQ ID NO:69  wildtype    CATGACCTTGAGCTGAAACTGCTGCAGAATATCACACCACATCACCGTGACAGGACAG   2100
SEQ ID NO:70  Sun1_plus4  CATGACCTTGAGCTGAAACTGCTGCAGAATATCACACCACATCACCGTGACAGGACAG   2100
SEQ ID NO:71  Sun1_del7   CATGACCTTGAGCTGAAACTGCTGCAGAATATCACACCACATCACCGTGACAGGACAG   2100
                          **********************************************************

SEQ ID NO:69  wildtype    GCCCCG----ACATCCGAGGCTATTGTGTCTGCCGTGAATCAGGCAGGGATTTCAGGAAT  2156
SEQ ID NO:70  Sun1_plus4  GCCCCGagaCACATCCGAGGCTATTGTGTCTGCCGTGAATCAGGCAGGGATTTCAGGAAT  2160
SEQ ID NO:71  Sun1_del7   GCCC------CGAGGCTATTGTGTCTGCCGTGAATCAGGCAGGGATTTCAGGAAT      2149
                          ****      ******************************************

SEQ ID NO:69  wildtype    CACAGAAGCGcaagcacacatatcattgtgaacaatgctctgaagctgtactcccaagacaa  2215
SEQ ID NO:70  Sun1_plus4  CACAGAAGCGcaagcacacatatcattgtgaacaatgctctgaagctgtactcccaagacaa  2220
SEQ ID NO:71  Sun1_del7   CACAGAAGCGcaagcacacatatcattgtgaacaatgctctgaagctgtactcccaagacaa  2209
                          ************************************************************
```

Fig. 40B

```
SEQ ID NO:72  wildtype    WLLEKLSSRFVSKDELQVLLHDLELKLLQNITHHITVTGQAPTSEAIVSAVNQAGISGIT  720
SEQ ID NO:73  Sun1_plus4  WLLEKLSSRFVSKDELQVLLHDLELKLLQNITHHITVTGQAPRHIRGYCVCRESGRDFRN  720
SEQ ID NO:74  Sun1_del7   WLLEKLSSRFVSKDELQVLLHDLELKLLQNITHHITVTGQAPRLLCLP----*------  708
                          ********************************************   *

SEQ ID NO:72  wildtype    EAQAHIIVNNALKLYSQDKTGMVDFALESGGGSILSTRCSETYETKTALLSLFGVLWYF  780
SEQ ID NO:73  Sun1_plus4  ------HRSASTYHCEQCSEAVLPRQDGDGGL----C------SGVWRW           753
SEQ ID NO:74  Sun1_del7   ----------------------------------------------------------  708

SEQ ID NO:72  wildtype    SQSPRVVIQPDIYPGNCWAFKGSQGYLVVRLSMKIYPTFTMEHIPKTLSPTGNISSAPK  840
SEQ ID NO:73  Sun1_plus4  QHPKHSVL*-------------------------------------------------  761
SEQ ID NO:74  Sun1_del7   ----------------------------------------------------------  708

SEQ ID NO:72  wildtype    DFAVYGLETEVQEEGQPLGRFTYDQEGDSLQMFHTLERPDQAFQIVELRVLSNWGHPEYT  900
SEQ ID NO:73  Sun1_plus4  ----------------------------------------------------------  761
SEQ ID NO:74  Sun1_del7   ----------------------------------------------------------  708

SEQ ID NO:72  wildtype    CLYRFRVHGEPIQ*  913
SEQ ID NO:73  Sun1_plus4  -------------   761
SEQ ID NO:74  Sun1_del7   -------------   708
```

```
SEQ ID NO:75  wildtype      TATTGGACTCACCTGCCTTGTACCCATGTCAGAGAAAGACTACAGCTGTGCCCTCTCCAA  180
SEQ ID NO:76  Syne1_CTdel8  TATTGGACTCACCTGCCTTGTACCCATGTCAGAGAAAGACTACAGCTGTGCCCTCTCCAA  180
                            ************************************************************

SEQ ID NO:75  wildtype      CAACTTTGCCCGATCCTTCCATCCGATGCTCAGATATACCAACGGTCCTCCTCCACTCTG  240
SEQ ID NO:76  Syne1_CTdel8  CAACTTTGCCCGATCCTTCCATCCG------ATATACCAACGGTCCTCCTCCACTCTG   232
                            *************************      *****************************

SEQ ID NO:75  wildtype      AAGCAAGCAGACATCCCCACACAAGTGcaggcagtaagagaggaggaatatcaaatggc   300
SEQ ID NO:76  Syne1_CTdel8  AAGCAAGCAGACATCCCCACACAAGTGcaggcagtaagagaggaggaatatcaaatggc   292
                            ************************************************************
```

B

```
SEQ ID NO:77  wildtype         STRDGSDSSRSDPRPERVGRAFLFRILRAALPFQLLLLLIGLTCLVPMSEKDYSCALSN   60
SEQ ID NO:78  Nesprin1_CTdel8  STRDGSDSSRSDPRPERVGRAFLFRILRAALPFQLLLLLIGLTCLVPMSEKDYSCALSN   60
                               ************************************************************

SEQ ID NO:77  wildtype         NFARSFHPMLRYTNGPPPL*------------------------------------      79
SEQ ID NO:78  Nesprin1_CTdel8  NFARSFHPIYQRSSSTLKQADIPTQVQAVRGEGISNGREAPKEKFNILNHQGNANQNNPE  120
                               ********:  :  : ..

SEQ ID NO:77  wildtype         -----------                                                   79
SEQ ID NO:78  Nesprin1_CTdel8  METNAPPCS*                                                   129
```

Fig. 41 (continued)
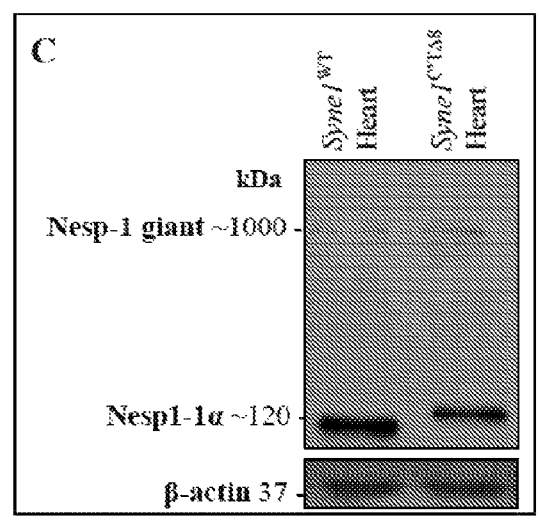
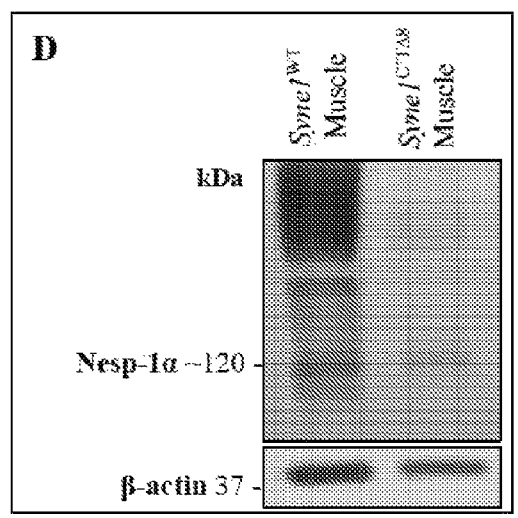

Fig. 42
A
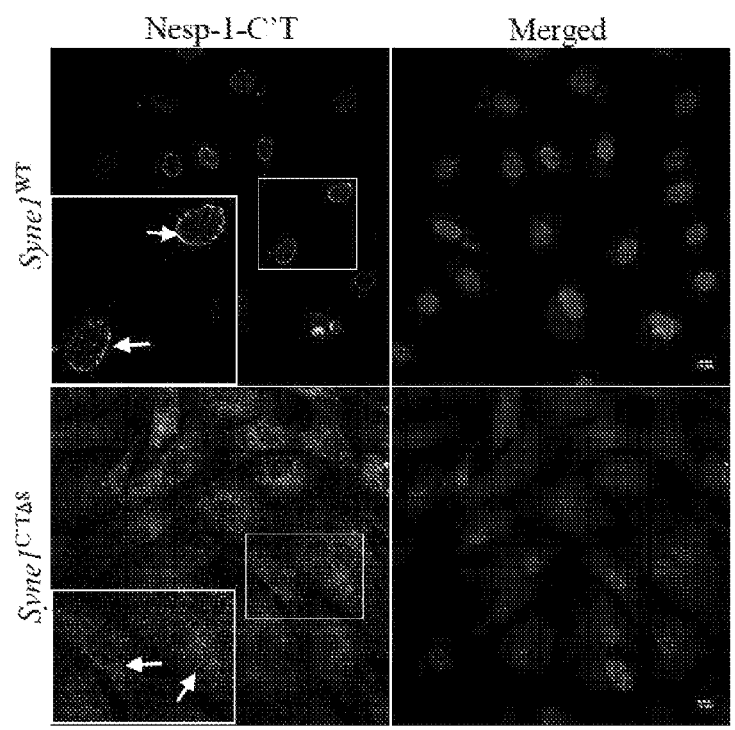
B
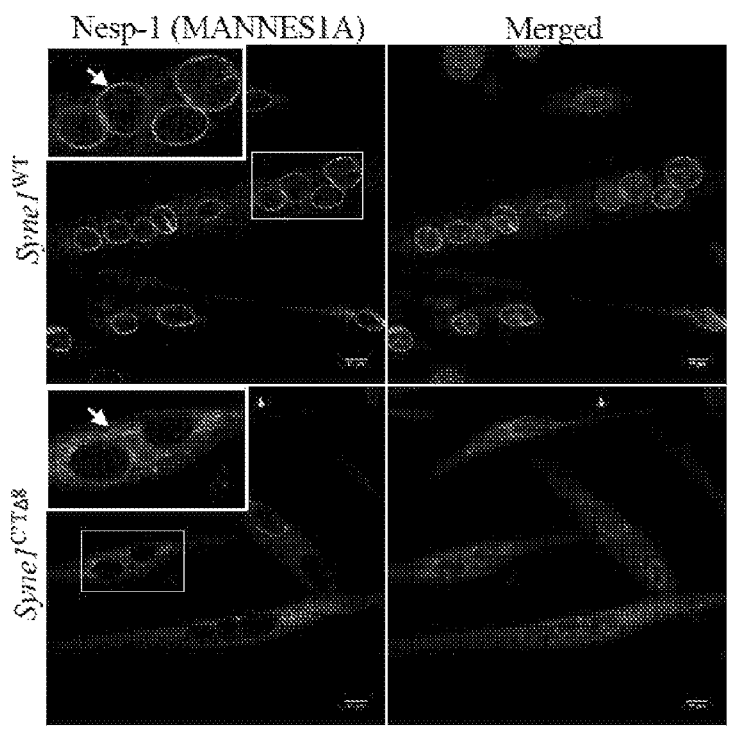

DISRUPTING THE LINC COMPLEX FOR TREATING LAMINOPATHY

RELATED APPLICATIONS

This application is a national stage filing under 35 U.S.C. 0 371 of international application number PCT/SG2019/50033, filed Jan. 18, 2019, which claims the benefit of Singapore application number 10201800530Q, filed Jan. 19, 2018, each of which is herein incorporated by reference in its entirety.

FIELD OF THE INVENTION

The present invention relates to use of expression vectors and other compounds in methods to disrupt the Linker of Nucleoskeleton and Cytoskeleton (LINC) complex, uncoupling the nucleus from its linkage to the cytoskeleton, resulting in amelioration of diseases caused by one or more Lmna mutations, so-called laminopathies. More particularly, the invention relates to the expression of dominant negative or mutated SUN domain protein and/or dominant negative or mutated KASH domain protein to disrupt the LINC complex in, for example, cardiomyocytes for suppressing disease progression in dilated cardiomyopathy (DCM).

BACKGROUND

Dilated Cardiomyopathy (DCM) is the most common disease affecting heart muscle, accounting for approximately 60% of all cardiomyopathies. It is characterized by reduced systolic (contractile) function due to enlargement and thinning of the left ventricular wall or in some cases both ventricles. DCM is associated with sudden heart failure and cardiac death, resulting in high rates of hospital admission, the need for heart transplantation and consequently a high cost burden [J. L. Jefferies and J. A. Towbin, *Lancet* 375: 752-762 (2010); R. E. Hershberger, et al., *Nat Rev Cardiol* 10: 531-547 (2013)]. The causes of DCM are varied, but include a variety of extrinsic factors, (viral, autoimmune infiltration, alcohol, and drugs). However 30-40% of all cases have a monogenic basis, with mutations in some 40 genes being linked to DCM. The most frequently mutated gene in DCM is TTN, that encodes the giant sarcomeric protein titin, with truncating variants in TTN accounting for almost 15-25% of all congenital forms of DCM [D. S. Herman et al., *N Engl J Med* 366: 619-628 (2012); U. Tayal, S. et al., *Genome Med* 9: 20 (2017)]. The second most frequently mutated gene is Lamin A (LMNA) accounts for as many as 6-8% of congenital DCM patients [U. Tayal, S. et al., *Genome Med* 9: 20 (2017)].

LMNA Induced DCM Is characterized by cardiac conduction disease manifested by electrophysiological (ECG) abnormalities, including atrioventricular block, ventricular arrhythmias and fibrillation. The risk of sudden cardiac death is greater in patients with LMNA-cardiomyopathy than patients with other forms of DCM [J. H. Van Berlo et al., *Hum Mol Genet* 14: 2839-2849 (2005)]. Some 450 different mutations have been Identified in the LMNA gene, most being missense, resulting in the majority of DCM cases being inherited as autosomal dominants, with this diversity of the mutations complicating genetic approaches to treating LMNA induced DCM. To a limited extent LMNA induced DCM can be treated by fitting a pacemaker. Ultimately, however, effective treatment at present is accomplished by heart transplantation (R. E. Hershberger and A. Morales, in *Gene Reviews((R))*, M. P. Adam et al., Eds. (Seattle (Wash.), 1993); G. Captur et al., *Heart* 104: 488-479 (2018)].

Mouse lines carrying Lmna mutations usually die within a few weeks after birth [T. Sullivan et al., *J Cell Biol* 147: 913-920 (1999); A. T. Bertrand et al., *Hum Mol Genet* 21: 1037-1048 (2012); V. Nikolova et al., *J Clin Invest* 113: 357-369 (2004); A. S. Wang, et al., *Differentiation; research in biological diversity*, (2015)]. The cause of early death in mice lacking Lmna is uncertain due to multiple tissues being affected. Cardiac myopathy is thought to be a major contributing cause, as Lmna mutant mice develop DCM with conduction abnormalities and focal myocyte degeneration [V. Nikolova et al., *J Clin Invest* 113: 357-369 (2004); L. C. Mounkes, et al., *Hum Mol Genet* 14: 2167-2180 (2005)], although effects on other, as yet undefined, skeletal muscles may contribute to early postnatal death.

The lamins are nuclear intermediate filament proteins and are the principal constituents of the nuclear lamina, the proteinaceous matrix underlying the inner nuclear membrane (INM). The lamina consists of the A-type lamins, consisting of 2 predominant forms, lamins A and lamin C, derived by alternate splicing of LMNA, whereas the two B type lamins (LMNB 1 and 2) are each encoded by two genes: LMNB1 and LMNB2 [B. Burke and C. L. Stewart, *Nat Rev Mod Cell Biol* 14: 13-24 (2013)]. The lamina provides structural and mechanical integrity to the nucleus, maintains nuclear shape and position within the cell, as well as being determinants of chromatin organization [T. Sullivan et al., *J Cell Biol* 147: 913-920 (1999); I. Solovei et al., *Cell* 152: 584-598 (2013)]. The lamins interact with numerous INM proteins, inducing Emerin, the Lamina-Associated Polypeptides (LAPs) and the SUN domain proteins [B. van Steensel and A. S. Belmont, *Cell* 169: 780-791 (2017)], many of which when either mutated or present as a variant are linked to heart disease [H. J. Worman, et al., *Cold Sprng Harbor perspectives in biology* 2: a000760 (2010); C. L. Stewart, et al., *Exp Cell Res* 313:2144-2156 (2007)]. Together these proteins comprise an integrated protein network, centered on the lamina, where loss or mutation of the lamins can result in either the mislocalization or a change in expression levels of many lamina associated proteins, (emerin, SUN1, LBR and Lap2α) [T. Sullivan et al., *J Cell Biol* 147: 913-920 (1999); I. Solovel et al., *Cell* 152: 584-598 (2013); C. Y. Chen et al., *Cell* 149: 565-577 (2012); T. V. Cohen et al., *Hum Mol Genet* 22: 2852-2869 (2013); F. Haque et al., *J Biol Chem* 285: 3487-3498 (2010)]. Among these proteins, where expression is affected by the loss of Lmna or mutation, are SUN1 and Lap2, both of whose levels are Increased. In the case of SUN1 the Increased level is due to reduced turnover, rather than increased expression, resulting in high levels accumulating in the Golgi which appeared to be cytotoxic at least in the Lmna$^{-/-}$ and LmnaΔ9 mouse disease models [C. Y. Chen et al., *Cell* 149: 565-577 (2012); C. Stewart and B. Burke, WO/2013/158046]. However, when SUN1 levels are genetically ablated in mice with Lmna mutations, this increases the longevity 3-fold and ameliorates much of the pathology [C. Y. Chen et al., *Cell* 149: 585-577 (2012); C. Stewart and B. Burke, WO/2013/158048]. The median survival of wild-type or Sun1$^{-/-}$ is >210 days in a 7 month follows up; Lmna$^{-/-}$ mice had median survival of 41 days; Lmna$^{-/-}$ Sun1$^{-/-}$ mice had a median survival of 54 days; Lmna$^{-/-}$ Sun1$^{-/-}$ mice had a median survival of 104 days (p<0.01 comparing Lmna$^{-/-}$ and Lmna$^{-/-}$ Sun1$^{-/-}$). Likewise, whereas all LmnaΔ9 mice expired by 30 days after birth, their LmnaΔ9Sun1$^{-/-}$ littermates thrived past this date, and most achieved life spans more than twice this duration [C. Y. Chen et al., *Cell* 149:

565-577 (2012)]. At the cellular level, human fibroblasts harbouring a LMNA mutation resulting in Hutchison-Gilford Progeria Syndrome also exhibited increased Sun1 levels. Depleting Sun1 in these cells alleviated nuclear morphology defects, again suggesting that excess Sun1 resulting from LMNA mutation is cytotoxic [C. Y. Chen et al., Cell 149: 565-577 (2012); C. Stewart and B. Burke, WO/2013/158046].

The SUN (Sad1p, UNC-84) domain proteins share a conserved C-terminal SUN domain and localize to the INM [C. J. Malone, et al., Development 126:3171-3181 (1999)]. In mammals, SUN1 and SUN2 are the 2 principal SUN proteins that are widely expressed in virtually all tissues. In the perinuclear space, between the INM and outer nuclear membrane (ONM), the C-termini of SUN1 and/or 2 bind to the C-termini (KASH domains) of the different Nesprins/SYNE/KASH proteins that traverse the ONM. Together these 2 families of proteins comprise the LINC complexes that physically couple the interphase nuclei to the cytoskeleton [M. Crisp et al., *J Cell Biol* 172: 41-53 (2006); E. C. Tapley and D. A. Starr, *Curr Opin Cell Biol* 25: 57-62 (2013)]. The N-termini of the SUN domain proteins protrude into the nudeoplasm and with SUN1, this region interacts with pre-laminA and nuclear pore complexes. Whether the N-terminus of SUN2 interacts with any nucleoplasmic/NE protein is unclear. In contrast, the bulk of the Nesprins/KASH domain proteins extend into the cytoplasm adjacent to the ONM. There, depending on the particular Nesprin/KASH protein, they interact directly or indirectly with all 3 cytoskeletal protein networks (microtubules, actin microfilaments and Intermediate filaments) [H. F. Horn, *Current topics in developmental biology* 109: 287-321 (2014)]. Together, the SUN and KASH/Nesprin proteins of the LINC complex establish a direct physical connection between the cytoplasmic cytoskeletal networks (and their connections e.g. cell adhesion complexes at the cell membrane) and the interphase nuclear interior or nucleoplasm. The LINC complex Is thought to mediate force transmission between the nucleus and cytoskeleton and consequently regulate changes in gene expression/chromatin organization in response to mechanical/physical stimuli [S. G. Alam et al., *Scientific reports* 6: 38003 (2016)]. Although loss of either SUN1 or SUN2 alone has no overt effect on postnatal growth and viability, SUN1 null mice are infertile and deaf. Simultaneous loss of Sun1 and Sun2 results in perinatal lethality, indicating a degree of redundancy during embryogenesis [K. Lei et al., *Proc Natl Acad Sci USA* 106: 10207-10212 (2009)].

There is a need to develop alternative methods to ameliorate the negative effects over-accumulation of Sun1 has on cells carrying Lmna mutations. The present disclosure aims at providing such a method.

SUMMARY OF INVENTION

Surprisingly, the inventors have found that disruption of the LINC complex rather than removal of accumulated Sun1 protein can ameliorate diseases caused by one or more Lmna mutations. One way of achieving the disruption is via an expression construct/vector comprising an operably linked transgene, the expression of which generates dominant negative SUN domain protein or mutated endogenous SUN domain protein and/or dominant negative KASH domain protein or mutated endogenous KASH domain protein. The exogenous dominant negative SUN domain and KASH domain proteins act as LINC complex binding competitors, thereby uncoupling the nucleus from its linkage to the cytoskeleton. The mutated SUN domain and KASH domain proteins are endogenous Sun and Nesprin proteins that have been mutated in the SUN or KASH domain, respectively, and cannot form a UNC complex because they cannot bind to their cognate LINC complex partner. These strategies may be used to disrupt the LINC complex to treat, for example, laminopathies. The result was achieved without actively reducing the endogenous SUN1 protein levels. Results shown herein support these claims.

According to a first aspect of the invention, there is provided an isolated nucleic acid molecule, wherein the nucleic acid molecule comprises an expression vector and a transgene, whereby the transgene is operably linked to the expression vector, wherein expression of the transgene in a transfected cell results in disruption of a LINC complex in the transfected cell.

In some embodiments, the expression vector is a cardiac- or cardiomyocyte-specific expression vector.

In some embodiments, the expression vector comprises a cardiac- or cardiomyocyte-specific promoter selected from the group comprising a cardiac troponin T promoter (cTnT), a α-myosin heavy chain (α-MHC) promoter and a myosin light chain (MLC2v) promoter. Preferably the promoter is cardiac troponin T promoter (cTnT).

In some embodiments, the cardiomyocyte-specific promoter is chicken cardiac troponin T promoter (cTnT).

In some embodiments, the expression vector has cardiac tropism/is cardiotropic.

In some embodiments, the expression vector is a virus expression vector.

In some embodiments, the virus expression vector Is selected from the group comprising Lentivirus, Adenovirus and Adeno-associated virus (AAV). Preferably the virus expression vector is adeno-associated virus (AAV).

In some embodiments, the AAV vector is selected from the group consisting of AAV9 (serotype 9), AAV1 (serotype 1), AAV6 (serotype 6), AAV8 (serotype 8), AAV218 and AAV9.45.

In some embodiments, the AAV vector is AAV9 (serotype 9).

In some embodiments, the transgene comprises nucleic acid sequences for expressing a lumenal domain of a SUN domain-containing protein, an N-terminal signal sequence, a signal peptidase cleavage site, and a C-terminal targeting peptide sequence.

In some embodiments the lumenal domain of the SUN domain-containing protein comprises a coiled coil domain and a SUN domain.

In a preferred embodiment the coiled coil domain is upstream of the SUN domain.

In some embodiments, the transgene further comprises nucleic acid sequences for expressing an N-terminal signal sequence, a signal peptidase cleavage site, and a C-terminal targeting peptide sequence.

In some embodiments, the transgene comprises nucleic acid sequences for expressing an N-terminal signal sequence, a signal peptidase cleavage site, and a C-terminal targeting peptide sequence, and either the luminal domain of the SUN domain-containing protein or the SUN domain.

Preferably, the SUN domain protein is SUN1 or SUN2.

In some embodiments the luminal domain of Sun1 comprises amino acids 458-913 of full-length mouse Sun1 (Uniprot Q9D666) or Its human equivalent comprising the coiled coil domain and the SUN domain and lacking the transmembrane domain. A schematic of the structure of a dominant negative form of Sun is shown in FIG. 7.

For SUN domain constructs it is expected that the SUN domain alone (crystal structure solved by the Kutay and Schwartz labs [Sosa et al., *Cell* 149(5):1035-47 (2012)], Instead of the entire luminal domain (coiled coil domain and SUN domain) is sufficient to disrupt the SUN-KASH interaction as it is capable of binding to the KASH domain. The human Sun1 SUN domain nucleic acid sequence is set forth in SEQ ID NO: 80. However, the presence of the signal sequence and the KDEL sequence are important for targeting the construct to the perinuclear space.

In some embodiments, the N-terminal signal sequence is derived from a secretory protein or a Type I transmembrane protein.

Preferably, the secretory protein or Type I transmembrane protein is selected from the group consisting of human serum albumin, proinsulin, transferrin receptor, EGF receptor, pre-pro-opiomelanocortin, pancreatic digestive enzymes (for example, proteases, amylases and lipases), endoplasmic reticulum luminal proteins, for example protein disulphide isomerases, GRP94 and combinations thereof. More preferably, the N-terminal signal sequence is derived from human serum albumin.

In some embodiments, the N-terminal signal sequence is not preceded at its N-terminus by any other tags.

In some embodiments, the signal peptidase cleavage site is a signal peptidase cleavage site derived from or is one of the group consisting of human serum albumin, proinsulin, transferrin receptor, EGF receptor, pre-pro-opiomelanocortin, pancreatic digestive enzymes (for example, proteases, amylases and lipases), endoplasmic reticulum lumenal proteins, such as protein disulphide isomerases, GRP94 and combinations thereof. Preferably, the signal peptidase cleavage site is a signal peptidase cleavage site derived from human serum albumin.

In some embodiments, the C-terminal targeting peptide sequence prevents secretion of a peptide expressed from the transgene according to any aspect of the invention.

In some embodiments, the C-terminal targeting peptide sequence is a KDEL tetrapeptide Golgi retrieval sequence. Examples of such structures are shown in FIGS. 11 and 12.

In some embodiments the transgene comprises a humanized Sun1DN nucleic acid sequence or a humanized Sun2DN nucleic acid sequence. In a preferred embodiment, the transgene comprises a signal sequence, a humanized Sun1DN nucleic acid sequence and a KDEL sequence as set forth in SEQ ID NO: 4; or the transgene comprises a signal sequence, a humanized Sun2DN nucleic acid sequence and a KDEL sequence as set forth in SEQ ID NO: 5.

In some embodiments, the transgene further comprises an epitope tag. Preferably the epitope tag is N-terminal, or located anywhere in the nucleic acid molecule except downstream of (after) the C-terminal targeting peptide sequence [for example KDEL], or located anywhere in the nucleic acid molecule except upstream of (before) the N-terminal signal sequence.

In some embodiments, the epitope tag is selected from the group consisting of cellulose binding domain (CBD), chloramphenicol acetyl transferase (CAT), dihydrofolate reductase (DHFR), one or more FLAG tags, glutathione S-transferase (GST), green fluorescent protein (GFP), haemagglutinin A (HA), histidine (His), Herpes simplex virus (HSV), luciferase, maltose-binding protein (MBP), c-Myc, Protein A, Protein G, streptavidin, T7, thioredoxin, V5, vesicular stomatitis virus glycoprotein (VSV-G), and combinations thereof. Preferably, the epitope tag is haemagglutinin A (HA).

In some embodiments, the nucleic acid molecule of the invention comprises an adeno-associated virus vector (AAV) comprising a chicken cardiac troponin T promoter (cTnT), a transgene according to any aspect of the invention comprising the luminal domain of the SUN domain-containing protein derived from SUN, an N-terminal signal sequence and a signal peptidase cleavage site which are each derived from human serum albumin, a C-terminal targeting peptide sequence which is a KDEL sequence, and wherein the transgene optionally further comprises haemagglutinin (HA) as an N-terminal epitope tag.

According to an embodiment an example of such a vector is shown in FIG. 10 and comprises the nucleic acid sequence set forth in SEQ ID NO: 3.

In some embodiments, the nucleic acid molecule of the invention comprises an adeno-associated virus vector (AAV) comprising a chicken cardiac troponin T promoter (cTnT), a transgene according to any aspect of the invention comprising the luminal domain of the SUN domain-containing protein derived from SUN2, an N-terminal signal sequence and a signal peptidase cleavage site which are each derived from human serum albumin, a C-terminal targeting peptide sequence which is a KDEL sequence, and wherein the transgene optionally further comprises hemagglutinin (HA) as the N-terminal epitope tag.

According to an embodiment an example nucleic acid molecule would comprise the vector structure shown in FIG. 10 and the transgene nucleic acid sequence set forth in SEQ ID NO: 5.

Rather than expressing components of a lumenal domain of a SUN domain-containing protein, a KASH domain may be expressed to disrupt a LINC complex by competing with endogenous Nesprins (which comprise a KASH domain) for binding to SUN1 and SUN2 domains.

Accordingly, in some embodiments of the nucleic acid molecule of the Invention, the transgene comprises nucleic acid sequences for expressing a KASH domain, and an N-terminal stabiliser polypeptide sequence.

Preferably, the KASH domain comprises a transmembrane domain and a SUN-interacting peptide.

Preferably the transgene comprises nucleic acid sequences for expressing a KASH domain that traverses the outer nuclear membrane, a SUN-interacting KASH peptide that extends into the perinuclear space at the C-terminus, and an N-terminal stabiliser polypeptide sequence in the cytoplasm.

It would be understood that KASH domain constructs with extensions after the last C-terminal amino acid of the naturally occurring KASH domain are not expected to work. i.e. C-terminal tags, or even an additional carboxy-terminal single amino acid, will disrupt KASH interaction with SUN. In addition, a signal sequence on the N-terminus of SUN domain constructs cannot be preceded by any tags.

In some embodiments, the KASH domain is selected from the group consisting of KASH1 (derived from Nesprin-1 (SYNE1 gene)), KASH2 (derived from Nesprin-2 (SYNE2 gene)), KASH3 (derived from Nesprin-3 (SYNE3 gene)), KASH4 (derived from Nesprin-4 (SYNE4 gene)) and KASH5 (derived from KASH5/CCDC155 (KASH5 gene)).

In preferred embodiments the KASH 1 domain comprises the human amino acid sequence set forth in SEQ ID NO: 7; the KASH 2 domain comprises the human amino acid sequence set forth in SEQ ID NO: 9; the KASH 3 domain comprises the human amino acid sequence set forth in SEQ ID NO: 11; the KASH 4 domain comprises the human amino acid sequence set forth in SEQ ID NO: 13; and the KASH 5 domain comprises the human amino acid sequence set forth in SEQ ID NO: 15. An alignment of the five KASH amino acid sequences is shown in FIG. 14.

In some embodiments the KASH domain nucleic acid sequence has at least 80%, at least 85%, at least 90%, at least 95% sequence identity or 100% sequence identity to the nucleic acid sequence of the KASH1 domain set forth in SEQ ID NO: 6; the nucleic acid sequence of the KASH2 domain set forth in SEQ ID NO: 8; the nucleic acid sequence of the KASH3 domain set forth in SEQ ID NO: 10; the nucleic acid sequence of the KASH4 domain set forth in SEQ ID NO: 12; or the nucleic acid sequence of the KASH5 domain set forth in SEQ ID NO: 14.

More preferably, for the purpose of clinical use, the KASH domain is the human KASH1 domain of SYNE1 having at least 80%, at least 85%, at least 90%, at least 95% sequence identity or 100% sequence identity to the nucleic acid sequence of the human KASH1 domain set forth in SEQ ID NO: 6.

It would be understood that due to the redundancy in the genetic code, a nucleic acid sequence may have less than 100% identity and still encode the same amino acid sequence.

In some embodiments, the KASH domain does not comprise any extensions after the last C-terminal amino acid compared to a naturally occurring KASH domain.

In some embodiments, the N-terminal stabiliser polypeptide sequence Is selected from the group consisting of green fluorescent protein (GFP), cellulose binding domain (CBD), chloramphenicol acetyl transferase (CAT), dihydrofolate reductase (DHFR), glutathione S-transferase (GST), luciferase, maltose-binding protein (MBP), Protein A, Protein G, streptavidin, thioredoxin, DHFR, including multiples and combinations thereof.

In some embodiments, the N-terminal stabilizer polypeptide sequence forms a discretely folded domain.

In some embodiments, the vector is the adeno-associated virus vector (AAV) comprising a cardiac troponin T promoter (cTnT), and the transgene comprises nucleic acid sequences for expressing a KASH domain, and an N-terminal stabiliser polypeptide sequence, wherein the KASH domain is selected from the group comprising KASH1, KASH2, KASH3, KASH4 and KASH5.

In some embodiments, the N-terminal stabiliser polypeptide sequence is green fluorescent protein (GFP).

Rather than expressing components of a lumenal domain of a SUN domain-containing protein or a KASH domain to disrupt a LINC complex by competing for binding with endogenous Nesprins (which comprise a KASH domain) or Sun1 and Sun2 (which comprise a SUN domain), another approach for disrupting the LINC complex is to modify the endogenous SUN domain or KASH domain so that it fails to bind to, or has reduced binding capacity for, its cognate LINC complex binding partner.

As both the SUN domain and the KASH domain are located at the C-termini of their respective proteins, one way of producing a modified SUN or KASH domain is to use a CRISPR/Cas system to modify the genes encoding SUN or KASH domain proteins to generate a premature stop codon at the 3' end of the respective protein sequences following CRISPR-induced non-homologous end joining. This would result in a truncated protein with its C-terminal SUN or KASH domain mutated. The truncated protein would be expressed and membrane-localized, but unable to interact with its cognate LINC complex partners.

Accordingly, in some embodiments of the nucleic acid molecule of the invention, the transgene comprises nucleic acid sequences for expressing a CRISPR-Cas or other synthetic nuclease system to modify nucleic acid that encodes the SUN domain or KASH domain of endogenous Sun or Nesprin protein, respectively.

Data shown herein (Example 6) suggests that modification of the SUN2 domain or KASH2 domain does not ameliorate Lmna pathology.

In some embodiments the CRISPR-Cas modifies the endogenous SUN domain or KASH domain of Sun1 or Nesprin-1 protein, respectively, to disrupt a LINC complex. The respective nucleic acids are Sun1 and Syne1.

In some embodiments, the transgene comprises nucleic acid sequences for expressing a CRISPR-Cas with a gRNA nucleic acid sequence comprising 5'-GCACAATAGCCTCGGATGTCG-3' (SEQ ID NO: 66) to modify the SUN domain of mouse Sun1.

In some embodiments, the transgene comprises nucleic acid sequences for expressing a CRISPR-Cas with a gRNA nucleic acid sequence targeting the human SUN1 domain set forth in SEQ ID NO: 80. Preferably, the gRNA nucleic acid sequence targets the end of axon 20 comprising a nucleic acid sequence set forth in SEQ ID NO: 81. More preferably, the gRNA nucleic acid sequence targets a SUN1 nucleic acid sequence selected from the group comprising SEQ ID NO: 55; SEQ ID NO: 56; SEQ ID NO: 57; SEQ ID NO: 58; SEQ ID NO: 59; SEQ ID NO: 60; SEQ ID NO: 61; SEQ ID NO: 62; SEQ ID NO: 63; SEQ ID NO: 64 and SEQ ID NO: 65 set forth in Table 3.

In some embodiments, the transgene comprises nucleic acid sequences for expressing a CRISPR-Cas with a gRNA nucleic acid sequence comprising 5'-CCGTTGGTATATCT-GAGCAT-3' (SEQ ID NO: 34) to modify the KASH domain of mouse Syne-1.

In some embodiments, the transgene comprises nucleic acid sequences for expressing a CRISPR-Cas with a gRNA nucleic acid sequence targeting the human KASH domain set forth in SEQ ID NO: 6. Preferably, the gRNA nucleic acid sequence comprises a nucleic sequence selected from the group comprising SEQ ID NO: 44; SEQ ID NO: 45; SEQ ID NO: 46; SEQ ID NO: 47; SEQ ID NO: 48; SEQ ID NO: 49; SEQ ID NO: 50; SEQ ID NO: 51; SEQ ID NO: 52; SEQ ID NO: 53 and SEQ ID NO: 54 set forth in Table 3.

In some embodiments, the transgene comprises nucleic acid sequences for expressing a CRISPR-Cas9 or variant thereof.

In preferred embodiments, the transgene is a dominant negative construct.

In some embodiments, the transgene is a humanised transgene.

In some embodiments, expression of the transgene results in the disruption of the protein-protein Interaction between SUN and KASH domains of the LINC complex. Preferably, the disruption of the protein-protein interaction between SUN and KASH of the LINC complex occurs between the protein interactions selected from the group consisting of Sun1$^{-/-}$ Nesprin-1, Sun2+Nesprin-1, Sun1$^{-/-}$ Nesprin-2, Sun1$^{-/-}$ Nesprin-3, Sun2+Nesprin-2, and Sun2+Nesprin-3. More preferably, the disruption of the protein-protein interaction between SUN and KASH of the LINC complex occurs between the protein interactions of Sun1 and Nesprin-1.

In some embodiments, the AAV vector is formulated for delivery into the myocardium of a subject.

According to a second aspect of the invention there is provided a nucleic acid molecule of any embodiment of the invention for use in treating a disease caused by one or more Lmna mutations in a subject.

In some embodiments of the second aspect, the disease is selected from the group consisting of restrictive dermopathy, familial partial lipodystrophy (for example, Dunnigan type), mandibuloacral dysplasia with type A lipodystrophy, metabolic syndrome, Charcot-Marie-Tooth disease type 2, Charcot-Marie-Tooth disease type 2B1 and diseases presented in normal font in Table 1.

TABLE 1

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 17811 | c.1771T > A | Substitution | p.Cys591Ser | Substitution | Tail | — | Acrogeria, Gottron Type | 201200 | # |
| 18255 | c.418_438dupCTGCTG AACTCCAAGGAGGCC | Duplication | p.Leu140_Ala146dup | Duplication | 1B | — | Arrhythmogenic cardiomyopathy | — | — |
| 17439 | c.1039G > A | Substitution | p.Glu347Lys | Substitution | 2B | ARVD7 | Arrhythmogenic right ventricular cardiomyopathy | 609160 | % |
| 18492 | c.1930C > T | Substitution | p.Arg644Cys | Substitution | Tail | ARVD7 | Arrhythmogenic right ventricular cardiomyopathy | 609160 | % |
| 9157 | c.1718C > T | Substitution | p.Ser573Leu | Substitution | Tail | — | Arthropathy syndrome, autosomal recessive | — | — |
| 18299 | c.1494G > A | Substitution | p.Trp498X | Substitution | Tail | AF | Atrial fibrillation | — | — |
| 18301 | c.175C > G | Substitution | p.Leu59Val | Substitution | 1A | APS | Atypical progeroid syndrome | — | — |
| 8885 | c.169G > C | Substitution | p.Ala57Pro | Substitution | 1A | WRN | Atypical Werner syndrome | 277700 | # |
| 8886 | c.398G > T | Substitution | p.Arg133Leu | Substitution | 1B | WRN | Atypical Werner syndrome | 277700 | # |
| 11462 | c.398G > T | Substitution | p.Arg133Leu | Substitution | 1B | WRN | Atypical Werner syndrome | 277700 | # |
| 9232 | c.398G > T | Substitution | p.Arg133Leu | Substitution | 1B | WRN | Atypical Werner syndrome | 277700 | # |
| 11509 | c.398G > T | Substitution | p.Arg133Leu | Substitution | 1B | WRN | Atypical Werner syndrome | 277700 | # |
| 11670 | c.419T > G | Substitution | p.Leu140Arg | Substitution | 1B | WRN | Atypical Werner syndrome | 277700 | # |
| 8888 | c.506delT | Deletion | p.Val169GlyfsX7 | Frame shift | 1B | WRN | Atypical Werner syndrome | 277700 | # |
| 13457 | c.898G > A | Substitution | p.Asp300Asn | Substitution | 2B | WRN | Atypical Werner syndrome | 277700 | # |
| 13350 | c.898G > A | Substitution | p.Asp300Asn | Substitution | 2B | WRN | Atypical Werner syndrome | 277700 | # |
| 17875 | c.1130G > T | Substitution | p.Arg377Leu | Substitution | 2B | AD-SMA | Autosomal dominant spinal muscular dystrophy | 182980 | # |
| 11767 | c.1477C > T | Substitution | p.Gln493X | Substitution | Tail | AD-SMA | Autosomal dominant spinal muscular dystrophy | 182980 | # |
| 11766 | c.? | Unknown | p.Glu33Asp | Substitution | 1A | — | Axonal neuropathy, muscular dystrophy, cardiac disease | 182980 | — |
| 9205 | | | | | | | | | |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 8994 | c.99G > T | Substitution | p.Glu33Asp | Substitution | 1A | — | Axonal neuropathy, muscular dystrophy, cardiac disease, leuconychia | — | — |
| 12416 | c.1621C > T | Substitution | p.Arg541Cys | Substitution | Tail | — | Cardiac arrhythmia | — | — |
| 12399 | c.673C > T | Substitution | p.Arg225X | Substitution | L12 | CCD | Cardiac conduction defect | 115080 | # |
| 17808 | c.695G > T | Substitution | p.Gly232Val | Substitution | L12 | CCD | Cardiac conduction defect | 115080 | # |
| 13449 | c.799T > C | Substitution | p.Tyr267His | Substitution | 2B | CCD | Cardiac conduction defect | 115080 | # |
| 14260 | c.178C > G | Substitution | p.Arg60Gly | Substitution | 1A | — | Cardiomyopathy with advanced AV block and arrhythmia | — | — |
| 14256 | c.184C > G | Substitution | p.Arg62Gly | Substitution | 1A | — | Cardiomyopathy with advanced AV block and arrhythmia | — | — |
| 14018 | c.497G > C | Substitution | p.Arg166Pro | Substitution | 1B | — | Cardiomyopathy with advanced AV block and arrhythmia | — | — |
| 14258 | c.575A > T | Substitution | p.Asp192Val | Substitution | 1B | — | Cardiomyopathy with advanced AV block and arrhythmia | — | — |
| 14007 | c.673C > T | Substitution | p.Arg225X | Substitution | L12 | — | Cardiomyopathy with advanced AV block and arrhythmia | — | — |
| 14015 | c.775T > C | Substitution | p.Tyr259His | Substitution | L2 | — | Cardiomyopathy with advanced AV block and arrhythmia | — | — |
| 14016 | c.775T > C | Substitution | p.Tyr259His | Substitution | L2 | — | Cardiomyopathy with advanced AV block and arrhythmia | — | — |
| 14011 | c.815_818delACAAins CCAGAC | Indel | p.Asp272AlafsX208 | Frame shift | 2B | — | Cardiomyopathy with advanced AV block and arrhythmia | — | — |
| 14012 | c.815_818delACAAins CCAGAC | Indel | p.Asp272AlafsX208 | Frame shift | 2B | — | Cardiomyopathy with advanced AV block and arrhythmia | — | — |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 11652 | c.-3_12delGCCATGGAGAGACCCG | Deletion | p.Met1_Pro4del | Deletion | Head | CMT2 | Charcot-Marie-Tooth disease type 2 | 118210 | # |
| 13374 | c.1496_1496delC | Deletion | p.Ala499ValfsX141 | Frame shift | Tail | CMT2 | Charcot-Marie-Tooth disease type 2 | 118210 | # |
| 17199 | c.1910T > C | Substitution | p.Phe637Ser | Substitution | Tail | CMT2 | Charcot-Marie-Tooth disease type 2 | 118210 | # |
| 8840 | c.892C > T | Substitution | p.Arg298Cys | Substitution | 2B | CMT2B1 | Charcot-Marie-Tooth disease type 2B1 | 605588 | # |
| 11415 | c.892C > T | Substitution | p.Arg298Cys | Substitution | 2B | CMT2B1 | Charcot-Marie-Tooth disease type 2B1 | 605588 | # |
| 11416 | c.892C > T | Substitution | p.Arg298Cys | Substitution | 2B | CMT2B1 | Charcot-Marie-Tooth disease type 2B1 | 605588 | # |
| 8997 | c.892C > T | Substitution | p.Arg298Cys | Substitution | 2B | CMT2B1 | Charcot-Marie-Tooth disease type 2B1 | 605588 | # |
| 11840 | c.892C > T | Substitution | p.Arg298Cys | Substitution | 2B | CMT2B1 | Charcot-Marie-Tooth disease type 2B1 | 605588 | # |
| 11839 | c.892C > T | Substitution | p.Arg298Cys | Substitution | 2B | CMT2B1 | Charcot-Marie-Tooth disease type 2B1 | 605588 | # |
| 11838 | c.892C > T | Substitution | p.Arg298Cys | Substitution | 2B | CMT2B1 | Charcot-Marie-Tooth disease type 2B1 | 605588 | # |
| 11837 | c.892C > T | Substitution | p.Arg298Cys | Substitution | 2B | CMT2B1 | Charcot-Marie-Tooth disease type 2B1 | 605588 | # |
| 12087 | c.892C > T | Substitution | p.Arg298Cys | Substitution | 2B | CMT2B1 | Charcot-Marie-Tooth disease type 2B1 | 605588 | # |
| 13414 | c.892C > T | Substitution | p.Arg298Cys | Substitution | 2B | CMT2B1 | Charcot-Marie-Tooth disease type 2B1 | 605588 | # |
| 13415 | c.892C > T | Substitution | p.Arg298Cys | Substitution | 2B | CMT2B1 | Charcot-Marie-Tooth disease type 2B1 | 605588 | # |
| 13416 | c.892C > T | Substitution | p.Arg298Cys | Substitution | 2B | CMT2B1 | Charcot-Marie-Tooth disease type 2B1 | 605588 | # |
| 13417 | c.892C > T | Substitution | p.Arg298Cys | Substitution | 2B | CMT2B1 | Charcot-Marie-Tooth disease type 2B1 | 605588 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 13418 | c.892C > T | Substitution | p.Arg298Cys | Substitution | 2B | CMT2B1 | Charcot-Marie-Tooth disease type 2B1 | 605588 | # |
| 13419 | c.892C > T | Substitution | p.Arg298Cys | Substitution | 2B | CMT2B1 | Charcot-Marie-Tooth disease type 2B1 | 605588 | # |
| 13420 | c.892C > T | Substitution | p.Arg298Cys | Substitution | 2B | CMT2B1 | Charcot-Marie-Tooth disease type 2B1 | 605588 | # |
| 13421 | c.892C > T | Substitution | p.Arg298Cys | Substitution | 2B | CMT2B1 | Charcot-Marie-Tooth disease type 2B1 | 605588 | # |
| 13422 | c.892C > T | Substitution | p.Arg298Cys | Substitution | 2B | CMT2B1 | Charcot-Marie-Tooth disease type 2B1 | 605588 | # |
| 13423 | c.892C > T | Substitution | p.Arg298Cys | Substitution | 2B | CMT2B1 | Charcot-Marie-Tooth disease type 2B1 | 605588 | # |
| 13424 | c.892C > T | Substitution | p.Arg298Cys | Substitution | 2B | CMT2B1 | Charcot-Marie-Tooth disease type 2B1 | 605588 | # |
| 13425 | c.892C > T | Substitution | p.Arg298Cys | Substitution | 2B | CMT2B1 | Charcot-Marie-Tooth disease type 2B1 | 605588 | # |
| 13426 | c.892C > T | Substitution | p.Arg298Cys | Substitution | 2B | CMT2B1 | Charcot-Marie-Tooth disease type 2B1 | 605588 | # |
| 13427 | c.892C > T | Substitution | p.Arg298Cys | Substitution | 2B | CMT2B1 | Charcot-Marie-Tooth disease type 2B1 | 605588 | # |
| 13428 | c.892C > T | Substitution | p.Arg298Cys | Substitution | 2B | CMT2B1 | Charcot-Marie-Tooth disease type 2B1 | 605588 | # |
| 13429 | c.892C > T | Substitution | p.Arg298Cys | Substitution | 2B | CMT2B1 | Charcot-Marie-Tooth disease type 2B1 | 605588 | # |
| 13430 | c.892C > T | Substitution | p.Arg298Cys | Substitution | 2B | CMT2B1 | Charcot-Marie-Tooth disease type 2B1 | 605588 | # |
| 13431 | c.892C > T | Substitution | p.Arg298Cys | Substitution | 2B | CMT2B1 | Charcot-Marie-Tooth disease type 2B1 | 605588 | # |
| 13432 | c.892C > T | Substitution | p.Arg298Cys | Substitution | 2B | CMT2B1 | Charcot-Marie-Tooth disease type 2B1 | 605588 | # |
| 13433 | c.892C > T | Substitution | p.Arg298Cys | Substitution | 2B | CMT2B1 | Charcot-Marie-Tooth disease type 2B1 | 605588 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 13434 | c.892C > T | Substitution | p.Arg298Cys | Substitution | 2B | CMT2B1 | Charcot-Marie-Tooth disease type 2B1 | 605588 | # |
| 13435 | c.892C > T | Substitution | p.Arg298Cys | Substitution | 2B | CMT2B1 | Charcot-Marie-Tooth disease type 2B1 | 605588 | # |
| 13436 | c.892C > T | Substitution | p.Arg298Cys | Substitution | 2B | CMT2B1 | Charcot-Marie-Tooth disease type 2B1 | 605588 | # |
| 13437 | c.892C > T | Substitution | p.Arg298Cys | Substitution | 2B | CMT2B1 | Charcot-Marie-Tooth disease type 2B1 | 605588 | # |
| 17886 | c.80C > T | Substitution | p.Thr27Ile | Substitution | Head | CFTDM | Congenital fiber type disproportion | 255310 | # |
| 18472 | c.907T > C | Substitution | p.Ser303Pro | Substitution | 2B | CFTDM | Congenital fiber type disproportion | 255310 | # |
| 18473 | c.907T > C | Substitution | p.Ser303Pro | Substitution | 2B | CFTDM | Congenital fiber type disproportion | 255310 | # |
| 18474 | c.907T > C | Substitution | p.Ser303Pro | Substitution | 2B | CFTDM | Congenital fiber type disproportion | 255310 | # |
| 18475 | c.907T > C | Substitution | p.Ser303Pro | Substitution | 2B | CFTDM | Congenital fiber type disproportion | 255310 | # |
| 18144 | c.91G > A | Substitution | p.Glu31Lys | Substitution | Head | CMD | Congenital muscular dystrophy | — | — |
| 18148 | c.91_93delGAG | Deletion | p.Glu31X | Substitution | Head | CMD | Congenital muscular dystrophy | — | — |
| 17813 | c.93G > C | Substitution | p.Glu31Asp | Substitution | Head | CMD | Congenital muscular dystrophy | — | — |
| 18146 | c.94_96delAAG | Deletion | p.Lys32X | Substitution | 1A | CMD | Congenital muscular dystrophy | — | — |
| 16402 | c.104T > C | Substitution | p.Leu35Pro | Substitution | 1A | CMD | Congenital muscular dystrophy | — | — |
| 16287 | c.115A > T | Substitution | p.Asn39Tyr | Substitution | 1A | CMD | Congenital muscular dystrophy | — | — |
| 18150 | c.117T > G | Substitution | p.Asn39Lys | Substitution | 1A | CMD | Congenital muscular dystrophy | — | — |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 18153 | c.143G > C | Substitution | p.Arg48Pro | Substitution | 1A | CMD | Congenital muscular dystrophy | — | — |
| 18156 | c.422T > C | Substitution | p.Leu141Pro | Substitution | 1B | CMD | Congenital muscular dystrophy | — | — |
| 13462 | c.745C > T | Substitution | p.Arg249Trp | Substitution | 2A | CMD | Congenital muscular dystrophy | — | — |
| 16404 | c.745C > T | Substitution | p.Arg249Trp | Substitution | 2A | CMD | Congenital muscular dystrophy | — | — |
| 17758 | c.745C > T | Substitution | p.Arg249Trp | Substitution | 2A | CMD | Congenital muscular dystrophy | — | — |
| 18158 | c.745C > T | Substitution | p.Arg249Trp | Substitution | 2A | CMD | Congenital muscular dystrophy | — | — |
| 11816 | c.1072G > A | Substitution | p.Glu358Lys | Substitution | 2B | CMD | Congenital muscular dystrophy | — | — |
| 18161 | c.1117A > G | Substitution | p.Ile373Val | Substitution | 2B | CMD | Congenital muscular dystrophy | — | — |
| 18166 | c.1118-T > A | Substitution | p.Ile373Asn | Substitution | 2B | CMD | Congenital muscular dystrophy | — | — |
| 13460 | c.1139-T > C | Substitution | p.Leu380Ser | Substitution | 2B | CMD | Congenital muscular dystrophy | — | — |
| 18169 | c.1147G > A | Substitution | p.Glu383Lys | Substitution | 2B | CMD | Congenital muscular dystrophy | — | — |
| 18171 | c.1147G > A | Substitution | p.Glu383Lys | Substitution | 2B | CMD | Congenital muscular dystrophy | — | — |
| 18163 | c.1151A > G | Substitution | p.Glu384Gly | Substitution | 2B | CMD | Congenital muscular dystrophy | — | — |
| 11817 | c.1162C > T | Substitution | p.Arg388Cys | Substitution | Tail | CMD | Congenital muscular dystrophy | — | — |
| 17473 | c.1330_1338dupGAGGTGGAT | Duplication | p.Glu444_Asp446dup | Duplication | Tail | CMD | Congenital muscular dystrophy | — | — |
| 11818 | c.1368_1370delCAA | Deletion | p.Asn456del | Deletion | Tail | CMD | Congenital muscular dystrophy | — | — |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 18238 | c.1489-14_1489-7delTTTCTCCT | Deletion | p.? | Unknown | Unknown | CMD | Congenital muscular dystrophy | – | – |
| 16951 | c.1445G > A | Substitution | p.Arg482Gln | Substitution | Tail | T2D | DIABETES MELLITUS, NONINSULIN-DEPENDENT, NIDDM | 125853 | # |
| 13171 | c.? | Unknown | p.Lys260Asn | Substitution | L2 | CMD1A | Dilated cardiomyopathy 1A | 115200 | # |
| 8832 | c.16C > T | Substitution | p.Gln6X | Substitution | Head | CMD1A | Dilated cardiomyopathy 1A | 115200 | # |
| 9397 | c.28_29insA | Insertion | p.Thr10AsnfsX31 | Frame shift | Head | CMD1A | Dilated cardiomyopathy 1A | 115200 | # |
| 11627 | c.31delC | Deletion | p.Arg11AlafsX85 | Frame shift | Head | CMD1A | Dilated cardiomyopathy 1A | 115200 | # |
| 14254 | c.73C > G | Substitution | p.Arg25Gly | Substitution | Head | CMD1A | Dilated cardiomyopathy 1A | 115200 | # |
| 13155 | c.82C > T | Substitution | p.Arg28Trp | Substitution | 1A | CMD1A | Dilated cardiomyopathy 1A | 115200 | # |
| 13563 | c.155T > C | Substitution | p.Leu52Pro | Substitution | 1A | CMD1A | Dilated cardiomyopathy 1A | 115200 | # |
| 13379 | c.176T > G | Substitution | p.Leu59Arg | Substitution | 1A | CMD1A | Dilated cardiomyopathy 1A | 115200 | # |
| 13378 | c.176T > G | Substitution | p.Leu59Arg | Substitution | 1A | CMD1A | Dilated cardiomyopathy 1A | 115200 | # |
| 8748 | c.178C > G | Substitution | p.Arg60Gly | Substitution | 1A | CMD1A | Dilated cardiomyopathy 1A | 115200 | # |
| 13192 | c.203_208delAGGTGG | Deletion | p.Glu68_Val69del | Deletion | 1A | CMD1A | Dilated cardiomyopathy 1A | 115200 | # |
| 17742 | c.232G > A | Substitution | p.Lys78Glu | Substitution | 1B | CMD1A | Dilated cardiomyopathy 1A | 115200 | # |
| 9163 | c.244G > A | Substitution | p.Glu82Lys | Substitution | 1B | CMD1A | Dilated cardiomyopathy 1A | 115200 | # |
| 16139 | c.244G > A | Substitution | p.Glu82Lys | Substitution | 1B | CMD1A | Dilated cardiomyopathy 1A | 115200 | # |
| 8749 | c.254T > G | Substitution | p.Leu85Arg | Substitution | 1B | CMD1A | Dilated cardiomyopathy 1A | 115200 | # |
| 8865 | c.266G > T | Substitution | p.Arg89Leu | Substitution | 1B | CMD1A | Dilated cardiomyopathy 1A | 115200 | # |
| 11618 | c.266G > T | Substitution | p.Arg89Leu | Substitution | 1B | CMD1A | Dilated cardiomyopathy 1A | 115200 | # |
| 13080 | c.266G > T | Substitution | p.Arg89Leu | Substitution | 1B | CMD1A | Dilated cardiomyopathy 1A | 115200 | # |
| 13157 | c.266G > T | Substitution | p.Arg89Leu | Substitution | 1B | CMD1A | Dilated cardiomyopathy 1A | 115200 | # |
| 14030 | c.266G > T | Substitution | p.Arg89Leu | Substitution | 1B | CMD1A | Dilated cardiomyopathy 1A | 115200 | # |
| 16966 | c.266G > T | Substitution | p.Arg89Leu | Substitution | 1B | CMD1A | Dilated cardiomyopathy 1A | 115200 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 17777 | c.266G > T | Substitution | p.Arg89Leu | Substitution | 1B | CMD1A | Dilated cardiomyopathy 1A | 115200 | # |
| 13613 | c.274C > T | Substitution | p.Leu92Phe | Substitution | 1B | CMD1A | Dilated cardiomyopathy 1A | 115200 | # |
| 8844 | c.289A > G | Substitution | p.Lys97Glu | Substitution | 1B | CMD1A | Dilated cardiomyopathy 1A | 115200 | # |
| 11620 | c.289A > G | Substitution | p.Lys97Glu | Substitution | 1B | CMD1A | Dilated cardiomyopathy 1A | 115200 | # |
| 13159 | c.289A > G | Substitution | p.Lys97Glu | Substitution | 1B | CMD1A | Dilated cardiomyopathy 1A | 115200 | # |
| 13082 | c.302G > C | Substitution | p.Arg101Pro | Substitution | 1B | CMD1A | Dilated cardiomyopathy 1A | 115200 | # |
| 16954 | c.302G > C | Substitution | p.Arg101Pro | Substitution | 1B | CMD1A | Dilated cardiomyopathy 1A | 115200 | # |
| 8843 | c.331G > T | Substitution | p.Glu111X | Substitution | 1B | CMD1A | Dilated cardiomyopathy 1A | 115200 | # |
| 11619 | c.331G > T | Substitution | p.Glu111X | Substitution | 1B | CMD1A | Dilated cardiomyopathy 1A | 115200 | # |
| 13199 | c.331G > T | Substitution | p.Glu111X | Substitution | 1B | CMD1A | Dilated cardiomyopathy 1A | 115200 | # |
| 16935 | c.348_349insG | Insertion | p.Lys117GlufsX10 | Frame shift | 1B | CMD1A | Dilated cardiomyopathy 1A | 115200 | # |
| 13089 | c.357-1G > T | Substitution | p.? | Unknown | Unknown | CMD1A | Dilated cardiomyopathy 1A | 115200 | # |
| 9148 | c.394G > C | Substitution | p.Ala132Pro | Substitution | 1B | CMD1A | Dilated cardiomyopathy 1A | 115200 | # |
| 17029 | c.394G > C | Substitution | p.Ala132Pro | Substitution | 1B | CMD1A | Dilated cardiomyopathy 1A | 115200 | # |
| 17028 | c.394G > C | Substitution | p.Ala132Pro | Substitution | 1B | CMD1A | Dilated cardiomyopathy 1A | 115200 | # |
| 9297 | c.425_426insGGCACTGGAGGCTCTGCTGAA | Insertion | p.Leu141_Asn142insLysAspLeuAspAlaLeuLeu | Insertion | 1B | CMD1A | Dilated cardiomyopathy 1A | 115200 | # |
| 9010 | c.427T > C | Substitution | p.Ser143Pro | Substitution | 1B | CMD1A | Dilated cardiomyopathy 1A | 115200 | # |
| 11473 | c.427T > C | Substitution | p.Ser143Pro | Substitution | 1B | CMD1A | Dilated cardiomyopathy 1A | 115200 | # |
| 11474 | c.427T > C | Substitution | p.Ser143Pro | Substitution | 1B | CMD1A | Dilated cardiomyopathy 1A | 115200 | # |
| 11475 | c.427T > C | Substitution | p.Ser143Pro | Substitution | 1B | CMD1A | Dilated cardiomyopathy 1A | 115200 | # |
| 11476 | c.427T > C | Substitution | p.Ser143Pro | Substitution | 1B | CMD1A | Dilated cardiomyopathy 1A | 115200 | # |
| 11477 | c.427T > C | Substitution | p.Ser143Pro | Substitution | 1B | CMD1A | Dilated cardiomyopathy 1A | 115200 | # |
| 9150 | c.427T > C | Substitution | p.Ser143Pro | Substitution | 1B | CMD1A | Dilated cardiomyopathy 1A | 115200 | # |
| 16162 | c.427T > C | Substitution | p.Ser143Pro | Substitution | 1B | CMD1A | Dilated cardiomyopathy 1A | 115200 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 16163 | c.427T > C | Substitution | p.Ser143Pro | Substitution | 1B | CMD1A | Dilated cardiomyopathy 1A | 115200 | # |
| 16164 | c.427T > C | Substitution | p.Ser143Pro | Substitution | 1B | CMD1A | Dilated cardiomyopathy 1A | 115200 | # |
| 16165 | c.427T > C | Substitution | p.Ser143Pro | Substitution | 1B | CMD1A | Dilated cardiomyopathy 1A | 115200 | # |
| 17038 | c.427T > C | Substitution | p.Ser143Pro | Substitution | 1B | CMD1A | Dilated cardiomyopathy 1A | 115200 | # |
| 17037 | c.427T > C | Substitution | p.Ser143Pro | Substitution | 1B | CMD1A | Dilated cardiomyopathy 1A | 115200 | # |
| 17036 | c.427T > C | Substitution | p.Ser143Pro | Substitution | 1B | CMD1A | Dilated cardiomyopathy 1A | 115200 | # |
| 17024 | c.427T > C | Substitution | p.Ser143Pro | Substitution | 1B | CMD1A | Dilated cardiomyopathy 1A | 115200 | # |
| 17022 | c.427T > C | Substitution | p.Ser143Pro | Substitution | 1B | CMD1A | Dilated cardiomyopathy 1A | 115200 | # |
| 17021 | c.427T > C | Substitution | p.Ser143Pro | Substitution | 1B | CMD1A | Dilated cardiomyopathy 1A | 115200 | # |
| 17020 | c.427T > C | Substitution | p.Ser143Pro | Substitution | 1B | CMD1A | Dilated cardiomyopathy 1A | 115200 | # |
| 17019 | c.427T > C | Substitution | p.Ser143Pro | Substitution | 1B | CMD1A | Dilated cardiomyopathy 1A | 115200 | # |
| 17018 | c.427T > C | Substitution | p.Ser143Pro | Substitution | 1B | CMD1A | Dilated cardiomyopathy 1A | 115200 | # |
| 17023 | c.427T > C | Substitution | p.Ser143Pro | Substitution | 1B | CMD1A | Dilated cardiomyopathy 1A | 115200 | # |
| 17661 | c.448A > T | Substitution | p.Thr150Ser | Substitution | 1B | CMD1A | Dilated cardiomyopathy 1A | 115200 | # |
| 8879 | c.481G > A | Substitution | p.Glu161Lys | Substitution | 1B | CMD1A | Dilated cardiomyopathy 1A | 115200 | # |
| 13161 | c.481G > A | Substitution | p.Glu161Lys | Substitution | 1B | CMD1A | Dilated cardiomyopathy 1A | 115200 | # |
| 13162 | c.481G > A | Substitution | p.Glu161Lys | Substitution | 1B | CMD1A | Dilated cardiomyopathy 1A | 115200 | # |
| 13163 | c.481G > A | Substitution | p.Glu161Lys | Substitution | 1B | CMD1A | Dilated cardiomyopathy 1A | 115200 | # |
| 13328 | c.481G > A | Substitution | p.Glu161Lys | Substitution | 1B | CMD1A | Dilated cardiomyopathy 1A | 115200 | # |
| 13617 | c.481G > A | Substitution | p.Glu161Lys | Substitution | 1B | CMD1A | Dilated cardiomyopathy 1A | 115200 | # |
| 13091 | c.497G > C | Substitution | p.Arg166Pro | Substitution | 1B | CMD1A | Dilated cardiomyopathy 1A | 115200 | # |
| 16968 | c.497G > C | Substitution | p.Arg166Pro | Substitution | 1B | CMD1A | Dilated cardiomyopathy 1A | 115200 | # |
| 16969 | c.497G > C | Substitution | p.Arg166Pro | Substitution | 1B | CMD1A | Dilated cardiomyopathy 1A | 115200 | # |
| 13165 | c.548T > C | Substitution | p.Leu183Pro | Substitution | 1B | CMD1A | Dilated cardiomyopathy 1A | 115200 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 18267 | c.563T > G | Substitution | p.Leu188Arg | Substitution | 1B | CMD1A | Dilated cardiomyopathy 1A | 115200 | # |
| 16160 | c.565C > T | Substitution | p.Arg189Trp | Substitution | 1B | CMD1A | Dilated cardiomyopathy 1A | 115200 | # |
| 8845 | c.568C > T | Substitution | p.Arg190Trp | Substitution | 1B | CMD1A | Dilated cardiomyopathy 1A | 115200 | # |
| 9011 | c.568C > T | Substitution | p.Arg190Trp | Substitution | 1B | CMD1A | Dilated cardiomyopathy 1A | 115200 | # |
| 11507 | c.568C > T | Substitution | p.Arg190Trp | Substitution | 1B | CMD1A | Dilated cardiomyopathy 1A | 115200 | # |
| 9149 | c.568C > T | Substitution | p.Arg190Trp | Substitution | 1B | CMD1A | Dilated cardiomyopathy 1A | 115200 | # |
| 11621 | c.568C > T | Substitution | p.Arg190Trp | Substitution | 1B | CMD1A | Dilated cardiomyopathy 1A | 115200 | # |
| 11782 | c.568C > T | Substitution | p.Arg190Trp | Substitution | 1B | CMD1A | Dilated cardiomyopathy 1A | 115200 | # |
| 11790 | c.568C > T | Substitution | p.Arg190Trp | Substitution | 1B | CMD1A | Dilated cardiomyopathy 1A | 115200 | # |
| 13167 | c.568C > T | Substitution | p.Arg190Trp | Substitution | 1B | CMD1A | Dilated cardiomyopathy 1A | 115200 | # |
| 16167 | c.568C > T | Substitution | p.Arg190Trp | Substitution | 1B | CMD1A | Dilated cardiomyopathy 1A | 115200 | # |
| 17034 | c.568C > T | Substitution | p.Arg190Trp | Substitution | 1B | CMD1A | Dilated cardiomyopathy 1A | 115200 | # |
| 17033 | c.568C > T | Substitution | p.Arg190Trp | Substitution | 1B | CMD1A | Dilated cardiomyopathy 1A | 115200 | # |
| 17032 | c.568C > T | Substitution | p.Arg190Trp | Substitution | 1B | CMD1A | Dilated cardiomyopathy 1A | 115200 | # |
| 17031 | c.568C > T | Substitution | p.Arg190Trp | Substitution | 1B | CMD1A | Dilated cardiomyopathy 1A | 115200 | # |
| 13093 | c.569G > A | Substitution | p.Arg190Gln | Substitution | 1B | CMD1A | Dilated cardiomyopathy 1A | 115200 | # |
| 13330 | c.569G > A | Substitution | p.Arg190Gln | Substitution | 1B | CMD1A | Dilated cardiomyopathy 1A | 115200 | # |
| 16976 | c.569G > A | Substitution | p.Arg190Gln | Substitution | 1B | CMD1A | Dilated cardiomyopathy 1A | 115200 | # |
| 9165 | c.575A > G | Substitution | p.Asp192Gly | Substitution | 1B | CMD1A | Dilated cardiomyopathy 1A | 115200 | # |
| 14200 | c.575A > G | Substitution | p.Asp192Gly | Substitution | 1B | CMD1A | Dilated cardiomyopathy 1A | 115200 | # |
| 8750 | c.585C > A | Substitution | p.Asn195Lys | Substitution | 1B | CMD1A | Dilated cardiomyopathy 1A | 115200 | # |
| 12393 | c.585C > A | Substitution | p.Asn195Lys | Substitution | 1B | CMD1A | Dilated cardiomyopathy 1A | 115200 | # |
| 11668 | c.607G > A | Substitution | p.Glu203Lys | Substitution | 1B | CMD1A | Dilated cardiomyopathy 1A | 115200 | # |
| 16978 | c.607G > A | Substitution | p.Glu203Lys | Substitution | 1B | CMD1A | Dilated cardiomyopathy 1A | 115200 | # |
| 8751 | c.6084 > G | Substitution | p.Glu203Gly | Substitution | 1B | CMD1A | Dilated cardiomyopathy 1A | 115200 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 13332 | c.608A > T | Substitution | p.Glu203Val | Substitution | 1B | CMD1A | Dilated cardiomyopathy 1A | 115200 | # |
| 13095 | c.629T > G | Substitution | p.Ile210Ser | Substitution | 1B | CMD1A | Dilated cardiomyopathy 1A | 115200 | # |
| 16971 | c.629T > G | Substitution | p.Ile210Ser | Substitution | 1B | CMD1A | Dilated cardiomyopathy 1A | 115200 | # |
| 8901 | c.640 – 10A > G | Substitution | p.? | Unknown | Unknown | CMD1A | Dilated cardiomyopathy 1A | 115200 | # |
| 8864 | c.644T > C | Substitution | p.Leu215Pro | Substitution | 1B | CMD1A | Dilated cardiomyopathy 1A | 115200 | # |
| 16980 | c.644T > C | Substitution | p.Leu215Pro | Substitution | 1B | CMD1A | Dilated cardiomyopathy 1A | 115200 | # |
| 13169 | c.656A > C | Substitution | p.Lys219Thr | Substitution | 1B | CMD1A | Dilated cardiomyopathy 1A | 115200 | # |
| 13335 | c.656A > C | Substitution | p.Lys219Thr | Substitution | 1B | CMD1A | Dilated cardiomyopathy 1A | 115200 | # |
| 11669 | c.673C > T | Substitution | p.Arg225X | Substitution | L12 | CMD1A | Dilated cardiomyopathy 1A | 115200 | # |
| 17607 | c.673C > T | Substitution | p.Arg225X | Substitution | L12 | CMD1A | Dilated cardiomyopathy 1A | 115200 | # |
| 17609 | c.673C > T | Substitution | p.Arg225X | Substitution | L12 | CMD1A | Dilated cardiomyopathy 1A | 115200 | # |
| 13097 | c.700C > T | Substitution | p.Gln234X | Substitution | L12 | CMD1A | Dilated cardiomyopathy 1A | 115200 | # |
| 13201 | c.736C > T | Substitution | p.Gln246X | Substitution | 2A | CMD1A | Dilated cardiomyopathy 1A | 115200 | # |
| 17786 | c.736C > T | Substitution | p.Gln246X | Substitution | 2A | CMD1A | Dilated cardiomyopathy 1A | 115200 | # |
| 17779 | c.767T > G | Substitution | p.Val256Gly | Substitution | 2A | CMD1A | Dilated cardiomyopathy 1A | 115200 | # |
| 11809 | c.8004 > G | Substitution | p.Tyr267Cys | Substitution | 2B | CMD1A | Dilated cardiomyopathy 1A | 115200 | # |
| 13173 | c.8004 > G | Substitution | p.Tyr267Cys | Substitution | 2B | CMD1A | Dilated cardiomyopathy 1A | 115200 | # |
| 11810 | c.855delG | Deletion | p.Ala287LeufsX191 | Frame shift | 2B | CMD1A | Dilated cardiomyopathy 1A | 115200 | # |
| 11613 | c.908_909delCT | Deletion | p.Ser303CysfsX26 | Frame shift | 2B | CMD1A | Dilated cardiomyopathy 1A | 115200 | # |
| 12384 | c.908_909delCT | Deletion | p.Ser303CysfsX26 | Frame shift | 2B | CMD1A | Dilated cardiomyopathy 1A | 115200 | # |
| 13206 | c.936 + 1G > T | Substitution | p.? | Unknown | Unknown | CMD1A | Dilated cardiomyopathy 1A | 115200 | # |
| 16805 | c.937 – 11C > G | Substitution | p.Leu313GlyIsX31 | Frame shift | 2B | CMD1A | Dilated cardiomyopathy 1A | 115200 | # |
| 8846 | c.949G > A | Substitution | p.Glu317Lys | Substitution | 2B | CMD1A | Dilated cardiomyopathy 1A | 115200 | # |
| 11617 | c.949G > A | Substitution | p.Glu317Lys | Substitution | 2B | CMD1A | Dilated cardiomyopathy 1A | 115200 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 13175 | c.949G > A | Substitution | p.Glu317Lys | Substitution | 2B | CMD1A | Dilated cardiomyopathy 1A | 115200 | # |
| 13176 | c.949G > A | Substitution | p.Glu317Lys | Substitution | 2B | CMD1A | Dilated cardiomyopathy 1A | 115200 | # |
| 13621 | c.949G > A | Substitution | p.Glu317Lys | Substitution | 2B | CMD1A | Dilated cardiomyopathy 1A | 115200 | # |
| 13100 | c.952G > A | Substitution | p.Ala318Thr | Substitution | 2B | CMD1A | Dilated cardiomyopathy 1A | 115200 | # |
| 16956 | c.952G > A | Substitution | p.Ala318Thr | Substitution | 2B | CMD1A | Dilated cardiomyopathy 1A | 115200 | # |
| 11700 | c.959delT | Deletion | p.Leu320fsX160 | Frame shift | 2B | CMD1A | Dilated cardiomyopathy 1A | 115200 | # |
| 9409 | c.959delT | Deletion | p.Leu320fsX160 | Frame shift | 2B | CMD1A | Dilated cardiomyopathy 1A | 115200 | # |
| 9391 | c.959delT | Deletion | p.Leu320fsX160 | Frame shift | 2B | CMD1A | Dilated cardiomyopathy 1A | 115200 | # |
| 14032 | c.959delT | Deletion | p.Leu320fsX160 | Frame shift | 2B | CMD1A | Dilated cardiomyopathy 1A | 115200 | # |
| 12389 | c.961C > T | Substitution | p.Arg321X | Substitution | 2B | CMD1A | Dilated cardiomyopathy 1A | 115200 | # |
| 14077 | c.961C > T | Substitution | p.Arg321X | Substitution | 2B | CMD1A | Dilated cardiomyopathy 1A | 115200 | # |
| 14093 | c.961C > T | Substitution | p.Arg321X | Substitution | 2B | CMD1A | Dilated cardiomyopathy 1A | 115200 | # |
| 17737 | c.961C > T | Substitution | p.Arg321X | Substitution | 2B | CMD1A | Dilated cardiomyopathy 1A | 115200 | # |
| 17738 | c.961C > T | Substitution | p.Arg321X | Substitution | 2B | CMD1A | Dilated cardiomyopathy 1A | 115200 | # |
| 9155 | c.976T > A | Substitution | p.Ser326Thr | Substitution | 2B | CMD1A | Dilated cardiomyopathy 1A | 115200 | # |
| 11760 | c.[992G > A; =] + [=; 1039G > A] | Substitution | p.[Arg331Glu; =] + [=; Glu347Lys] | Substitution | 2B | CMD1A | Dilated cardiomyopathy 1A | 115200 | # |
| 11811 | c.992G > C | Substitution | p.Arg331Pro | Substitution | 2B | CMD1A | Dilated cardiomyopathy 1A | 115200 | # |
| 14075 | c.992G > A | Substitution | p.Arg331Gln | Substitution | 2B | CMD1A | Dilated cardiomyopathy 1A | 115200 | # |
| 17477 | c.1003C > T | Substitution | p.Arg335Trp | Substitution | 2B | CMD1A | Dilated cardiomyopathy 1A | 115200 | # |
| 18486 | c.1039G > A | Substitution | p.Glu347Lys | Substitution | 2B | CMD1A | Dilated cardiomyopathy 1A | 115200 | # |
| 9012 | c.1046G > T | Substitution | p.Arg349Leu | Substitution | 2B | CMD1A | Dilated cardiomyopathy 1A | 115200 | # |
| 13561 | c.1048G > C | Substitution | p.Ala350Pro | Substitution | 2B | CMD1A | Dilated cardiomyopathy 1A | 115200 | # |
| 14204 | c.1057C > A | Substitution | p.Gln353Lys | Substitution | 2B | CMD1A | Dilated cardiomyopathy 1A | 115200 | # |
| 14072 | c.1063C > T | Substitution | p.Gln355X | Substitution | 2B | CMD1A | Dilated cardiomyopathy 1A | 115200 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 17475 | c.1070A > C | Substitution | p.Asp357Ala | Substitution | 2B | CMD1A | Dilated cardiomyopathy 1A | 115200 | # |
| 13116 | c.1072G > T | Substitution | p.Glu358X | Substitution | 2B | CMD1A | Dilated cardiomyopathy 1A | 115200 | # |
| 9152 | c.1085_1085delT | Deletion | p.Leu363TrpfsX117 | Frame shift | 2B | CMD1A | Dilated cardiomyopathy 1A | 115200 | # |
| 17026 | c.1085_1085delT | Deletion | p.Leu362TrpfsX117 | Frame shift | 2B | CMD1A | Dilated cardiomyopathy 1A | 115200 | # |
| 16157 | c.1102_1130dupGCCC TGGACATGGAGATCC ACGCCTACCG | Duplication | p.Lys378ProfsX112 | Frame shift | 2B | CMD1A | Dilated cardiomyopathy 1A | 115200 | # |
| 13102 | c.1114delG | Deletion | p.Glu372ArgfsX107 | Frame shift | 2B | CMD1A | Dilated cardiomyopathy 1A | 115200 | # |
| 8866 | c.1130G > A | Substitution | p.Arg377His | Substitution | 2B | CMD1A | Dilated cardiomyopathy 1A | 115200 | # |
| 8869 | c.1130G > A | Substitution | p.Arg377His | Substitution | 2B | CMD1A | Dilated cardiomyopathy 1A | 115200 | # |
| 8880 | c.1130G > A | Substitution | p.Arg377His | Substitution | 2B | CMD1A | Dilated cardiomyopathy 1A | 115200 | # |
| 9160 | c.1130G > A | Substitution | p.Arg377His | Substitution | 2B | CMD1A | Dilated cardiomyopathy 1A | 115200 | # |
| 9162 | c.1130G > A | Substitution | p.Arg377His | Substitution | 2B | CMD1A | Dilated cardiomyopathy 1A | 115200 | # |
| 12330 | c.1130G > A | Substitution | p.Arg377His | Substitution | 2B | CMD1A | Dilated cardiomyopathy 1A | 115200 | # |
| 13178 | c.1130G > T | Substitution | p.Arg377Leu | Substitution | 2B | CMD1A | Dilated cardiomyopathy 1A | 115200 | # |
| 13623 | c.1130G > A | Substitution | p.Arg377His | Substitution | 2B | CMD1A | Dilated cardiomyopathy 1A | 115200 | # |
| 14034 | c.1130G > A | Substitution | p.Arg377His | Substitution | 2B | CMD1A | Dilated cardiomyopathy 1A | 115200 | # |
| 17664 | c.1150G > T | Substitution | p.Glu384X | Substitution | 2B | CMD1A | Dilated cardiomyopathy 1A | 115200 | # |
| 17482 | C.1157 + 1G > T | Substitution | p.Arg386SerfsX21 | Frame shift | 2B | CMD1A | Dilated cardiomyopathy 1A | 115200 | # |
| 13104 | c.1163G > A | Substitution | p.Arg388His | Substitution | Tail | CMD1A | Dilated cardiomyopathy 1A | 115200 | # |
| 16958 | c.1163G > A | Substitution | p.Arg388His | Substitution | Tail | CMD1A | Dilated cardiomyopathy 1A | 115200 | # |
| 13106 | c.1195C > T | Substitution | p.Arg399Cys | Substitution | Tail | CMD1A | Dilated cardiomyopathy 1A | 115200 | # |
| 16960 | c.1195C > T | Substitution | p.Arg399Cys | Substitution | Tail | CMD1A | Dilated cardiomyopathy 1A | 115200 | # |
| 17782 | c.1197_1240delTGGCC GTGCTTCCTCTCACTC ATCCCAGACACAGGG TGGGGGCA | Deletion | p.Gly400ArgfsX11 | Frame shift | Tail | CMD1A | Dilated cardiomyopathy 1A | 115200 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 17789 | c.1292C > G | Substitution | p.Ser431X | Substitution | Tail | CMD1A | Dilated cardiomyopathy 1A | 115200 | # |
| 14082 | c.1294C > T | Substitution | p.Gln432X | Substitution | Tail | CMD1A | Dilated cardiomyopathy 1A | 115200 | # |
| 14084 | c.1294C > T | Substitution | p.Gln432X | Substitution | Tail | CMD1A | Dilated cardiomyopathy 1A | 115200 | # |
| 14085 | c.1294C > T | Substitution | p.Gln432X | Substitution | Tail | CMD1A | Dilated cardiomyopathy 1A | 115200 | # |
| 14086 | c.1294C > T | Substitution | p.Gln432X | Substitution | Tail | CMD1A | Dilated cardiomyopathy 1A | 115200 | # |
| 13108 | c.1307_1308insGCAC | Insertion | p.Ser437HisfsX1 | Frame shift | Tail | CMD1A | Dilated cardiomyopathy 1A | 115200 | # |
| 16962 | c.1307_1308insGCAC | Insertion | p.Ser437HisfsX1 | Frame shift | Tail | CMD1A | Dilated cardiomyopathy 1A | 115200 | # |
| 14088 | c.1318G > A | Substitution | p.Val440Met | Substitution | Tail | CMD1A | Dilated cardiomyopathy 1A | 115200 | # |
| 14090 | c.1318G > A | Substitution | p.Val440Met | Substitution | Tail | CMD1A | Dilated cardiomyopathy 1A | 115200 | # |
| 14091 | c.1318G > A | Substitution | p.Val440Met | Substitution | Tail | CMD1A | Dilated cardiomyopathy 1A | 115200 | # |
| 11812 | c.1370delA | Deletion | p.Lys457SerfsX21 | Frame shift | Tail | CMD1A | Dilated cardiomyopathy 1A | 115200 | # |
| 12397 | c.1380 + 1G > A | Substitution | p.? | Unknown | Unknown | CMD1A | Dilated cardiomyopathy 1A | 115200 | # |
| 9413 | c.1397_1397delA | Deletion | p.Asn466IlefsX14 | Frame shift | Tail | CMD1A | Dilated cardiomyopathy 1A | 115200 | # |
| 9161 | c.1397_1397delA | Deletion | p.Asn466IlefsX14 | Frame shift | Tail | CMD1A | Dilated cardiomyopathy 1A | 115200 | # |
| 13110 | c.1412G > A | Substitution | p.Arg471His | Substitution | Tail | CMD1A | Dilated cardiomyopathy 1A | 115200 | # |
| 16973 | c.1412G > A | Substitution | p.Arg471His | Substitution | Tail | CMD1A | Dilated cardiomyopathy 1A | 115200 | # |
| 13112 | c.1424_1425insAGA | Insertion | p.Gly474_Asp475insGlu | Insertion | Tail | CMD1A | Dilated cardiomyopathy 1A | 115200 | # |
| 11508 | c.1443C > G | Substitution | p.Tyr481X | Substitution | Tail | CMD1A | Dilated cardiomyopathy 1A | 115200 | # |
| 17791 | c.1443C > G | Substitution | p.Tyr481X | Substitution | Tail | CMD1A | Dilated cardiomyopathy 1A | 115200 | # |
| 17480 | c.1489 − 1G > T | Substitution | p.Ile497_Glu536del | Deletion | Tail | CMD1A | Dilated cardiomyopathy 1A | 115200 | # |
| 13180 | c.1492T > A | Substitution | p.Trp498Arg | Substitution | Tail | CMD1A | Dilated cardiomyopathy 1A | 115200 | # |
| 9153 | c.1493_1493delG | Deletion | p.Ala499LeufsX47 | Frame shift | Tail | CMD1A | Dilated cardiomyopathy 1A | 115200 | # |
| 12395 | c.1512_1513insAG | Insertion | p.Thr505ArgfsX44 | Frame shift | Tail | CMD1A | Dilated cardiomyopathy 1A | 115200 | # |
| 17784 | c.1526_1527insC | Insertion | p.Thr510TyrfsX42 | Frame shift | Tail | CMD1A | Dilated cardiomyopathy 1A | 115200 | # |
| 17797 | c.1526_1527insA | Insertion | p.Thr510TyrfsX42 | Frame shift | Tail | CMD1A | Dilated cardiomyopathy 1A | 115200 | # |

TABLE 1-continued

| Database ID | cDNA Variant | Protein Variant | cDNA Variant Types | Protein Variant Types | Domain | Disease Abbreviation | Disease Name | Omim ID | Omim Symbol |
|---|---|---|---|---|---|---|---|---|---|
| 17486 | c.1549C > T | p.Gln517X | Substitution | Substitution | Tail | CMD1A | Dilated cardiomyopathy 1A | 115200 | # |
| 17484 | c.1560G > A | p.Trp520X | Substitution | Substitution | Tail | CMD1A | Dilated cardiomyopathy 1A | 115200 | # |
| 13625 | c.1567G > A | p.Gly523Arg | Substitution | Substitution | Tail | CMD1A | Dilated cardiomyopathy 1A | 115200 | # |
| 11624 | c.1579_1580insCTGC | p.Arg527ProfsX26 | Insertion | Frame shift | Tail | CMD1A | Dilated cardiomyopathy 1A | 115200 | # |
| 17558 | c.1583C > T | p.Thr528Met | Substitution | Substitution | Tail | CMD1A | Dilated cardiomyopathy 1A | 115200 | # |
| 9307 | c.1621C > T | p.Arg541Cys | Substitution | Substitution | Tail | CMD1A | Dilated cardiomyopathy 1A | 115200 | # |
| 9283 | c.1621C > A | p.Arg541Ser | Substitution | Substitution | Tail | CMD1A | Dilated cardiomyopathy 1A | 115200 | # |
| 9151 | c.1621C > A | p.Arg541Ser | Substitution | Substitution | Tail | CMD1A | Dilated cardiomyopathy 1A | 115200 | # |
| 13592 | c.1621C > T | p.Arg541Cys | Substitution | Substitution | Tail | CMD1A | Dilated cardiomyopathy 1A | 115200 | # |
| 14202 | c.1621C > A | p.Arg541Ser | Substitution | Substitution | Tail | CMD1A | Dilated cardiomyopathy 1A | 115200 | # |
| 16472 | c.1621C > G | p.Arg541Gly | Substitution | Substitution | Tail | CMD1A | Dilated cardiomyopathy 1A | 115200 | # |
| 17774 | c.1621C > T | p.Arg541Cys | Substitution | Substitution | Tail | CMD1A | Dilated cardiomyopathy 1A | 115200 | # |
| 17775 | c.1621C > T | p.Arg541Cys | Substitution | Substitution | Tail | CMD1A | Dilated cardiomyopathy 1A | 115200 | # |
| 13559 | c.1622G > A | p.Arg541His | Substitution | Substitution | Tail | CMD1A | Dilated cardiomyopathy 1A | 115200 | # |
| 9392 | c.1718C > T | p.Ser573Leu | Substitution | Substitution | Tail | CMD1A | Dilated cardiomyopathy 1A | 115200 | # |
| 13182 | c.1718C > T | p.Ser573Leu | Substitution | Substitution | Tail | CMD1A | Dilated cardiomyopathy 1A | 115200 | # |
| 13183 | c.1718C > T | p.Ser573Leu | Substitution | Substitution | Tail | CMD1A | Dilated cardiomyopathy 1A | 115200 | # |
| 14038 | c.1718C > T | p.Ser573Leu | Substitution | Substitution | Tail | CMD1A | Dilated cardiomyopathy 1A | 115200 | # |
| 17667 | c.1879C > T | p.Arg624Cys | Substitution | Substitution | Tail | CMD1A | Dilated cardiomyopathy 1A | 115200 | # |
| 13565 | c.1904G > A | p.Gly635Asp | Substitution | Substitution | Tail | CMD1A | Dilated cardiomyopathy 1A | 115200 | # |
| 8833 | c.1930C > T | p.Arg644Cys | Substitution | Substitution | Tail | CMD1A | Dilated cardiomyopathy 1A | 115200 | # |
| 9018 | c.1930C > T | p.Arg644Cys | Substitution | Substitution | Tail | CMD1A | Dilated cardiomyopathy 1A | 115200 | # |
| 11500 | c.1930C > T | p.Arg644Cys | Substitution | Substitution | Tail | CMD1A | Dilated cardiomyopathy 1A | 115200 | # |
| 11501 | c.1930C > T | p.Arg644Cys | Substitution | Substitution | Tail | CMD1A | Dilated cardiomyopathy 1A | 115200 | # |
| 11502 | c.1930C > A | p.Arg644His | Substitution | Substitution | Tail | CMD1A | Dilated cardiomyopathy 1A | 115200 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 13185 | c.1930C > T | Substitution | p.Arg644Cys | Substitution | Tail | CMD1A | Dilated cardiomyopathy 1A | 115200 | # |
| 13337 | c.1930C > T | Substitution | p.Arg644Cys | Substitution | Tail | CMD1A | Dilated cardiomyopathy 1A | 115200 | # |
| 14080 | c.1930C > T | Substitution | p.Arg644Cys | Substitution | Tail | CMD1A | Dilated cardiomyopathy 1A | 115200 | # |
| 13114 | c.1960C > T | Substitution | p.Arg654X | Substitution | Tail | CMD1A | Dilated cardiomyopathy 1A | 115200 | # |
| 16964 | c.1960C > T | Substitution | p.Arg654X | Substitution | Tail | CMD1A | Dilated cardiomyopathy 1A | 115200 | # |
| 11788 | c.? | Unknown | p.Tyr481X | Substitution | Tail | DCM-CD | Dilated cardiomyopathy with conduction system defects | — | — |
| 17886 | c.80C > T | Substitution | p.Thr27Ile | Substitution | Head | DCM-CD | Dilated cardiomyopathy with conduction system defects | — | — |
| 13486 | c.106C > T | Substitution | p.Gln36X | Substitution | 1A | DCM-CD | Dilated cardiomyopathy with conduction system defects | — | — |
| 11792 | c.158A > T | Substitution | p.Glu53Val | Substitution | 1A | DCM-CD | Dilated cardiomyopathy with conduction system defects | — | — |
| 18301 | c.175C > G | Substitution | p.Leu59Val | Substitution | 1A | DCM-CD | Dilated cardiomyopathy with conduction system defects | — | — |
| 11791 | c.481G > A | Substitution | p.Glu161Lys | Substitution | 1B | DCM-CD | Dilated cardiomyopathy with conduction system defects | — | — |
| 13204 | c.514 – 1G > A | Unknown | p.? | Unknown | Unknown | DCM-CD | Dilated cardiomyopathy with conduction system defects | — | — |
| 11793 | c.556G > A | Substitution | p.Glu186Lys | Substitution | 1B | DCM-CD | Dilated cardiomyopathy with conduction system defects | — | — |
| 11789 | c.568C > T | Substitution | p.Arg190Trp | Substitution | 1B | DCM-CD | Dilated cardiomyopathy with conduction system defects | — | — |
| 11787 | c.575A > G | Substitution | p.Asp192Gly | Substitution | 1B | DCM-CD | Dilated cardiomyopathy with conduction system defects | — | — |
| 18470 | c.683A > T | Substitution | p.Glu228Val | Substitution | L12 | DCM-CD | Dilated cardiomyopathy with conduction system defects | — | — |
| 17868 | c.871G > A | Substitution | p.Glu291Lys | Substitution | 2B | DCM-CD | Dilated cardiomyopathy with conduction system defects | — | — |
| 17870 | c.949G > A | Substitution | p.Glu317Lys | Substitution | 2B | DCM-CD | Dilated cardiomyopathy with conduction system defects | — | — |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 13078 | c.1069G > C | Substitution | p.Asp357His | Substitution | 2B | DCM-CD | Dilated cardiomyopathy with conduction system defects | — | — |
| 13208 | c.1157 + 1G > A | Substitution | p.? | Unknown | Unknown | DCM-CD | Dilated cardiomyopathy with conduction system defects | — | — |
| 18490 | c.1412G > A | Substitution | p.Arg471His | Substitution | Tail | DCM-CD | Dilated cardiomyopathy with conduction system defects | — | — |
| 11814 | c.1526_1527insC | Insertion | p.Thr510TyrfsX42 | Frame shift | Tail | DCM-CD | Dilated cardiomyopathy with conduction system defects | — | — |
| 9008 | c.1621C > T | Substitution | p.Arg541Cys | Substitution | Tail | DCM-CD | Dilated cardiomyopathy with conduction system defects | — | — |
| 17578 | c.1711C > A | Substitution | p.= | Silent | Not affected | DCM-CD | Dilated cardiomyopathy with conduction system defects | — | — |
| 17880 | c.1930C > T | Substitution | p.Arg644Cys | Substitution | Tail | DCM-CD | Dilated cardiomyopathy with conduction system defects | — | — |
| 18305 | c.1774G > A | Substitution | p.Gly592Arg | Substitution | Tail | DAPJ | Distal acroosteolysis, poikiloderma and joint stiffness | — | — |
| 13581 | c.1930C > T | Substitution | p.Arg644Cys | Substitution | Tail | — | Distal motor neuropathy | — | — |
| 17813 | c.93G > C | Substitution | p.Glu31Asp | Substitution | Head | — | Dropped head syndrome | — | — |
| 9020 | c.94_96delAAG | Deletion | p.Lys32del | Deletion | 1A | — | Dropped head syndrome | — | — |
| 13476 | c.116A > G | Substitution | p.Asn39Ser | Substitution | 1A | — | Dropped head syndrome | — | — |
| 13466 | c.149G > C | Substitution | p.Arg50Pro | Substitution | 1A | — | Dropped head syndrome | — | — |
| 13464 | c.745C > T | Substitution | p.Arg249Trp | Substitution | 2A | — | Dropped head syndrome | — | — |
| 13470 | c.905T > C | Substitution | p.Leu302Pro | Substitution | 2B | — | Dropped head syndrome | — | — |
| 13468 | c.1072G > A | Substitution | p.Glu358Lys | Substitution | 2B | — | Dropped head syndrome | — | — |
| 13482 | c.1072G > A | Substitution | p.Glu358Lys | Substitution | 2B | — | Dropped head syndrome | — | — |
| 13484 | c.1072G > A | Substitution | p.Glu358Lys | Substitution | 2B | — | Dropped head syndrome | — | — |
| 13474 | c.1358C > C | Substitution | p.Arg453Pro | Substitution | Tail | — | Dropped head syndrome | — | — |
| 13472 | c.1364G > C | Substitution | p.Arg455Pro | Substitution | Tail | — | Dropped head syndrome | — | — |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 13478 | c.1366A > G | Substitution | p.Asn456Asp | Substitution | Tail | — | Dropped head syndrome | — | — |
| 13480 | c.1381-2A > G | Substitution | p.? | Unknown | Unknown | — | Dropped head syndrome | — | — |
| 11652 | c.-3_12delGCCATGGAGAGACCCCG | Deletion | p.Met1_Pro4del | Deletion | Head | EDMD2 | Emery-Dreifuss muscular dystrophy, autosomal dominant | 181350 | # |
| 8743 | c.16C > T | Substitution | p.Gln6X | Substitution | Head | EDMD2 | Emery-Dreifuss muscular dystrophy, autosomal dominant | 181350 | # |
| 8796 | c.16C > T | Substitution | p.Gln6X | Substitution | Head | EDMD2 | Emery-Dreifuss muscular dystrophy, autosomal dominant | 181350 | # |
| 11746 | c.31delC | Deletion | p.Arg11AlafsX85 | Frame shift | Head | EDMD2 | Emery-Dreifuss muscular dystrophy, autosomal dominant | 181350 | # |
| 9262 | c.73C > G | Substitution | p.Arg25Gly | Substitution | Head | EDMD2 | Emery-Dreifuss muscular dystrophy, autosomal dominant | 181350 | # |
| 9376 | c.74G > C | Substitution | p.Arg25Pro | Substitution | Head | EDMD2 | Emery-Dreifuss muscular dystrophy, autosomal dominant | 181350 | # |
| 9177 | c.94_96delAAG | Deletion | p.Lys32del | Deletion | 1A | EDMD2 | Emery-Dreifuss muscular EDMD2 dystrophy, autosomal dominant | 181350 | # |
| 8998 | c.94_96delAAG | Deletion | p.Lys32del | Deletion | 1A | EDMD2 | Emery-Dreifuss muscular dystrophy, autosomal dominant | 181350 | # |
| 9014 | c.94_96delAAG | Deletion | p.Lys32del | Deletion | 1A | EDMD2 | Emery-Dreifuss muscular dystrophy, autosomal dominant | 181350 | # |
| 13594 | c.98A > G | Substitution | p.Glu33Gly | Substitution | 1A | EDMD2 | Emery-Dreifuss muscular dystrophy, autosomal dominant | 181350 | # |
| 11747 | c.99G > C | Substitution | p.Glu33Asp | Substitution | 1A | EDMD2 | Emery-Dreifuss muscular dystrophy, autosomal dominant | 181350 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 8999 | c.103C > G | Substitution | p.Leu35Val | Substitution | 1A | EDMD2 | Emery-Dreifuss muscular dystrophy, autosomal dominant | 181350 | # |
| 11748 | c.116A > G | Substitution | p.Asn39Ser | Substitution | 1A | EDMD2 | Emery-Dreifuss muscular dystrophy, autosomal dominant | 181350 | # |
| 16329 | c.116A > G | Substitution | p.Asn39Ser | Substitution | 1A | EDMD2 | Emery-Dreifuss muscular dystrophy, autosomal dominant | 181350 | # |
| 18174 | c.116A > G | Substitution | p.Asn39Ser | Substitution | 1A | EDMD2 | Emery-Dreifuss muscular dystrophy, autosomal dominant | 181350 | # |
| 9377 | c.127G > A | Substitution | p.Ala43Thr | Substitution | 1A | EDMD2 | Emery-Dreifuss muscular dystrophy, autosomal dominant | 181350 | # |
| 8797 | c.134A > G | Substitution | p.Tyr45Cys | Substitution | 1A | EDMD2 | Emery-Dreifuss muscular dystrophy, autosomal dominant | 181350 | # |
| 16331 | c.134A > G | Substitution | p.Tyr45Cys | Substitution | 1A | EDMD2 | Emery-Dreifuss muscular dystrophy, autosomal dominant | 181350 | # |
| 13605 | c.136A > G | Substitution | p.Ile46Val | Substitution | 1A | EDMD2 | Emery-Dreifuss muscular dystrophy, autosomal dominant | 181350 | # |
| 13545 | c.139G > C | Substitution | p.Asp47His | Substitution | 1A | EDMD2 | Emery-Dreifuss muscular dystrophy, autosomal dominant | 181350 | # |
| 9378 | c.148C > A | Substitution | p.Arg50Ser | Substitution | 1A | EDMD2 | Emery-Dreifuss muscular dystrophy, autosomal dominant | 181350 | # |
| 8798 | c.149G > C | Substitution | p.Arg50Pro | Substitution | 1A | EDMD2 | Emery-Dreifuss muscular dystrophy, autosomal dominant | 181350 | # |
| 8799 | c.188T > G | Substitution | p.Ile63Ser | Substitution | 1A | EDMD2 | Emery-Dreifuss muscular dystrophy, autosomal dominant | 181350 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 9175 | c.188T > A | Substitution | p.Ile63Asn | Substitution | 1A | EDMD2 | Emery-Dreifuss muscular dystrophy, autosomal dominant | 181350 | # |
| 11633 | c.188T > A | Substitution | p.Ile63Asn | Substitution | 1A | EDMD2 | Emery-Dreifuss muscular dystrophy, autosomal dominant | 181350 | # |
| 13192 | c.203_208delAGGTGG | Deletion | p.Glu68_Val69del | Deletion | 1A | EDMD2 | Emery-Dreifuss muscular dystrophy, autosomal dominant | 181350 | # |
| 12477 | c.265C > T | Substitution | p.Arg89Cys | Substitution | 1B | EDMD2 | Emery-Dreifuss muscular dystrophy, autosomal dominant | 181350 | # |
| 13596 | c.265C > T | Substitution | p.Arg89Cys | Substitution | 1B | EDMD2 | Emery-Dreifuss muscular dystrophy, autosomal dominant | 181350 | # |
| 17193 | c.266G > T | Substitution | p.Arg89Leu | Substitution | 1B | EDMD2 | Emery-Dreifuss muscular dystrophy, autosomal dominant | 181350 | # |
| 9410 | c.334_336delGAG | Deletion | p.Glu112del | Deletion | 1B | EDMD2 | Emery-Dreifuss muscular dystrophy, autosomal dominant | 181350 | # |
| 9000 | c.334_336delGAG | Deletion | p.Glu112del | Deletion | 1B | EDMD2 | Emery-Dreifuss muscular dystrophy, autosomal dominant | 181350 | # |
| 16291 | c.357C > T | Substitution | p.= | Silent | Not affected | EDMD2 | Emery-Dreifuss muscular dystrophy, autosomal dominant | 181350 | # |
| 17182 | c.367_369delAAG | Deletion | p.Lys123del | Deletion | 1B | EDMD2 | Emery-Dreifuss muscular dystrophy, autosomal dominant | 181350 | # |
| 9379 | c.398G > C | Substitution | p.Arg133Pro | Substitution | 1B | EDMD2 | Emery-Dreifuss muscular dystrophy, autosomal dominant | 181350 | # |
| 11632 | c.419T > C | Substitution | p.Leu140Pro | Substitution | 1B | EDMD2 | Emery-Dreifuss muscular dystrophy, autosomal dominant | 181350 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 9015 | c.428C > T | Substitution | p.Ser143Phe | Substitution | 1B | EDMD2 | Emery-Dreifuss muscular dystrophy, autosomal dominant | 181350 | # |
| 12609 | c.428C > T | Substitution | p.Ser143Phe | Substitution | 1B | EDMD2 | Emery-Dreifuss muscular dystrophy, autosomal dominant | 181350 | # |
| 8795 | c.448A > C | Substitution | p.Thr150Pro | Substitution | 1B | EDMD2 | Emery-Dreifuss muscular dystrophy, autosomal dominant | 181350 | # |
| 16334 | c.448A > C | Substitution | p.Thr150Pro | Substitution | 1B | EDMD2 | Emery-Dreifuss muscular dystrophy, autosomal dominant | 181350 | # |
| 13453 | c.485T > C | Substitution | p.Leu162Pro | Substitution | 1B | EDMD2 | Emery-Dreifuss muscular dystrophy, autosomal dominant | 181350 | # |
| 16396 | c.566_567delGGinsCC | Indel | p.Arg189Pro | Substitution | 1B | EDMD2 | Emery-Dreifuss muscular dystrophy, autosomal dominant | 181350 | # |
| 16299 | c.568_570dupCGG | Duplication | p.Arg190dup | Duplication | 1B | EDMD2 | Emery-Dreifuss muscular dystrophy, autosomal dominant | 181350 | # |
| 9380 | c.588_596delGCTGCAGAC | Deletion | p.Arg196_Thr199delinsSer | Indel | 1B | EDMD2 | Emery-Dreifuss muscular dystrophy, autosomal dominant | 181350 | # |
| 16301 | c.618C > G | Substitution | p.Phe206Leu | Substitution | 1B | EDMD2 | Emery-Dreifuss muscular dystrophy, autosomal dominant | 181350 | # |
| 12382 | c.625delA | Deletion | p.Asn209ThrfsX271 | Frame shift | 1B | EDMD2 | Emery-Dreifuss muscular dystrophy, autosomal dominant | 181350 | # |
| 8800 | c.665A > C | Substitution | p.His222Pro | Substitution | L12 | EDMD2 | Emery-Dreifuss muscular dystrophy, autosomal dominant | 181350 | # |
| 13547 | c.694G > C | Substitution | p.Gly232Arg | Substitution | L12 | EDMD2 | Emery-Dreifuss muscular dystrophy, autosomal dominant | 181350 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 8801 | c.695G > A | Substitution | p.Gly232Glu | Substitution | L12 | EDMD2 | Emery-Dreifuss muscular dystrophy, autosomal dominant | 181350 | # |
| 12485 | c.695G > A | Substitution | p.Gly232Glu | Substitution | L12 | EDMD2 | Emery-Dreifuss muscular dystrophy, autosomal dominant | 181350 | # |
| 9001 | c.743T > C | Substitution | p.Leu248Pro | Substitution | 2A | EDMD2 | Emery-Dreifuss muscular dystrophy, autosomal dominant | 181350 | # |
| 16336 | c.745C > T | Substitution | p.Arg249Trp | Substitution | 2A | EDMD2 | Emery-Dreifuss muscular dystrophy, autosomal dominant | 181350 | # |
| 16337 | c.745C > T | Substitution | p.Arg249Trp | Substitution | 2A | EDMD2 | Emery-Dreifuss muscular dystrophy, autosomal dominant | 181350 | # |
| 16338 | c.745C > T | Substitution | p.Arg249Trp | Substitution | 2A | EDMD2 | Emery-Dreifuss muscular dystrophy, autosomal dominant | 181350 | # |
| 16342 | c.[745C > T; 1930C > T] | Substitution | p.[Arg249Trp; Arg644Cys] | Substitution | 2A, Tail | EDMD2 | Emery-Dreifuss muscular dystrophy, autosomal dominant | 181350 | # |
| 8783 | c.746G > A | Substitution | p.Arg249Gln | Substitution | 2A | EDMD2 | Emery-Dreifuss muscular dystrophy, autosomal dominant | 181350 | # |
| 11380 | c.746G > A | Substitution | p.Arg249Gln | Substitution | 2A | EDMD2 | Emery-Dreifuss muscular dystrophy, autosomal dominant | 181350 | # |
| 11381 | c.746G > A | Substitution | p.Arg249Gln | Substitution | 2A | EDMD2 | Emery-Dreifuss muscular dystrophy, autosomal dominant | 181350 | # |
| 8802 | c.746G > A | Substitution | p.Arg249Gln | Substitution | 2A | EDMD2 | Emery-Dreifuss muscular dystrophy, autosomal dominant | 181350 | # |
| 9002 | c.746G > A | Substitution | p.Arg249Gln | Substitution | 2A | EDMD2 | Emery-Dreifuss muscular dystrophy, autosomal dominant | 181350 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 9023 | c.746G > A | Substitution | p.Arg249Gln | Substitution | 2A | EDMD2 | Emery-Dreifuss muscular dystrophy, autosomal dominant | 181350 | # |
| 11631 | c.746G > A | Substitution | p.Arg249Gln | Substitution | 2A | EDMD2 | Emery-Dreifuss muscular dystrophy, autosomal dominant | 181350 | # |
| 11749 | c.746G > A | Substitution | p.Arg249Gln | Substitution | 2A | EDMD2 | Emery-Dreifuss muscular dystrophy, autosomal dominant | 181350 | # |
| 11750 | c.746G > A | Substitution | p.Arg249Gln | Substitution | 2A | EDMD2 | Emery-Dreifuss muscular dystrophy, autosomal dominant | 181350 | # |
| 13552 | c.746G > A | Substitution | p.Arg249Gln | Substitution | 2A | EDMD2 | Emery-Dreifuss muscular dystrophy, autosomal dominant | 181350 | # |
| 16344 | c.746G > A | Substitution | p.Arg249Gln | Substitution | 2A | EDMD2 | Emery-Dreifuss muscular dystrophy, autosomal dominant | 181350 | # |
| 16345 | c.746G > A | Substitution | p.Arg249Gln | Substitution | 2A | EDMD2 | Emery-Dreifuss muscular dystrophy, autosomal dominant | 181350 | # |
| 18176 | c.746G > A | Substitution | p.Arg249Gln | Substitution | 2A | EDMD2 | Emery-Dreifuss muscular dystrophy, autosomal dominant | 181350 | # |
| 11751 | c.775T > G | Substitution | p.Tyr259Asp | Substitution | L2 | EDMD2 | Emery-Dreifuss muscular dystrophy, autosomal dominant | 181350 | # |
| 9640 | c.781_783delAAG | Deletion | p.Lys261del | Deletion | L2 | EDMD2 | Emery-Dreifuss muscular dystrophy, autosomal dominant | 181350 | # |
| 9411 | c.781_783delAAG | Deletion | plys261del | Deletion | L2 | EDMD2 | Emery-Dreifuss muscular dystrophy, autosomal dominant | 181350 | # |
| 9381 | c.781_783delAAG | Deletion | plys261del | Deletion | L2 | EDMD2 | Emery-Dreifuss muscular EDMD2 dystrophy, autosomal dominant | 181350 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 13584 | c.781_783delAAGinsG TGGAGCAGTATAAGA AA | Indel | p.Lys261delinsValGlu GlnTyrLysLys | Indel | L2 | EDMD2 | Emery-Dreifuss muscular dystrophy, autosomal dominant | 181350 | # |
| 16149 | c.788T > C | Substitution | p.Leu263Pro | Substitution | L2 | EDMD2 | Emery-Dreifuss muscular dystrophy, autosomal dominant | 181350 | # |
| 17403 | c.788T > C | Substitution | p.Leu263Pro | Substitution | L2 | EDMD2 | Emery-Dreifuss muscular dystrophy, autosomal dominant | 181350 | # |
| 17751 | c.788T > C | Substitution | p.Leu263Pro | Substitution | L2 | EDMD2 | Emery-Dreifuss muscular dystrophy, autosomal dominant | 181350 | # |
| 17405 | c.799T > C | Substitution | p.Tyr267His | Substitution | 2B | EDMD2 | Emery-Dreifuss muscular dystrophy, autosomal dominant | 181350 | # |
| 9003 | c.800A > G | Substitution | p.Tyr267Cys | Substitution | 2B | EDMD2 | Emery-Dreifuss muscular dystrophy, autosomal dominant | 181350 | # |
| 11809 | c.800A > G | Substitution | p.Tyr267Cys | Substitution | 2B | EDMD2 | Emery-Dreifuss muscular dystrophy, autosomal dominant | 181350 | # |
| 13173 | c.800A > G | Substitution | p.Tyr267Cys | Substitution | 2B | EDMD2 | Emery-Dreifuss muscular dystrophy, autosomal dominant | 181350 | # |
| 16303 | c.802T > C | Substitution | p.Ser268Pro | Substitution | 2B | EDMD2 | Emery-Dreifuss muscular dystrophy, autosomal dominant | 181350 | # |
| 16305 | c.810G > A | Substitution | p.= | Silent | Not affected | EDMD2 | Emery-Dreifuss muscular dystrophy, autosomal dominant | 181350 | # |
| 16307 | c.810G > A | Substitution | p.= | Silent | Not affected | EDMD2 | Emery-Dreifuss muscular dystrophy, autosomal dominant | 181350 | # |
| 16309 | c.810 + 1G > A | Substitution | p.? | Unknown | Unknown | EDMD2 | Emery-Dreifuss muscular dystrophy, autosomal dominant | 181350 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 16347 | c.812T > C | Substitution | p.Leu271Pro | Substitution | 2B | EDMD2 | Emery-Dreifuss muscular dystrophy, autosomal dominant | 181350 | # |
| 18186 | c.832G > C | Substitution | p.Ala278Pro | Substitution | 2B | EDMD2 | Emery-Dreifuss muscular dystrophy, autosomal dominant | 181350 | # |
| 8803 | c.881A > C | Substitution | p.Gln294Pro | Substitution | 2B | EDMD2 | Emery-Dreifuss muscular dystrophy, autosomal dominant | 181350 | # |
| 16349 | c.881A > C | Substitution | p.Gln294Pro | Substitution | 2B | EDMD2 | Emery-Dreifuss muscular dystrophy, autosomal dominant | 181350 | # |
| 16311 | c.883T > C | Substitution | p.Ser295Pro | Substitution | 2B | EDMD2 | Emery-Dreifuss muscular dystrophy, autosomal dominant | 181350 | # |
| 8863 | c.907T > C | Substitution | p.Ser303Pro | Substitution | 2B | EDMD2 | Emery-Dreifuss muscular dystrophy, autosomal dominant | 181350 | # |
| 16351 | c.907T > C | Substitution | p.Ser303Pro | Substitution | 2B | EDMD2 | Emery-Dreifuss muscular dystrophy, autosomal dominant | 181350 | # |
| 8786 | c.1007G > A | Substitution | p.Arg336Gln | Substitution | 2B | EDMD2 | Emery-Dreifuss muscular dystrophy, autosomal dominant | 181350 | # |
| 16314 | c.1064_1066delAGC | Deletion | p.Gln355del | Deletion | 2B | EDMD2 | Emery-Dreifuss muscular dystrophy, autosomal dominant | 181350 | # |
| 8804 | c.1072G > A | Substitution | p.Glu358Lys | Substitution | 2B | EDMD2 | Emery-Dreifuss muscular dystrophy, autosomal dominant | 181350 | # |
| 11388 | c.1072G > A | Substitution | p.Glu358Lys | Substitution | 2B | EDMD2 | Emery-Dreifuss muscular dystrophy, autosomal dominant | 181350 | # |
| 11816 | c.1072G > A | Substitution | p.Glu358Lys | Substitution | 2B | EDMD2 | Emery-Dreifuss muscular dystrophy, autosomal dominant | 181350 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 9167 | c.1072G > A | Substitution | p.Glu358Lys | Substitution | 2B | EDMD2 | Emery-Dreifuss muscular dystrophy, autosomal dominant | 181350 | # |
| 11478 | c.1072G > A | Substitution | p.Glu358Lys | Substitution | 2B | EDMD2 | Emery-Dreifuss muscular dystrophy, autosomal dominant | 181350 | # |
| 11479 | c.1072G > A | Substitution | p.Glu358Lys | Substitution | 2B | EDMD2 | Emery-Dreifuss muscular dystrophy, autosomal dominant | 181350 | # |
| 11480 | c.1072G > A | Substitution | p.Glu358Lys | Substitution | 2B | EDMD2 | Emery-Dreifuss muscular dystrophy, autosomal dominant | 181350 | # |
| 11752 | c.1072G > A | Substitution | p.Glu358Lys | Substitution | 2B | EDMD2 | Emery-Dreifuss muscular dystrophy, autosomal dominant | 181350 | # |
| 12479 | c.1072G > A | Substitution | p.Glu358Lys | Substitution | 2B | EDMD2 | Emery-Dreifuss muscular dystrophy, autosomal dominant | 181350 | # |
| 12483 | c.1072G > A | Substitution | p.Glu358Lys | Substitution | 2B | EDMD2 | Emery-Dreifuss muscular dystrophy, autosomal dominant | 181350 | # |
| 13598 | c.1072G > A | Substitution | p.Glu358Lys | Substitution | 2B | EDMD2 | Emery-Dreifuss muscular dystrophy, autosomal dominant | 181350 | # |
| 13603 | c.1072G > A | Substitution | p.Glu358Lys | Substitution | 2B | EDMD2 | Emery-Dreifuss muscular dystrophy, autosomal dominant | 181350 | # |
| 16353 | c.1072G > A | Substitution | p.Glu358Lys | Substitution | 2B | EDMD2 | Emery-Dreifuss muscular dystrophy, autosomal dominant | 181350 | # |
| 16354 | c.1072G > A | Substitution | p.Glu358Lys | Substitution | 2B | EDMD2 | Emery-Dreifuss muscular dystrophy, autosomal dominant | 181350 | # |
| 16355 | c.1072G > A | Substitution | p.Glu358Lys | Substitution | 2B | EDMD2 | Emery-Dreifuss muscular dystrophy, autosomal dominant | 181350 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 16316 | c.1081G > A | Substitution | p.Glu361Lys | Substitution | 2B | EDMD2 | Emery-Dreifuss muscular dystrophy, autosomal dominant | 181350 | # |
| 8806 | c.1112T > A | Substitution | p.Met371Lys | Substitution | 2B | EDMD2 | Emery-Dreifuss muscular dystrophy, autosomal dominant | 181350 | # |
| 18184 | c.1124C > G | Substitution | p.Ala375Gly | Substitution | 2B | EDMD2 | Emery-Dreifuss muscular dystrophy, autosomal dominant | 181350 | # |
| 11634 | c.1130G > T | Substitution | p.Arg377Leu | Substitution | 2B | EDMD2 | Emery-Dreifuss muscular dystrophy, autosomal dominant | 181350 | # |
| 11693 | c.1130G > A | Substitution | p.Arg377His | Substitution | 2B | EDMD2 | Emery-Dreifuss muscular dystrophy, autosomal dominant | 181350 | # |
| 12405 | c.1130G > A | Substitution | p.Arg377His | Substitution | 2B | EDMD2 | Emery-Dreifuss muscular dystrophy, autosomal dominant | 181350 | # |
| 18223 | c.1130G > A | Substitution | p.Arg377His | Substitution | 2B | EDMD2 | Emery-Dreifuss muscular dystrophy, autosomal dominant | 181350 | # |
| 12474 | c.1142A > C | Substitution | p.Glu381Ala | Substitution | 2B | EDMD2 | Emery-Dreifuss muscular dystrophy, autosomal dominant | 181350 | # |
| 11629 | c.1157G > A | Substitution | p.Arg386Lys | Substitution | 2B | EDMD2 | Emery-Dreifuss muscular dystrophy, autosomal dominant | 181350 | # |
| 13653 | c.1157G > T | Substitution | p.Arg386Met | Substitution | 2B | EDMD2 | Emery-Dreifuss muscular dystrophy, autosomal dominant | 181350 | # |
| 16357 | c.1157G > A | Substitution | p.Arg386Lys | Substitution | 2B | EDMD2 | Emery-Dreifuss muscular dystrophy, autosomal dominant | 181350 | # |
| 16358 | c.1157G > A | Substitution | p.Arg386Lys | Substitution | 2B | EDMD2 | Emery-Dreifuss muscular dystrophy, autosomal dominant | 181350 | # |

TABLE 1-continued

| Database ID | cDNA Variant | Protein Variant | cDNA Variant Types | Protein Variant Types | Domain | Disease Abbreviation | Disease Name | Omim ID | Omim Symbol |
|---|---|---|---|---|---|---|---|---|---|
| 16319 | c.1158-2A?G | p.? | Substitution | Unknown | Unknown | EDMD2 | Emery-Dreifuss muscular dystrophy, autosomal dominant | 181350 | # |
| 11817 | c.1162C > T | p.Arg388Cys | Substitution | Substitution | Tail | EDMD2 | Emery-Dreifuss muscular dystrophy, autosomal dominant | 181350 | # |
| 9281 | c.1187A > G | p.Gln396Arg | Substitution | Substitution | Tail | EDMD2 | Emery-Dreifuss muscular dystrophy, autosomal dominant | 181350 | # |
| 8862 | c.1201C > T | p.Arg401Cys | Substitution | Substitution | Tail | EDMD2 | Emery-Dreifuss muscular dystrophy, autosomal dominant | 181350 | # |
| 9176 | c.1201C > T | p.Arg401Cys | Substitution | Substitution | Tail | EDMD2 | Emery-Dreifuss muscular dystrophy, autosomal dominant | 181350 | # |
| 9302 | c.1201C > T | p.Arg401Cys | Substitution | Substitution | Tail | EDMD2 | Emery-Dreifuss muscular dystrophy, autosomal dominant | 181350 | # |
| 9004 | c.1337A > T | p.Asp446Val | Substitution | Substitution | Tail | EDMD2 | Emery-Dreifuss muscular dystrophy, autosomal dominant | 181350 | # |
| 16321 | c.1346G > A | p.Gly449Asp | Substitution | Substitution | Tail | EDMD2 | Emery-Dreifuss muscular dystrophy, autosomal dominant | 181350 | # |
| 18192 | c.1346G?T | p.Gly449Val | Substitution | Substitution | Tail | EDMD2 | Emery-Dreifuss muscular dystrophy, autosomal dominant | 181350 | # |
| 8744 | c.1357C > T | p.Arg453Trp | Substitution | Substitution | Tail | EDMD2 | Emery-Dreifuss muscular dystrophy, autosomal dominant | 181350 | # |
| 8787 | c.1357C > T | p.Arg453Trp | Substitution | Substitution | Tail | EDMD2 | Emery-Dreifuss muscular dystrophy, autosomal dominant | 181350 | # |
| 11382 | c.1357C > T | p.Arg453Trp | Substitution | Substitution | Tail | EDMD2 | Emery-Dreifuss muscular dystrophy, autosomal dominant | 181350 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 11383 | c.1357C > T | Substitution | p.Arg453Trp | Substitution | Tail | EDMD2 | Emery-Dreifuss muscular dystrophy, autosomal dominant | 181350 | # |
| 11384 | c.1357C > T | Substitution | p.Arg453Trp | Substitution | Tail | EDMD2 | Emery-Dreifuss muscular dystrophy, autosomal dominant | 181350 | # |
| 8807 | c.1357C > T | Substitution | p.Arg453Trp | Substitution | Tail | EDMD2 | Emery-Dreifuss muscular dystrophy, autosomal dominant | 181350 | # |
| 11389 | c.1357C > T | Substitution | p.Arg453Trp | Substitution | Tail | EDMD2 | Emery-Dreifuss muscular dystrophy, autosomal dominant | 181350 | # |
| 11390 | c.1357C > T | Substitution | p.Arg453Trp | Substitution | Tail | EDMD2 | Emery-Dreifuss muscular dystrophy, autosomal dominant | 181350 | # |
| 8836 | c.1357C > T | Substitution | p.Arg453Trp | Substitution | Tail | EDMD2 | Emery-Dreifuss muscular dystrophy, autosomal dominant | 181350 | # |
| 9005 | c.1357C > T | Substitution | p.Arg453Trp | Substitution | Tail | EDMD2 | Emery-Dreifuss muscular dystrophy, autosomal dominant | 181350 | # |
| 9304 | c.1357C > T | Substitution | p.Arg453Trp | Substitution | Tail | EDMD2 | Emery-Dreifuss muscular dystrophy, autosomal dominant | 181350 | # |
| 11614 | c.1357C > T | Substitution | p.Arg453Trp | Substitution | Tail | EDMD2 | Emery-Dreifuss muscular dystrophy, autosomal dominant | 181350 | # |
| 11753 | c.1357C > T | Substitution | p.Arg453Trp | Substitution | Tail | EDMD2 | Emery-Dreifuss muscular dystrophy, autosomal dominant | 181350 | # |
| 12481 | c.1357C > T | Substitution | p.Arg453Trp | Substitution | Tail | EDMD2 | Emery-Dreifuss muscular dystrophy, autosomal dominant | 181350 | # |
| 13590 | c.1357C > T | Substitution | p.Arg453Trp | Substitution | Tail | EDMD2 | Emery-Dreifuss muscular dystrophy, autosomal dominant | 181350 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 13607 | c.1357C > T | Substitution | p.Arg453Trp | Substitution | Tail | EDMD2 | Emery-Dreifuss muscular dystrophy, autosomal dominant | 181350 | # |
| 13609 | c.1357C > T | Substitution | p.Arg453Trp | Substitution | Tail | EDMD2 | Emery-Dreifuss muscular dystrophy, autosomal dominant | 181350 | # |
| 13611 | c.1357C > T | Substitution | p.Arg453Trp | Substitution | Tail | EDMD2 | Emery-Dreifuss muscular dystrophy, autosomal dominant | 181350 | # |
| 16363 | c.1357C > T | Substitution | p.Arg453Trp | Substitution | Tail | EDMD2 | Emery-Dreifuss muscular dystrophy, autosomal dominant | 181350 | # |
| 16364 | c.1357C > T | Substitution | p.Arg453Trp | Substitution | Tail | EDMD2 | Emery-Dreifuss muscular dystrophy, autosomal dominant | 181350 | # |
| 16365 | c.1357C > T | Substitution | p.Arg453Trp | Substitution | Tail | EDMD2 | Emery-Dreifuss muscular dystrophy, autosomal dominant | 181350 | # |
| 16366 | c.1357C > T | Substitution | p.Arg453Trp | Substitution | Tail | EDMD2 | Emery-Dreifuss muscular dystrophy, autosomal dominant | 181350 | # |
| 16367 | c.1357C > T | Substitution | p.Arg453Trp | Substitution | Tail | EDMD2 | Emery-Dreifuss muscular dystrophy, autosomal dominant | 181350 | # |
| 16368 | c.1357C > T | Substitution | p.Arg453Trp | Substitution | Tail | EDMD2 | Emery-Dreifuss muscular dystrophy, autosomal dominant | 181350 | # |
| 16323 | c.1361T > C | Substitution | p.Leu454Pro | Substitution | Tail | EDMD2 | Emery-Dreifuss muscular dystrophy, autosomal dominant | 181350 | # |
| 9513 | c.1367A > T | Substitution | p.Asn456Ile | Substitution | Tail | EDMD2 | Emery-Dreifuss muscular dystrophy, autosomal dominant | 181350 | # |
| 8810 | c.1368C > A | Substitution | p.Asn456Lys | Substitution | Tail | EDMD2 | Emery-Dreifuss muscular dystrophy, autosomal dominant | 181350 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 11818 | c.1368_1370delCAA | Deletion | p.Asn456del | Deletion | Tail | EDMD2 | Emery-Dreifuss muscular dystrophy, autosomal dominant | 181350 | # |
| 17446 | c.1368_1370delCAA | Deletion | p.Asn456del | Deletion | Tail | EDMD2 | Emery-Dreifuss muscular dystrophy, autosomal dominant | 181350 | # |
| 17447 | c.1368_1370delCAA | Deletion | p.Asn456del | Deletion | Tail | EDMD2 | Emery-Dreifuss muscular dystrophy, autosomal dominant | 181350 | # |
| 16370 | c.1381-2A > G | Substitution | p.? | Unknown | Unknown | EDMD2 | Emery-Dreifuss muscular dystrophy, autosomal dominant | 181350 | # |
| 16372 | c.[1381-1G > T; 1381G > T] | Substitution | p.?; Asp461Tyr | Unknown, Substitution | Tail | EDMD2 | Emery-Dreifuss muscular dystrophy, autosomal dominant | 181350 | # |
| 16325 | c.1399T > C | Substitution | p.Trp467Arg | Substitution | Tail | EDMD2 | Emery-Dreifuss muscular dystrophy, autosomal dominant | 181350 | # |
| 8791 | c.1406T > C | Substitution | p.Ile469Thr | Substitution | Tail | EDMD2 | Emery-Dreifuss muscular dystrophy, autosomal dominant | 181350 | # |
| 18194 | c.1466T > C | Substitution | p.Leu489Pro | Substitution | Tail | EDMD2 | Emery-Dreifuss muscular dystrophy, autosomal dominant | 181350 | # |
| 16327 | c.1488 + 1G > A | Substitution | p.? | Unknown | Unknown | EDMD2 | Emery-Dreifuss muscular dystrophy, autosomal dominant | 181350 | # |
| 13180 | c.1492T > A | Substitution | p.Trp498Arg | Substitution | Tail | EDMD2 | Emery-Dreifuss muscular dystrophy, autosomal dominant | 181350 | # |
| 16375 | c.1526dupC | Duplication | p.Thr510TyrfsX42 | Frame shift | Tail | EDMD2 | Emery-Dreifuss muscular dystrophy, autosomal dominant | 181350 | # |
| 18188 | c.1540T > A | Substitution | p.Trp514Arg | Substitution | Tail | EDMD2 | Emery-Dreifuss muscular dystrophy, autosomal dominant | 181350 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 18190 | c.1540T > A | Substitution | p.Trp514Arg | Substitution | Tail | EDMD2 | Emery-Dreifuss muscular dystrophy, autosomal dominant | 181350 | # |
| 12434 | c.1558T > G | Substitution | p.Trp520Gly | Substitution | Tail | EDMD2 | Emery-Dreifuss muscular dystrophy, autosomal dominant | 181350 | # |
| 18179 | c.1558T > C | Substitution | p.Trp520Arg | Substitution | Tail | EDMD2 | Emery-Dreifuss muscular dystrophy, autosomal dominant | 181350 | # |
| 8811 | c.1559G > C | Substitution | p.Trp520Ser | Substitution | Tail | EDMD2 | Emery-Dreifuss muscular dystrophy, autosomal dominant | 181350 | # |
| 8745 | c.1580G > C | Substitution | p.Arg527Pro | Substitution | Tail | EDMD2 | Emery-Dreifuss muscular dystrophy, autosomal dominant | 181350 | # |
| 11344 | c.1580G > C | Substitution | p.Arg527Pro | Substitution | Tail | EDMD2 | Emery-Dreifuss muscular dystrophy, autosomal dominant | 181350 | # |
| 8792 | c.1580G > C | Substitution | p.Arg527Pro | Substitution | Tail | EDMD2 | Emery-Dreifuss muscular dystrophy, autosomal dominant | 181350 | # |
| 8812 | c.1580G > C | Substitution | p.Arg527Pro | Substitution | Tail | EDMD2 | Emery-Dreifuss muscular dystrophy, autosomal dominant | 181350 | # |
| 11391 | c.1580G > C | Substitution | p.Arg527Pro | Substitution | Tail | EDMD2 | Emery-Dreifuss muscular dystrophy, autosomal dominant | 181350 | # |
| 8838 | c.1580G > C | Substitution | p.Arg527Pro | Substitution | Tail | EDMD2 | Emery-Dreifuss muscular dystrophy, autosomal dominant | 181350 | # |
| 8859 | c.1580G > C | Substitution | p.Arg527Pro | Substitution | Tail | EDMD2 | Emery-Dreifuss muscular dystrophy, autosomal dominant | 181350 | # |
| 11423 | c.1580G > C | Substitution | p.Arg527Pro | Substitution | Tail | EDMD2 | Emery-Dreifuss muscular dystrophy, autosomal dominant | 181350 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 11630 | c.1580G > C | Substitution | p.Arg527Pro | Substitution | Tail | EDMD2 | Emery-Dreifuss muscular dystrophy, autosomal dominant | 181350 | # |
| 11754 | c.1580G > C | Substitution | p.Arg527Pro | Substitution | Tail | EDMD2 | Emery-Dreifuss muscular dystrophy, autosomal dominant | 181350 | # |
| 16377 | c.1580G > C | Substitution | p.Arg527Pro | Substitution | Tail | EDMD2 | Emery-Dreifuss muscular dystrophy, autosomal dominant | 181350 | # |
| 18182 | c.1580G > C | Substitution | p.Arg527Pro | Substitution | Tail | EDMD2 | Emery-Dreifuss muscular dystrophy, autosomal dominant | 181350 | # |
| 8793 | c.1583C > A | Substitution | p.Thr528Lys | Substitution | Tail | EDMD2 | Emery-Dreifuss muscular dystrophy, autosomal dominant | 181350 | # |
| 8814 | c.1583C > A | Substitution | p.Thr528Lys | Substitution | Tail | EDMD2 | Emery-Dreifuss muscular dystrophy, autosomal dominant | 181350 | # |
| 11392 | c.1583C > A | Substitution | p.Thr528Lys | Substitution | Tail | EDMD2 | Emery-Dreifuss muscular dystrophy, autosomal dominant | 181350 | # |
| 9006 | c.1583C > G | Substitution | p.Thr528Arg | Substitution | Tail | EDMD2 | Emery-Dreifuss muscular dystrophy, autosomal dominant | 181350 | # |
| 16379 | c.1583C > A | Substitution | p.Thr528Lys | Substitution | Tail | EDMD2 | Emery-Dreifuss muscular dystrophy, autosomal dominant | 181350 | # |
| 16381 | c.1583C > G | Substitution | p.Thr528Arg | Substitution | Tail | EDMD2 | Emery-Dreifuss muscular dystrophy, autosomal dominant | 181350 | # |
| 16382 | c.1583C > G | Substitution | p.Thr528Arg | Substitution | Tail | EDMD2 | Emery-Dreifuss muscular dystrophy, autosomal dominant | 181350 | # |
| 16407 | c.1583C > G | Substitution | p.Thr528Arg | Substitution | Tail | EDMD2 | Emery-Dreifuss muscular dystrophy, autosomal dominant | 181350 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 18196 | c.1583C > G | Substitution | p.Thr528Arg | Substitution | Tail | EDMD2 | Emery-Dreifuss muscular dystrophy, autosomal dominant | 181350 | # |
| 18297 | c.1588C > T | Substitution | p.Leu530Phe | Substitution | Tail | EDMD2 | Emery-Dreifuss muscular dystrophy, autosomal dominant | 181350 | # |
| 8747 | c.1589T > C | Substitution | p.Leu530Pro | Substitution | Tail | EDMD2 | Emery-Dreifuss muscular dystrophy, autosomal dominant | 181350 | # |
| 16384 | c.1621C > A | Substitution | p.Arg541Ser | Substitution | Tail | EDMD2 | Emery-Dreifuss muscular dystrophy, autosomal dominant | 181350 | # |
| 9007 | c.1622G > A | Substitution | p.Arg541His | Substitution | Tail | EDMD2 | Emery-Dreifuss muscular dystrophy, autosomal dominant | 181350 | # |
| 16387 | c.1622G > C | Substitution | p.Arg541Pro | Substitution | Tail | EDMD2 | Emery-Dreifuss muscular dystrophy, autosomal dominant | 181350 | # |
| 13588 | c.1633C > T | Substitution | p.Arg545Cys | Substitution | Tail | EDMD2 | Emery-Dreifuss muscular dystrophy, autosomal dominant | 181350 | # |
| 16389 | c.1804G > A | Substitution | p.Arg541Pro | Substitution | Tail | EDMD2 | Emery-Dreifuss muscular dystrophy, autosomal dominant | 181350 | # |
| 9383 | c.1871G > A | Substitution | p.Arg624His | Substitution | Tail | EDMD2 | Emery-Dreifuss muscular dystrophy, autosomal dominant | 181350 | # |
| 9154 | c.1930C > T | Substitution | p.Arg644Cys | Substitution | Tail | EDMD2 | Emery-Dreifuss muscular dystrophy, autosomal dominant | 181350 | # |
| 13570 | c.1930C > T | Substitution | p.Arg644Cys | Substitution | Tail | EDMD2 | Emery-Dreifuss muscular dystrophy, autosomal dominant | 181350 | # |
| 13571 | c.1930C > T | Substitution | p.Arg644Cys | Substitution | Tail | EDMD2 | Emery-Dreifuss muscular dystrophy, autosomal dominant | 181350 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 13572 | c.1930C > T | Substitution | p.Arg644Cys | Substitution | Tail | EDMD2 | Emery-Dreifuss muscular dystrophy, autosomal dominant | 181350 | # |
| 13573 | c.1930C > T | Substitution | p.Arg644Cys | Substitution | Tail | EDMD2 | Emery-Dreifuss muscular dystrophy, autosomal dominant | 181350 | # |
| 16392 | c.1930C > T | Substitution | p.Arg644Cys | Substitution | Tail | EDMD2 | Emery-Dreifuss muscular dystrophy, autosomal dominant | 181350 | # |
| 9523 | c.664C > T | Substitution | p.His222Tyr | Substitution | L12 | EDMD3 | Emery-Dreifuss muscular dystrophy, autosomal recessive | 604929 | # |
| 17407 | c.674G > A | Substitution | p.Arg225Gln | Substitution | L12 | EDMD3 | Emery-Dreifuss muscular dystrophy, autosomal recessive | 604929 | # |
| 17573 | c.1445G > A | Substitution | p.Arg482Gln | Substitution | Tail | EDMD3 | Emery-Dreifuss muscular dystrophy, autosomal recessive | 604929 | # |
| 13319 | c.1580G > C | Substitution | p.Arg527Pro | Substitution | Tail | EDMD3 | Emery-Dreifuss muscular dystrophy, autosomal recessive | 604929 | # |
| 18345 | c.? | Unknown | p.Arg482Trp | Substitution | Tail | FPLD2 | Familial partial lipodystrophy (Dunnigan type) | 151660 | # |
| 8847 | c.82C > T | Substitution | p.Arg28Trp | Substitution | Head | FPLD2 | Familial partial lipodystrophy (Dunnigan type) | 151660 | # |
| 18291 | c.139G > A | Substitution | p.Asp47Asn | Substitution | 1A | FPLD2 | Familial partial lipodystrophy (Dunnigan type) | 151660 | # |
| 8861 | c.178C > G | Substitution | p.Arg60Gly | Substitution | 1A | FPLD2 | Familial partial lipodystrophy (Dunnigan type) | 151660 | # |
| 14260 | c.178C > G | Substitution | p.Arg60Gly | Substitution | 1A | FPLD2 | Familial partial lipodystrophy (Dunnigan type) | 151660 | # |
| 8848 | c.184C > G | Substitution | p.Arg62Gly | Substitution | 1A | FPLD2 | Familial partial lipodystrophy (Dunnigan type) | 151660 | # |
| 14256 | c.184C > G | Substitution | p.Arg62Gly | Substitution | 1A | FPLD2 | Familial partial lipodystrophy (Dunnigan type) | 151660 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 12100 | c.398G > T | Substitution | p.Arg133Leu | Substitution | 1B | FPLD2 | Familial partial lipodystrophy (Dunnigan type) | 151660 | # |
| 14258 | c.575A > T | Substitution | p.Asp192Val | Substitution | 1B | FPLD2 | Familial partial lipodystrophy (Dunnigan type) | 151660 | # |
| 17624 | c.667G > A | Substitution | p.Glu223Lys | Substitution | L12 | FPLD2 | Familial partial lipodystrophy (Dunnigan type) | 151660 | # |
| 11775 | c.688G > A | Substitution | p.Asp230Asn | Substitution | L12 | FPLD2 | Familial partial lipodystrophy (Dunnigan type) | 151660 | # |
| 11776 | c.1195C > T | Substitution | p.Arg399Cys | Substitution | Tail | FPLD2 | Familial partial lipodystrophy (Dunnigan type) | 151660 | # |
| 17066 | c.1232G > A | Substitution | p.Gly411Asp | Substitution | Tail | FPLD2 | Familial partial lipodystrophy (Dunnigan type) | 151660 | # |
| 12096 | c.1315C > T | Substitution | pArg439Cys | Substitution | Tail | FPLD2 | Familial partial lipodystrophy (Dunnigan type) | 151660 | # |
| 17208 | c.1315C > T | Substitution | p.Arg439Cys | Substitution | Tail | FPLD2 | Familial partial lipodystrophy (Dunnigan type) | 151660 | # |
| 11542 | c.[1318G > A; =] + [=; 1445G > A] | Substitution | p.[Val440Met; =] + [=; Arg482Gln] | Substitution | Tail | FPLD2 | Familial partial lipodystrophy (Dunnigan type) | 151660 | # |
| 8781 | c.1394G > A | Substitution | p.Gly465Asp | Substitution | Tail | FPLD2 | Familial partial lipodystrophy (Dunnigan type) | 151660 | # |
| 12601 | c.14110 > G | Substitution | p.Arg471Gly | Substitution | Tail | FPLD2 | Familial partial lipodystrophy (Dunnigan type) | 151660 | # |
| 8754 | c.1444C > T | Substitution | p.Arg482Trp | Substitution | Tail | FPLD2 | Familial partial lipodystrophy (Dunnigan type) | 151660 | # |
| 11358 | c.1444C > T | Substitution | p.Arg482Trp | Substitution | Tail | FPLD2 | Familial partial lipodystrophy (Dunnigan type) | 151660 | # |
| 11359 | c.1444C > T | Substitution | p.Arg482Trp | Substitution | Tail | FPLD2 | Familial partial lipodystrophy (Dunnigan type) | 151660 | # |
| 11360 | c.1444C > T | Substitution | p.Arg482Trp | Substitution | Tail | FPLD2 | Familial partial lipodystrophy (Dunnigan type) | 151660 | # |
| 11361 | c.1444C > T | Substitution | p.Arg482Trp | Substitution | Tail | FPLD2 | Familial partial lipodystrophy (Dunnigan type) | 151660 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 11362 | c.1444C > T | Substitution | p.Arg482Trp | Substitution | Tail | FPLD2 | Familial partial lipodystrophy (Dunnigan type) | 151660 | # |
| 11363 | c.1444C > T | Substitution | p.Arg482Trp | Substitution | Tail | FPLD2 | Familial partial lipodystrophy (Dunnigan type) | 151660 | # |
| 11364 | c.1444C > T | Substitution | p.Arg482Trp | Substitution | Tail | FPLD2 | Familial partial lipodystrophy (Dunnigan type) | 151660 | # |
| 11365 | c.1444C > T | Substitution | p.Arg482Trp | Substitution | Tail | FPLD2 | Familial partial lipodystrophy (Dunnigan type) | 151660 | # |
| 8773 | c.1444C > T | Substitution | p.Arg482Trp | Substitution | Tail | FPLD2 | Familial partial lipodystrophy (Dunnigan type) | 151660 | # |
| 11374 | c.1444C > T | Substitution | p.Arg482Trp | Substitution | Tail | FPLD2 | Familial partial lipodystrophy (Dunnigan type) | 151660 | # |
| 11375 | c.1444C > T | Substitution | p.Arg482Trp | Substitution | Tail | FPLD2 | Familial partial lipodystrophy (Dunnigan type) | 151660 | # |
| 11376 | c.1444C > T | Substitution | p.Arg482Trp | Substitution | Tail | FPLD2 | Familial partial lipodystrophy (Dunnigan type) | 151660 | # |
| 11377 | c.1444C > T | Substitution | p.Arg482Trp | Substitution | Tail | FPLD2 | Familial partial lipodystrophy (Dunnigan type) | 151660 | # |
| 11378 | c.1444C > T | Substitution | p.Arg482Trp | Substitution | Tail | FPLD2 | Familial partial lipodystrophy (Dunnigan type) | 151660 | # |
| 11379 | c.1444C > T | Substitution | p.Arg482Trp | Substitution | Tail | FPLD2 | Familial partial lipodystrophy (Dunnigan type) | 151660 | # |
| 8816 | c.1444C > T | Substitution | p.Arg482Trp | Substitution | Tail | FPLD2 | Familial partial lipodystrophy (Dunnigan type) | 151660 | # |
| 11393 | c.1444C > T | Substitution | p.Arg482Trp | Substitution | Tail | FPLD2 | Familial partial lipodystrophy (Dunnigan type) | 151660 | # |
| 11394 | c.1444C > T | Substitution | p.Arg482Trp | Substitution | Tail | FPLD2 | Familial partial lipodystrophy (Dunnigan type) | 151660 | # |
| 11395 | c.1444C > T | Substitution | p.Arg482Trp | Substitution | Tail | FPLD2 | Familial partial lipodystrophy (Dunnigan type) | 151660 | # |
| 11396 | c.1444C > T | Substitution | p.Arg482Trp | Substitution | Tail | FPLD2 | Familial partial lipodystrophy (Dunnigan type) | 151660 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 11397 | c.1444C > T | Substitution | p.Arg482Trp | Substitution | Tail | FPLD2 | Familial partial lipodystrophy (Dunnigan type) | 151660 | # |
| 8834 | c.1444C > T | Substitution | p.Arg482Trp | Substitution | Tail | FPLD2 | Familial partial lipodystrophy (Dunnigan type) | 151660 | # |
| 9213 | c.1444C > T | Substitution | p.Arg482Trp | Substitution | Tail | FPLD2 | Familial partial lipodystrophy (Dunnigan type) | 151660 | # |
| 9156 | c.1444C > T | Substitution | p.Arg482Trp | Substitution | Tail | FPLD2 | Familial partial lipodystrophy (Dunnigan type) | 151660 | # |
| 11543 | c.1444C > T | Substitution | p.Arg482Trp | Substitution | Tail | FPLD2 | Familial partial lipodystrophy (Dunnigan type) | 151660 | # |
| 11544 | c.1444C > T | Substitution | p.Arg482Trp | Substitution | Tail | FPLD2 | Familial partial lipodystrophy (Dunnigan type) | 151660 | # |
| 11662 | c.1444C > T | Substitution | p.Arg482Trp | Substitution | Tail | FPLD2 | Familial partial lipodystrophy (Dunnigan type) | 151660 | # |
| 11692 | c.1444C > T | Substitution | p.Arg482Trp | Substitution | Tail | FPLD2 | Familial partial lipodystrophy (Dunnigan type) | 151660 | # |
| 11699 | c.1444C > T | Substitution | p.Arg482Trp | Substitution | Tail | FPLD2 | Familial partial lipodystrophy (Dunnigan type) | 151660 | # |
| 12101 | c.1444C > T | Substitution | p.Arg482Trp | Substitution | Tail | FPLD2 | Familial partial lipodystrophy (Dunnigan type) | 151660 | # |
| 12102 | c.1444C > T | Substitution | p.Arg482Trp | Substitution | Tail | FPLD2 | Familial partial lipodystrophy (Dunnigan type) | 151660 | # |
| 12103 | c.1444C > T | Substitution | p.Arg482Trp | Substitution | Tail | FPLD2 | Familial partial lipodystrophy (Dunnigan type) | 151660 | # |
| 12104 | c.1444C > T | Substitution | p.Arg482Trp | Substitution | Tail | FPLD2 | Familial partial lipodystrophy (Dunnigan type) | 151660 | # |
| 12105 | c.1444C > T | Substitution | p.Arg482Trp | Substitution | Tail | FPLD2 | Familial partial lipodystrophy (Dunnigan type) | 151660 | # |
| 14066 | c.1444C > T | Substitution | p.Arg482Trp | Substitution | Tail | FPLD2 | Familial partial lipodystrophy (Dunnigan type) | 151660 | # |
| 16433 | c.1444C > T | Substitution | p.Arg482Trp | Substitution | Tail | FPLD2 | Familial partial lipodystrophy (Dunnigan type) | 151660 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 16434 | c.1444C > T | Substitution | p.Arg482Trp | Substitution | Tail | FPLD2 | Familial partial lipodystrophy (Dunnigan type) | 151660 | # |
| 16682 | c.1444C > T | Substitution | p.Arg482Trp | Substitution | Tail | FPLD2 | Familial partial lipodystrophy (Dunnigan type) | 151660 | # |
| 17866 | c.1444C > T | Substitution | p.Arg482Trp | Substitution | Tail | FPLD2 | Familial partial lipodystrophy (Dunnigan type) | 151660 | # |
| 17195 | c.1444C > T | Substitution | p.Arg482Trp | Substitution | Tail | FPLD2 | Familial partial lipodystrophy (Dunnigan type) | 151660 | # |
| 17464 | c.1444C > T | Substitution | p.Arg482Trp | Substitution | Tail | FPLD2 | Familial partial lipodystrophy (Dunnigan type) | 151660 | # |
| 17465 | c.1444C > T | Substitution | p.Arg482Trp | Substitution | Tail | FPLD2 | Familial partial lipodystrophy (Dunnigan type) | 151660 | # |
| 17466 | c.1444C > T | Substitution | p.Arg482Trp | Substitution | Tail | FPLD2 | Familial partial lipodystrophy (Dunnigan type) | 151660 | # |
| 17467 | c.1444C > T | Substitution | p.Arg482Trp | Substitution | Tail | FPLD2 | Familial partial lipodystrophy (Dunnigan type) | 151660 | # |
| 17733 | c.1444C > T | Substitution | p.Arg482Trp | Substitution | Tail | FPLD2 | Familial partial lipodystrophy (Dunnigan type) | 151660 | # |
| 17735 | c.1444C > T | Substitution | p.Arg482Trp | Substitution | Tail | FPLD2 | Familial partial lipodystrophy (Dunnigan type) | 151660 | # |
| 17744 | c.1444C > T | Substitution | p.Arg482Trp | Substitution | Tail | FPLD2 | Familial partial lipodystrophy (Dunnigan type) | 151660 | # |
| 17936 | c.1444C > T | Substitution | p.Arg482Trp | Substitution | Tail | FPLD2 | Familial partial lipodystrophy (Dunnigan type) | 151660 | # |
| 18484 | c.1444C > T | Substitution | p.Arg482Trp | Substitution | Tail | FPLD2 | Familial partial lipodystrophy (Dunnigan type) | 151660 | # |
| 8753 | c.1445G > A | Substitution | p.Arg482Gln | Substitution | Tail | FPLD2 | Familial partial lipodystrophy (Dunnigan type) | 151660 | # |
| 11354 | c.1445G > A | Substitution | p.Arg482Gln | Substitution | Tail | FPLD2 | Familial partial lipodystrophy (Dunnigan type) | 151660 | # |
| 11355 | c.1445G > A | Substitution | p.Arg482Gln | Substitution | Tail | FPLD2 | Familial partial lipodystrophy (Dunnigan type) | 151660 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 11356 | c.1445G > A | Substitution | p.Arg482Gln | Substitution | Tail | FPLD2 | Familial partial lipodystrophy (Dunnigan type) | 151660 | # |
| 11357 | c.1445G > A | Substitution | p.Arg482Gln | Substitution | Tail | FPLD2 | Familial partial lipodystrophy (Dunnigan type) | 151660 | # |
| 8763 | c.1445G > A | Substitution | p.Arg482Gln | Substitution | Tail | FPLD2 | Familial partial lipodystrophy (Dunnigan type) | 151660 | # |
| 8764 | c.1445G > T | Substitution | p.Arg482Leu | Substitution | Tail | FPLD2 | Familial partial lipodystrophy (Dunnigan type) | 151660 | # |
| 8768 | c.1445G > A | Substitution | p.Arg482Gln | Substitution | Tail | FPLD2 | Familial partial lipodystrophy (Dunnigan type) | 151660 | # |
| 11370 | c.1445G > A | Substitution | p.Arg482Gln | Substitution | Tail | FPLD2 | Familial partial lipodystrophy (Dunnigan type) | 151660 | # |
| 11371 | c.1445G > A | Substitution | p.Arg482Gln | Substitution | Tail | FPLD2 | Familial partial lipodystrophy (Dunnigan type) | 151660 | # |
| 11372 | c.1445G > A | Substitution | p.Arg482Gln | Substitution | Tail | FPLD2 | Familial partial lipodystrophy (Dunnigan type) | 151660 | # |
| 11373 | c.1445G > A | Substitution | p.Arg482Gln | Substitution | Tail | FPLD2 | Familial partial lipodystrophy (Dunnigan type) | 151660 | # |
| 8822 | c.1445G > A | Substitution | p.Arg482Gln | Substitution | Tail | FPLD2 | Familial partial lipodystrophy (Dunnigan type) | 151660 | # |
| 8868 | c.1445G > A | Substitution | p.Arg482Gln | Substitution | Tail | FPLD2 | Familial partial lipodystrophy (Dunnigan type) | 151660 | # |
| 9305 | c.1445G > T | Substitution | p.Arg482Leu | Substitution | Tail | FPLD2 | Familial partial lipodystrophy (Dunnigan type) | 151660 | # |
| 11663 | c.1445G > A | Substitution | p.Arg482Gln | Substitution | Tail | FPLD2 | Familial partial lipodystrophy (Dunnigan type) | 151660 | # |
| 11667 | c.1445G > A | Substitution | p.Arg482Gln | Substitution | Tail | FPLD2 | Familial partial lipodystrophy (Dunnigan type) | 151660 | # |
| 12098 | c.1445G > A | Substitution | p.Arg482Gln | Substitution | Tail | FPLD2 | Familial partial lipodystrophy (Dunnigan type) | 151660 | # |
| 12387 | c.1445G > A | Substitution | p.Arg482Gln | Substitution | Unknown | FPLD2 | Familial partial lipodystrophy (Dunnigan type) | 151660 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 12418 | c.1445G > A | Substitution | p.Arg482Gln | Substitution | Unknown | FPLD2 | Familial partial lipodystrophy (Dunnigan type) | 151660 | # |
| 12423 | c.1445G > A | Substitution | p.Arg482Gln | Substitution | Tail | FPLD2 | Familial partial lipodystrophy (Dunnigan type) | 151660 | # |
| 13150 | c.1445G > A | Substitution | p.Arg482Gln | Substitution | Tail | FPLD2 | Familial partial lipodystrophy (Dunnigan type) | 151660 | # |
| 13367 | c.1445G > A | Substitution | p.Arg482Gln | Substitution | Tail | FPLD2 | Familial partial lipodystrophy (Dunnigan type) | 151660 | # |
| 16285 | c.1445G > A | Substitution | p.Arg482Gln | Substitution | Tail | FPLD2 | Familial partial lipodystrophy (Dunnigan type) | 151660 | # |
| 16436 | c.1445G > A | Substitution | p.Arg482Gln | Substitution | Tail | FPLD2 | Familial partial lipodystrophy (Dunnigan type) | 151660 | # |
| 16437 | c.1445G > A | Substitution | p.Arg482Gln | Substitution | Tail | FPLD2 | Familial partial lipodystrophy (Dunnigan type) | 151660 | # |
| 16438 | c.1445G > A | Substitution | p.Arg482Gln | Substitution | Tail | FPLD2 | Familial partial lipodystrophy (Dunnigan type) | 151660 | # |
| 16439 | c.1445G > A | Substitution | p.Arg482Gln | Substitution | Tail | FPLD2 | Familial partial lipodystrophy (Dunnigan type) | 151660 | # |
| 16440 | c.1445G > A | Substitution | p.Arg482Gln | Substitution | Tail | FPLD2 | Familial partial lipodystrophy (Dunnigan type) | 151660 | # |
| 18138 | c.1445G > A | Substitution | p.Arg482Gln | Substitution | Tail | FPLD2 | Familial partial lipodystrophy (Dunnigan type) | 151660 | # |
| 8765 | c.1458G > C | Substitution | p.Lys486Asn | Substitution | Tail | FPLD2 | Familial partial lipodystrophy (Dunnigan type) | 151660 | # |
| 11366 | c.1458G > C | Substitution | p.Lys486Asn | Substitution | Tail | FPLD2 | Familial partial lipodystrophy (Dunnigan type) | 151660 | # |
| 8767 | c.1458G > T | Substitution | p.Lys486Asn | Substitution | Tail | FPLD2 | Familial partial lipodystrophy (Dunnigan type) | 151660 | # |
| 9319 | c.1488 + 5G > C | Substitution | p.Ile497_Met664delins ValThrGlyArgAlaLeu GlyThrLeuGlyArgPro TrpValAlaMetGlyAla LeuGlyX | Indel | Tail | FPLD2 | Familial partial lipodystrophy (Dunnigan type) | 151660 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 17455 | c.1683G > C | Substitution | p.= | Silent | Not affected | FPLD2 | Familial partial lipodystrophy (Dunnigan type) | 151660 | # |
| 11777 | c.1718C > T | Substitution | p.Ser573Leu | Substitution | Tail | FPLD2 | Familial partial lipodystrophy (Dunnigan type) | 151660 | # |
| 8780 | c.1745G > A | Substitution | p.Arg582His | Substitution | Tail | FPLD2 | Familial partial lipodystrophy (Dunnigan type) | 151660 | # |
| 16429 | c.1745G > A | Substitution | p.Arg582His | Substitution | Tail | FPLD2 | Familial partial lipodystrophy (Dunnigan type) | 151660 | # |
| 16430 | c.1745G > A | Substitution | p.Arg582His | Substitution | Tail | FPLD2 | Familial partial lipodystrophy (Dunnigan type) | 151660 | # |
| 16431 | c.1745G > A | Substitution | p.Arg582His | Substitution | Tail | FPLD2 | Familial partial lipodystrophy (Dunnigan type) | 151660 | # |
| 9452 | c.1751G > A | Substitution | p.Arg584His | Substitution | Tail | FPLD2 | Familial partial lipodystrophy (Dunnigan type) | 151660 | # |
| 11545 | c.1751G > A | Substitution | p.Arg584His | Substitution | Tail | FPLD2 | Familial partial lipodystrophy (Dunnigan type) | 151660 | # |
| 12429 | c.1772C > T | Substitution | p.Arg156Cys | Substitution | 1B | FPLD2 | Familial partial lipodystrophy (Dunnigan type) | 151660 | # |
| 17068 | c.1892G > A | Substitution | p.Gly631Asp | Substitution | Tail | FPLD2 | Familial partial lipodystrophy (Dunnigan type) | 151660 | # |
| 13575 | c.1930C > T | Substitution | p.Arg644Cys | Substitution | Tail | FPLD2 | Familial partial lipodystrophy (Dunnigan type) | 151660 | # |
| 13576 | c.1930C > T | Substitution | p.Arg644Cys | Substitution | Tail | FPLD2 | Familial partial lipodystrophy (Dunnigan type) | 151660 | # |
| 13579 | c.1930C > T | Substitution | p.Arg644Cys | Substitution | Tail | FPLD2 | Familial partial lipodystrophy (Dunnigan type) | 151660 | # |
| 17461 | c.1930C > T | Substitution | p.Arg644Cys | Substitution | Tail | FPLD2 | Familial partial lipodystrophy (Dunnigan type) | 151660 | # |
| 12601 | c.1411C > G | Substitution | p.Arg471Gly | Substitution | Tail | FPLD1 | Familial partial lipodystrophy (Köbberling) | 608600 | % |
| 11482 | c.[1583C > T; =] + [=; 1748C > T] | Substitution | p.[Thr528Met; =] + [=; Ser583Leu | Substitution | Tail | FPLD1 | Familial partial lipodystrophy (Köbberling) | 608600 | % |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 9183 | c.1748C > T | Substitution | p.Ser583Leu | Substitution | Tail | FPLD1 | Familial partial lipodystrophy (Köbberling) | 608600 | % |
| 11481 | c.1748C > T | Substitution | p.Ser583Leu | Substitution | Tail | FPLD1 | Familial partial lipodystrophy (Köbberling) | 608600 | % |
| 13490 | c.29C > T | Substitution | p.Thr10Ile | Substitution | Head | — | Generalized lipoatrophy syndrome | — | — |
| 8867 | c.398G > T | Substitution | p.Arg133Leu | Substitution | 1B | — | Generalized lipoatrophy syndrome | — | — |
| 17762 | c.1609-12T > G | Substitution | p.Glu536fsX14 | Frame shift | Tail | HSS | Hallermann-Streiff syndrome | 234100 | % |
| 17260 | c.1930C > T | Substitution | p.Arg644Cys | Substitution | Tail | HSS | Hallermann-Streiff syndrome | 234100 | % |
| 13153 | c.1609-12T > G | Substitution | p.Glu536fsX14 | Frame shift | Tail | — | Heart-hand syndrome, Slovenian Type | 610140 | % |
| 14097 | c.11C > G | Substitution | p.Pro4Arg | Substitution | Head | HGPS | Hutchinson-Gilford progeria syndrome | 176670 | # |
| 14112 | c.11C > G | Substitution | p.Pro4Arg | Substitution | Head | HGPS | Hutchinson-Gilford progeria syndrome | 176670 | # |
| 9172 | c.29C > T | Substitution | p.Thr10Ile | Substitution | Head | HGPS | Hutchinson-Gilford progeria syndrome | 176670 | # |
| 14108 | c.29C > T | Substitution | p.Thr10Ile | Substitution | Head | HGPS | Hutchinson-Gilford progeria syndrome | 176670 | # |
| 14110 | c.29C > T | Substitution | p.Thr10Ile | Substitution | Head | HGPS | Hutchinson-Gilford progeria syndrome | 176670 | # |
| 14101 | c.331G > T | Substitution | p.Glu111Lys | Substitution | 1B | HGPS | Hutchinson-Gilford progeria syndrome | 176670 | # |
| 14095 | c.406G > C | Substitution | p.Asp136His | Substitution | 1B | HGPS | Hutchinson-Gilford progeria syndrome | 176670 | # |
| 17070 | c.412G > A | Substitution | p.Glu138Lys | Substitution | 1B | HGPS | Hutchinson-Gilford progeria syndrome | 176670 | # |
| 9016 | c.428C > T | Substitution | p.Ser143Phe | Substitution | 1B | HGPS | Hutchinson-Gilford progeria syndrome | 176670 | # |
| 12609 | c.428C > T | Substitution | p.Ser143Phe | Substitution | 1B | HGPS | Hutchinson-Gilford progeria syndrome | 176670 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 8871 | c.433G > A | Substitution | p.Glu145Lys | Substitution | 1B | HGPS | Hutchinson-Gilford progeria syndrome | 176670 | # |
| 14106 | c.475G > A | Substitution | p.Glu159Lys | Substitution | 1B | HGPS | Hutchinson-Gilford progeria syndrome | 176670 | # |
| 17626 | c.899A > G | Substitution | p.Asp300Gly | Substitution | 2B | HGPS | Hutchinson-Gilford progeria syndrome | 176670 | # |
| 17903 | c.917T > G | Substitution | p.ꝏ | Substitution | 2B | HGPS | Hutchinson-Gilford progeria syndrome | 176670 | # |
| 14114 | c.1303C > T | Substitution | p.Arg435Cys | Substitution | Tail | HGPS | Hutchinson-Gilford progeria syndrome | 176670 | # |
| 9393 | c.1411C > T | Substitution | p.Arg471Cys | Substitution | Tail | HGPS | Hutchinson-Gilford progeria syndrome | 176670 | # |
| 12615 | c.1411C > T | Substitution | p.Arg471Cys | Substitution | Tail | HGPS | Hutchinson-Gilford progeria syndrome | 176670 | # |
| 9394 | c.1579C?T | Substitution | p.Arg527Cys | Substitution | Tail | HGPS | Hutchinson-Gilford progeria syndrome | 176670 | # |
| 13119 | c.1579C | Substitution | p.Arg527Cys | Substitution | Tail | HGPS | Hutchinson-Gilford progeria syndrome | 176670 | # |
| 13651 | c.1579C > T | Substitution | p.Arg527Cys | Substitution | Tail | HGPS | Hutchinson-Gilford progeria syndrome | 176670 | # |
| 11671 | c.[1583C > T; =] + [=; 1619T > C] | Substitution | p.[Thr528Met; =] + [=; Met540Thr] | Substitution | Tail | HGPS | Hutchinson-Gilford progeria syndrome | 176670 | # |
| 9013 | c.1626G > C | Substitution | p.Lys542Asn | Substitution | Tail | HGPS | Hutchinson-Gilford progeria syndrome | 176670 | # |
| 9173 | c.1733A > T | Substitution | p.Glu578Val | Substitution | Tail | HGPS | Hutchinson-Gilford progeria syndrome | 176670 | # |
| 14099 | c.1762-T > C | Substitution | p.Cys588Arg | Substitution | Tail | HGPS | Hutchinson-Gilford progeria syndrome | 176670 | # |
| 14104 | c.1762-T > C | Substitution | p.Cys588Arg | Substitution | Tail | HGPS | Hutchinson-Gilford progeria syndrome | 176670 | # |
| 11785 | c.1821G > A | Substitution | p.= | Silent | Not affected | HGPS | Hutchinson-Gilford progeria syndrome | 176670 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 9527 | c.1822G > A | Substitution | p.Gly608Ser | Substitution | Tail | HGPS | Hutchinson-Gilford progeria syndrome | 176670 | # |
| 8876 | c.1822G > A | Substitution | p.Gly608Ser | Substitution | Tail | HGPS | Hutchinson-Gilford progeria syndrome | 176670 | # |
| 9396 | c.1824C > T | Substitution | p.[=, Val607_Gln656del] | Silent, Deletion | Tail | HGPS | Hutchinson-Gilford progeria syndrome | 176670 | # |
| 9398 | c.1824C > T | Substitution | p.[=, Val607_Gln656del] | Silent, Deletion | Tail | HGPS | Hutchinson-Gilford progeria syndrome | 176670 | # |
| 11428 | c.1824C > T | Substitution | p.[=, Val607_Gln656del] | Silent, Deletion | Tail | HGPS | Hutchinson-Gilford progeria syndrome | 176670 | # |
| 11429 | c.1824C > T | Substitution | p.[=, Val607_Gln656del] | Silent, Deletion | Tail | HGPS | Hutchinson-Gilford progeria syndrome | 176670 | # |
| 11430 | c.1824C > T | Substitution | p.[=, Val607_Gln656del] | Silent, Deletion | Tail | HGPS | Hutchinson-Gilford progeria syndrome | 176670 | # |
| 11431 | c.1824C > T | Substitution | p.[=, Val607_Gln656del] | Silent, Deletion | Tail | HGPS | Hutchinson-Gilford progeria syndrome | 176670 | # |
| 11432 | c.1824C > T | Substitution | p.[=, Val607_Gln656del] | Silent, Deletion | Tail | HGPS | Hutchinson-Gilford progeria syndrome | 176670 | # |
| 11433 | c.1824C > T | Substitution | p.[=, Val607_Gln656del] | Silent, Deletion | Tail | HGPS | Hutchinson-Gilford progeria syndrome | 176670 | # |
| 11434 | c.1824C > T | Substitution | p.[=, Val607_Gln656del] | Silent, Deletion | Tail | HGPS | Hutchinson-Gilford progeria syndrome | 176670 | # |
| 11435 | c.1824C > T | Substitution | p.[=, Val607_Gln656del] | Silent, Deletion | Tail | HGPS | Hutchinson-Gilford progeria syndrome | 176670 | # |
| 11436 | c.1824C > T | Substitution | p.[=, Val607_Gln656del] | Silent, Deletion | Tail | HGPS | Hutchinson-Gilford progeria syndrome | 176670 | # |
| 11437 | c.1824C > T | Substitution | p.[=, Val607_Gln656del] | Silent, Deletion | Tail | HGPS | Hutchinson-Gilford progeria syndrome | 176670 | # |
| 11438 | c.1824C > T | Substitution | p.[=, Val607_Gln656del] | Silent, Deletion | Tail | HGPS | Hutchinson-Gilford progeria syndrome | 176670 | # |
| 11439 | c.1824C > T | Substitution | p.[=, Val607_Gln656del] | Silent, Deletion | Tail | HGPS | Hutchinson-Gilford progeria syndrome | 176670 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 11440 | c.1824C > T | Substitution | p.[=, Val607_Gln656del] | Silent, Deletion | Tail | HGPS | Hutchinson-Gilford progeria syndrome | 176670 | # |
| 11441 | c.1824C > T | Substitution | p.[=, Val607_Gln656del] | Silent, Deletion | Tail | HGPS | Hutchinson-Gilford progeria syndrome | 176670 | # |
| 11442 | c.1824C > T | Substitution | p.[=, Val607_Gln656del] | Silent, Deletion | Tail | HGPS | Hutchinson-Gilford progeria syndrome | 176670 | # |
| 11443 | c.1824C > T | Substitution | p.[=, Val607_Gln656del] | Silent, Deletion | Tail | HGPS | Hutchinson-Gilford progeria syndrome | 176670 | # |
| 11444 | c.1824C > T | Substitution | p.[=, Val607_Gln656del] | Silent, Deletion | Tail syndrome | HGPS | Hutchinson-Gilford progeria syndrome | 176670 | # |
| 9395 | c.1824C > T | Substitution | p.? | Unknown | Unknown | HGPS | Hutchinson-Gilford progeria syndrome | 176670 | # |
| 11449 | c.1824C > T | Substitution | p.? | Unknown | Unknown | HGPS | Hutchinson-Gilford progeria syndrome | 176670 | # |
| 11450 | c.1824C > T | Substitution | p.? | Unknown | Unknown | HGPS | Hutchinson-Gilford progeria syndrome | 176670 | # |
| 11451 | c.1824C > T | Substitution | p.? | Unknown | Unknown | HGPS | Hutchinson-Gilford progeria syndrome | 176670 | # |
| 11452 | c.1824C > T | Substitution | p.? | Unknown | Unknown | HGPS | Hutchinson-Gilford progeria syndrome | 176670 | # |
| 9171 | c.1824C > T | Substitution | p.[=, Val607_Gln656del] | Silent, Deletion | Tail | HGPS | Hutchinson-Gilford progeria syndrome | 176670 | # |
| 9017 | c.1824C > T | Substitution | p.[=, Val607_Gln656del] | Silent, Deletion | Tail | HGPS | Hutchinson-Gilford progeria syndrome | 176670 | # |
| 9019 | c.1824C > T | Substitution | p.[=, Val607_Gln656del] | Silent, Deletion | Tail | HGPS | Hutchinson-Gilford progeria syndrome | 176670 | # |
| 12074 | c.1824C > T | Substitution | p.[=, Val607_Gln656del] | Silent, Deletion | Not affected | HGPS | Hutchinson-Gilford progeria syndrome | 176670 | # |
| 12075 | c.1824C > T | Substitution | p.[=, Val607_Gln656del] | Silent, Deletion | Not affected | HGPS | Hutchinson-Gilford progeria syndrome | 176670 | # |
| 12076 | c.1824C > T | Substitution | p.[=, Val607_Gln656del] | Silent, Deletion | Not affected syndrome | HGPS | Hutchinson-Gilford progeria syndrome | 176670 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 12085 | c.1824C > T | Substitution | p.[=, Val607_Gln656del] | Silent, Deletion | Not affected | HGPS syndrome | Hutchinson-Gilford progeria | 176670 | # |
| 12354 | c.1824C > T | Substitution | p.= | Silent | Not affected | HGPS | Hutchinson-Gilford progeria syndrome | 176670 | # |
| 13533 | c.1824C > T | Substitution | p.[=, Val607_Gln656del] | Silent, Deletion | Tail | HGPS | Hutchinson-Gilford progeria syndrome | 176670 | # |
| 17393 | c.1824C > T | Substitution | p.= | Silent | Not affected | HGPS | Hutchinson-Gilford progeria syndrome | 176670 | # |
| 17395 | c.1824C > T | Substitution | p.= | Silent | Not affected | HGPS | Hutchinson-Gilford progeria syndrome | 176670 | # |
| 17564 | c.1824C > T | Substitution | p.= | Silent | Not affected | HGPS | Hutchinson-Gilford progeria syndrome | 176670 | # |
| 17729 | c.1824C > T | Substitution | p.= | Silent | Not affected | HGPS | Hutchinson-Gilford progeria syndrome | 176670 | # |
| 17818 | c.1824C > T | Substitution | p.= | Silent | Not affected | HGPS | Hutchinson-Gilford progeria syndrome | 176670 | # |
| 9009 | c.1868C > G | Substitution | p.[Thr623Ser, Val622_Gln656del] | Deletion, Substitution | Tail | HGPS | Hutchinson-Gilford progeria syndrome | 176670 | # |
| 12457 | c.1868C > G | Substitution | p.[Thr623Ser, Val622_Gln656del] | Deletion, Substitution | Tail | HGPS | Hutchinson-Gilford progeria syndrome | 176670 | # |
| 9174 | c.1930C > T | Substitution | p.Arg644Cys | Substitution | Tail | HGPS | Hutchinson-Gilford progeria syndrome | 176670 | # |
| 11615 | c.1960C > T | Substitution | p.Arg654X | Substitution | Tail | HGPS | Hutchinson-Gilford progeria syndrome | 176670 | % |
| 17159 | c.1968G > A | Substitution | p.= | Silent | Not affected | HGPS | Hutchinson-Gilford progeria syndrome | 176670 | # |
| 11784 | c.1968 + 1G > A | Substitution | p.Val607_Gln656del | Deletion | Tail | HGPS | Hutchinson-Gilford progeria syndrome | 176670 | # |
| 17161 | c.1968 + 5G > A | Substitution | p.Val607_Gln656del | Deletion | Tail | HGPS | Hutchinson-Gilford progeria syndrome | 176670 | # |
| 12615 | c.1411C > T | Substitution | p.Arg471Cys | Substitution | Tail | — | Lamin-related rigid spine muscular dystrophy | — | — |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 17426 | c.31delC | Deletion | p.Arg11AlafsX85 | Frame shift | Head | LGMD1B | Limb-girdle muscular dystrophy type 1B | 159001 | # |
| 14254 | c.73C > G | Substitution | p.Arg25Gly | Substitution | Head | LGMD1B | Limb-girdle muscular dystrophy type 1B | 159001 | # |
| 17886 | c.80C > T | Substitution | p.Thr27Ile | Substitution | Head | LGMD1B | Limb-girdle muscular dystrophy type 1B | 159001 | # |
| 18488 | c.80C?T | Substitution | p.Thr27Ile | Substitution | Head | LGMD1B | Limb-girdle muscular dystrophy type 1B | 159001 | # |
| 17428 | c.99G > C | Substitution | p.Glu33Asp | Substitution | 1A | LGMD1B | Limb-girdle muscular dystrophy type 1B | 159001 | # |
| 17429 | c.99G > C | Substitution | p.Glu33Asp | Substitution | 1A | LGMD1B | Limb-girdle muscular dystrophy type 1B | 159001 | # |
| 17430 | c.99G > C | Substitution | p.Glu33Asp | Substitution | 1A | LGMD1B | Limb-girdle muscular dystrophy type 1B | 159001 | # |
| 17434 | c.194A > G | Substitution | p.Glu65Gly | Substitution | 1A | LGMD1B | Limb-girdle muscular dystrophy type 1B | 159001 | # |
| 17435 | c.194A > G | Substitution | p.Glu65Gly | Substitution | 1A | LGMD1B | Limb-girdle muscular dystrophy type 1B | 159001 | # |
| 16283 | c.302G > C | Substitution | p.Arg101Pro | Substitution | 1B | LGMD1B | Limb-girdle muscular dystrophy type 1B | 159001 | # |
| 17399 | c.388G > T | Substitution | p.Ala130Ser | Substitution | 1B | LGMD1B | Limb-girdle muscular dystrophy type 1B | 159001 | # |
| 17755 | c.388G > T | Substitution | p.Ala130Ser | Substitution | 1B | LGMD1B | Limb-girdle muscular dystrophy type 1B | 159001 | # |
| 17432 | c.471G > A | Substitution | p.= | Silent | Not affected | LGMD1B | Limb-girdle muscular dystrophy type 1B | 159001 | # |
| 9216 | c.513G > A | Substitution | p.= | Silent | Not affected | LGMD1B | Limb-girdle muscular dystrophy type 1B | 159001 | # |
| 17575 | c.513 + 1G > A | Substitution | p.? | Unknown | Unknown | LGMD1B | Limb-girdle muscular dystrophy type 1B | 159001 | # |
| 17437 | c.565C > T | Substitution | p.Arg189Trp | Substitution | 1B | LGMD1B | Limb-girdle muscular dystrophy type 1B | 159001 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 9639 | c.622_624delAAG | Deletion | p.Lys208del | Deletion | 1B | LGMD1B | Limb-girdle muscular dystrophy type 1B | 159001 | # |
| 12403 | c.624_626delGAA | Deletion | p.Lys208del | Deletion | 1B | LGMD1B | Limb-girdle muscular dystrophy type 1B | 159001 | # |
| 16145 | c.673C > T | Substitution | p.Arg225X | Substitution | L12 | LGMD1B | Limb-girdle muscular dystrophy type 1B | 159001 | # |
| 17401 | c.673C > T | Substitution | p.Arg225X | Substitution | L12 | LGMD1B | Limb-girdle muscular dystrophy type 1B | 159001 | # |
| 17753 | c.673C > T | Substitution | p.Arg225X | Substitution | L12 | LGMD1B | Limb-girdle muscular dystrophy type 1B | 159001 | # |
| 13555 | c.746G > A | Substitution | p.Arg249Gln | Substitution | 2A | LGMD1B | Limb-girdle muscular dystrophy type 1B | 159001 | # |
| 9164 | c.777T > A | Substitution | p.Tyr259X | Substitution | L2 | LGMD1B | Limb-girdle muscular dystrophy type 1B | 159001 | # |
| 12401 | c.777T > A | Substitution | p.Tyr259X | Substitution | L2 | LGMD1B | Limb-girdle muscular dystrophy type 1B | 159001 | # |
| 17760 | c.777T > A | Substitution | p.Tyr259X | Substitution | L2 | LGMD1B | Limb-girdle muscular dystrophy type 1B | 159001 | # |
| 11810 | c.855delG | Deletion | p.Ala287LeufsX191 | Frame shift | 2B | LGMD1B | Limb-girdle muscular dystrophy type 1B | 159001 | # |
| 9021 | c.864_867delCCAC | Deletion | p.His289ArgfsX190 | Frame shift | 2B | LGMD1B | Limb-girdle muscular dystrophy type 1B | 159001 | # |
| 11759 | c.864_867delCCAC | Deletion | p.His289ArgfsX190 | Frame shift | 2B | LGMD1B | Limb-girdle muscular dystrophy type 1B | 159001 | # |
| 12384 | c.908_909delCT | Deletion | p.Ser303CysfsX26 | Frame shift | 2B | LGMD1B | Limb-girdle muscular dystrophy type 1B | 159001 | # |
| 11811 | c.992G > C | Substitution | p.Arg331Pro | Substitution | 2B | LGMD1B | Limb-girdle muscular dystrophy type 1B | 159001 | # |
| 18309 | c.1001_1003delGCC | Deletion | p.Ser334del | Deletion | 2B | LGMD1B | Limb-girdle muscular dystrophy type 1B | 159001 | # |
| 8794 | c.1130G > A | Substitution | p.Arg377His | Substitution | 2B | LGMD1B | Limb-girdle muscular dystrophy type 1B | 159001 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 8850 | c.1130G > T | Substitution | p.Arg377Leu | Substitution | 2B | LGMD1B | Limb-girdle muscular dystrophy type 1B | 159001 | # |
| 9301 | c.1130G > A | Substitution | p.Arg377His | Substitution | 2B | LGMD1B | Limb-girdle muscular dystrophy type 1B | 159001 | # |
| 9024 | c.1130G?T | Substitution | p.Arg377Leu | Substitution | 2B | LGMD1B | Limb-girdle muscular dystrophy type 1B | 159001 | # |
| 11762 | c.1130G > A | Substitution | p.Arg377His | Substitution | 2B | LGMD1B | Limb-girdle muscular dystrophy type 1B | 159001 | # |
| 13557 | c.1130G > A | Substitution | p.Arg377His | Substitution | 2B | LGMD1B | Limb-girdle muscular dystrophy type 1B | 159001 | # |
| 11755 | c.1146C > T | Substitution | p.= | Silent | Not affected | LGMD1B | Limb-girdle muscular dystrophy type 1B | 159001 | # |
| 11756 | c.1357C > T | Substitution | p.Arg453Trp | Substitution | Tail | LGMD1B | Limb-girdle muscular dystrophy type 1B | 159001 | # |
| 17443 | c.1357C > T | Substitution | p.Arg453Trp | Substitution | Tail | LGMD1B | Limb-girdle muscular dystrophy type 1B | 159001 | # |
| 11812 | c.1370delA | Deletion | p.Lys457SerfsX21 | Frame shift | Tail | LGMD1B | Limb-girdle muscular dystrophy type 1B | 159001 | # |
| 17441 | c.1380 + 1G > A | Substitution | KO | Unknown | Unknown | LGMD1B | Limb-girdle muscular dystrophy type 1B | 159001 | # |
| 8839 | c.1441T > C | Substitution | p.Tyr481His | Substitution | Tail | LGMD1B | Limb-girdle muscular dystrophy type 1B | 159001 | # |
| 13376 | c.1488 + 5G > A | Substitution | p.? | Unknown | Unknown | LGMD1B | Limb-girdle muscular dystrophy type 1B | 159001 | # |
| 9181 | c.1494G > T | Substitution | p.Trp498Cys | Substitution | Tail | LGMD1B | Limb-girdle muscular dystrophy type 1B | 159001 | # |
| 9158 | c.1494G > T | Substitution | p.Trp498Cys | Substitution | Tail | LGMD1B | Limb-girdle muscular dystrophy type 1B | 159001 | # |
| 16442 | c.1494G > T | Substitution | p.Trp498Cys | Substitution | Tail | LGMD1B | Limb-girdle muscular dystrophy type 1B | 159001 | # |
| 9159 | c.1535T > C | Substitution | p.Leu512Pro | Substitution | Tail | LGMD1B | Limb-girdle muscular dystrophy type 1B | 159001 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 11763 | c.1535T > C | Substitution | p.Leu512Pro | Substitution | Tail | LGMD1B | Limb-girdle muscular dystrophy type 1B | 159001 | # |
| 17449 | c.1535-T > C | Substitution | p.Leu512Pro | Substitution | Tail | LGMD1B | Limb-girdle muscular dystrophy type 1B | 159001 | # |
| 17452 | c.1535T > C | Substitution | p.Leu512Pro | Substitution | Tail | LGMD1B | Limb-girdle muscular dystrophy type 1B | 159001 | # |
| 11758 | c.1583C > A | Substitution | p.Thr528Lys | Substitution | Tail | LGMD1B | Limb-girdle muscular dystrophy type 1B | 159001 | # |
| 13446 | c.1608 + 1G > A | Substitution | p.? | Unknown | Unknown | LGMD1B | Limb-girdle muscular dystrophy type 1B | 159001 | # |
| 9412 | c.1608 + 5G > C | Substitution | p.Glu537ValfsX36 | Frame shift | Tail | LGMD1B | Limb-girdle muscular dystrophy type 1B | 159001 | # |
| 13151 | c.1609-3C?G | Substitution | p.? | Unknown | Unknown | LGMD1B | Limb-girdle muscular dystrophy type 1B | 159001 | # |
| 11764 | c.1718C > T | Substitution | p.Ser573Leu | Substitution | Tail | LGMD1B | Limb-girdle muscular dystrophy type 1B | 159001 | # |
| 13505 | c.373G > A | Substitution | p.Gly125Ser | Substitution | 1B | LAF | Lone atrial fibrillation | — | — |
| 13509 | c.[373G > A; =] + [=; 1243G > A] | Substitution | p.[Gly125Ser; =] + [=; Val415Ile] | Substitution | 1B, Tail | LAF | Lone atrial fibrillation | — | — |
| 13492 | c.1310 + 63C > A | Substitution | p.? | Unknown | Unknown | LAF | Lone atrial fibrillation | — | — |
| 13495 | c.937 - 46A > G | Substitution | p.? | Unknown | Unknown | LAF | Lone atrial fibrillation | — | — |
| 13501 | c.1149G > A | Substitution | p.= | Silent | Not affected | LAF | Lone atrial fibrillation | — | — |
| 13497 | c.1158 - 44C > T | Substitution | p.? | Unknown | Unknown | LAF | Lone atrial fibrillation | — | — |
| 13499 | c.1158 - 44C > T | Substitution | p.? | Unknown | Unknown | LAF | Lone atrial fibrillation | — | — |
| 13507 | c.1243G > A | Substitution | p.Val415Ile | Substitution | Tail | LAF | Lone atrial fibrillation | — | — |
| 13511 | c.1462A > C | Substitution | p.Thr488Pro | Substitution | Tail | LAF | Lone atrial fibrillation | — | — |
| 13503 | c.1803C > T | Substitution | p.= | Silent | Not affected | LAF | Lone atrial fibrillation | — | — |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 11783 | c.176T > G | Substitution | p.Leu59Arg | Substitution | 1A | MADA | Mandibuloacral dysplasia with type A lipodystrophy | 248370 | # |
| 18470 | c.683A > T | Substitution | p.Glu228Val | Substitution | L12 | MADA | Mandibuloacral dysplasia with type A lipodystrophy | 248370 | # |
| 12380 | c.[1318G > A; =] + [=; 1580G > A] | Substitution | p.[Val1440Met; =] + [=; Arg527His] | Substitution | Tail | MADA | Mandibuloacral dysplasia with type A lipodystrophy | 248370 | # |
| 12615 | c.1411C > T | Substitution | p.Arg471Cys | Substitution | Tail | MADA | Mandibuloacral dysplasia with type A lipodystrophy | 248370 | # |
| 13119 | c.1579C > T | Substitution | p.Arg527Cys | Substitution | Tail | MADA | Mandibuloacral dysplasia with type A lipodystrophy | 248370 | # |
| 17878 | c.1579C > T | Substitution | p.Arg527Cys | Substitution | Tail | MADA | Mandibuloacral dysplasia with type A lipodystrophy | 248370 | # |
| 8851 | c.1580G > A | Substitution | p.Arg527His | Substitution | Tail | MADA | Mandibuloacral dysplasia with type A lipodystrophy | 248370 | # |
| 11419 | c.1580G > A | Substitution | p.Arg527His | Substitution | Tail | MADA | Mandibuloacral dysplasia with type A lipodystrophy | 248370 | # |
| 11420 | c.1580G > A | Substitution | p.Arg527His | Substitution | Tail | MADA | Mandibuloacral dysplasia with type A lipodystrophy | 248370 | # |
| 11421 | c.1580G > A | Substitution | p.Arg527His | Substitution | Tail | MADA | Mandibuloacral dysplasia with type A lipodystrophy | 248370 | # |
| 11422 | c.1580G > A | Substitution | p.Arg527His | Substitution | Tail | MADA | Mandibuloacral dysplasia with type A lipodystrophy | 248370 | # |
| 8877 | c.1580G > A | Substitution | p.Arg527His | Substitution | Tail | MADA | Mandibuloacral dysplasia with type A lipodystrophy | 248370 | # |
| 11453 | c.1580G > A | Substitution | p.Arg527His | Substitution | Tail | MADA | Mandibuloacral dysplasia with type A lipodystrophy | 248370 | # |
| 8995 | c.1580G > A | Substitution | p.Arg527His | Substitution | Tail | MADA | Mandibuloacral dysplasia with type A lipodystrophy | 248370 | # |
| 9224 | c.1580G > A | Substitution | p.Ala527His | Substitution | Tail | MADA | Mandibuloacral dysplasia with type A lipodystrophy | 248370 | # |
| 17602 | c.1580G > T | Substitution | p.Arg527Leu | Substitution | Tail | MADA | Mandibuloacral dysplasia with type A lipodystrophy | 248370 | # |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 17603 | c.1580G > T | Substitution | p.Arg527Leu | Substitution | Tail | MADA | Mandibuloacral dysplasia with type A lipodystrophy | 248370 | # |
| 17747 | c.1580G > T | Substitution | p.Arg527Leu | Substitution | Tail | MADA | Mandibuloacral dysplasia with type A lipodystrophy | 248370 | # |
| 17748 | c.1580G > T | Substitution | p.Arg527Leu | Substitution | Tail | MADA | Mandibuloacral dysplasia with type A lipodystrophy | 248370 | # |
| 12598 | c.1585G > A | Substitution | p.Ala529Thr | Substitution | Tail | MADA | Mandibuloacral dysplasia with type A lipodystrophy | 248370 | # |
| 9317 | c.1586C > T | Substitution | p.Ala529Val | Substitution | Tail | MADA | Mandibuloacral dysplasia with type A lipodystrophy | 248370 | # |
| 18478 | c.1620C > A | Substitution | p. | Substitution | Tail | MADA | Mandibuloacral dysplasia with type A lipodystrophy | 248370 | # |
| 13054 | c.82C > T | Substitution | p.Arg28Trp | Substitution | Head | — | Metabolic syndrome | — | — |
| 13056 | c.274C > T | Substitution | p.Leu92Phe | Substitution | 1B | — | Metabolic syndrome | — | — |
| 13059 | c.1159G > G | Substitution | p.Leu387Val | Substitution | 2B | — | Metabolic syndrome | — | — |
| 13061 | c.1184C > T | Substitution | p.Ser395Leu | Substitution | Not affected | — | Metabolic syndrome | — | — |
| 13063 | c.1196G > A | Substitution | p.Arg399His | Substitution | Tail | — | Metabolic syndrome | — | — |
| 13065 | c.1262T > C | Substitution | p.Leu421Pro | Substitution | Tail | — | Metabolic syndrome | — | — |
| 13067 | c.1315C > T | Substitution | p.Arg439Cys | Substitution | Tail | — | Metabolic syndrome | — | — |
| 13069 | c.1516C > G | Substitution | p.His506Asp | Substitution | Tail | — | Metabolic syndrome | — | — |
| 13047 | c.1698C > T | Substitution | p.= | Silent | Not affected | — | Metabolic syndrome | — | — |
| 13071 | c.1961_1962insG | Insertion | p.Thr655AsnfsX49 | Frame shift | Tail | — | Metabolic syndrome | — | — |
| 12408 | c.73C > T | Substitution | p.Arg25Cys | Substitution | Head | — | Muscular dystrophy | — | — |
| 12410 | c.1130G > T | Substitution | p.Arg377Leu | Substitution | 2B | — | Muscular dystrophy | — | — |
| 12412 | c.1622G > C | Substitution | p.Arg541Pro | Substitution | Tail | — | Muscular dystrophy | — | — |
| 12414 | c.1045C > T | Substitution | p.Arg349Trp | Substitution | 2B | — | Muscular dystrophy and lipodystrophy | — | — |

TABLE 1-continued

| Database ID | cDNA Variant | cDNA Variant Types | Protein Variant | Protein Variant Types | Domain | Disease Abbreviation | Disease Name | Omim ID | Omim Symbol |
|---|---|---|---|---|---|---|---|---|---|
| 17411 | c.1821G > A | Substitution | p.= | Silent | Not affected | WRS | Progeroid syndrome, neonatal | 264090 | % |
| 18482 | c.1940T > G | Substitution | p.Leu647Arg | Substitution | Tail | WRS | Progeroid syndrome, neonatal | 264090 | % |
| 17009 | c.1303C > T | Substitution | p.Arg435Cys | Substitution | Tail | RD | Restrictive dermopathy | 275210 | # |
| 17731 | c.1303C > T | Substitution | p.Arg435Cys | Substitution | Tail | RD | Restrictive dermopathy | 275210 | # |
| 17801 | c.1303C > T | Substitution | p.Arg435Cys | Substitution | Tail | RD | Restrictive dermopathy | 275210 | # |
| 9166 | c.1824C > T | Substitution | p.[=, Val607_Gln656del] | Silent, Deletion | Tail | RD | Restrictive dermopathy | 275210 | # |
| 9208 | c.1968 + 1G > A | Substitution | p.Gly567_Gln656del | Deletion | Tail | RD | Restrictive dermopathy | 275210 | # |
| 17980 | c.1057C > T | Substitution | p.Gln353X | Substitution | 2B | — | Spinal muscular atrophy with cardiac involvment | — | — |
| 18424 | c.868G > A | Substitution | p.Glu290Lys | Substitution | 2B | SCD | Sudden cardiac death | 115080 | # |
| 17189 | c.908_909delCT | Deletion | p.Ser303CysfsX26 | Frame shift | 2B | SCD | Sudden cardiac death | 115080 | # |
| 17901 | c.1334T > A | Substitution | p.Val445Glu | Substitution | Tail | SCD | Sudden cardiac death | 115080 | # |
| 9022 | c.1804G > A | Substitution | p.Gly602Ser | Substitution | Tail | — | Type A insulin resistance syndrome | — | — |

In some embodiments, the nucleic acid molecule according to any aspect of the invention is for use in treating cardiovascular disease in a subject.

In some embodiments, the disease or the cardiovascular disease Is characterised by the presence of at least one Lmna mutation.

Preferably, the cardiovascular disease is selected from the group consisting of laminopethy, cardiomyopathy, such as dilated cardiomyopathy (DCM), dilated cardiomyopathy 1A, dilated cardiomyopathy with conduction system defects, cardiomyopathy with advanced AV block and arrhythmia, lone atrial fibrillation; muscular dystrophy (often associated with cardiomyopathy), such as cardiomyopathy associated with Emery-Dreifuss muscular dystrophy (autosomal dominant), cardiomyopathy associated with Emery-Dreifuss muscular dystrophy (autosomal recessive), cardiomyopathy associated with Limb-girdle muscular dystrophy type 1B, cardiomyopathy associated with congenital muscular dystrophy; premature aging syndromes (thought to be primarily vascular, but may have cardiac involvement) such as cardiomyopathy associated with Atypical Werner syndrome, cardiomyopathy associated with Hutchinson-Gilford progeria syndrome and the like, as well as diseases presented in bold font in Table 1.

According to a third aspect of the invention there is provided an adeno-associated virus vector (AAV) comprising a cardiac troponin T promoter (cTnT), and the transgene according to any aspect of the invention.

According to a fourth aspect of the invention there is provided a pharmaceutical composition comprising the nucleic acid molecule according to any embodiment of the invention for treating a disease.

In some embodiments the disease is a laminopathy.

In some embodiments the pharmaceutical composition comprising the nucleic acid molecule according to the invention is for use in treating a cardiovascular disease in a subject.

According to a fifth aspect of the invention there is provided a method of treating a disease in a subject, the method comprising administration of a pharmaceutically effective amount of the nucleic acid molecule according to any embodiment of the invention, or the pharmaceutical composition of the invention.

In some embodiments of the method of treating a disease in a subject, the disease is characterised by the presence of at least one Lmna mutation.

In some embodiments of the method of treating a disease in a subject, the method comprises:

(i) testing a sample obtained from a subject suspected of having a disease for the presence or absence of at least one Lmna mutation;

wherein the presence of at least one Lmna mutation indicates that the subject is to be administered the pharmaceutical composition of the invention or the nucleic acid molecule of the invention.

In some embodiments of the method of treating a disease in a subject, the Lmna mutation(s) affect(s) lamin A isoform, or lamin C isoform of the Lmna gene, or both lamin A/C isoforms.

In some embodiments of the method of treating a disease in a subject, the disease is selected from the group consisting of restrictive dermopathy, familial partial lipodystrophy (for example, Dunnigan type), mandibuloacral dysplasia with type A lipodystrophy, metabolic syndrome, Charcot-Marie-Tooth disease type 2, Charcot-Marie-Tooth disease type 2B1 and diseases presented in normal font in Table 1.

In some embodiments of the method of treating a disease in a subject, the disease is a cardiovascular disease, wherein the cardiovascular disease is selected from the group consisting of laminopathy, cardiomyopathy, such as dilated cardiomyopathy (DCM), dilated cardiomyopathy 1A, dilated cardiomyopathy with conduction system defects, cardiomyopathy with advanced AV block and arrhythmia, lone atrial fibrillation; muscular dystrophy (often associated with cardiomyopathy), such as cardiomyopathy associated with Emery-Dreifuss muscular dystrophy (autosomal dominant), cardiomyopathy associated with Emery-Dreifuss muscular dystrophy (autosomal recessive), cardiomyopathy associated with Limb-girdle muscular dystrophy type 1B, cardiomyopathy associated with congenital muscular dystrophy; premature aging syndromes (thought to be primarily vascular, but may have cardiac involvement) such as cardiomyopathy associated with Atypical Werner syndrome, cardiomyopathy associated with Hutchinson-Gilford progeria syndrome; and diseases presented in bold font in Table 1.

In some embodiments of the method of treating a disease in a subject, the subject is a non-human mammal, such as a mouse, or a human.

In some embodiments of the method, the mouse is an N195K mouse (Lmna N195K/N195K), or a Lmna conditional knockout (Lmnaflox/flox).

According to a sixth aspect of the invention there is provided use of the pharmaceutical composition according to the invention or the nucleic acid molecule according to the invention in the manufacture of a medicament for treating a disease caused by one or more Lmna mutations.

In some embodiments the disease is Lmna mutation-related cardiovascular disease.

In some embodiments the disease is selected from the group consisting of restrictive dermopathy, familial partial lipodystrophy (for example, Dunnigan type), mandibuloacral dysplasia with type A lipodystrophy, metabolic syndrome, Charcot-Marie-Tooth disease type 2, Charcot-Marie-Tooth disease type 2B1 and diseases presented in normal font in Table 1.

In some embodiments the cardiovascular disease is selected from the group consisting of laminopathy, cardiomyopathy, such as dilated cardiomyopathy (DCM), dilated cardiomyopathy 1A, dilated cardiomyopathy with conduction system defects, cardiomyopathy with advanced AV block and arrhythmia, lone atrial fibrillation; muscular dystrophy (often associated with cardiomyopathy), such as cardiomyopathy associated with Emery-Dreifuss muscular dystrophy (autosomal dominant), cardiomyopathy associated with Emery-Dreifuss muscular dystrophy (autosomal recessive), cardiomyopathy associated with Limb-girdle muscular dystrophy type 1B, cardiomyopathy associated with congenital muscular dystrophy; premature aging syndromes (thought to be primarily vascular, but may have cardiac involvement) such as cardiomyopathy associated with Atypical Werner syndrome, cardiomyopathy associated with Hutchinson-Gilford progeria syndrome and the like, as well as diseases presented in bold font in Table 1.

According to a seventh aspect of the invention there is provided a method for screening for drug candidates capable of inhibiting or disrupting the LINC complex in a cell.

Accordingly, in some embodiments there is provided a method for screening for drug candidates capable of inhibiting the interaction of the proteins of a LINC complex in a cell, which comprises:

(a) combining the proteins of said LINC complex in the presence of a drug to form a first complex;

(b) combining the proteins in the absence of said drug to form a second complex;
(c) measuring the amount of said first complex and said second complex; and
(d) comparing the amount of said first complex with the amount of said second complex, wherein if the amount of said first complex is less than the amount of said second complex, then the drug is a drug candidate for inhibiting the interaction of the proteins of said UNC complex in a cell.

In some embodiments the drug candidate disrupts the protein-protein interaction between SUN and KASH of the LINC complex. Preferably the drug candidate disrupts the interaction between Sun1 and Nesprin-1 proteins.

In some embodiments said screening is an in vitro screening.

In some embodiments said complex is measured by an ELISA method.

In some embodiments recombinant SUN domain is immobilized on a solid surface and recombinant KASH domain is labelled with an enzyme that can generate a colorimetric or chemiluminescent readout. Compounds that fail to inhibit the SUN-KASH interaction will result in a well in the plate where the recombinant SUN would bind to the enzyme-linked KASH domain. Following wash steps and incubation with colorimetric or chemiluminescent enzyme substrates, the presence of the SUN-KASH interaction can be detected in standard plate readers. If the compound can inhibit SUN-KASH interaction, then following the wash step, the KASH domain would be removed, and there would be reduced or no enzymatic reaction in the well.

In some embodiments if the amount of said first complex is less than the amount of said second complex, then said drug is a drug candidate for inhibiting the interaction of said proteins.

In some embodiments said complex is measured by a fluorescence anisotropy method.

In some embodiments the fluorescence anisotropy method employs recombinant SUN and KASH domains. In some embodiments the KASH domain is fluorescently labelled with a fluorescein moiety and fluorescence anisotropy of the KASH domain interacting with SUN domain may be measured using standard equipment such as a plate reader incorporating a fluorescence spectrometer function.

In some embodiments if the amount of said first complex is less than the amount of said second complex there will be a difference in the fluorescence anisotropy of the fluorescent KASH and said drug is a drug candidate for inhibiting the interaction of said proteins.

BRIEF DESCRIPTION OF THE FIGURES

FIG. 3 shows a schematic of the connections between the nucleus and the extracellular matrix via the LINC complex and how mutations in lamin A/C might result in DCM. The plasma membrane, cytoskeleton and nucleus form a mechanically and physically linked entity. In Lmna mutants, the nucleus is structurally weak. It is much more susceptible to mechanical stress from cytoskeletal forces. This leads to severe damage to the myocyte nuclei that in turn leads to a cascade of events such as apoptosis and fibrosis that results finally in DCM.

FIG. 4 shows the effect of microinjection of dextran into the nucleus of $Lmna^{-/-}$ and $Lmna^{-/-}$ mice under low pressure. In the wildtype cells, the dextran stays in the nucleus, while in the Lmna mutant cells the dextran leaks out of the nucleus into the cytoplasm.

FIG. 13 shows a schematic of the region of Sun1 protein used in dominant negative constructs.

FIG. 14 shows an alignment of KASH1-KASH5 domain amino acid sequences with conserved residues (SEQ ID Nos: 7, 9, 11, 13 and 15, respectively).

(FIG. 26A) Wild type (C57/Bl6) mice with or without Sun1 have a normal lifespan, whereas the average postnatal lifespan of the Lmna$^{Flx/Flx:Zp3}$ mice in which LaminA is deleted in all tissues was 17.5 days (*P=<0.0001; Log-rank test). On a Sun1$^{-/-}$ background longevity is increased to 32.5 days. (FIG. 26B) When Lmna$^{Flx/Flx}$ was deleted specifically and constitutively in hearts by crossing the mice with the Cre$^{\alpha MyHC}$ line, the Lmna$^{Flx/Flx:\alpha MyHC}$ mice lived on average 26.5 days. On a Sun1$^{-/-}$ background these mice lived for longer than 6 months. (FIG. 26C) 3-5 month old Lmna$^{Flx/Flx}$ were crossed with the Tmx inducible cardiomyocyte specific Cre Tg(Myh6-cre/Esr1), (abbreviated to mcm), after a single injection of Tmx the mice die within 3-4 weeks. On a Sun1$^{-/-}$ background these mice lived for more than 1 year. (FIG. 26D) Lmna$^{N195K/N195K}$ mice lived for an average of 78 days compared to Lmna$^{N195K/N195K}$ Sun1$^{-/-}$ mice which had an average lifespan of 111 days. (*P=<0.0001, **P=0.0073 Log-rank test).

(FIG. 27A) The average lifespan of the Lmna$^{Flx/Flx:mcm}$ mice was 27 days after a single Tmx injection (*P=<0.0001; Log-rank test). (FIG. 27B) PCR detected the floxed (deleted) Lmna gene (arrow head) only in heart tissue after Tmx injection and not in other tissues or when Tmx was not injected (FIG. 27C) Lmna$^{Flx/Flx:mcm}$+Tmx mice developed kyphosis (arrow head) by 21 days after injection. (FIG. 27D) LaminA/C protein, detected by immunofluorescence, were present in control (i, iii), but reduced/absent in cardiomyocyte (CM) nuclei in both isolated CMs (ii second panel) and heart sections (iv) (white arrowheads) with CM nuclei being detected by PCM-1 staining, 21 days after Tmx. (FIG. 27E) LaminA/C levels were quantified by Western analysis of whole heart lysates 21 days after injection. A significant reduction (*P=<0.0001; T-test) in A-type Lamin protein was detected, although Lamin C levels were not reduced as much in the Lmna$^{Flx/Flx:mcm}$+Tmx mice compared to Lmna$^{Flx/Flx:mcm}$+CTL.

(FIG. 28A) Lmna$^{Flx/Flx:mcm}$+Tmx mice show reduced cardiac contractile function. (FIG. 28B) Lmna$^{Flx/Flx:mcm}$ hearts show reduced EF % and FS %, and increased LVID (*P=<0.0001, P=0.0010 Two way ANOVA). (FIG. 28C) Histological analysis of the hearts revealed increased infiltration of nucleated cells and intercellular spaces in Lmna$^{Flx/Flxmcm}$ hearts (i and ii). Significantly fewer viable (brick-like) CMs were isolated from Lmna$^{Flx/Flx:mcm}$ hearts compared to Lmna$^{Flx/Flx:mcm}$ controls (iii). With higher magnification, the isolated cardiomyocytes from Lmna$^{Flx/Flx:mcm}$ hearts contained large intracellular vacuoles (arrow head, iv). (FIG. 28D) The left ventricular lumen in Lmna$^{Flx/Flx:mcm}$ hearts was enlarged (i) together with increased fibrosis (ii) (*P=0.0007 visible as lighter grey areas in the 28D ii, middle panels and iv left panel) and apoptotic nuclei revealed by TUNEL staining (*P=0.0220; One way ANOVA) (iii and iv right panel). All samples and analyses were performed on hearts 21 days post Tmx injection.

(FIG. 29A) CM nuclei with reduced or absent Lamin A/C expression are indicated by white arrow heads (1, 3). CM nuclei (2, 4) with normal Lamin A/C levels are indicated by grey arrowheads. LMNA protein levels, measured by both fluorescence intensity (5) and Western blot (6), were significantly reduced in Lmna$^{Flx/Flx:mcm}$ Sun1$^{+/+}$+Tmx (***P=0.0009; T-test) and Lmna$^{Flx/Flx:mcm}$ Sun1$^{-/-}$+Tmx (*P=0.0359; T-test) compared to Lmna$^{Flx/Flxmcm}$ Sun1$^{+/+}$ controls (lower graph, 6) (FIG. 29B). Left ventricular (LV) enlargement was apparent in the Lmna$^{Flx/Flx:mcm}$ Sun1$^{+/+}$+Tmx hearts (panel 1) but not in the LV of the Lmna$^{Flx/Flx:mcm}$ Sun1$^{-/-}$+Tmx hearts (panel 2). The Lmna$^{Flx/Flx:mcm}$ Sun1$^{+/+}$+Tmx mice had significantly increased fibrosis (panel 3, fibrosis in grey) compared to controls, but there was no significant increase in fibrosis in the Lmna$^{Flx/Flxmcm}$ Sun1$^{-/-}$+Tmx hearts (panel 3) compared to controls (panel 4, quantified in panel 5, P=0.0001; One way ANOVA). Cardiac papillary muscle active force measurements were significantly reduced from the Lmna$^{Flx/Flx:mcm}$ Sun1$^{+/+}$+Tmx mice compared to Lmna$^{Flx/Flx:mcm}$ Sun 1$^{+/+}$ controls (P=0.0047; T-test) and Lmna$^{Flx/Flx:mcm}$ Sun1$^{+/+}$+Tmx (*P=0.0113; T-test) (panel 6). (FIG. 29C) CM nuclear morphologies were significantly altered in Lmna$^{Flx/Flx:mcm}$ Sun1$^{-/-}$+Tmx mice (Panel 1, solid arrow heads). In the absence of TMX, control heart sections (CTL, panel 2) display few nuclear abnormalities. In the absence of Sun1, Lmna$^{Flx/Flx:mcm}$ Sun1$^{-/-}$+Tmx cardiomyocytes showed no nuclear abnormalities (Panels 3 and 4). In summary FIG. 29C panel 5 reveals that, 70% of CM in Lmna$^{Flx/Flx:mcm}$ Sun1$^{+/+}$+Tmx mice had NE ruptures/distortions or misshapen nuclei compared to less than 1% of CM nuclei in Lmna$^{Flx/Flx:mcm}$ Sun1$^{-/-}$+Tmx mice. (FIG. 29D) Echo analyses on TMX-treated and control mice were performed following Tmx induction. Echocardiograms (ECGs) performed at 28 days after Tmx injection on 3-5 month old mice (panel 1). ECGs performed before and after Cre induction revealed a progressive worsening of cardiac contractility in Lmna$^{Flx/Flx:mcm}$ Sun1$^{+/+}$+Tmx mice (solid black line) compared to Lmna$^{Flx/Flx:mcm}$ Sun1$^{-/-}$+Tmx mice (panels 2-4). The loss of SUN1 preserved EF (panel 2), FS (panel 3) and Global Longitudinal Strain (GLS, panel 4) in Lmna$^{Flx/Flx:mcm}$ Sun1$^{-/-}$+Tmx mice compared to Lmna$^{Flx/Flx:mcm}$ Sun1$^{+/+}$+Tmx mice.

(FIG. 30A) The absence of Sun1 significantly increases the lifespan of Lmna$^{N195K/Flx:mcm}$ Sun1$^{-/-}$+Tmx mice compared to Lmna$^{N195K/Flx:mcm}$ Sun1$^{+/+}$+Tmx mice (*P=0.0101; Log-rank test). Mice with only one copy of the N195K mutation (Lmna$^{N195K/-:mcm}$ Sun1$^{+/+}$+Tmx) had an average lifespan of 47 days, approximately half the lifespan of mice homozygous i.e. with two copies of the N195K allele. (FIG. 30B) Echocardiograms (ECGs) performed before and after Cre induction revealed progressive worsening of cardiac contractility in Lmna$^{N195K/-:mcm}$ Sun1$^{+/+}$+Tmx mice compared to Lmna$^{N195K/-:mcm}$ Sun1$^{-/-}$+Tmx mice over time. ECGs images were recorded at 28 days after Tmx injection (left-hand side panels). The loss of SUN1 preserved EF, FS and GLS in Lmna$^{N195K/Flx:mcm}$ Sun1$^{-/-}$+Tmx mice compared to Lmna$^{N195K/Flx:mcm}$ Sun1$^{+/+}$+Tmx mice (right-hand side bottom 3 panels).

FIGS. 31A-31G show Lmna$^{Flxx/Flx:mcm}$+Tmx mice expressing an AAV transduced DNSun1 exhibit improved cardiac function and increased longevity. (FIG. 31A) Protocol for AAV-mediated transduction of the DN-Sun1 miniprotein into Lmna$^{Flx/Flx:mcm}$+Tmx mice. A single Tmx (IP) injection is given at D14 postnatally to induce Lmna deletion. AAV9-DNSun1 or AAV9-GFP viral particles are then injected into the chest cavity on D15 postnatally. The experimental endpoint was set at 100 days after Tmx. (FIG. 31B) The DNSun1 miniprotein competes with endogenous Sun1 for binding to the KASH domain of the Nesprins (in CMs this is Nesprin1). The miniprotein competes with endogenous SUN1 in binding to the KASH domain of the Nesprins. As the DNSun1 miniprotein is not anchored in the INM this effectively disconnects the endogenous SUN proteins from binding to the KASH domains so breaking the LINC. (FIG. 31C) The presence of the recombined Lmna gene following Tmx injection was confirmed by PCR of the heart tissues (upper panel). Robust expression of both AAV9-DNSun1 and AAV9-GFP protein (Dosage: 5×10$^{\wedge}$10 vg/g of mouse) was detected in extracts from whole hearts 99 days post AAV injection (lower panel). (FIG. 31D) CMs derived from human iPS stem cells were transduced with the DNSun1 using AW-DJ as the vector. In CMs expressing high levels of DNSun1, indicated by grey arrows, Nesprin1 localization to the NE Is reduced or absent. Nesprin localization to the NE is maintained in CMs either not expressing the AW-DJ-DNSun1 or when expressed at lower levels (white arrow heads). (FIG. 31E) The Lmna$^{Flx/Flx:mcm}$+Tmx+AAV9-GFP mice lived for an average of 34.5 d after Tmx induction, whereas Lmna$^{Flx/Flx:mcm}$+Tmx mice injected with AA9-DNSun1 (5×10$^{\wedge}$10 vg/g/mouse) lived significantly longer (**P=0.0038; Log-rank test) to at least 100 D post Tmx, after which the mice were sacrificed for analysis. This set of data was derived from that shown in FIG. 20, adjusted by removing mice that were female and those with a different dose of virus. FIG. E(i) represents male mice and FIG. E(ii) represents female mice. (FIG. 31F) At 35 d after Tmx, extensive fibrosis (blue in original image, grey here) and ventricular enlargement was detected in Lmna$^{Flx/Flx:mcm}$+Tmx+AAV9-GFP hearts compared to Lmna$^{Flx/Flx:mcm}$+Tmx+AAV9-DNSun1 hearts. (FIG. 31G) ECG analysis confirmed Lmna$^{Flx/Flx:mcm}$+Tmx+AAV9-DNSun1 hearts had better cardiac function compared to the Lmna$^{Flx/Flx:mcm}$+Tmx+AAV9-GFP hearts at 35 d days after Tmx injection.

(FIG. 32B) The loss of or introduction of a mutation within the Lmna gene results in loss/or incorrect assembly of the nuclear lamina, which weakens the Lamina/NE. The weakened nuclei are damaged due to the tension/stress forces exerted via the LINC complex from the contractile sarcomeres of the cardiomyocytes. (FIGS. 32C, D). In the absence of SUN1 or by disrupting its binding to the KASH domains by expression of DNSun1, the untethered LINC complexes exert less tensional force on the cardiomyocyte nuclei, enabling survival of the Lmna mutant cardiomyocytes.

(FIG. 37A) Histological analysis of the aged Lmna$^{Flx/Flx:mcm}$ Sun1$^{+/+}$ hearts, 12-14 months after the Tmx injection, revealing no significant morphological changes e.g. LV enlargement or (FIG. 37B) in fibrosis compared to the controls. (FIG. 37C) PCR analysis confirmed the sustained deletion of Lmna gene. (FIG. 37D) Protein quantification revealed a significant reduction of LMNA levels in Lmna$^{Flx/Flx:mcm}$ Sun1$^{-/-}$+Tmx hearts at 14 months after TMX. (FIG. 37E) Echocardiograms (left-hand side panel) from the aged mice showed reduced EF and FS (right-hand side panels) in both Lmna$^{Flx/Flx:mcm}$ Sun1$^{+/+}$+CTL and Lmna$^{Flx/Flx:mcm}$ Sun1$^{-/-}$+Tmx aged mice.

(FIG. 39A) LaminA/C levels were significantly reduced following Tmx induction, and the presence of either AAV9-DNSun1 or AAV9-GFP protein did not alter LMNA protein levels (Quantification of LaminA/C immunofluorescence intensity). The amount of LaminA/C, DNSun1 and GFP protein in whole hearts were also quantified by Western analysis (lower 3 graphs). (Analysis performed 35 days after Tmx). (FIG. 39B) The expression of both DNSun1 and GFP proteins were dependent on the concentration of viral particles injected. (FIG. 39C) Immunofluorescence revealed the majority of CMs were successfully infected and expressed GFP with 5×10^10 vg/g of AAV9-GFP (left image) compared to infection with a 10-fold lower (5×10^9 AAV9-GFP, right image) concentration of viral particles.

FIGS. 40A-40C show CRISPR targeting of Sun1 SUN domain results in loss of Sun1 protein. (A, B) Clustal alignment of Sun1 DNA (FIG. 40A) and amino acid (FIG. 40B) sequence (SEQ ID Nos: 69 and 72, respectively) adjacent to CRISPR-induced mutation in wildtype Sun1, Sun1 with 4 bp insertion (Sun1_plus4; SEQ ID NOs: 70 and 73, respectively) and Sun1 with 7 bp deletion (Sun1_del7; SEQ ID NOs: 71 and 74, respectively). Numbering is of Sun1 coding sequence (A) and protein sequence (B). Bold letters in (B) indicate SUN domain. (FIG. 40C) Immunofluorescence staining of mouse adult fibroblasts derived from wildtype and Sun1 mutant mice. Sun1 expression is lost in mutant mice, but Sun2 and Nesprin-1 expression is similar in all 3 genotypes. Scale bar=10 μm.

FIG. 41A-D shows CRISPR targeting of Syne1 C-terminus results in expression of a mutant Nesprin-1 protein. (A, B) Clustal alignment of wildtype Nesprin-1 DNA (SEQ ID NO; 75) and Nesprin-1C'TΔ8 (Nesprn1_CTdel8) (SEQ ID NO: 76) (A) and amino acid sequence adjacent to CRISPR-induced mutation in wildtype Nesprin-1 (SEQ ID NO: 77) and Nesprin-1C'TΔ8 (Nesprin1_CTdel8) (SEQ ID NO: 78) (B). TGA in bold indicates stop codon of Syne1/Nesprin-1 gene. (C, D) Immunoblots of Nesprin-1 from Syne1/Nesprin-1 wildtype and Syne1/Nesprin-1C'TΔ8 mutant heart and muscle tissue.

FIG. 42A-B are photomicrographs showing CRISPR-Induced Syne1 mutation results in mislocalized, "KASH-less" Nesprin-1 protein. Immunofluorescence staining of mouse adult fibroblasts (A) and primary myotubes (B) derived from widtype (WT) and Syne1C'TΔ8 mutant mice. Nesprin-1 is mislocalized from the nuclear envelope in the mutant samples. Merged images shows Nesprin-1 and DNA staining. Scale bar=10 μm.

(FIG. 46A) Design of IRES-βgal PGK-Neo targeting construct for generating Syne2 mutation. (FIG. 46B) Immunofluorescence staining of mouse adult fibroblasts derived from wildtype (WT) and Syne2 mutant mice showing loss of Nesprin-2. (FIG. 46C) Images of newborn pups. Top row are of mice with at least 1 wildtype Syne1 or Syne2 allele that appear a healthy pink. Bottom row shows cyanotic double mutant Syne1$^{C'T\Delta8/C'T\Delta8}$:Syne2$^{-/-}$ pups which appear blue and die at birth.

DETAILED DESCRIPTION OF PREFERRED EMBODIMENTS

Definitions

Figure 1:
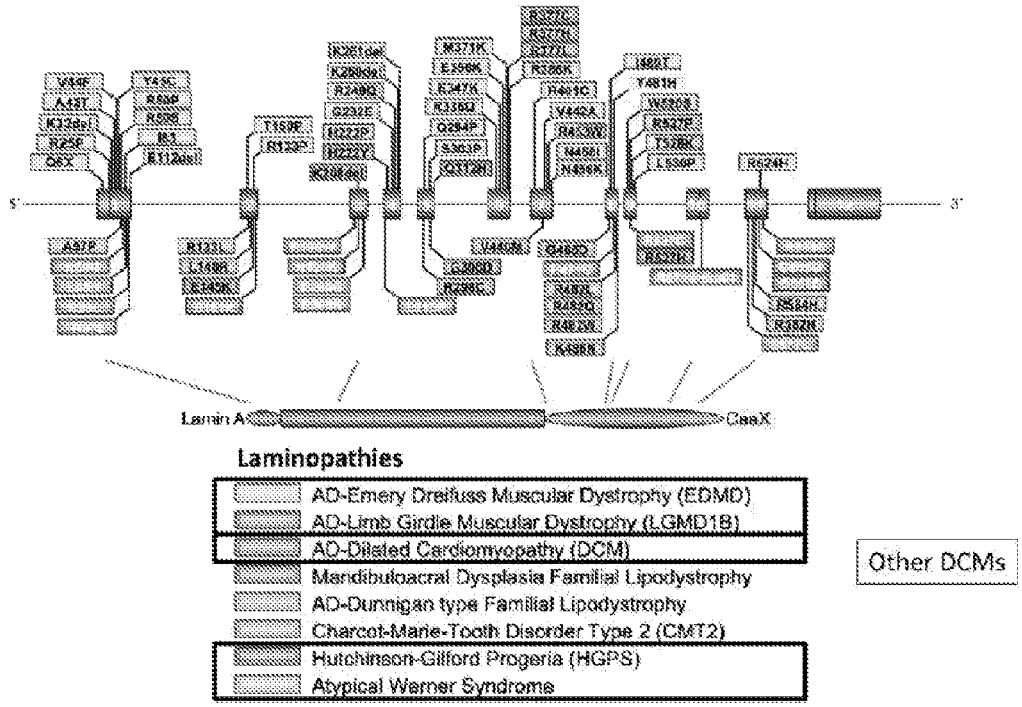
FIG. 1 shows a schematic of the mutations in the lamin A/C gene LMNA and the laminopathies resulting from the mutations.
Figure 2:
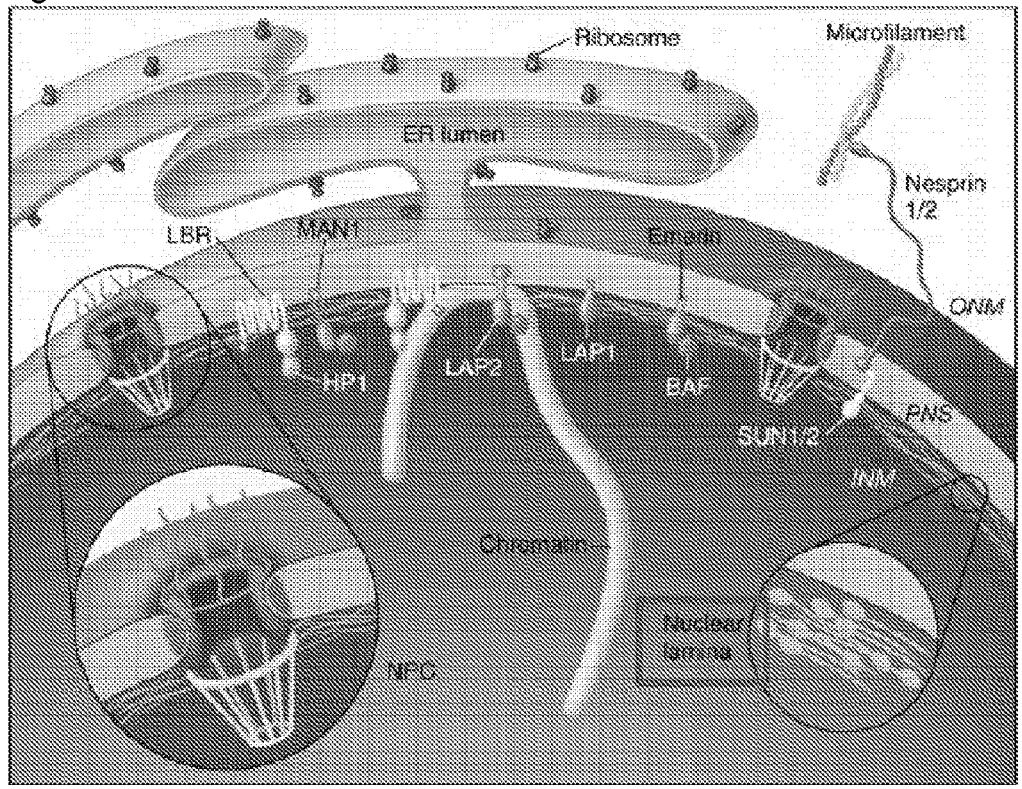
FIG. 2 shows a schematic of the positioning of components of the nuclear envelope membrane and lamina.

Certain terms employed in the specification, examples and appended claims are collected here for convenience.

The terms "amino acid" or "amino acid sequence," as used herein, refer to an oligopeptide, peptide, polypeptide, or protein sequence, or a fragment of any of these, and to naturally occurring or synthetic molecules. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

As used herein, the term "comprising" or "including" is to be interpreted as specifying the presence of the stated features, integers, steps or components as referred to, but does not preclude the presence or addition of one or more features, integers, steps or components, or groups thereof. However, in context with the present disclosure, the term "comprising" or "including" also includes "consisting of". The variations of the word "comprising", such as "comprise" and "comprises", and "including", such as "include" and "includes", have correspondingly varied meanings.

As used herein, the terms "CRISPR-Cas" and "CRISPR" system are used somewhat interchangeably to refer to a microbial adaptive immune system that uses RNA-guided nucleases to cleave foreign genetic elements. It comprises clustered regularly intersperced short palindromic repeats (CRISPRs), a CRISPR-associated (Cas) endonuclease and a synthetic guide RNA that can be programmed to identify and introduce a double strand break at a specific site within a targeted gene sequence. The palindromic repeats are interspaced by short variable sequences derived from exogenous DNA targets known as protospacers, and together they constitute the CRISPR RNA (crRNA) array. Within the DNA target, each protospacer is always associated with a protospacer adjacent motif (PAM), which can vary depending on the specific CRISPR system. CRISPR-Cas9 is a specific version of the system referring to use of RNA-guided Cas9 nuclease, originally derived from *Streptococcus pyogenes*, whereby the target DNA must immediately precede a 5'-NGG PAM. Variations of the CRISPR-Cas9 system are known [Ran F A, at al., *Nat. Protoc* 8, 2281-2308 (2013); Ran F A, et al., *Cell* 154, 1380-1389 (2013)], including CRISPR-Cpf1, and although CRISPR-Cas9 has been used herein in the Examples, it is not intended that the present invention be limited to a particular CRISPR-Cas system.

As used herein, the term "dominant negative" refers to a mutation whose gene product adversely affects the normal, wild-type gene product within the same cell. This usually occurs if the product can still interact with the same elements as the wild-type product, but block some aspect of its function. In one example, the transgene is expressed as a protein, and said protein that is functional as a dimer. A mutation that removes the functional domain, but retains the dimerization domain would cause a dominant negative phenotype, because some fraction of protein dimers would be missing one of the functional domains.

As used herein, the term "normal font" in reference to diseases listed in Table 1 refers to those diseases that are in plain text and not in bold text. The term "bold text" has its ordinary meaning.

As used herein, the term "stabiliser polypeptide" or "stabiliser protein" refers to an inert polypeptide which folds into a discrete domain, thereby ensuring that the remainder of the peptide maintains, for example, the proper topology. In one example, the stabiliser protein ensures that the KASH protein maintains proper topology on the endoplasmic reticulum membrane and the outer nuclear membrane. In another example, the stabiliser polypeptide prevents an attached polypeptide from translocating into, for example, the perinuclear space.

As used herein, the term "operably linked" means that the components to which the term is applied are in a relationship that allows them to carry out their inherent functions under suitable conditions. For example, a control sequence which is "operably linked" to a protein coding sequence is ligated thereto, so that expression of the protein coding sequence is achieved under conditions compatible with the transcriptional activity of the control sequences. By way of an example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

As used herein, there term "extension" refers to one or more amino acids that can be found attached to the N- or the C-terminus of a desired peptide.

As used herein, the terms "polypeptide", "peptide" or "protein" refer to one or more chains of amino acids, wherein each chain comprises amino acids covalently linked by peptide bonds, and wherein said polypeptide or peptide can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. A "polypeptide", "peptide" or "protein" can comprise one (termed "a monomer") or a plurality (termed "a multimer") of amino acid chains.

The term "subject" is herein defined as vertebrate, particularly mammal, more particularly human. For purposes of research, the subject may particularly be at least one animal model, e.g., a mouse, rat and the like. In particular, for treatment or prophylaxis of a laminopthy, such as DCM, the subject may be a human.

The term "treatment", as used in the context of the invention refers to ameliorating, therapeutic or curative treatment.

Without being bound by theory, the inventors submit that the whole basis of the therapy is that disrupting LINC complex function suppresses Lmna mutation. It is further noted that the target of the claimed methods is the SUN-KASH interaction in the LINC complex. The endogenous protein levels should not be affected.

It is also further noted that the transgene (for example, the dominant negative transgene) will not work if the full length SUN domain protein is inserted between the signal sequence and the KDEL, as it will invert the membrane topology of the protein such that the SUN domain is no longer in the perinuclear space/ER lumen. Only the regions following the transmembrane domain can be used, i.e. the luminal domain.

A person skilled in the art will appreciate that the present invention may be practiced without undue experimentation according to the methods given herein. The methods, techniques and chemicals are as described in the references given or from protocols in standard biotechnology and molecular biology text books.

EXAMPLES

Example 1

Materials and Methods

Figure 33:
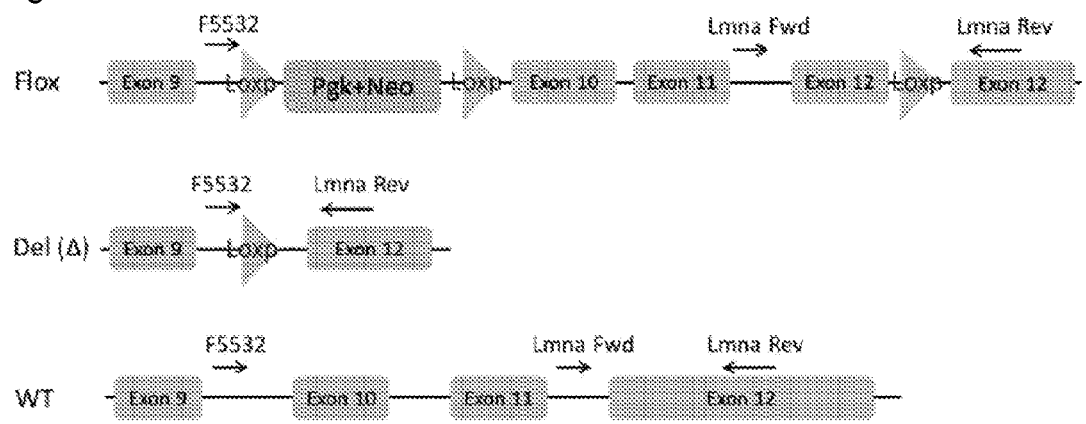
FIG. 33: shows the structure of the Lmna$^{Flx/Flx}$ conditional allele. Primer locations for genotyping the Lmna gene both before and after Cre recombination are indicated for the Lmna$^{Flx}$ allele (Flox), the Lmna deleted allele (A) and the wildtype alele [A. S. Wang, et al., *Differentiation* 89: 11-21 (2015)].
Figure 35:
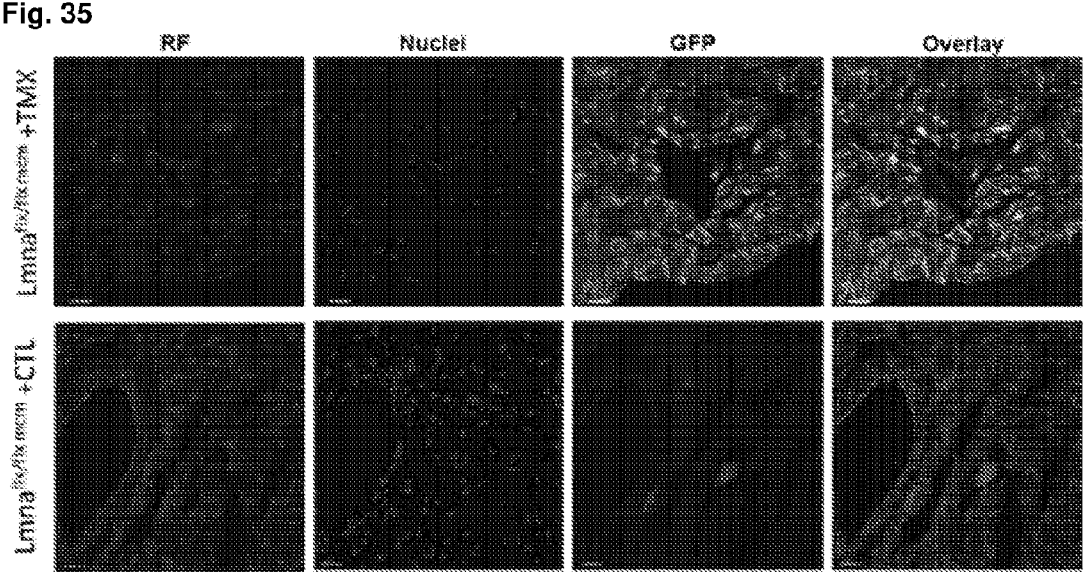
FIG. 35 shows photomicrographs of cardiomyocyte specific expression of Cre recombinase after Tmx injection. The Lmna$^{Flx/Flx:mcm}$ mice were crossed with the mT/mG (JAX: Gt(ROSA)26Sortm4(ACTB-tdTomato,-EGFP)Luo/J) reporter mice. In the absence of Cre, RFP is expressed. When Cre is induced, GFP is expressed. Only CMs of Lmna$^{Flx/Flx:mcm}$ mice express GFP upon TMX injection. Heart tissues were analyzed 7 days after Tmx injection.

Mice were maintained at the A*STAR Biological Resource Centre facility and the NUS Animal Facility in accordance with the guidelines of the Institutional Animal Care and Use Committee for each facility. The $Lmna^{Flx/Flx}$ mice were generated and characterized as previously described [A. S. Wang, at al., *Differentation; research in biological diversity*, (2015); I. Solovei et al., *Cell* 152: 584-598 (2013)] (FIG. 33). To derive mice with a global deletion Lmna ($Lmna^{\Delta/\Delta}$), we crossed the floxed allele ($Lmna^{Flx/Flx}$) to mice in which Cre recombinase is driven by the regulatory sequences of the mouse zona pellucida 3 gene (Zp3;Tg(Zp3-cre)93Knw, JAX stock 003651) [W. N. de Vries et al., *Genesis* 28:110-112 (2000)]. To obtain cardiomyocyte-specific deletion of Lmna ($Lmna^{Flx/Flx/NlMhc}$), we first crossed the $Lmna^{Flx/Flx}$ mice to mice in which Cre expression was driven by the cardiac-specific murine alpha myosin-heavy chain (Myh6, myosin, heavy polypeptide 6, cardiac muscle, alpha) promoter (MyHC;Tg(Myhca-cre) 2182Mds, JAX stock 011038). To obtain a tamoxifen inducible cardiomyocyte-specific deletion of Lmna (LmnFlx/Flx: mcm), we crossed the $Lmna^{Flx/Flx}$ with mice in which Cre expression was driven by the mouse cardiac-specific alpha-myosin heavy chain promoter ($\alpha$MHC or alpha-MHC; Myh6) that expressed a tamoxifen-inducible Cre recombinase (MerCreMer) specifically in juvenile and adult cardiac myocytes (mcm;Tg(Myh6-cre/Esr1*)1Jmk, JAX stock 005657). The specificity of mcm Cre expression to cardiomyocytes was confirmed by crossing Cre lines to the mT/mG reporter mice [M. D. Muzumdar, et al., *Genesis* 45: 593-605 (2007)] (FIG. 35). Generation of the $Sun1^{-/-}$ mice was previously described [Y. H. Chi et al., *Development* 136: 965-973 (2009)] as were the $Lmna^{N195K/N195K}$ mice [L. C. Mounkes, et al., *Hum Mol Genet* 14: 2167-2180 (2005)]. The $Lmna^{\Delta/\Delta}$:$Sun1^{-/-}$ and $Lmna^{Flx/Flx}$mcm:$Sun1^{-/-}$ mice were obtained by crossing the respective Lamin-Cre mice strains with $Sun1^{+/-}$ mice as $Sun1^{-/-}$ mice are infertile.

To test for the insertion of loxP sites and conditional deleted allele, genotyping was performed with a duplex PCR protocol with the following primers were used:

```
FLX/FLX-F1:
                               SEQ ID NO: 16
5'-CCAGCTTACAGAGCACCGAGCT-3',

FLX/FLX-F2:
                               SEQ ID NO: 17
5'-TCCTTGCAGTCCCTCTTGCATC-3',

FLX/FLX-R1:
                               SEQ ID NO: 18
5'-AGGCACCATTGTCACAGGGTC-3'.
```

To test for Sun1 deletion, the following primers were used:

```
Sun1-F:
                               SEQ ID NO: 19
5'-GGC AAG TGG ATC TCT TGT GAA TTC TTG AC-3'

Sun1-R:
                               SEQ ID NO: 20
5'-GTA GCA CCC ACC TTG GTG AGC TGG TAC-3'

Sun1-E8:
                               SEQ ID NO: 21
5'-AGC CAC ATA ACC ACC TGG AG-3'
```

To test for the MyHC transgene, the following primers were used:

```
MyHC-tF:
                               SEQ ID NO: 22
5'-ATG ACA GAC AGA TCC CTC CTA TCT CC-3'

MyHC-tR:
                               SEQ ID NO: 23
5'-CTC ATC ACT CGT TGC ATC ATC GAC-3'

MyHC-F:
                               SEQ ID NO: 24
5'-CAA ATG TTG CTT GTC TGG TG-3'

MyHC-R:
                               SEQ ID NO: 25
5'-GTC AGT CGA GTG CAC AGT TT-3'
```

To test for the presence of mcm transgene, the following primers were used:

```
mcm-3798t:
                               SEQ ID NO: 26
5'-AGG TGG ACC TGA TCA TGG AG-3' mcm-8346t:
                               SEQ ID NO: 27
5'-ATA CCG GAG ATC ATG CAA GC-3' mcm-7338:
                               SEQ ID NO: 28
5'-CTA GGC CAC AGA ATT GAA AGA TCT-3' mcm-7339:
                               SEQ ID NO: 29
5'-GTA GGT GGA AAT TCT AGC ATC ATC C-3'
```

Tamoxifen Injection and Tissue Collection

Young mice (14 days old) and adult mice (3-5 months old) were injected once with 40 mg/kg of Tamoxifen (Sigma) dissolved in Corn Oil (Sigma). Mice were sacrificed by $CO_2$ euthanasia or anesthetised with a gaseous mixture of 1.5% Isoflurane (BioMac) and $1.5LO_2$ at various time points after tamoxifen injection. Cardiac arrest was induced by injection of 15% KCl, followed by flushing with PBS to remove blood. Hearts for paraffin embedding were additionally flushed with 4% paraformaidehyde (PFA), left in 4% paraformaldehyde (PFA) overnight, dehydrated in 70% ethanol for at least 24 hr and embedded in paraffin. Hearts for cryosection were embedded in tragacanth gum (Sigma), frozen in isopentane (BDH-AnalaR) cooled in liquid $N_2$, cut 9 µm sections by cryostat (Leica CM3050), collected onto charged slides and stored at −20° C. for histological and immunofluorescence staining. Hearts for protein and RNA extraction were snap frozen in liquid N2 and stored for further processing.

Cardiomyocyte Isolation

Cardiomyocyte isolation was carried out as per standard protocol [M. Ackers-Johnson et al., *Circulation Research* 119: 909 (2016)]. Briefly, mice were anaesthetised with isoflurane (100% $O_2$ at 0.5 L/min, isoflurane atomiser dial at 4%). Mice hearts were stopped with 15% KCl, descending aorta was cut and hearts were flushed with 7 mL of EDTA buffer into the right ventricle. Ascending aorta was clamped using Reynolds forceps, the entire heart removed and placed in a 60 mm dish containing fresh EDTA buffer. Hearts were digested by sequential injections of 10 mL EDTA buffer, 3 mL Perfusion buffer and 30-50 mL Collagenase buffer into the left ventricle. Forceps were used to gently pull the digested heart into smaller pieces ~1 mm and gentle trituration. Enzymatic activity was inhibited by addition of 5 ml of Stop buffer. Cell suspension was passed through a 100 um filter, and four sequential rounds of gravity settling to enrich for myocytes, ultimately obtaining a highly pure myocyte fraction. The myocyte pellet was snap frozen in liquid $N_2$ and stored a $-80°$ C. until further processing.

Histological and Immunofluorescence Microscopy

For histological studies, sections (9 µm) were stained with standard Hematoxylin and Eosin for cell morphology, Masson's trichrome stain to detect collagen and TUNEL assay to detect apoptotic nuclei. Images were obtained on a Zeiss Axio Imager Microscope. For immunofluorescence on frozen heart sections, sections were warmed to room temperature, rehydrated with PBS, blocked with M.O.M block (Vector Shields) and donkey serum (Sigma-Aldrich), incubated with primary antibodies overnight at 4° C. The slides were then washed in PBS and incubated with secondary antibodies and Hoechst dye (Sigma-Aldrich) for 60 mins, washed with PBS and mounted in Prolong-Gold Anti-fade reagent (Invitrogen). Primary antibodies: LMNA/C N-18 (goat, 1:50, Santa Cruz), Sun1 monoclonal (mouse, neat, from B. Burke), PCM-1 (rabbit, 1:200, Sigma) and sarcomere-α-actinin (mouse, 1:100, abcam); Secondary antibodies were: Alexa Fluor 488, 568 and 847 (1:250, Invitrogen). For isolated cardiomyocyte immunofluorescence, myocytes were stained in suspension and spun down gently for each solution change then plated on glass slides for imaging with a Zeiss LSM510 inverted confocal microscope.

Western Analysis for LMNA, SUN1, Ha-Tag and GFP.

Whole Hearts and Quadriceps muscles were homogenized in RIPA lysis buffer and spun at 13,200 g, 10 min, 4° C. Total cell lysates were electrophoresed and transferred to PVDF membrane and blocked with Odyssey Blocking Buffer (Li-Cor Biosciences). The membrane was incubated with primary antibodies for 2 h at room temperature. After which, membrane was washed in TBST washing solution and incubated in Odyssey IRDye secondary antibodies for 1 h before visualization on the Odyssey Infrared Imaging System (Li-Cor Biosciences). The primary antibodies used for detection of LMNA/C (Rabbit, Cell Signalling) that is specific to an epitope in the first 50 amino acids in LMNA, Sun1 monoclonal (mouse, 1:500, Burke) and control beta-tubulin (rabbit, 1:1000, Abcam).

Active Force Measurement of Cardiac Papillary Muscle.

Mouse papillary muscle from mouse left ventricle was prepared according to the methods described before [C. N. Toepfer, et al., *J Physiol* 594: 5237-5254 (2016)]. Briefly, explanted mouse heart was immediately rinsed with oxygenated ice-cold Krebs-Henseleit solution with 12 unit/mL heparin sodium (EDQM) and 30 mM 2,3-Butanedione monoxime (BDM, Sigma) and excess blood was removed. After that, the heart was transferred to ice-cold Krebs-Henseleit solution in a glass petri-dish under a dissection microscope with a cooling stage. Cylindrical papillary (200-300 µm in diameter and 1.5-2 mm in length) were excised from the left ventricle. T-shaped aluminium clips with a hole were crimped onto the ends of a papillary preparation and the prepared papillary chunks were fixed using pins onto a glass petri-dish with a layer of PDMS sylgard 184 (Dow Corning). Papillary preparations were immersed in a 2% Triton X-100 solution at 4° C. overnight.

Force measurement was performed as previously described [C. Toepfer et al., *J Biol Chem* 288: 13448-13454 (2013)]. The T-shaped aluminium clips at the ends of the papillary preparations were attached to the hooks of a force transducer (AE801, HJK Sensoren+Systeme) and servomotor in the experimental rig and were glued with shellac in ethanol (Sigma) to minimize the movement during the experiment. Papillary contraction force was measured at 20° C. The max contraction force was measured in activing solution (100 mM TES, 6.5 Mm MgCl2, 25 mM Ca-EGTA, 5.7 mM Na2ATP, 20 mM Glutathione, 21.5 mM sodium creatine phosphate, pH=7.1, Ionic strength is 150 mmol/L) with 32 µmol/L free Ca2+. The data were collected and processed from the force transducer and DAQ data acquisition device (National Instrument) using a customized software programmed by LabVIEW 2013 (National instrument). At least 5 fibres were tested in each mouse, and at least 3 mice were tested for each experimental group.

AAV9-N-Sun1 and AAV9-GFP Virus

The DN-Sun1 (SS-HA-Sun1L-KDEL) and GFP (SS-GFP-KDEL) vectors were as described [M. Crisp et al., *J Cell Biol.* 172: 41-53 (200)]. Briefly, almost the entire lumenal domain of Sun1 was tagged at its $NH_2$ terminus with HA (HA-Sun1L). To introduce the HA-Sun1L as a soluble form into the lumen of the ER and PNS, signal sequence and signal peptidase cleavage site of human serum albumin was fused onto the $NH_2$ terminus of HA-Sun1L to yield SS-HA-Sun1L To prevent its secretion, a KDEL tetrapeptide was fused to the COOH terminus of SS-HA-Sun1L to form the final SS-HA-Sun1L-KDEL. The HA-Sun1L region was replaced with GFP sequence to generate the SS-GFP-KDEL.

Figure 10:
FIG. 10 shows a schematic of an AAV expression construct (SEQ ID NO: 3) comprising cardiac-specific promoter and Sun1 dominant negative sequence.
Figure 11:
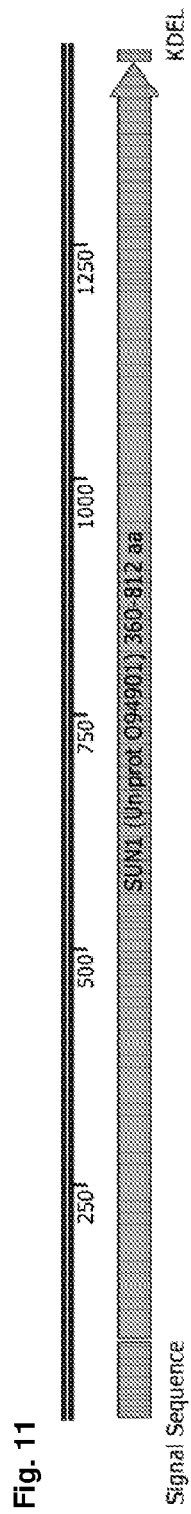
FIG. 11 shows a schematic of the features of the dominant negative Sun1 protein, Including a signal sequence, coiled-coil sequence, SUN domain sequence and KDEL sequence (SEQ ID NO: 4).
Figure 12:
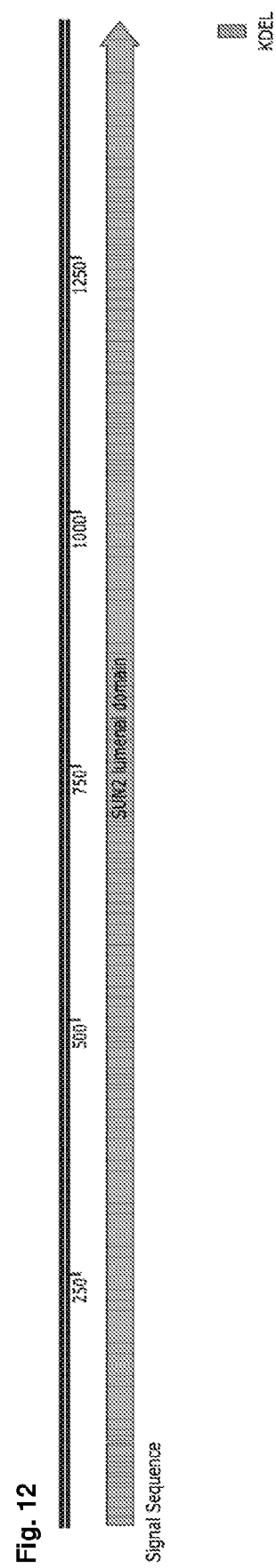
FIG. 12 shows a schematic of the features of a dominant negative Sun2 protein, including a signal sequence, lumenal domain sequence and KDEL sequence (SEQ ID NO: 5).

The DN-Sun1 and GFP fragments were amplified with the primers listed below (same forward primer was used for both fragments) and ligated into pENN-AAV-cTnT-Pl-eGFP plasmid (kind gift from Dr J. Jian), digested with NcoI and KpnI, to produce Penn-AAV-cTnT-Sun1DN (FIG. 10; SEQ ID NO: 3).

aav Sun1 F
SEQ ID NO: 30
5'-CgagaattcacgcgggccgccATGAAGTGGGTAACCTTTATTTC-3' aav Sun1 R
SEQ ID NO: 31
5'-CgggtcgactctagaggtaccttaCTACAACTCATCTTTCTGGATG-3' aav GFP Sun R
SEQ ID NO: 32
5'-CgggtcgactctagaggtacttaCTACAACTCATCTTIGGATCC-3'

All restriction enzymes were purchased from NEB. PCR reactions were conducted using Q54 Hot Start High-Fidelity 2× Master Mix (NEB, M0494L). Ligations were conducted using isothermal assembly with NEBuilder® HiFi DNA Assembly Master Mix (NEB, E2621L). Primers used for constructing the plasmids were ordered from IDT.

AAV Viruses were produced as per standard protocol [H. Wakimoto, et al., in *Current Protocols in Molecular Biology*. (John Wiley & Sons, Inc., 2001)]. Materials supplied by R. Foo: pAAV2/9- the trans-plasmid encoding AAV replicase and capsid gene (SEQ ID NO: 2; available from University of Pennsylvania Penn Vector Core); pAdDeltaF6—the adenoviral helper plasmid (SEQ ID NO: 1) (available from University of Pennsylvania Penn Vector Core); QIAGEN Plasmid Maxi Kit; HEK293T cells (ATCC); Transfection reagent (polyethylenimine e.g., Polysciences). AAV-DJ capsid was obtained from Cell Biolabs, Inc. The pAAV2/9, AAV-DJ, pAdDeltaF6, DN-Sun1 and GFP plasmids were purified using a QIAGEN Plasmid Maxi Kit HEK293T cells were transfected with the virus combination of pAAV2/9, pAdDeltaF6 and either DN-Sun1 or GFP plasmids. Cells were collected and virus purified by Iodixnol gradient ultracentrifugation.

The following timeline was used for infection of the mouse hearts. Mice were genotyped at 10 days postnatally. They were then subjected to 1 IP injection of Tmx (40 mg/kg of mouse weight) at 14 days postnatally, followed by a concentration of 5×10^10 vg/g AAV9-DN-Sun1 or AAV9-GFP virus injected into the thoracic cavity at 15 days postnatally. Adult mice (3-5 months old) were injected IP with a single dose of Tmx (40 mg/kg of mouse weight), followed by injection of AAV at a concentration of 5×10^10 vg/g AAV9-DN-Sun1 or AAV9-GFP virus into the thoracic cavity. Young and adult mice were anesthetised with a gaseous mixture of 1.5% Isoflurane (BioMac) and 1.5 L $O_2$ before virus injections.

Plasmid Construction and Generation of Cas9 mRNA and sgRNAs pX330 was obtained from Addgene (#42230, Cambridge, MA, USA). The 20 nt Sun1 and Syne1 single guide RNA (sgRNA) sequences were designed with the help of CRISPR Design Tool (crispr.genome-engineerng.org). A region of the gene of interest was submitted to the tool to identify suitable target sites. Since off-target mutations are possible in CRISPR/Cas9-mediated targeted mutagenesis in the mouse, the CRISPR Design Tool is able to experimentally assess off-target genomic modifications for each gRNA target sites and provide computationally predicted off-target sites for each intended target, ranking the target sequence according to quantitative specificity analysis on the effects of base-pairing mismatch identity, position and distribution. Complimentary oligonucleotides containing the gRNA target sequences were annealed and cloned into the BbsI site of pX330. Guide RNA sequences were as follows:

```
                                    (SEQ ID NO: 33)
5'-GCACAATAGCCTCGGATGTCG-3' for Sun1ΔSUN, (SEQ ID NO: 34)
5'-CCGTTGGTATATCTGAGCAT-3' for Syne1-stop, (SEQ ID NO: 35)
5'-GGTTATGGCCGATAGGTGCAT-3' for Tyrosinase4a
```

These plasmids (pSun1ΔSUN, pSyne1-stop and pTyrosinase4a) were then sequenced to verify correct insertion of the target sequences. For in vitro transcription, PCR was performed to generate the appropriate transcription templates using a common reverse primer (AAAAGCACCGACTCGGTGCC-3'; SEQ ID NO: 36) and gRNA-specific forward primers that encoded the T7 promoter sequence as follows:

```
Sun1ΔSUN:
                                    (SEQ ID NO: 37)
5'-TTAATACGACTCACTATAGCACAATAGCCTCGGATGTCG-3';

Syne1-stop:
                                    (SEQ ID NO: 38)
5'-TTAATACGACTCACTATAGCCGTTGGTATATCTGAGCAT-3';

Tyrosinase4a:
                                    (SEQ ID NO: 39)
5'-TTAATACGACTCACTATAGGTTATGGCCGATAGGTGCAT-3'
```

The gRNA PCR products were then subjected to agarose gel electrophoresis (1.5% agarose) to confirm successful PCR, gel purified and used as templates for in vitro transcription using the MEGAshortscript T7 kit (Life Technologies). The gRNAs were purified using MEGAclear kit (Life Technologies) and eluted in RNase-free water. A sample of purified gRNAs were then subjected to agarose gel electrophoresis for quality checks before injecting into zygotes.

Generation of Mutant Mice Using CRISPR/Cas9

3 to 4 weeks old C57BL/6N females were superovulated with Pregnant Mare Serum gonadotropin (Calbiochem, 38722, 5 IU/ml). 48 hours later, the females were injected with human chorionic gonadotropin (Sigma, CG10, 5 IU/ml) and were mated with C57BL6 males. The following day, fertilized 0.5 dpc embryos were collected from the oviducts. Cas9 mRNA (Sigma, CAS9MRNA, 100 ng/ul), Tyrosinase4a gRNA (50 ng/ul) and gene-specific gRNA (50 ng/ul) were co-injected into the cytoplasm of the embryos in M2 medium (EmbryoMax® Sigma) using a microinjection system (Nikon). Syne1-stop sgRNA were used to derive Syne1 C'T mutant mice and Sun1ΔSUN sgRNA were used to derive Sun1ΔSUN mutant mice. The injected zygotes were cultured in KSOM with amino acids (EmbryoMax® Sigma) in an incubator maintained at 37° C. with 5% $CO_2$ and 5% $O_2$ for 2 hours before implanting into 0.5 dpc pseudopregnant C3H-ICR females.

DNA Extraction for Genotyping of CRISPR/Cas9 Mice

Mouse tails were clipped and each placed in a 1.5 ml Eppendorf tube. 80 μl of lysis buffer (25 mM NaOH, 0.2 mM EDTA, pH 12) was dispensed into the tube and heated at 95° C. for 60 minutes. After heating, the buffer was neutralized with an equal volume of 40 mM Tris-HCl, pH 5. For certain applications, DNA was extracted and purified from mouse tails using DNeasy Blood and Tissue Kit (QIAGEN).

Genotyping of CRISPR/Cas9 Mice

CRISPR modified mutant mice were genotyped by PCR followed by gel electrophoresis using a high resolution agarose (2% MetaPhor agarose, Lonza).

Primers for Syne1CT'Δ8 Mice were:

```
Forward:
                                    SEQ ID NO: 40
5'-TGCTCCTGCTGCTGCTTATT-3'
and Reverse:
                                    SEQ ID NO: 41
5'- ACATGGTGGAGCATTTGTCTCC -3'
```

Primers for Sun1 CRISPR Mice were:

```
Forward:
                                    SEQ ID NO: 42
5'-TGACCTTGAGCTGAAACTGC-3'
and Reverse:
                                    SEQ ID NO: 43
5'-TCAGAACACTGGCACACACA-3'
```

Lmna mutant mice were genotyped as described in Example 1. To determine sequence of CRISPR-Induced mutations, PCR products from mouse tall DNA were subjected to TOPO cloning (Zero Blunt™ TOPO™ PCR Cloning Kit, 450245, Thermo Fisher Scientific). Plasmid DNA from at least 10 bacterial colonies were isolated using a mini-prep kit (QIAGEN, QIAprepSpin, Miniprep Kit) and sent for Sanger sequencing.

Derivation of Myoblasts, Fibroblasts and Cell Culture for CRISPR/Cas9 Study

To isolate myoblasts, limbs were obtained from euthanized mice and muscles were dissected from bone. Tissue digestion was performed by incubating the muscle tissues in enzyme solution consisting of equal volumes of dispase II (Roche, cat. 04942078001) at a concentration of 2.4 U/ml and 1% collagenase II (GIBCO® Invitrogen, cat 17101-015) in a 37° C. water bath for 30 minutes, with occasional mixing at 10 minutes interval. After 30 minutes, enzyme solution was neutralized in D10 media (Dulbeco's Modified Eagle Medium (DMEM) with 10% fetal bovine serum). Mixture is then filtered through 70 μm sterile filter (BD Falcon™, cat 352350) and 40 μm sterile filter (BD Falcon™, cat 352340). The suspension was then centrifuged, supernatant removed and subsequently resuspended in F10 media (GIBCO® Invitrogen, cat. 11550043) supplemented with 10 μg/ml bFGF (GIBCO®, cat PHG0264) and plated in 100 mm plates. Mouse adult fibroblasts were allowed to settle for 2 to 3 hours before collecting the supernatant (with floating myoblasts) and replated into 60 mm plates coated with 0.15% Gelatin (Sigma, cat G1393). D10 media was added to the 100 mm plates with MAFs. To terminally differentiate myoblasts to myotubes, the media was changed to DMEM supplemented with 2% horse serum (Thermo Fisher Scientific GIBCO®, cat 16050122).

Immunoblotting for CRISPR/Cas9 Study

Whole cell lysates were generated using the Lysis-M kit solution (cOmplete; Roche). Cells were washed in ice-cold PBS and lysed with Roche Lysis M buffer, and centrifuged at 14,000 g for 10 minutes to remove cell debris. To extract protein from tissue sample, small slices of tissue were rapidly placed into Lysing Matrix D tubes (MP Biomedicals), and snap frozen in liquid nitrogen. After snap freezing, the tubes were either stored at −80° C. or used directly for protein analysis. Protein extraction buffer (50 mM Tris (pH7.4), 500 mM NaCl, 0.4% SDS, 5 mM EDTA (pH7.4), 1× Protease inhibitor (cOmplete™ EDTA-free Protease Inhibitor cocktail, Cat no. 04693159001, Roche), 2% Triton, 1 mM Dithiothreitol, in distilled water) was added to tissues, which were then homogenized using the FastPrep™-24 Instrument (MP Biomedicals). Samples were then centrifuged at 14,000 g for 10 minutes to remove cell debris. Protein concentration was quantified using bicinchoninic acid (BCA) protein kit (Bio-Rad) before loading protein samples onto a polyacrylamide gel to ensure equal amounts were being analyzed. All protein samples were resolved by SDS-PAGE gel analysis and transferred onto polyvinylidene fluoride (PVDF) membrane (Millipore) by wet transfer for 48 hours at 20V at 4° C. Membranes were blocked in TBS containing 0.1% Tween 20 (TBST) supplemented 5% milk powder (Anlene) for 1 hour at room temperature. Western Blot analysis was performed using primary antibodies diluted in 5% milk powder (diluted in TBST). Membranes were incubated for 2 hours at room temperature or overnight at 4° C. For secondary antibodies, horseradish-peroxidase (HRP) (Invitrogen) conjugated antibodies were used for chemiluminescent imaging. The membranes were incubated for 1 hour at room temperature with the secondary antibodies. For immunoblots visualized by chemiluminescence, membranes were incubated in ECL substrate (Pierce) for 1 minute before being exposed to a chemiluminescence sensitive film (Thermo Scientific) and subsequently processed.

Immunofluorescence for CRISPR/Cas9 Study

Cells were grown in 8-well slides (Ibidi) and fixed in ice-cold methanol for 15 minutes at −20° C. They were then rinsed in PBS twice and permeabilized and blocked with 0.1% Triton X, 3% BSA in PBS for 15 minutes at room temperature. The fixed and permeabilized cells were then rinsed in PBS three times. Samples were then incubated with primary antibodies (Table 2) for 2 hours at room temperature or overnight at 4° C. Samples were then washed with PBS three times and subsequently incubated with secondary antibodies (Life Technologies) and DAPI (Life Technologies) for 1 hour at room temperature. After three washes in PBS, cells were mounted in Anti-fade (1% DABCO, 90% Glycerol, 10% PBS) and inspected using a Zeiss 510 Meta Confocal microscope or Axiovert 200 inverted epifluorescence microscope (Zeiss). Images were recorded and analysed using Zeiss ZEN, Metamorph or Image J (NIH) software.

TABLE 2

Antibodies used for immunofluorescence study.

| Antibody | Type and Source | Concentration |
| --- | --- | --- |
| Akap450, HPA-026109 | Polyclonal, Sigma | 1:500 |
| MF20 | Monoclonal, DSHB | 1:25 |
| Nesp1 (MANNES1A) | Monoclonal, Glenn Morris | 1:1000 (Western) 1:50 (IF) |
| Nesp1-CT | Monoclonal, Brian Burke | Undiluted supernatant |
| LaminA, ab8984 | Monoclonal, Abcam | 1:200 |
| LaminA, SSD | Monoclonal, Brian Burke | 1:200 |
| Pcm-1, HPA-023374 | Polyclonal, Sigma | 1:100 |
| Pcnt, ab4448 | Polyclonal, Abcam | 1:100 |
| Sun1-9F10 | Monoclonal, Brian Burke | 1:200 |
| Sun2-3.1E | Monoclonal, Brian Burke | 1:500 |
| Nesprin-2 | Polyclonal, MyBiosource.com | 1:500 |

Mouse Genetics

Lmna mice and tamoxifen injection were described in Example 1. To obtain $Lmna^{\Delta/\Delta}$:$Syne1^{C'T\Delta 8/C'T\Delta 8}$ and $Lmna^{Flx/Flxmcm}$:$Syne1^{C'T\Delta 8/C'T\Delta 8}$ double mutant mice, $Lmna^{\Delta/+}$ or $Lmna^{Flx/Flx:mcm}$ mice were intercrossed with $Syne1^{C'T\Delta 8/C'T\Delta 8}$ mice. In the Syne2 mouse model, a IRES-β-gal neomycin selectable cassette (PgkNeo) flanked by loxP sites was inserted into the Syne2 gene, resulting in deletion of part of axon 102 and all of exons 103-104. The neomycin cassette was subsequently removed by crossing with Cre recombinase mice. $Syne1^{C'T\Delta 8/+}$ or $Syne1^{C'T\Delta 8/C'T\Delta 8}$ mice were crossed with $Syne2^{+/-}$ or $Syne2^{-/-}$ mice to obtain mice with mutant Syne1 and Syne2 alleles, which were intercrossed to obtain double mutant mice. Kaplan-Meier method was used to draw the survival curves.

Human Guide RNA Sequences

Potential guide RNA sequences to disrupt human SYNE1 KASH domain or SUN1 SUN domain were determined using CRISPR tool in Benchling software (Benchling Inc. USA) and are shown in Table 3.

TABLE 3

Potential guide RNA sequences to target final exons in human SYNE1 (Nesprin-1) or SUN1 genes

| Gene Name | ENSEMBL gene ID | Chromosome | Position | Strand | Sequence | PAM | CRISPR enzyme | SEQ ID NO: |
|---|---|---|---|---|---|---|---|---|
| SYNE1 | ENSG00000131018 | 6 | 515330 | − | TCGTGTATCTGAGCATGGGG | TGGAAT | saCas9 | 44 |
| SYNE1 | ENSG00000131018 | 6 | 515335 | − | GCCATTCGTGTATCTGAGCA | TGGGGT | saCas9 | 45 |
| SYNE1 | ENSG00000131018 | 6 | 515340 | + | TCCACCCCATGCTCAGATAC | ACGAAT | saCas9 | 46 |
| SYNE1 | ENSG00000131018 | 6 | 515320 | − | GAGCATGGGGTGGAATGACC | GGG | spCas9 | 47 |
| SYNE1 | ENSG00000131018 | 6 | 515321 | − | TGAGCATGGGGTGGAATGAC | CGG | spCas9 | 48 |
| SYNE1 | ENSG00000131018 | 6 | 515330 | − | TCGTGTATCTGAGCATGGGG | TGG | spCas9 | 49 |
| SYNE1 | ENSG00000131018 | 6 | 515333 | − | CATTCGTGTATCTGAGCATG | GGG | spCas9 | 50 |
| SYNE1 | ENSG00000131018 | 6 | 515334 | − | CCATTCGTGTATCTGAGCAT | GGG | spCas9 | 51 |
| SYNE1 | ENSG00000131018 | 6 | 515335 | − | GCCATTCGTGTATCTGAGCA | TGG | spCas9 | 52 |
| SYNE1 | ENSG00000131018 | 6 | 515345 | + | CCCATGCTCAGATACACGAA | TGG | spCas9 | 53 |
| SYNE1 | ENSG00000131018 | 6 | 515333 | + | CCCGGTCATTCCACCCCATG | TTTG | Cpf1 | 54 |
| SUN1 | ENSG00000164828 | 7 | 873276 | + | TTTTTCTAACTGGGGCCATC | CTGAGT | saCas9 | 55 |
| SUN1 | ENSG00000164828 | 7 | 873285 | − | CCGATACAGACAGGTATACT | CAGGAT | saCas9 | 56 |
| SUN1 | ENSG00000164828 | 7 | 873266 | + | AACTTCGGATTTTTTCTAAC | TGG | spCas9 | 57 |
| SUN1 | ENSG00000164828 | 7 | 873267 | + | ACTTCGGATTTTTTCTAACT | GGG | spCas9 | 58 |
| SUN1 | ENSG00000164828 | 7 | 873268 | + | CTTCGGATTTTTTCTAACTG | GGG | spCas9 | 59 |
| SUN1 | ENSG00000164828 | 7 | 873280 | − | ACAGACAGGTATACTCAGGA | TGG | spCas9 | 60 |
| SUN1 | EN5G00000164828 | 7 | 873296 | + | CTGAGTATACCTGTCTGTAT | CGG | spCas9 | 61 |
| SUN1 | ENSG00000164828 | 7 | 873281 | + | TTCTAACTGGGGCCATCCTG | TTTT | Cpf1 | 62 |
| SUN1 | ENSG00000164828 | 7 | 873282 | + | TCTAACTGGGGCCATCCTGA | TTTT | Cpf1 | 63 |
| SUN1 | ENSG00000164828 | 7 | 873283 | + | CTAACTGGGGCCATCCTGAG | TTTT | Cpf1 | 64 |
| SUN1 | ENSG00000164828 | 7 | 873284 | + | TAACTGGGGCCATCCTGAGT | TTTC | Cpf1 | 65 |

PAM, protospacer adjacent motif; saCas9, *Staphylococcus aureus* Cas9; spCas9, *Streptococcus pyogenes* Cas9; Cpf1, CRISPR from *Prevotella* and *Francisella* 1.

Statistical Analysis

All statistical analysis was performed using Graphpad Prism software.

Example 2

Cardiomyocyte Specific Loss of Lmna Results in the Rapid Onset of Heart Failure

Figure 26A:
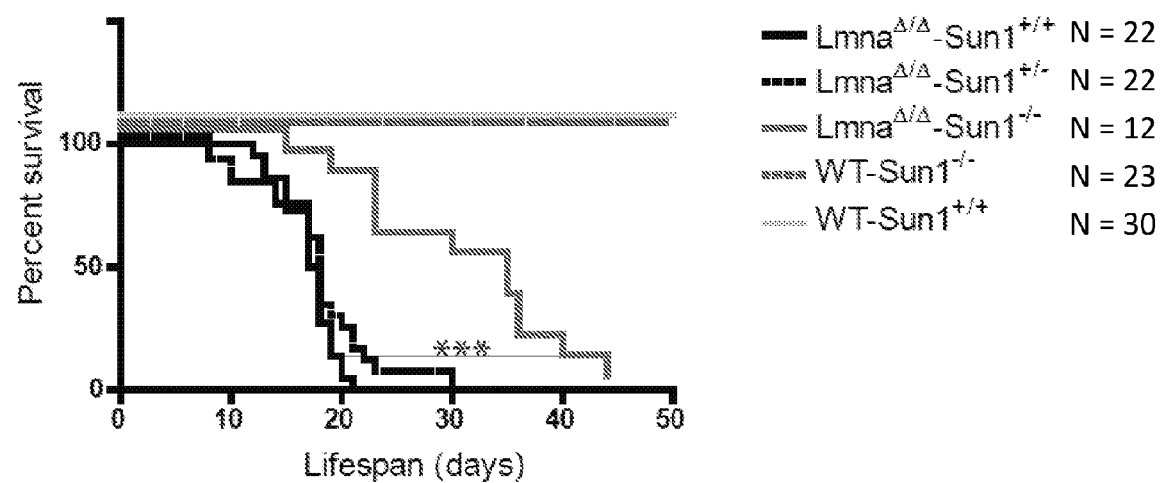
FIGS. 26A-26D show Kaplan Meier curves of Sun1 loss extending the longevity of Lmna mutant mice.
Figure 26B:
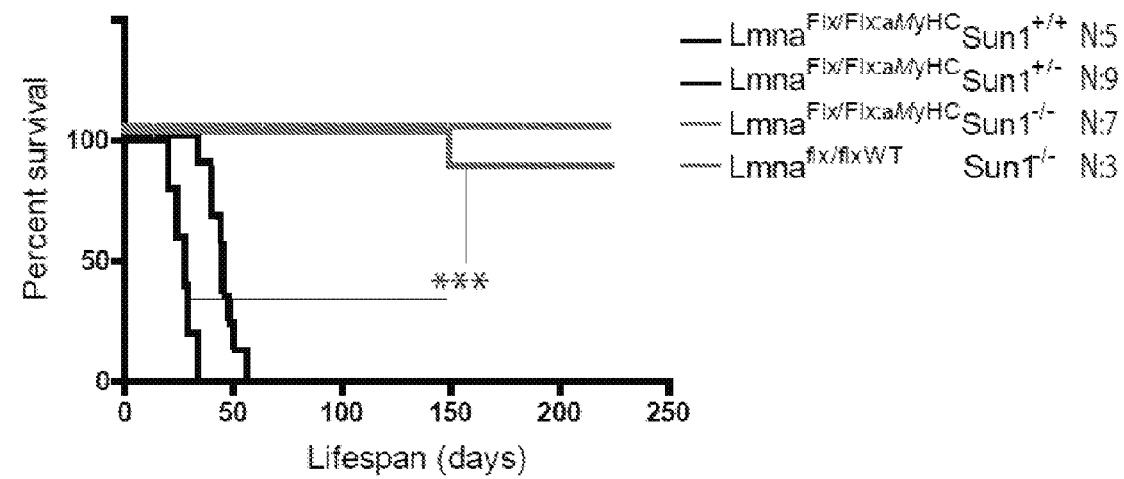
Figure 26C:
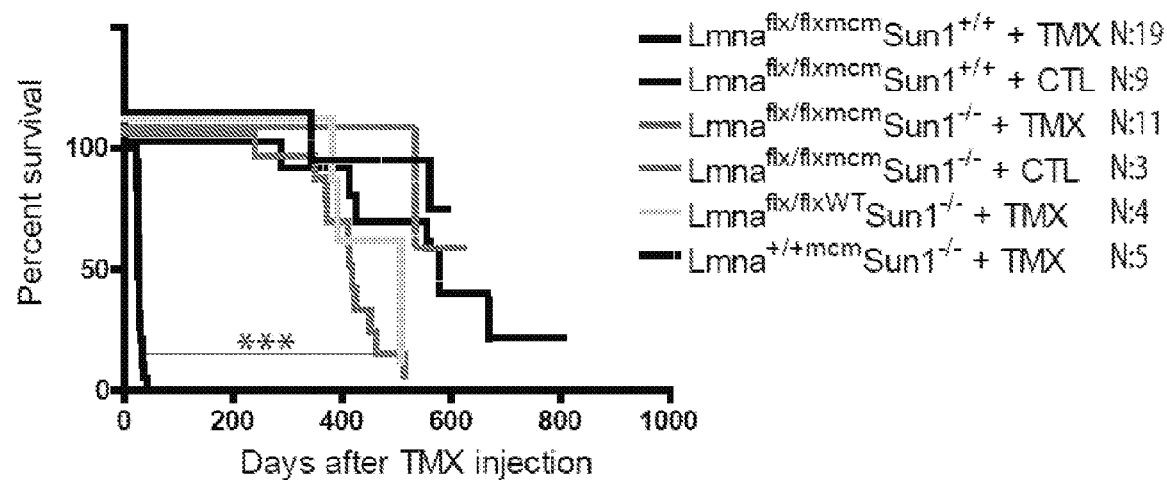
Figure 28A:
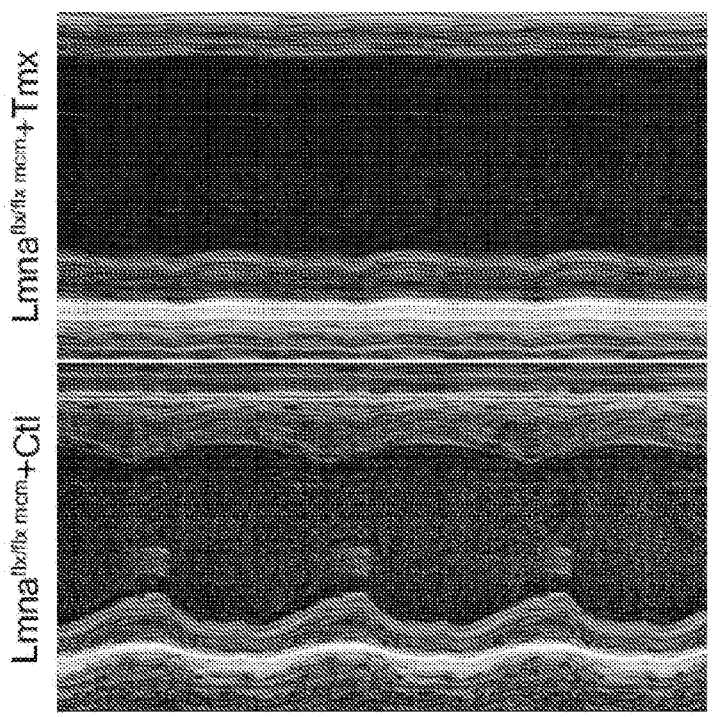
FIGS. 28A-28D show echocardiograms, heart function and histology of Lmna$^{Flx/Flxmcm}$+Tmx mice.
Figure 36:
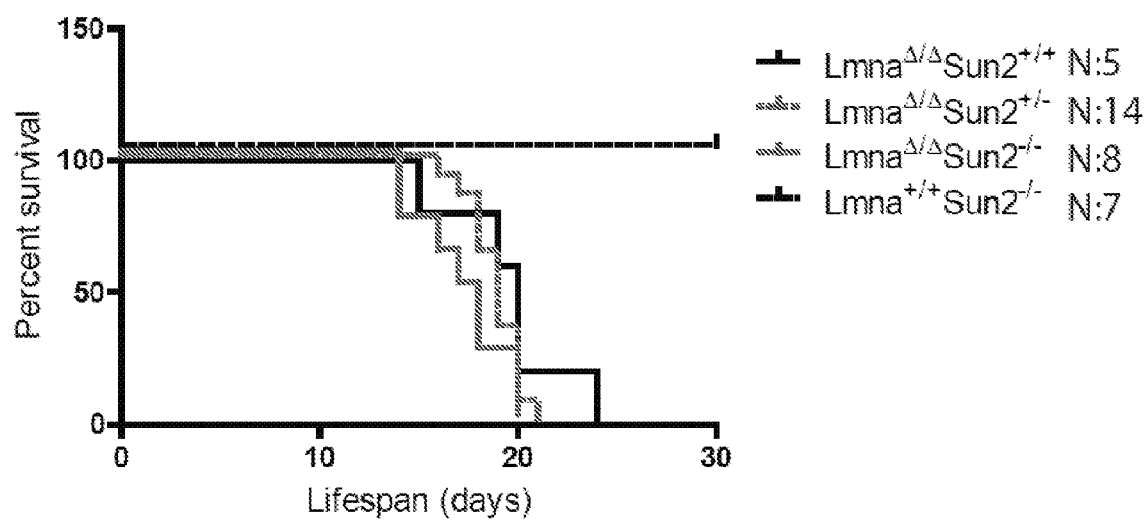
FIG. 36 shows that loss of Sun2 does not rescue loss of Lmna. Loss of Sun2 does not extend the lifespan of Lmna$^{\Delta/\Delta}$ Sun2$^{-/-}$ mice.

To further define the interaction between Sun1 and Lmna in postnatal pathology in mice, we specifically ablated the Lmna gene in different tissues by using a conditional Lmna$^{Flx/Flx}$ line of mice (FIG. 33), that when recombined by Cre activation, results in the complete loss of LaminA/C protein [A. S. Wang, et al., *Differentiation; research in biological diversity*, (2015); I. Solovei et al., *Cell* 152: 584-598 (2013)]. When Lmna$^{Flx/Flx}$ was constitutively deleted in all tissues by crossing the Lmna$^{Flx/Flx}$ mice with Zp3-Cre mice [W. N. de Vries et al., *Genesis* 26: 110-112 (2000)], the mean postnatal lifespan was 17.5 days (FIG. 26A). When the same deletion was induced in the absence of Sun1, the Lmna$^{Δ/Δ}$:Sun1$^{−/−}$ mice lived to a mean of 32.5 days, almost a doubling in longevity (FIG. 28A). Performing the same Lmna deletion on a Sun2 null background did not extend the longevity of Lmna$^{Δ/Δ}$ mice, revealing the longevity extension is specific to the loss of Sun1 (FIG. 36). Since the A-type lamins are widely expressed in almost all adult tissues, we then determined to what extent, Lmna deletion, specifically in cardiomyocytes, contributes to the early postnatal death of Lmn$^{Δ/Δ}$ mice. Furthermore, the inventors wished to ascertain whether loss of Sun1 would increase longevity in these mice harbouring Lmna deficient cardiomyocytes. We first crossed the Lmna$^{Flx/Flx}$ with a constitutive myh6 Cre [R. Agah et al., *J Clin Invest* 100: 169-179 (1997)], in which Cre expression, though constitutive, is restricted to cardiomyocytes but commences during embryogenesis. These mice survived slightly longer than the Lmna$^{Δ/Δ}$ to an average of 26.5 days postnatally (FIG. 26C). When the same cardiomyocyte specific deletion was performed on a Sun1$^{−/−}$ background, this resulted in a significant increase in longevity to at least 6 months and beyond after birth (FIG. 26C). To further define the loss of Lmna and its effect in postnatal/adult cardiomyocytes we derived mice homozygous for the Lmn$^{Flx/Flx}$ allele carrying the inducible cardiomyocyte specific Cre Tg(Myh6-cre/

Figure 27A:
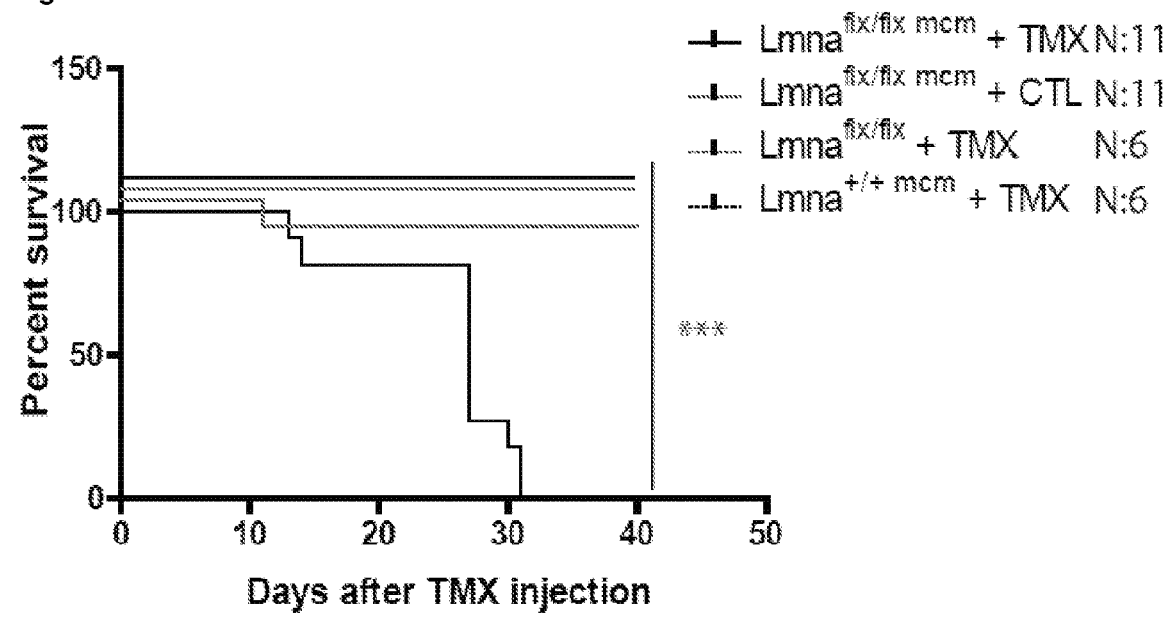
FIGS. 27A-27E show the lifespan and phenotype of Lmna$^{Flx/Flx:mcm}$+Tmx mice.
Figure 27B:
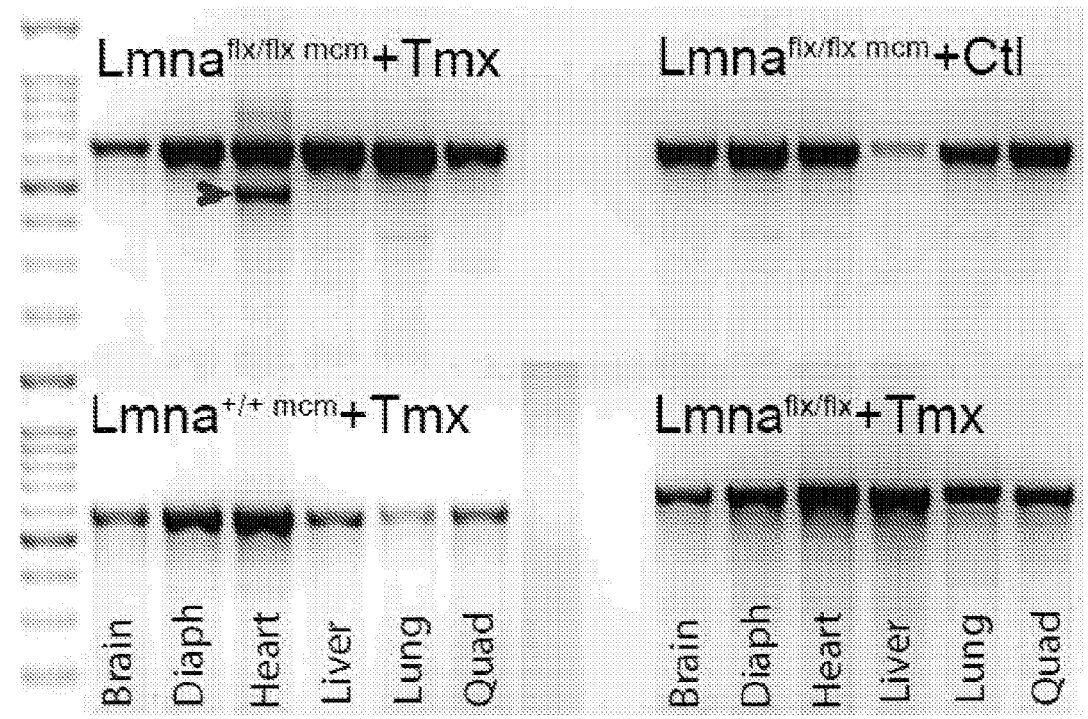
Figure 27C:
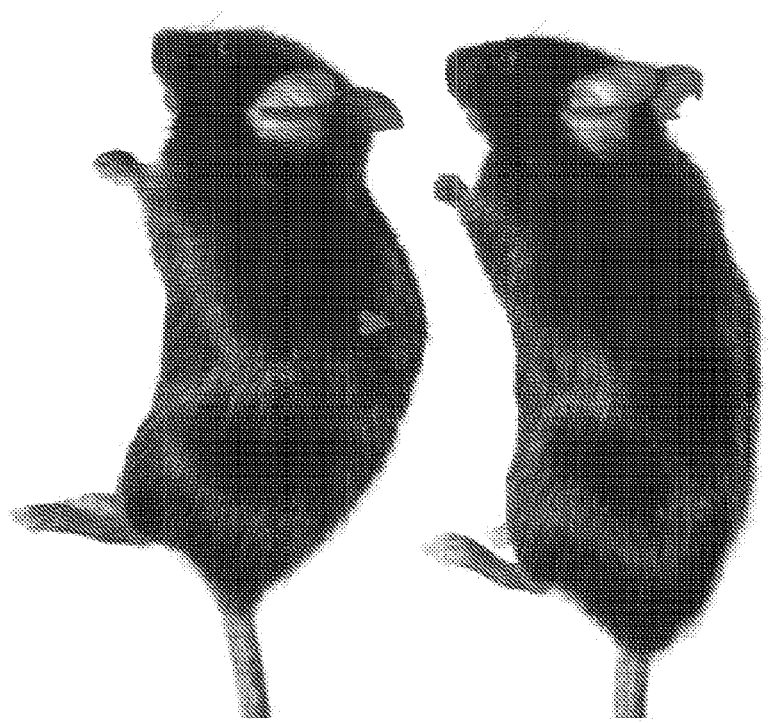
Figure 27D:
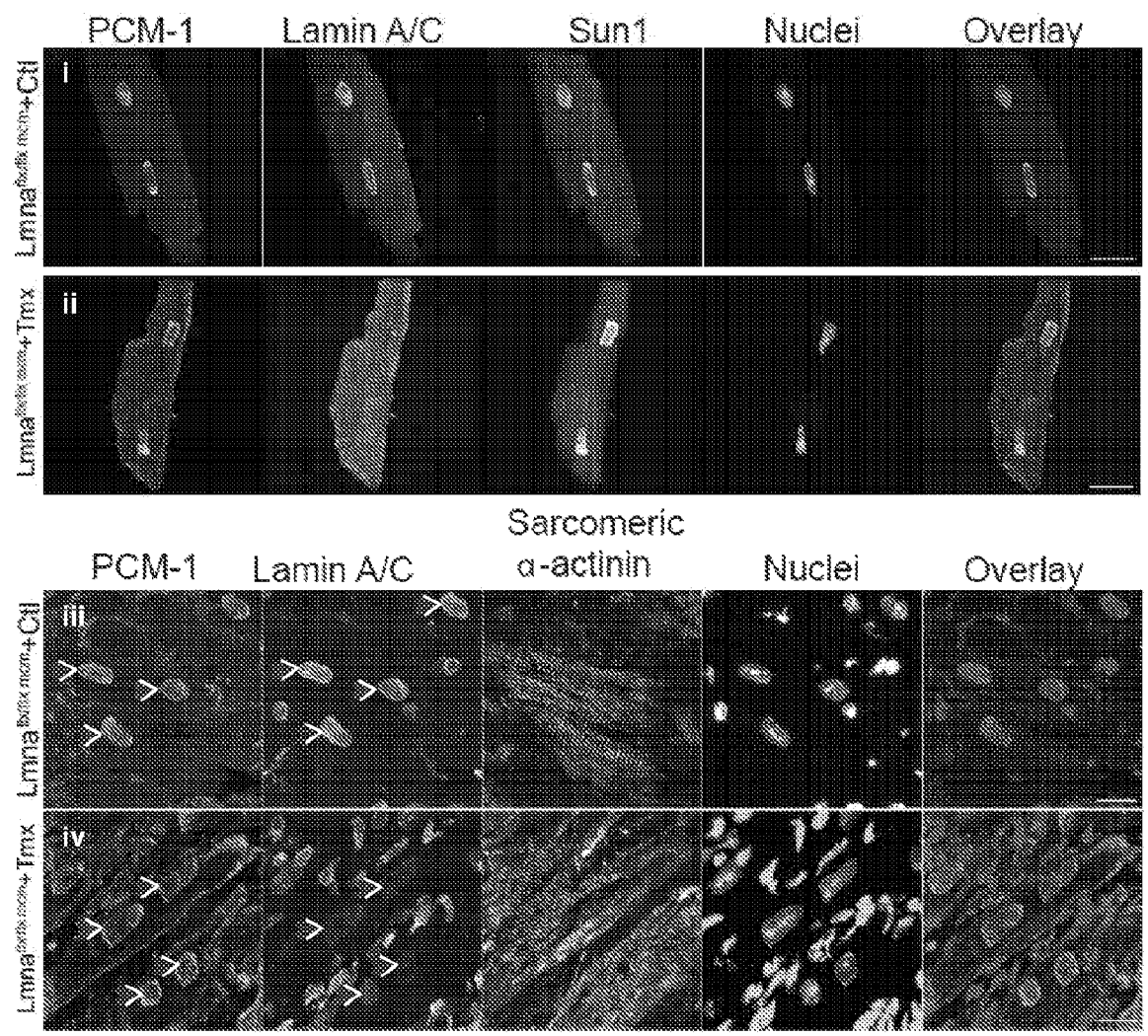
Figure 27E:
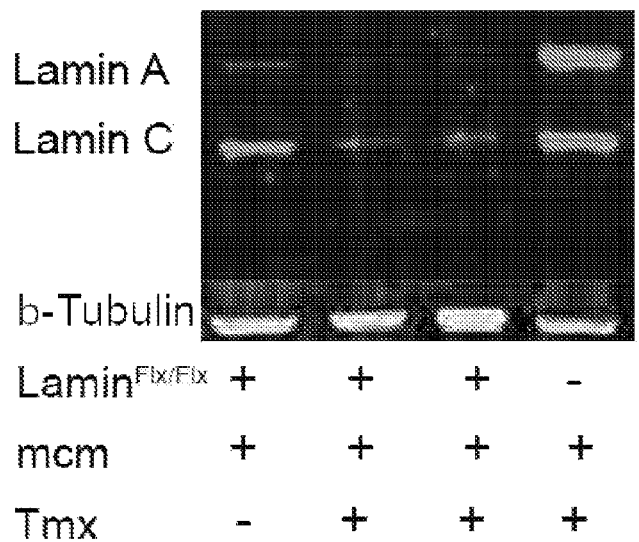
Figure 27F:
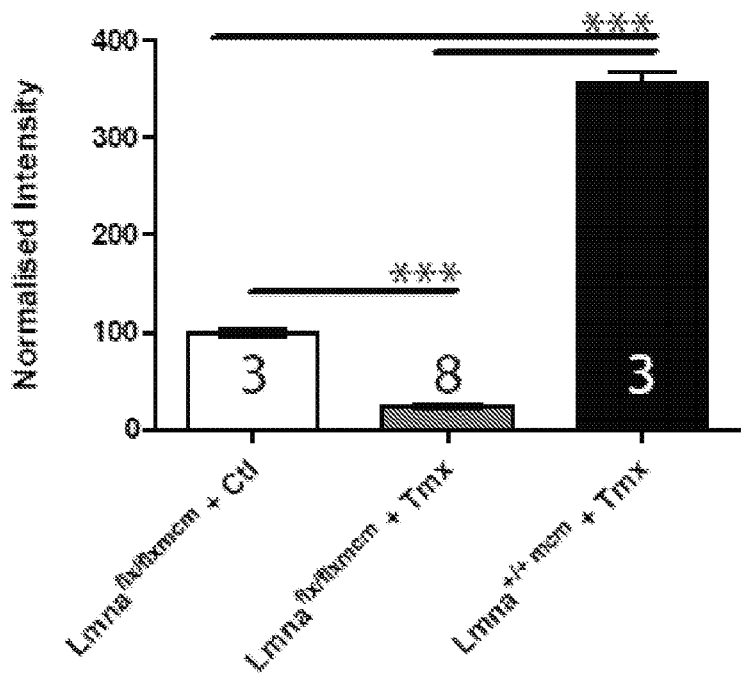
(FIG. 27F) Quantitative analysis was performed at 21 days post Tmx. The presence of the LoxP sites in the WT-Lmna gene (Lmna$^{Flx/Flx}$) results in a reduction in Lmna transcript levels compared to Lmna$^{Wt/Wt}$ levels, although this had no overt effect on longevity or growth/viability.
Figure 28B:
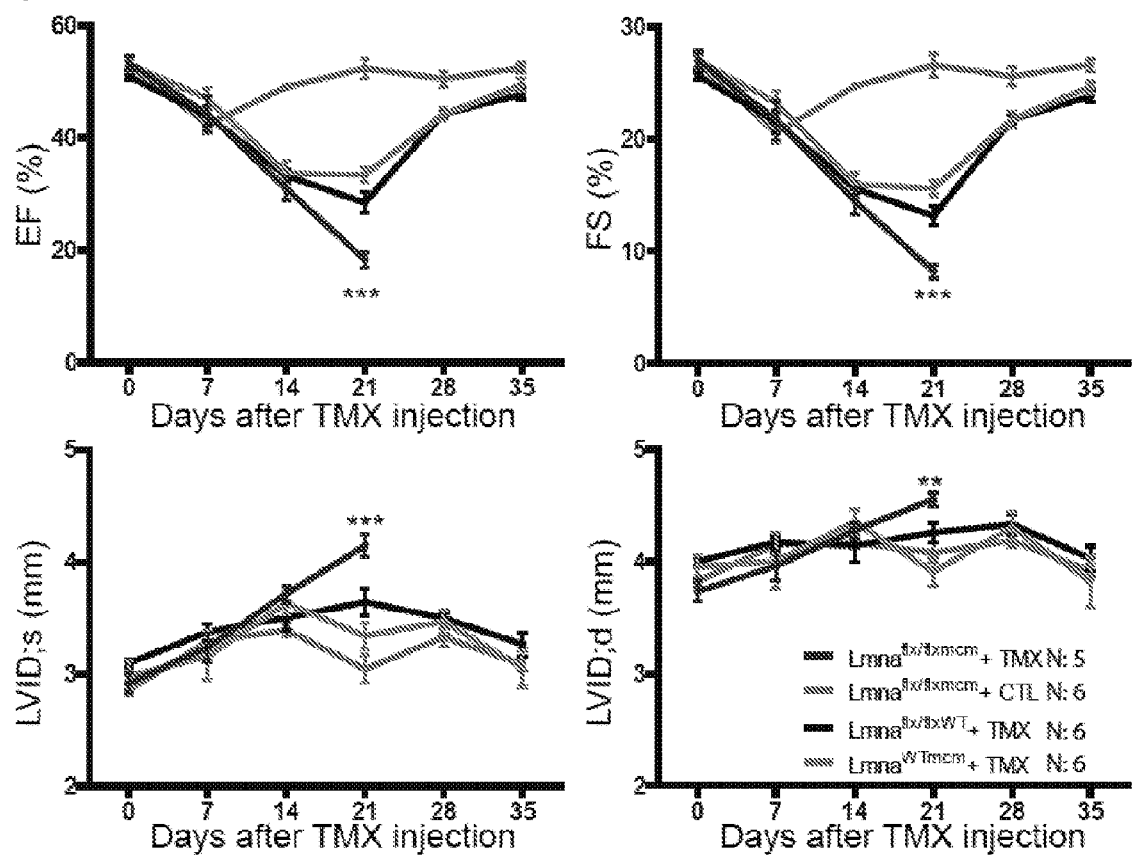
Figure 28C:
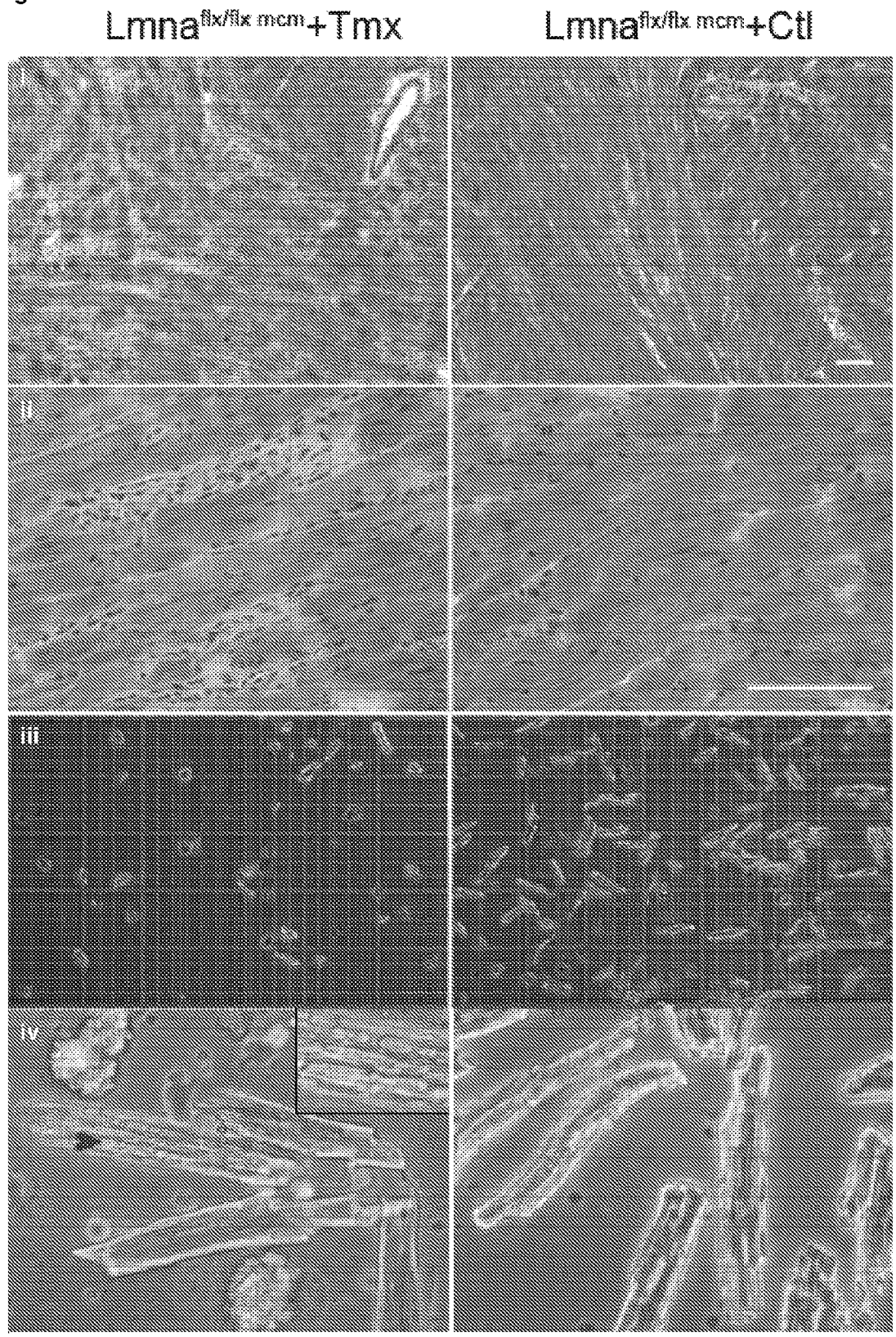
Figure 28D:
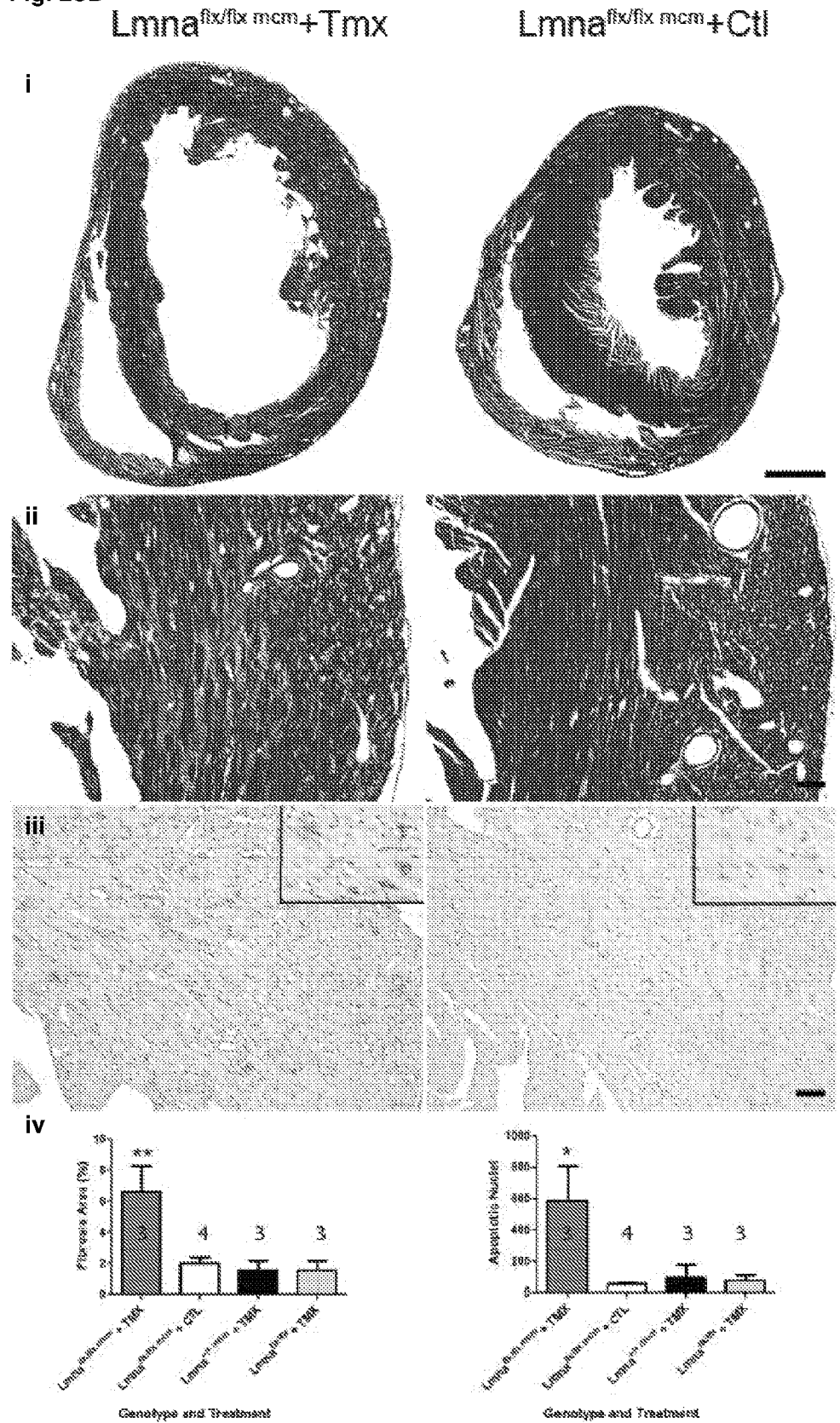

Esr1), (here abbreviated to mcm) in which Cre is induced by a single injection of tamoxifen (Tmx) [D. S. Sohal et al., Circ Res 89: 20-25 (2001)]. From this cross, the average lifespan of 3-5 month old Lmna$^{Flx/Flx:mcm}$ mice, following Cre induction was 27 days (FIG. 27A). Controls were unaffected by Tmx injection. PCR and immunofluorescence analysis confirmed the Lmna deletion was specific to the Lmna$^{Flx/Flx:mcm}$ cardiomyocytes, with no detectable recombination occurring in the brain, diaphragm, lung, liver and skeletal muscle, or in wild-type control animals (FIG. 27B). By 21 days post injection, Lmna$^{Flx/Flx:mcm}$ mice showed laboured breathing, a dishevelled, ungroomed appearance, increased lethargy and kyphosis (FIG. 27C). Immunofluorescence analysis of isolated cardiomyocytes (CM) and sections of Lmna$^{Flx/Flx:mcm}$ hearts showed reduced levels of LaminA protein and cardiomyocyte nuclei without any LaminA expression (FIG. 27D). LaminA protein levels were decreased 3.5 fold in Lmna$^{Flx/Flx:mcm}$ hearts after Cre induction compared to uninduced Lmna$^{Flx/Flx:mcm}$ and Lmna$^{+/+/mcm}$ hearts (FIG. 27E). By sampling Lmna$^{Flx/Flx:mcm}$ mice at specific time points after Tmx injection, it was estimated that it takes 7-14 days after Cre induction for LMNA protein levels to fall by 50% (data not shown), a rate consistent with a study using siRNA LMNA knockdown in human fibroblasts by 1.3-fold after 48 hrs and a further 4-fold reduction after 10.5 days [A. Buchwalter and M. W. Hetzer, Nature communications 8: 328 (2017); T. Sieprath et al., Nucleus 6: 236-248 (2015)]. Echocardiograms (ECGs) performed at 21 days after Cre induction revealed poor cardiac contractility in Lmna$^{Flx/Flx:mcm}$ mice compared to Lmna$^{Flx/Flx:mcm}$ controls (FIG. 28A). There was a significant reduction in the Ejection Fraction (EF %) and Fractional shortening (FS %) (P<0.0001) (FIG. 28B). The left systolic and diastolic ventricular internal diameters (LVID) were enlarged, compared to Lmna$^{Flx/Flx:mcm}$ controls (FIG. 28B). Significantly fewer viable (brick-like) cardiomyocytes were isolated from Lmna$^{Flx/Flx:mcm}$+Tmx hearts compared to Lmna$^{Flx/Flx:mcm}$ controls (FIG. 28C). Visual analysis revealed the isolated cardiomyocytes from Lmna$^{Flx/Flx:mcm}$+Tmx hearts contained large intracellular vacuoles (FIG. 28C). Histological analysis of Lmna$^{Flx/Flx:mcm}$+Tmx hearts, revealed infiltration of nucleated cells and increased intercellular spaces between cardiomyocytes compared to Lmna$^{Flx/Flx:mcm}$ control hearts (FIG. 28D). The left ventricular lumen in Lmna$^{Flx/Flx:mcm}$+Tmx hearts was significantly enlarged, together with significantly increased levels (P=0.0098) of fibrosis were noted in Lmna$^{Flx/Flx:mcm}$+Tmx hearts compared to in Lmna$^{Flx/Flx:mcm}$ controls (FIG. 28D). Increased numbers of apoptotic cells were also identified in Lmna$^{Flx/Flx:mcm}$+Tmx hearts compared to control hearts (FIG. 28D). However there was no evidence of extensive DNA damage detectable in the cardiomyocytes, as assessed by Rad51, MRE11, H2AX phosphor-Ser and 53BP1 immunostaining (Data not shown).

Example 3

Deletion of Sun1 Amellorates Cardiac Pathology Induced by Lmna Loss

Figure 29A:
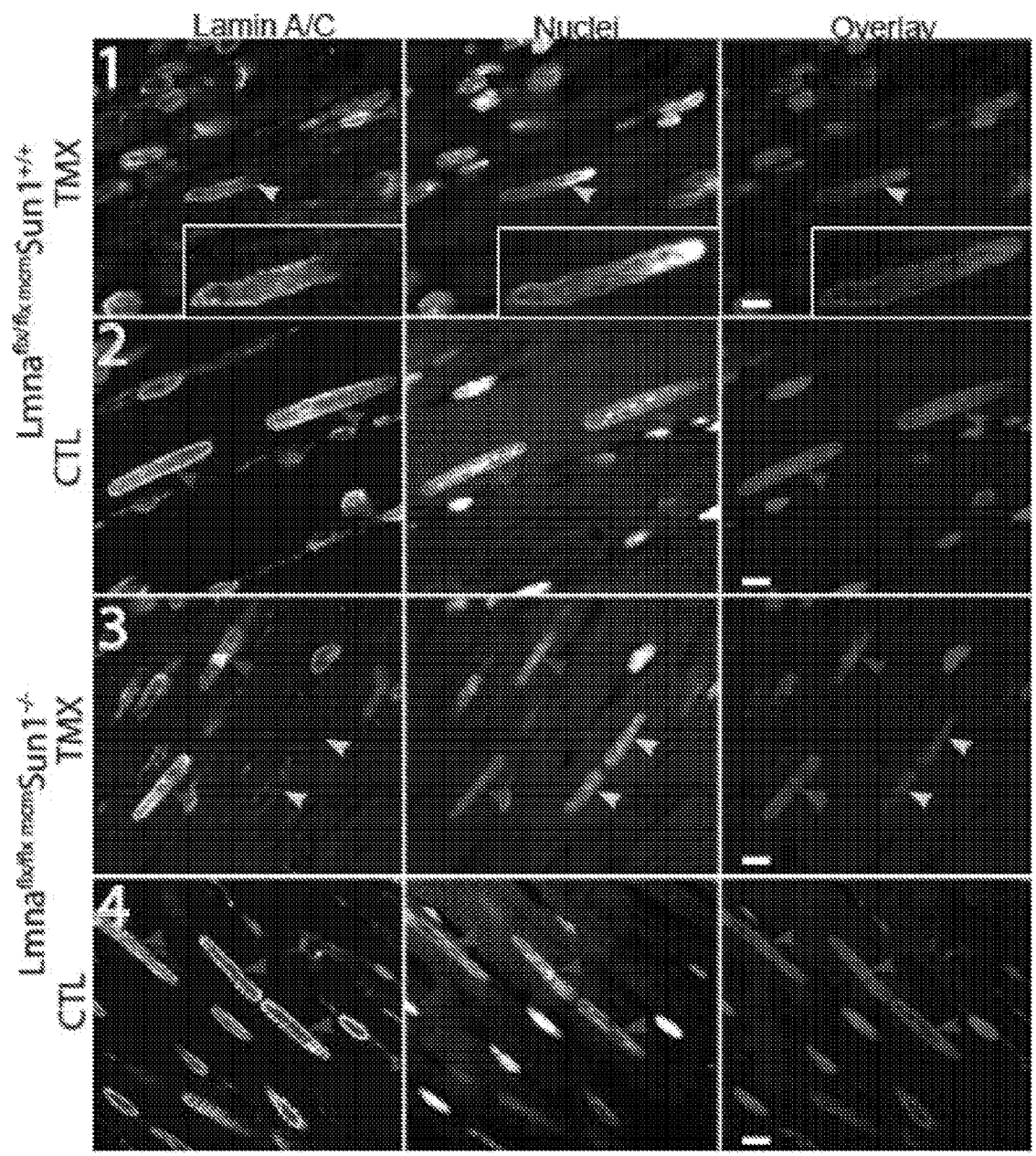
FIGS. 29A-29D shows changes in nuclear morphologies and heart structure with and without Sun1 in the Lmna$^{Flx/Flx:mcm}$ after Tmx injection.

Mice with Lmna mutations show a significant increase in longevity and health in the absence of Sun1 [C. Y. Chen et al., Cell 149: 565-577 (2012)]. As described, induced deletion of Lmna in cardiomyocytes (Lmna$^{Flx/Flx:mcm}$+Tmx) results in death within 1 month post Cre induction (FIG. 26C). Strikingly, when the same deletion was induced on a Sun1 null background the mice survived for more than 1 year after Cre induction (FIG. 26C). Hearts from Lmna$^{Flx/Flx:mcm}$Sun1$^{-/-}$+Tmx mice, 3 weeks after induction, were compared to those from Lmna$^{Flx/Flx:mcm}$ Sun1$^{+/+}$+Tmx to determine the extent to which SUN1 loss ameliorated the pathological changes induced by Lmna loss in cardiomyocytes. Immunofluorescent imaging for Lamin A/C identified many elongated and distorted nuclei. In some of these, residual Lamin A/C was displaced to one pole of the nucleus (FIG. 29A panel 1 and insert) in the Lmna$^{Flx/Flx:mcm}$Sun1$^{+/+}$+Tmx hearts. In contrast in the Lmna$^{Flx/Flx:mcm}$Sun1$^{-/-}$+Tmx hearts, while there were many elongated nuclei, these showed few if any distortions, even when there was no Lamin A/C staining (FIG. 29A panel 3 yellow arrow heads). Western analysis of whole hearts revealed a significant reduction in Lamin A/C in the Lmna$^{Flx/Flx:mcm}$Sun1$^{-/-}$+Tmx hearts (P=0.0359) lysates compared to Lmna$^{Flx/Flx:mcm}$Sun1$^{+/+}$ controls (FIG. 29A lower panels). The Lmna$^{Flx/Flx:mcm}$Sun1$^{+/+}$+Tmx cardiomyocyte nuclei exhibited increased longitudinal length, together with a segmented appearance, with the segments connected by narrow bridges (FIGS. 29A and C, panel 1 arrows). However, in the absence of Sun1, Lmna$^{Flx/Flx:mcm}$ Sun1$^{-/-}$ cardiomyocyte nuclei exhibited no abnormalities or segmentation (FIG. 29C panels 3 and 4). In total, 70% of cardiomyocytes in Lmna$^{Flx/Flx:mcm}$Sun1$^{+/+}$ mice had ruptured or misshapen nuclei compared to fewer than 1% of the cardiomyocytes from the Lmna$^{Flx/Flx:mcm}$Sun1$^{-/-}$ (FIG. 29C panel 5).

Figure 29B:
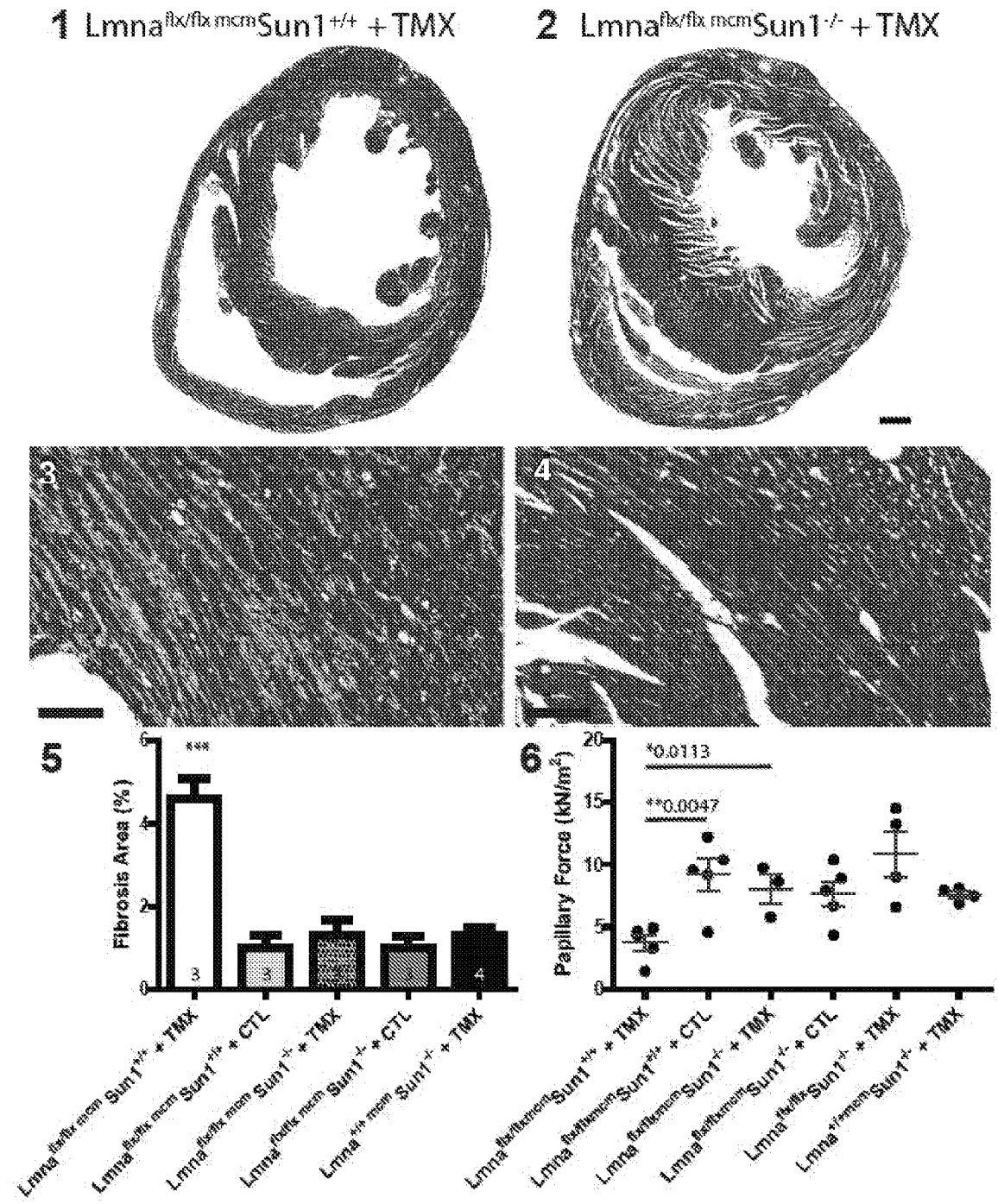
Figure 29C:
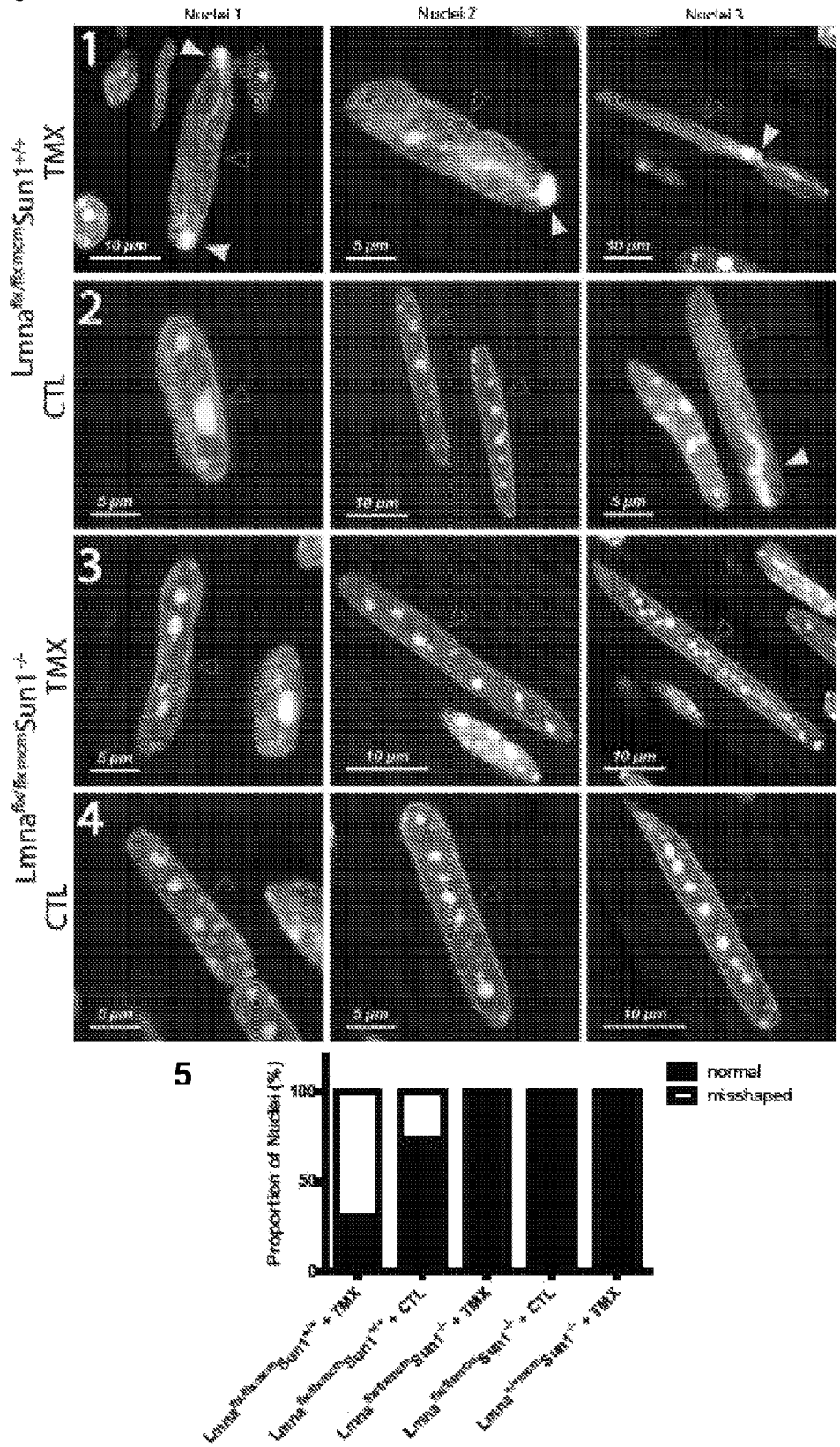

Clear enlargement of the left ventricle (LV) was evident in the Lmna$^{Flx/Flx:mcm}$Sun1$^{+/+}$ mice but not in the LVs of the Lmna$^{Flx/Flx:mcm}$Sun1$^{-/-}$+Tmx hearts (FIG. 29B, panels 1 and 2). The Lmna$^{Flx/Flx:mcm}$Sun1$^{+/+}$ hearts exhibited significantly increased levels of fibrosis (P<0.0001) compared to controls, whereas there was no significant fibrosis in the Lmna$^{Flx/Flx:mcm}$Sun1$^{-/-}$ hearts (FIG. 29B, panels 3-5).

As a model for ventricular muscle mechanics we measured the active force in cardiac papillary muscle. The active force was significantly reduced by 66% in Lmna$^{Flx/Flx:mcm}$: Sun1$^{+/+}$+Tmx papillary muscle (P=0.0028) compared to Lmna$^{Flx/Flx:mcm}$ Sun1$^{+/+}$+CTL. In the absence of SUN1, Lmna$^{Flx/Flx:mcm}$Sun1$^{-/-}$+Tmx cardiac papillary active force was maintained at levels not significantly different from those of controls (FIG. 29B panel 6).

Figure 29D:
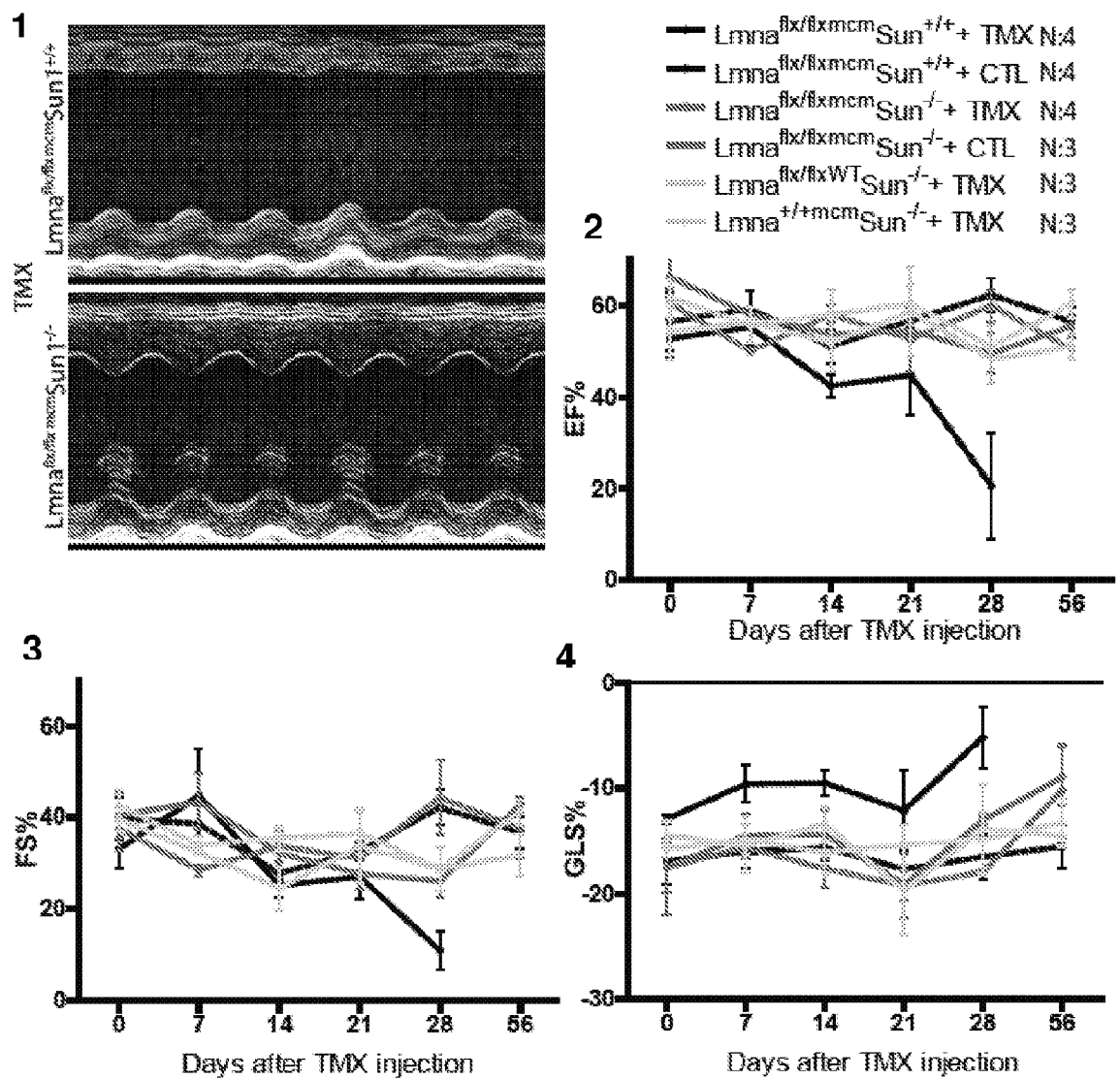

Echocardiograms performed before and after Cre induction revealed progressive worsening of cardiac contractility in the Lmna$^{Flx/Flx:mcm}$ Sun1$^{+/+}$+Tmx mice compared to Lmna$^{Flx/Flx:mcm}$Sun1$^{-/-}$+Tmx mice (FIG. 29D). Loss of SUN1 preserved both EF, FS and Global Longitudinal Strain (GLS) (GLS is a separate parameter used to assess myocardial contractility, and Is a better predictor of heart failure) In Lmna$^{Flx/Flx:mcm}$Sun1$^{-/-}$+Tmx mice compared to Lmna$^{Flx/Flx:mcm}$ Sun1$^{+/+}$+Tmx mice.

Figure 37A:
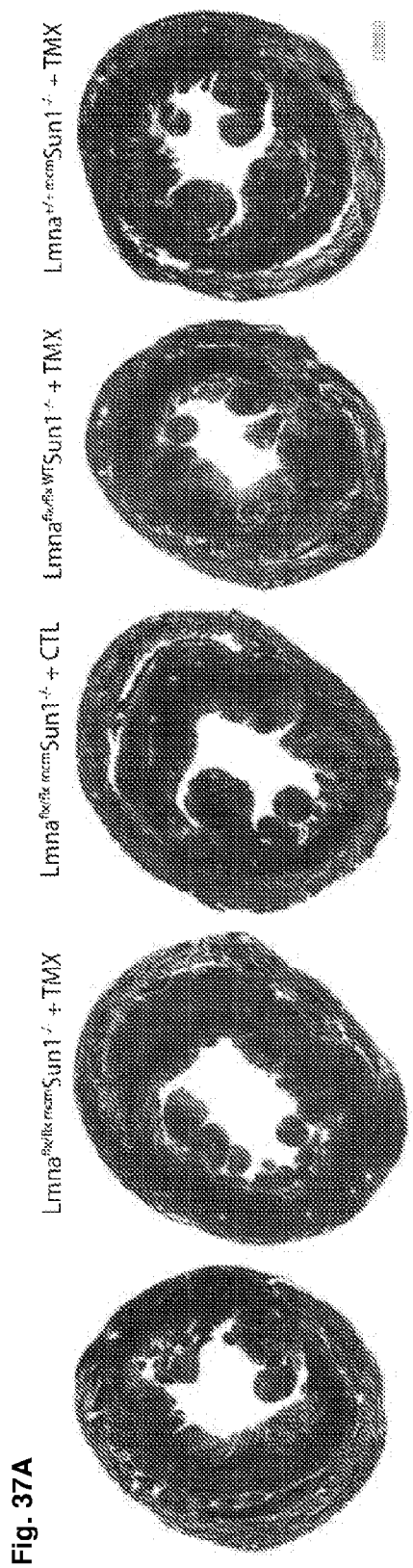
FIGS. 37A-37E show the phenotypes of Lmna$^{Flx/Flxmcm}$ Sun1$^{+/+}$ and Lmna$^{Flx/Flxmcm}$ Sun1$^{-/-}$ hearts at 12-14 months after Tmx injection.
Figures 37B, 37C:
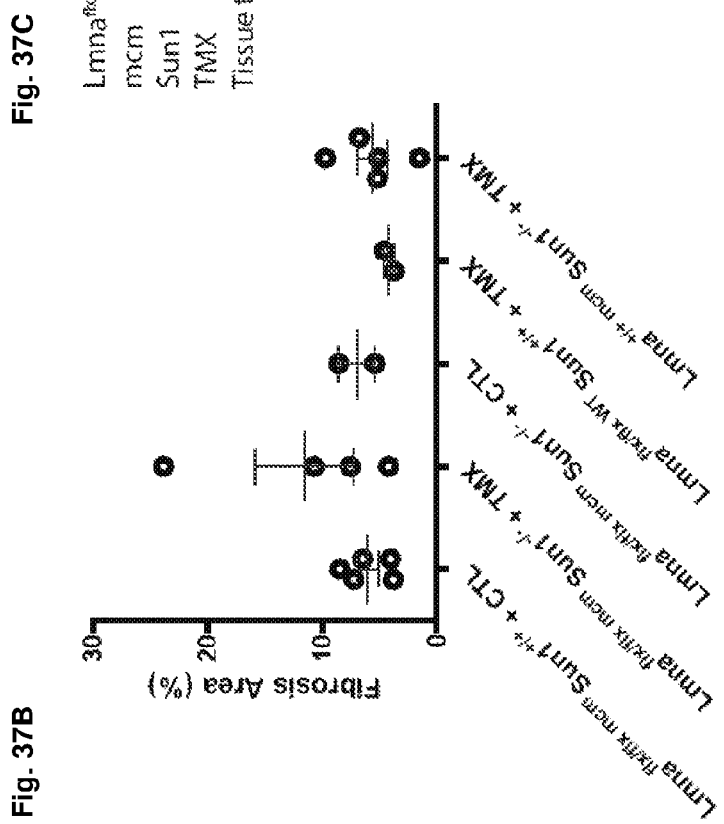
Figure 37D:
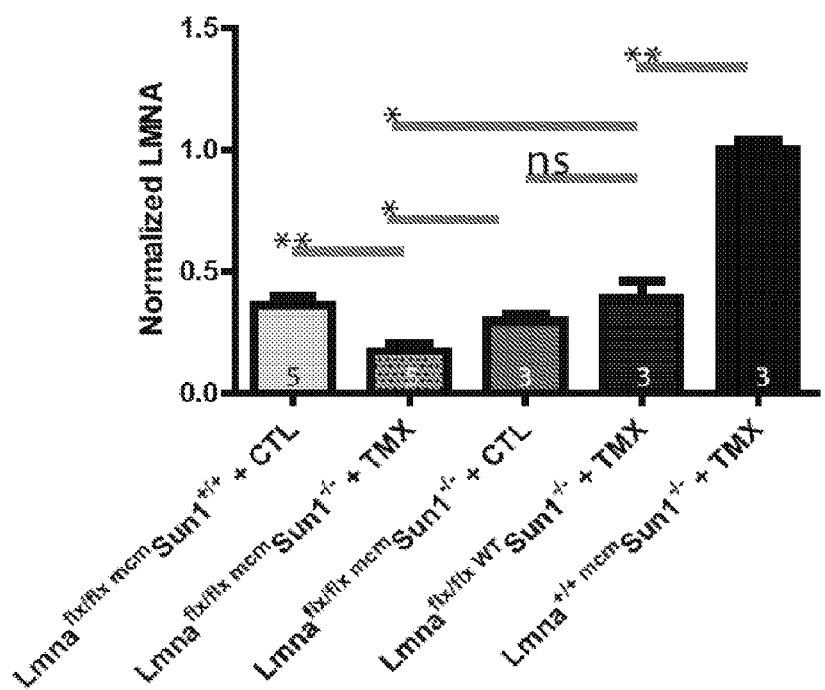
Figure 37E:
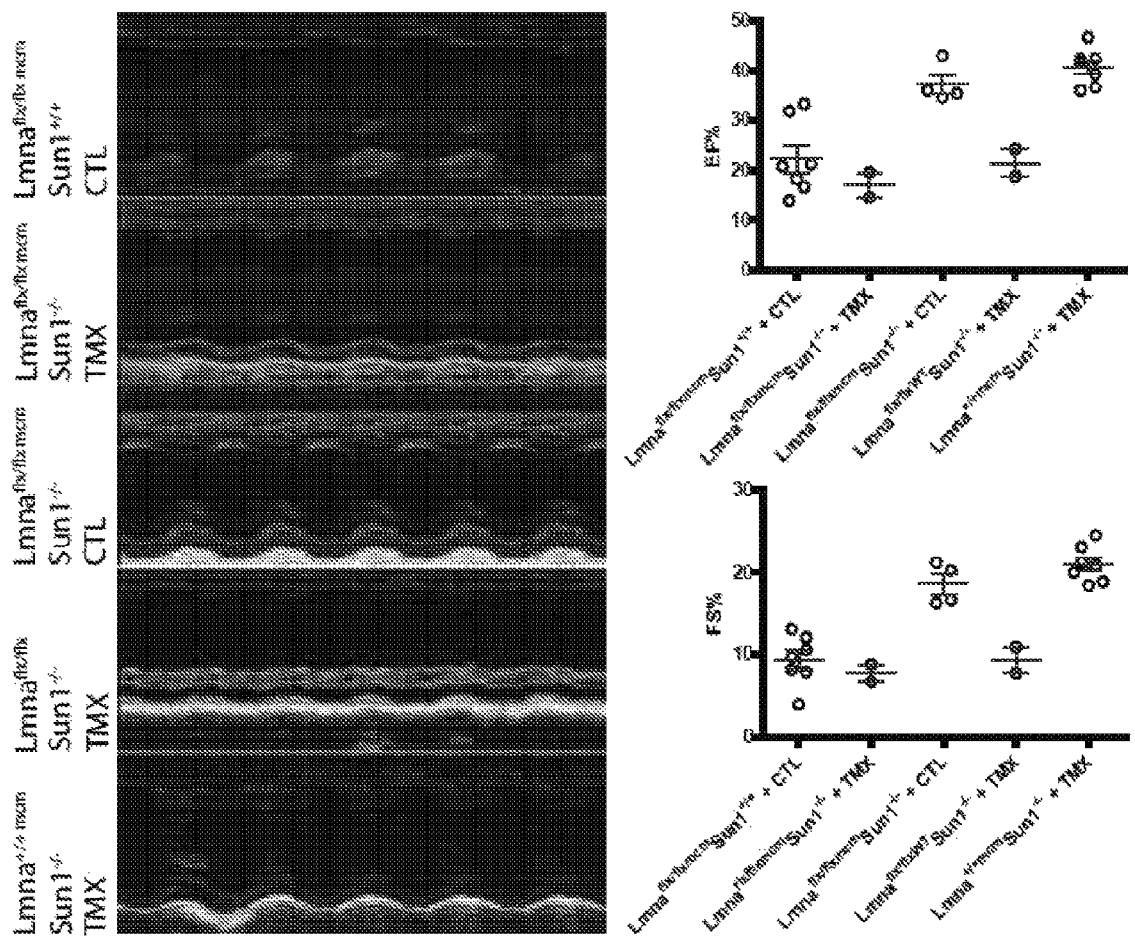

PCR analysis of the aged Lmna$^{Flx/Flx:mcm}$Sun1$^{-/-}$ Tmx hearts 12-14 months after Tmx injection confirmed the sustained deletion of Lmna gene (FIG. 37C), while protein quantification revealed a significant reduction of LMNA levels in Lmna$^{Flx/Flx:mcm}$ Sun1$^{-/-}$+Tmx hearts 12-14 months after Tmx (FIG. 37D). Histological analysis of the 12-14 month Lmna$^{Flx/Flx:mcm}$ Sun1$^{-/-}$+Tmx hearts revealed no significant increase in fibrosis compared to controls (FIGS. 37A and B). However, echocardiograms on these aged mice showed reduced EF and FS in both Lmna$^{Flx/Flx:mcm}$ Sun1$^{+/+}$+CTL and Lmna$^{Flx/Flxmcm}$Sun1$^{-/-}$+Tmx mice (FIG. 37E), although the average lifespan of Lmna$^{Flx/Flx}$ mice is 13-14 months (FIG. 26C and so the reduced contractile function may have been due to ageing. Together these findings demonstrate that loss of Lmna, in adult (2-3 month old) cardiomyocytes is sufficient to result in cardiac failure within 3-4 weeks after Cre activation, but the pathology is strikingly reduced by deleting Sun1, with this reduction being sustained for a year.

Example 4

Loss of SUN1 Extends Longevity of Lmna Missense Mutants

Figure 26D:
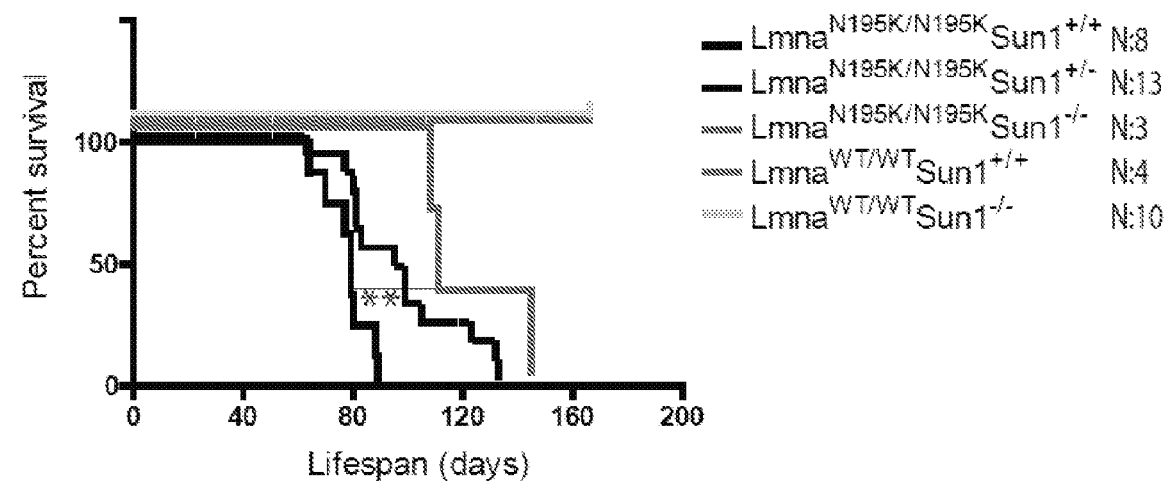
Figure 30A:
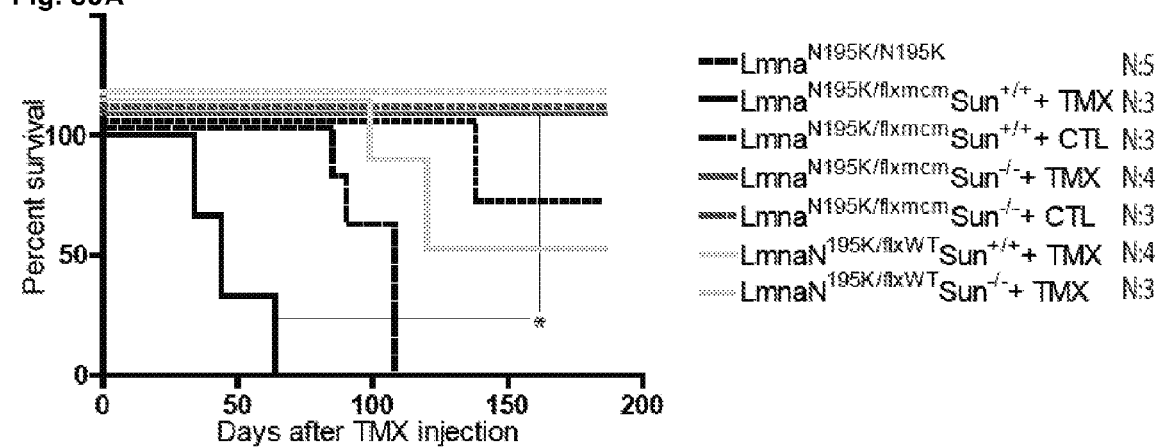
FIGS. 30A-30B show Kaplan Meier graph and heart function effects of deletion of SUN1 on cardiac pathology induced by a missense mutation in the Lmna gene (N195K).

As most cases of LMNA induced DCM result from missense mutations, we determined what effect loss of SUN1 had on the longevity and cardiac function of a previously described Lmna mutant mouse line carrying the N195K missense mutation that dies from DCM [L. C. Mounkes, et al., *Hum Mol Genet* 14: 2167-2180 (2005)], with this mutation having been identified in 2 unrelated patients diagnosed with AD-EDMD [D. Fatkin et al., *N Engl J Med* 341: 1715-1724 (1999); J. P. van Tintelen et al., *Am Heart J* 154: 1130-1139 (2007)]. Here too, we found that the absence of SUN significantly extended the lifespan of this mutant mouse line with improved cardiac function (FIG. 26D). We extended these findings by deriving mice heterozygous for the N195K mutation, with the WT-Lmna allele being floxed i.e. $Lmna^{N195K/Flx} \times Sun1^{+/+}$. Inducing the Tmx inducible cardiomyocyte Cre allele in these mice ($Lmna^{N195K/Flx:mcm}$+Tmx) resulted in the deletion of the WT floxed Lmna allele making the cardiomyocytes hemizygous for the $Lmna^{N195K/-}$ mutation. These mice had a mean lifespan of less than 50 days, a longevity half that of the original $Lmna^{N195K/N195K}$ homozygotes (FIG. 30A). When the $Lmna^{N195K/flx:mcm}$+Tmx mutation was induced on a Sun1 null background longevity was significantly extended from <50 days to >200 days (FIG. 30A), revealing that loss of Sun1 is also effective at preventing DCM caused by Lmna missense mutations specifically in cardiomyocytes.

Figure 30B:
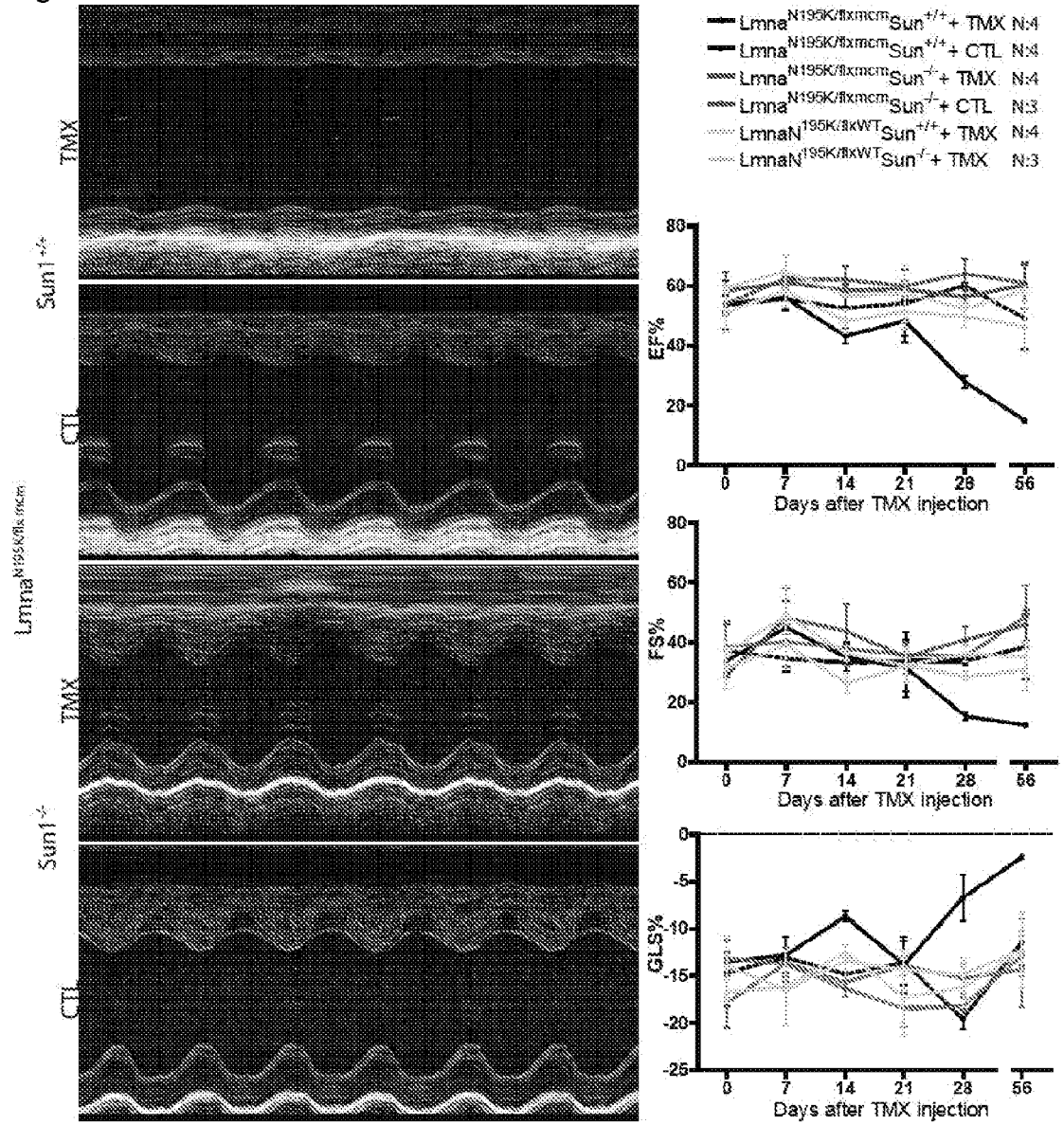

Echocardiograms performed before and after Cre induction revealed progressive worsening of cardiac contractility in the $Lmna^{N195K/Flx:mcm}$ $Sun1^{+/+}$ mice compared to $Lmna^{N195K/Flx:mcm}$ $Sun1^{-/-}$ mice (FIG. 30B). Loss of SUN1 preserved both EF, FS and Global Longitudinal Strain (GLS) in $Lmna^{N195K/-:mcm}$ $Sun1^{-/-}$ mice compared to $Lmna^{N195K/-:mcm}$ $Sun1^{+/+}$ mice (FIG. 30S).

Example 5

AAV9 Mediated Transduction and Expression of a DNSun1 Prolongs the Lifespan of the $Lmna^{Flx/Flx:mcm}$+Tmx Mice.

Figure 15:
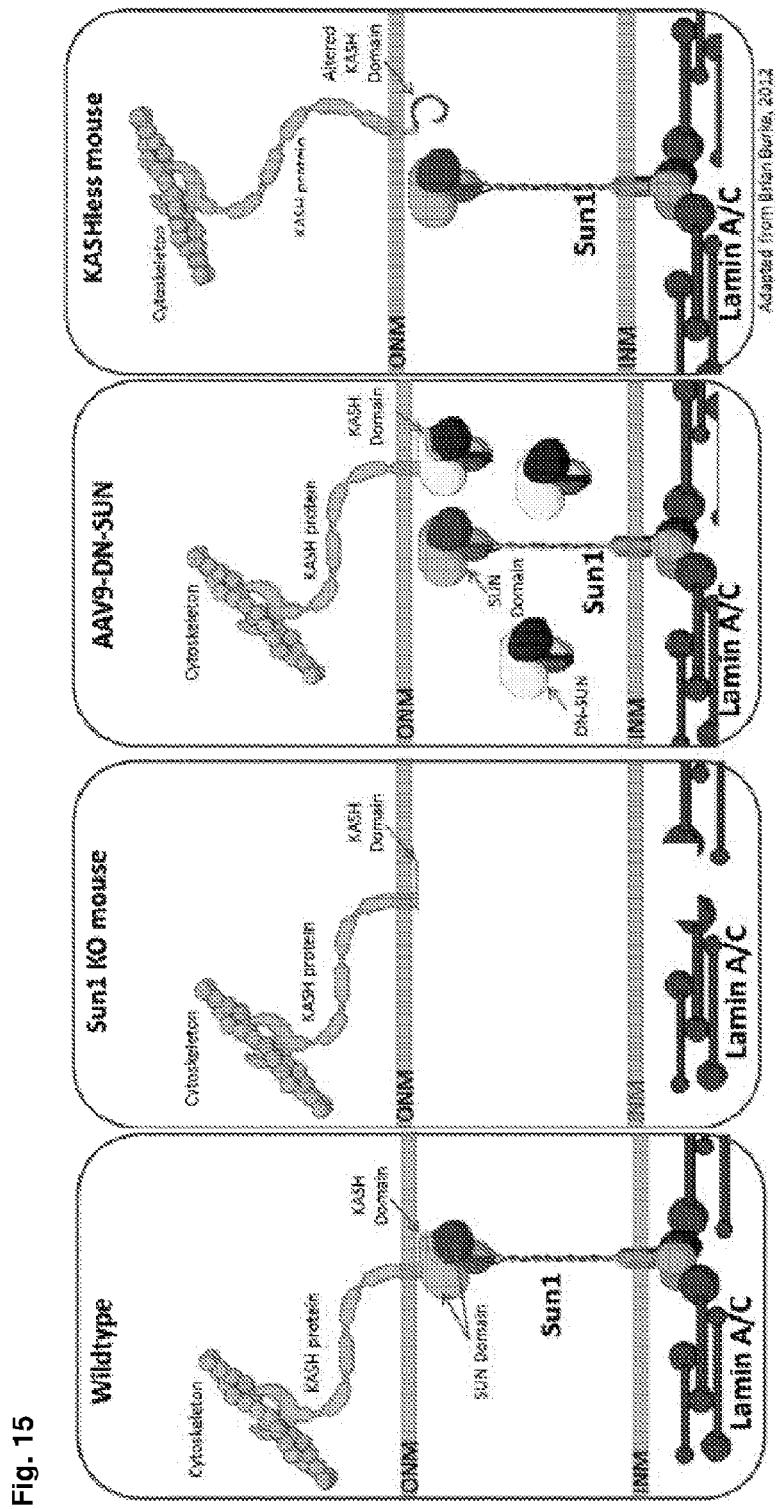
FIG. 15 shows a schematic of the LINC complex in wildtype mice, Sun1 KO mice, AAV dominant negative SUN mice and mice with altered KASH domain. The schematic for wildtype mice is obtained from Brian Burke, 2012. The schematic for Sun1 KO mice represents the results from Chen et al., 2012. The AAV dominant negative SUN and the altered KASH domain schematics represent Inventor proposals at the priority date on methods for LINC complex disruption to ameliorate laminopathies, based on data obtained at that time.
Figure 16:
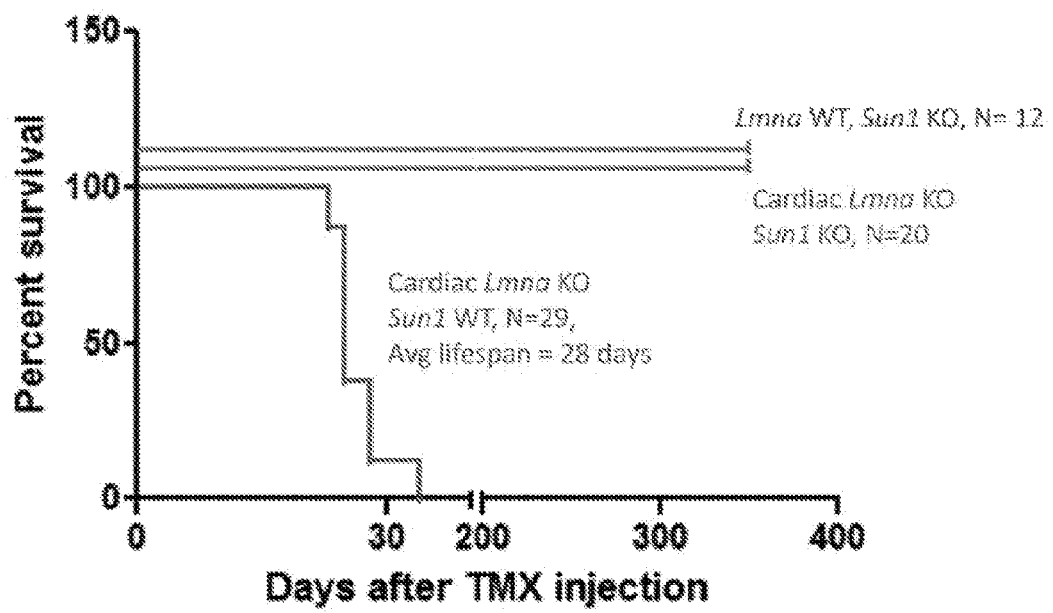
FIG. 16 shows a Kaplan Meier curve of Lmna KO mice surviving for an average of 28 days, Sun1 KO mice living beyond 300 days and cardiac Lmna KO/Sun1 KO mice living beyond 300 days.
Figure 17:
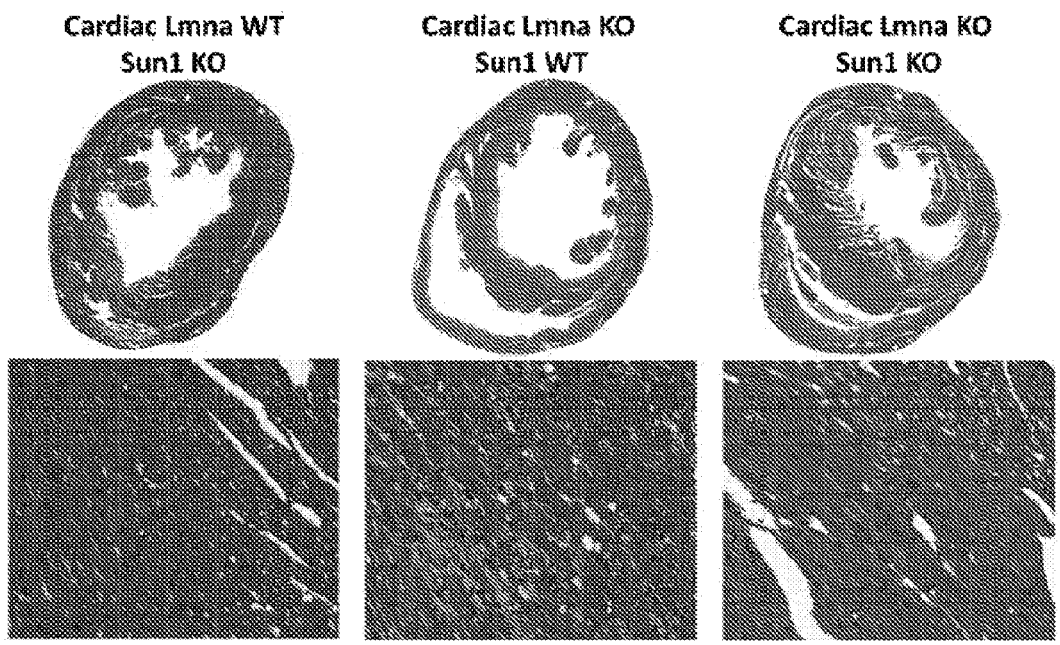
FIG. 17 shows H&E stained sections of hearts from Sun1 KO mice, cardiac Lmna KO mice and cardiac Lmna KO/Sun1 KO mice, with LmnaKO/Sun1WT hearts showing enlargement of the left ventricle (DCM) compared to WT and LmnaKo/Sun1KO hearts.
Figure 18:
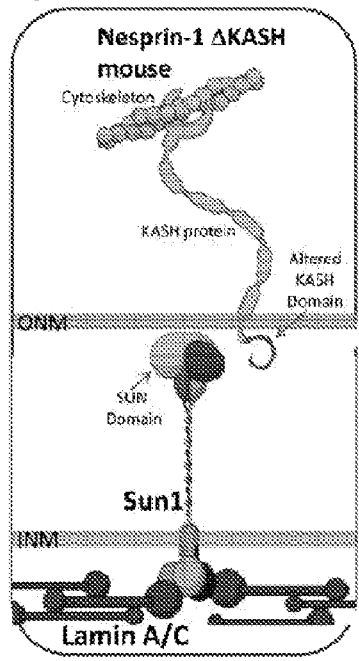
FIG. 18 shows a schematic of disruption of a LINC complex in a Nesprin-1 ΔKASH mouse. LmnaKO Nesprin-WT mice have a lifespan of about 20 days. LmnaKO Nesprin-1-ΔKASH survive about 40 days, which is similar to LmnaKOSun1KO mice.
Figure 19A:
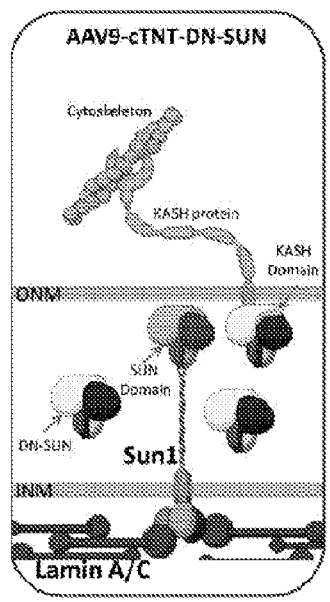
FIGS. 19A-19B show a schematic of anticipated AAV-cTNT-DN-SUN expression and competition between exogenous DN-SUN and native Sun1 for binding to the KASH domain (FIG. 19A) with the DN-SUN shown in 19B (upper panel) and the effect of transfected DN-SUN on native Nesprin2G positioning in cells where the 2 nuclei in the middle panel express the DN-SUN and in the merge panel both show loss of Nesprin2 from the nuclear membranes (FIG. 19B).
Figure 19B:
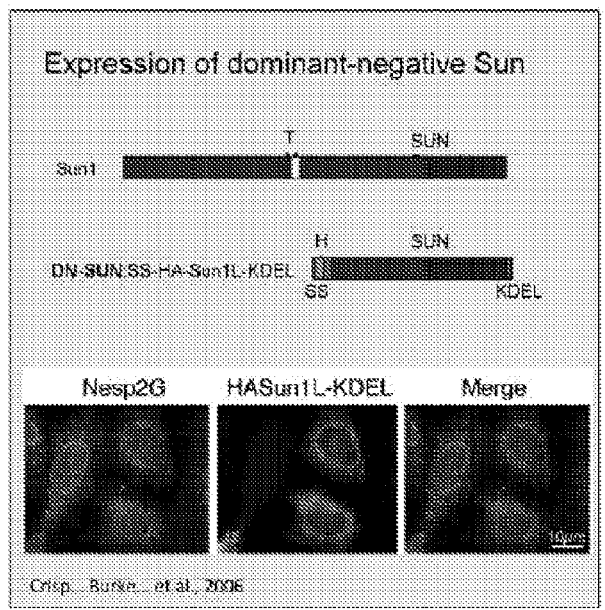
Figure 31A:
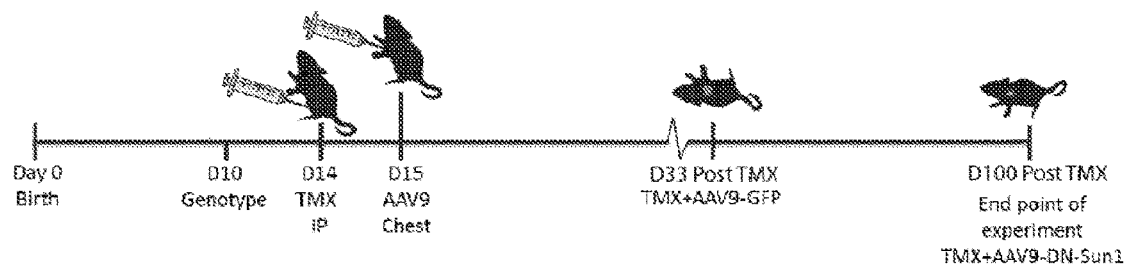
Figure 31B:
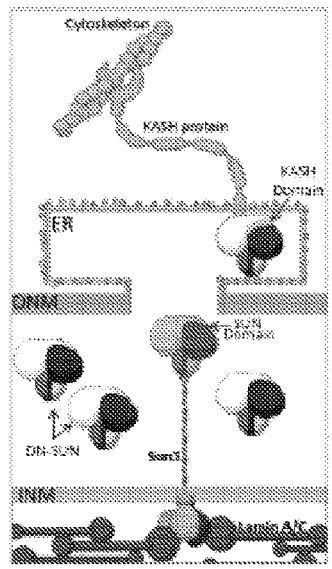
Figure 34:
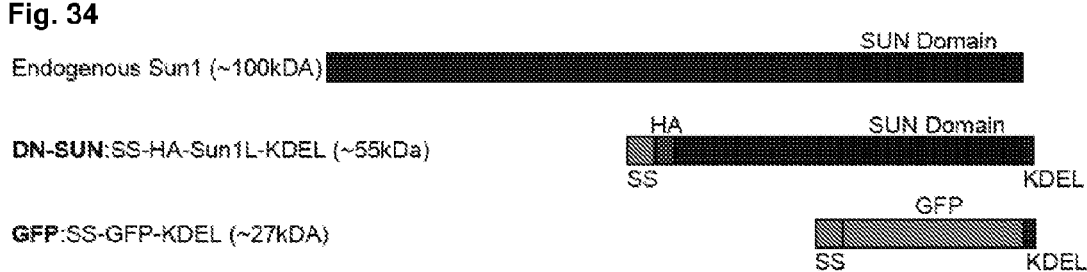
FIG. 34 shows a diagram of the recombinant AAV9-DNSun1 and AAV9-GFP miniproteins. The DN-Sun1 includes the Sun domain, an HA tag, a Signal Sequence (SS, for targeting the protein to the ER), and the KDEL (ER retention signal) [M. Crisp et al., *J Cell Biol.* 172: 41-53 (2006)]. The AAV9-GFP includes the SS and KDEL sequences. GFP was used as a control in place of the Sun1L-KDEL.

The above results demonstrated that genetically ablating SUN1's functions or reducing SUN levels could be of therapeutic value in treating DCM. We then tested whether this was due to the complete ablation of SUN1's functions to overcome its toxic over-abundance versus leaving its levels untouched and specifically disrupting its LINC complex-associated role in tethering KASH-domain proteins in the ONM, thereby tethering the nucleus to components of the cytoskeleton. To distinguish between these 2 possibilities, Adenovirus Associated Virus (AAV) was utilized to transduce and express, specifically in cardiomyocytes, a dominant negative SUN minigene whose protein product would compete with both SUN1- and SUN2-KASH binding in the cardiomyocyte perinuclear space [M. Crisp et al., *J Cell Biol* 172: 41-53 (2006)]. A region corresponding to the entire luminal domain of the Sun1 gene was tagged at its N terminus with an HA (HA-Sun1L) epitope. To localize the resulting protein product to the endoplasmic reticulum (ER) and perinuclear space (between the INM and ONM-PNS), the signal sequence and signal peptidase cleavage site of human serum albumin was fused to the N terminus of HA-Sun1L to yield SS-HA-Sun1L. To prevent the miniprotein's secretion, a KDEL tetrapeptide was linked to the C-terminus of SS-HA-Sun1L, forming SS-HA-Sun1L-KDEL (FIG. 34). The signal sequence would ensure the HA-Sun1KDEL accumulates intracellularly within the contiguous peripheral ER and PNS lumen. The cDNA sequence encoding the minigene was fused to the chicken cardiotroponin promoter (cTnT) to ensure the minigene is only transcribed in cardiomyocytes [K. M. Prasad, et al., *Gene Ther* 18: 43-52 (2011)]. A diagram of how SS-HA-Sun1L (DN-Sun1) displaces the KASH domain proteins from the LINC complex in the PNS to the ER is presented in FIG. 15 (third panel) and FIG. 31B.

Figure 31C:
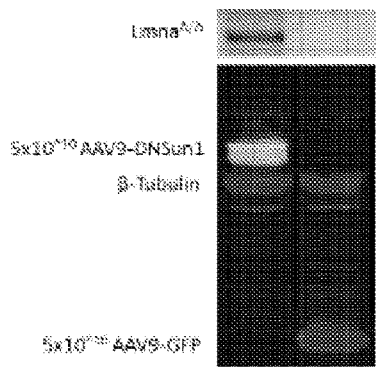
Figure 31D:
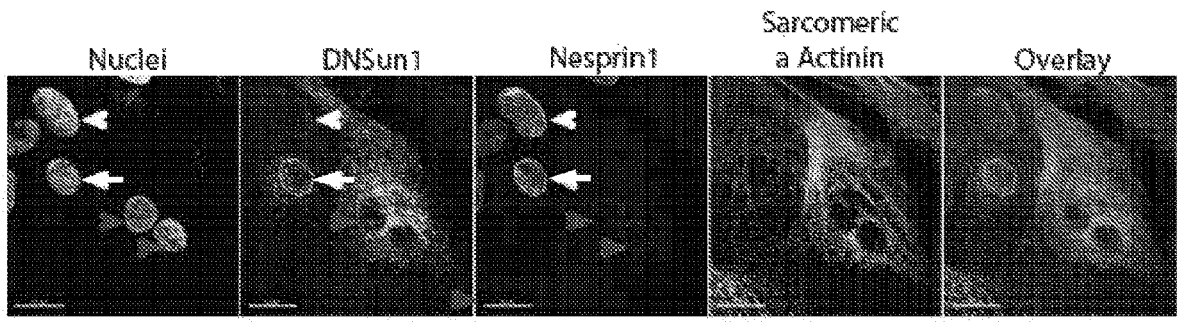

To verify that the DN-Sun1 functioned in cardiomyocytes (CM) we initially transduced human CMs derived from PS stem cells using the AAV-DJ system [D. Grimm, et al., *J Virol.* 82(12):5887-911 (2008)] that provides for a higher infectivity rate in cultured cells than the AAV9 serotype used to transduce the DN-Sun1, under transcriptional control of the cTnT promoter, in the mouse hearts. The DN-Sun1 was effective at displacing Nesprin-1 from the nuclear envelopes in the CMs that were expressing the DN-Sun1 as shown in FIG. 31D. Cells expressing high levels and low levels of DN-Sun1 are indicated by grey and white arrowheads respectively. High levels of DN-Sun1 expression resulted in the displacement of Nesprin-1 from the nuclear envelope. This confirmed that the DN-Sun1 was effective at disrupting the LINC complex in CMs.

Figure 38:
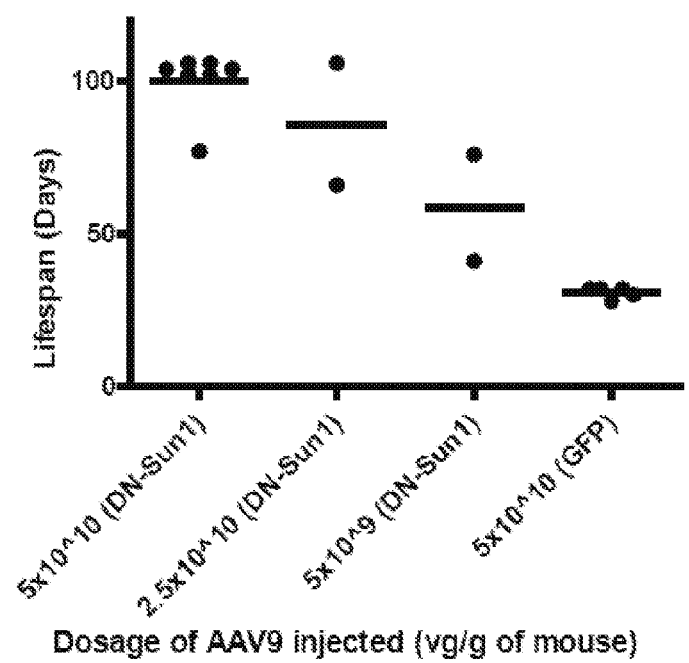
FIG. 38 shows the rescue by AAV9-DNSun1 depends on the dosage of viral particles injected. Lifespan of Lmna$^{Flx/Flx:mcm}$+TMX mice depends of the dosage of AAV9-DNSun1 with, with a lower concentrations resulting in shorter lifespans. Each dot represents a mouse, horizontal lines indicate mean.
Figure 39A:
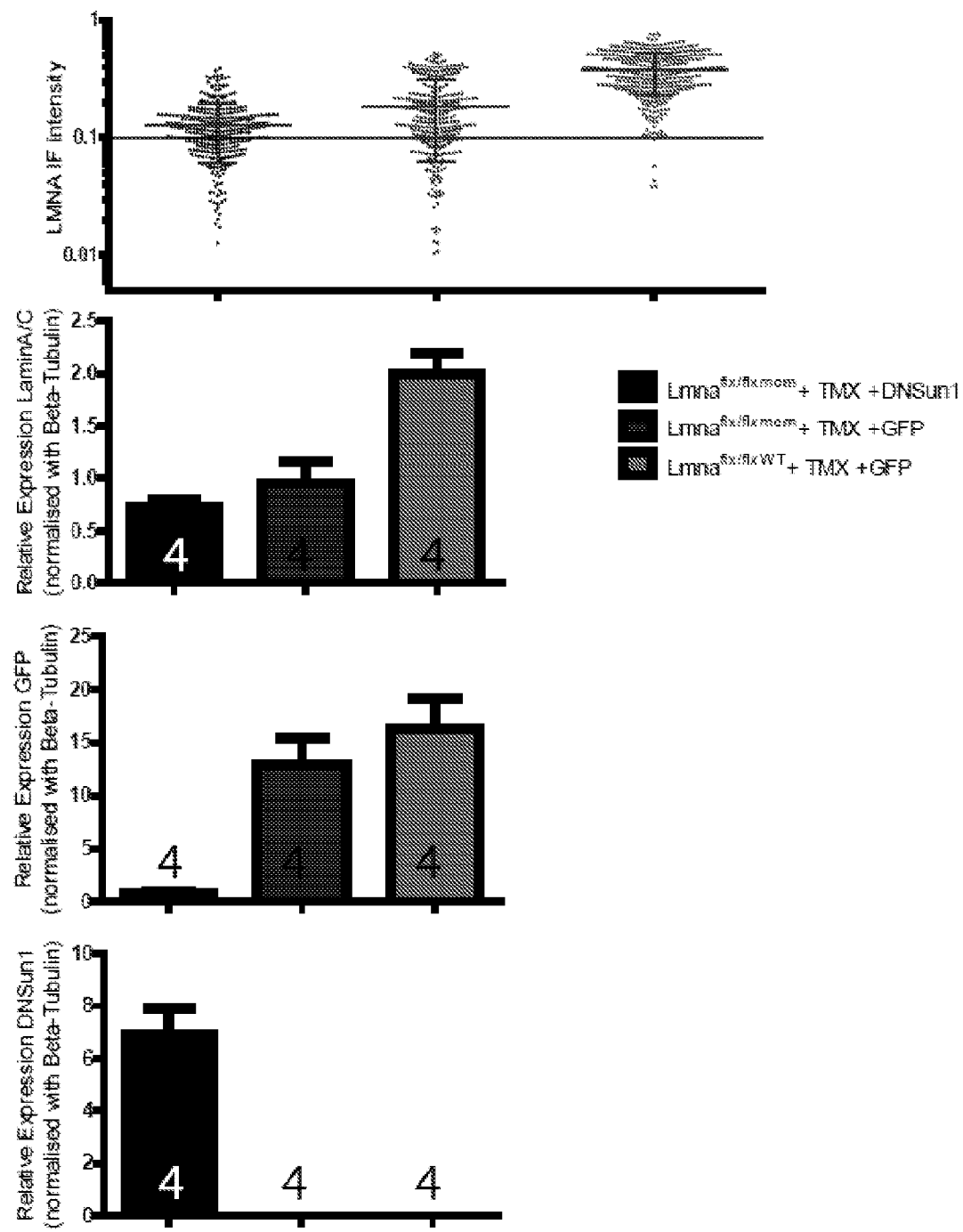
FIGS. 39A-39C show levels of LamiA/C following Tmx induction and expression of AAV-expressed proteins.
Figure 39B:
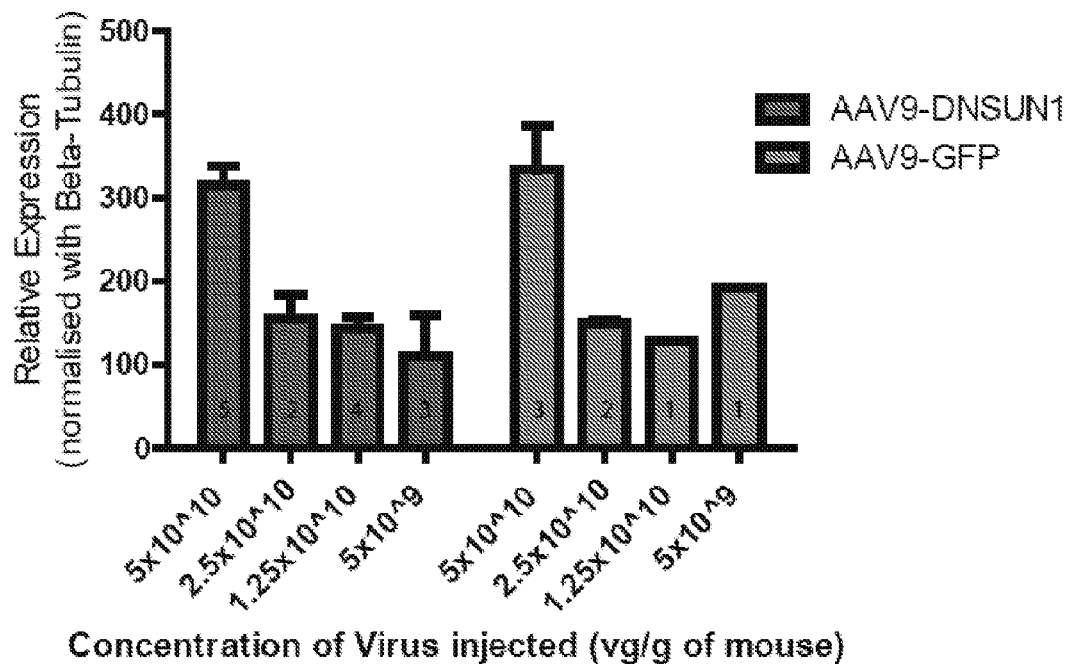
Figure 39C:
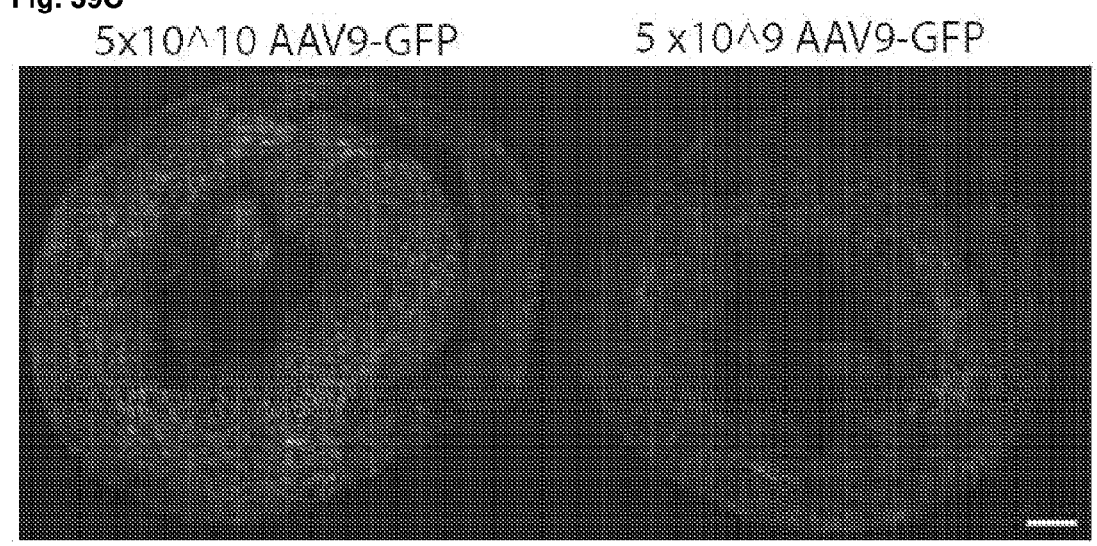

We used AAV (serotype 9) to transduce and express the DN-Sun1 minigene in the hearts of postnatal mice by intrathoracic injection. The procedure is summarized in FIG. 31A and all mice were sacrificed at 100 days after Tmx injection for analysis. Detection by PCR of the Lmna deletion in the hearts confirmed Cre induction by Tmx injection (FIG. 31C). To determine the localization and expression levels of the DN-Sun1 minigene, total protein was extracted from half the heart. Western analysis revealed robust expression of both AAV9-DNSun1 and AAV9-GFP control protein (Dose injected: 5×10^10 vg/g of mouse) 99 days after AAV injection (FIG. 31C) with the expression levels of both proteins being dependent on the dose of viral particles injected (FIG. 38). The expression of either AAV9-DNSun1 or AAV9-GFP proteins did not affect LMNA protein levels (FIG. 39A). Immunofluorescence analysis revealed that a larger percentage of cardiomyocytes were expressing GFP with 5×10^10 vg/g of AAV9-GFP compared to the levels resulting from a 10-fold lower dose of viral particles (5×10^9 AAV9-GFP) (FIG. 39B and FIG. 39C).

Figure 20:
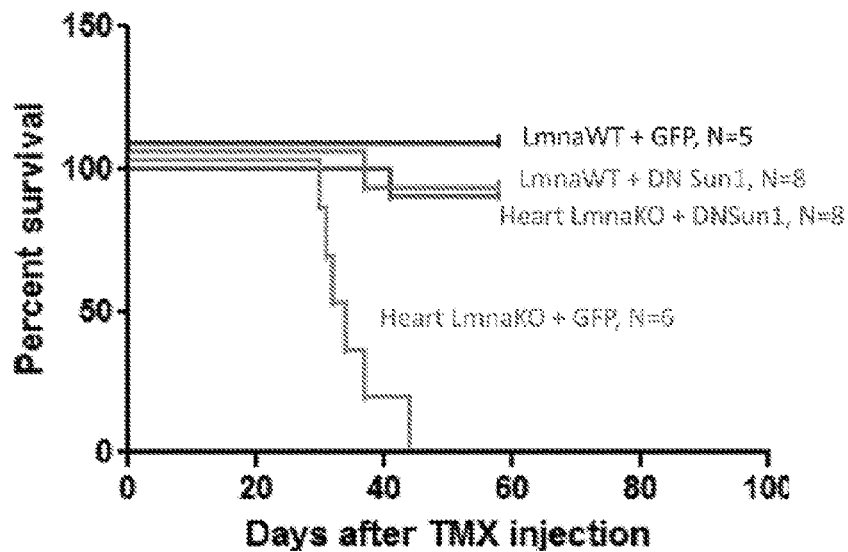
FIG. 20 is a Kaplan Meier curve showing disruption of SUN-KASH interaction in vivo, using AAV9-cTNT-dominant negative Sun1 (DNSun1), extends the longevity of the heart-specific Lmna KO in male and female mice.
Figure 31F:
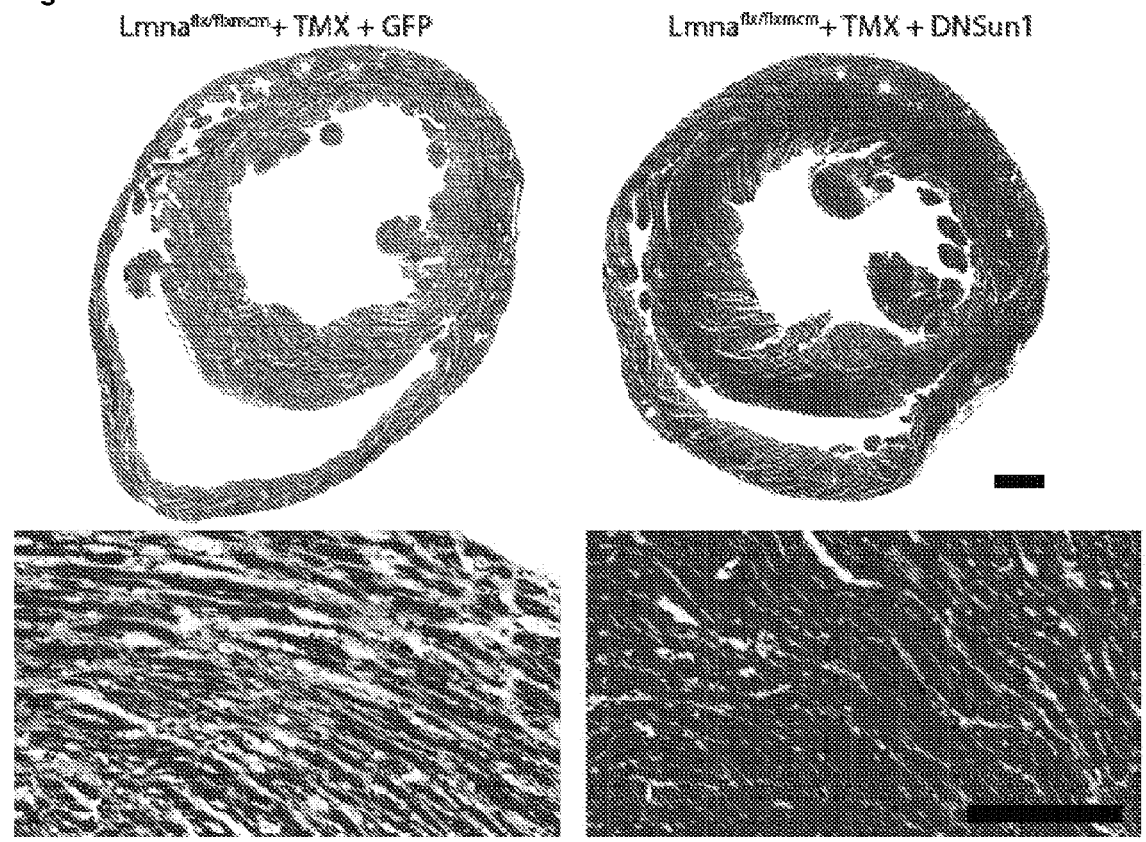
Figure 31G:
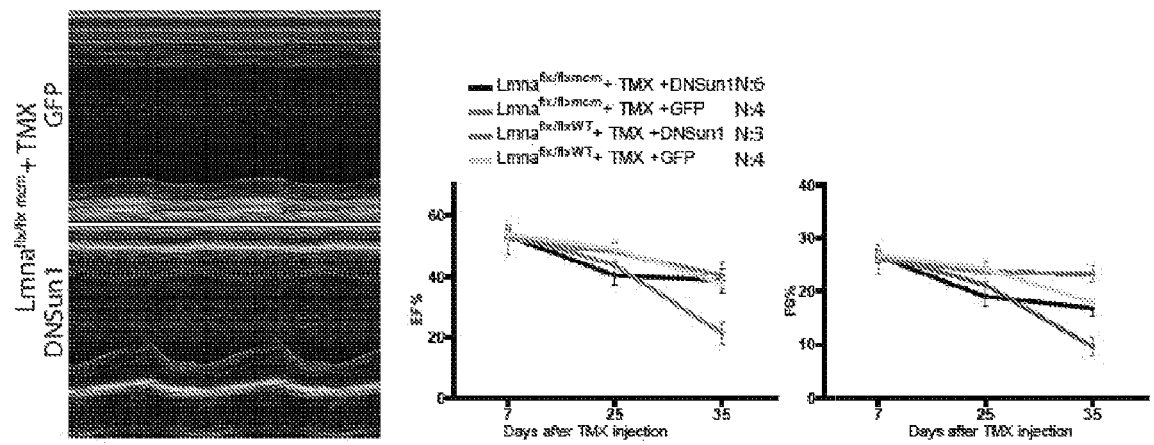

The $Lmna^{Flx/Flx:mcm}$+Tmx mice, injected with AAV9-GFP control, lived an average of 34.5 days after Tmx, whereas $Lmna^{Flx/Flx:mcm}$+Tmx mice injected with AA9-DNSun1 (5×10^10 vg/g of mouse) lived significantly longer with the majority surviving at least 100 days after Tmx, before their termination for analysis (P=0.0002) (FIG. 20 shows early time period results with male and female mice; FIG. 31E shows results at 100 days with separate graphs for male and female mice and mice with different virus injection titre removed). Echo analysis confirmed $Lmna^{Flx/Flx:mcm}$+Tmx+AAV9-DNSun1 hearts were functioning better than $Lmna^{Flx/Flx:mcm}$+Tmx+AAV9-GFP hearts at 35 days post Tmx (FIG. 31G). Although the $Lmna^{Flx/Flx:mcm}$+Tmx+AAV9-DNSun1 mice were alive at 100 days after induction both EF % and FS % were significantly lower compared to control $Lmna^{Flx/Flx:mcm}$+Tmx mice (FIG. 31G). At 35 days post Tmx, increased fibrosis was detected in both the $Lmna^{Flx/Flx:mcm}$+Tmx+AAV9-DNSun1 and Lmna$^{Flx/Flx:mcm}$+Tmx+AAV9-GFP hearts (FIG. 31F), although fibrosis in the Lmna$^{Flx/Flx:mcm}$+Tmx+AAV9-DN-Sun1 hearts was significantly lower than in Lmna$^{Flx/Flx:mcm}$+Tmx+AAV9-GFP hearts (FIG. 31F lower panels).

Example 6

Disruption of the LINC Complex in Mice Using CRISPR/Cas9

Mice harboring a variety of Lmna mutations, both global and cardiac-specific, show a significant increase in longevity and health in the absence of Sun1 [(Chen et al., Cell 149: 565-577 (2012) and Examples 2-4]. Prior to the findings described in Examples 2-5, the mechanism of this rescue was unclear, but was speculated to be due to the toxic effects of excess Sun1 in Lmna mutants [Chen et al., Cell 149: 55-577 (2012)]. AAV-mediated expression of a dominant negative LINC-complex-disrupting transgene ameliorates the pathology associated with Lmna mutation [Example 5]. The findings in Examples 2-5 are consistent with the idea that LINC complex function, rather than excess Sun1, is the molecular driver of Lmna pathology. This was surprising, as genetic disruption of the LINC complex via loss of Sun1 and Sun2 [K. Lei at al., Proc Nat Acad Sci USA 106: 10207-10212 (2009)], or cardiac-specific disruption of Nesprin-1 and Nesprin-2 [Banerjee at al., PLOS Genet 10(2): e1004114 (2014)], in mice, resulted in various pathologies.

To develop alternative means of disrupting the LINC complex in vivo, the possibility of using CRISPR/Cas9 genome editing to disable the SUN and KASH domains of the proteins constituting the LINC complex was examined. As both the SUN domain and the KASH domain are located at the C-termini of their respective proteins, we hypothesized that a CRISPR guide RNA targeted to the 3' end of the genes encoding SUN or KASH domain proteins would result in a premature stop codon following CRISPR-induced non-homologous end joining. This would result in a truncated protein with its C-terminal SUN or KASH domain mutated. The truncated protein would be expressed and membrane-localized, but unable to interact with its cognate LINC complex partners. In Example 2, we found that loss of Sun2 did not ameliorate Lmna-associated pathologies. Thus we chose to target the Sun1 SUN domain using CRISPR as Sun1 appears to be the dominant SUN domain protein mediating Lmna pathology. Of the KASH domain proteins, only Nesprin-1, Nesprin-2 and Nesprin-3 are broadly expressed [H. F. Horn, Current topics in developmental biology 109: 287-321 (2014)). Nesprin-1 and Nesprin-2 are close paralogues that are functionally redundant. They interact with the actin and microtubule cytoskeleton, whereas Nesprin-3 appears to interact specifically with intermediate filaments [Kim et al., Biol. Chem. 396: 295-310 (2015)]. As we already had Nesprin-2 and Nesprin-3 mutant mouse strains derived by conventional gene targeting available in the laboratory, we chose to target the KASH domain of Nesprin-1 using CRISPR to test the possibility of using CRISPR/Cas9 in vivo for treatment of laminopathies.

The Sun1 gene and the Syne1 gene encoding Nesprin-1 protein were directly targeted in vivo by microinjecting C57/B16 mouse zygotes with Cas9 mRNA and gRNA targeting the SUN1 (5'-GCACAATAGCCTCGGATGTCG-3'; SEQ ID NO: 66) or KASH1 (5'-CCGTTGGTATATCT-GAGCAT-3' SEQ ID NO: 67) domains, followed by implantation into surrogate mothers. Note the SUN gRNA targeted Sun1 upstream of the SUN domain so as to ablate the SUN domain. A gRNA (5'-GGTTATGGCCGATAGGTGCAT-3'; SEQ ID NO: 68) targeting the tyrosinase gene was co-injected—progeny that had undergone CRISPR genome editing would have white or mosaic coat color resulting from tyrosinase disruption. These pups were genotyped to confirm successful gene disruption and used as founder animals to establish Sun1 or Nesprin-1 mutant colonies.

Characterization of Mutant Mice

Figure 40C:
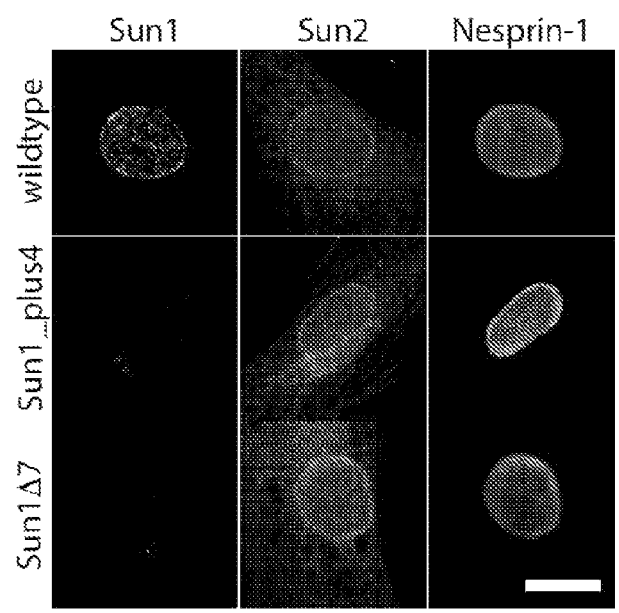

Following Sanger sequencing of founder animals and F1 progeny, we focused on characterizing Sun1 mutant alleles (FIG. 40A) with a 7 bp deletion (Sun1_del7, or Sun1Δ7; SEQ ID NO: 71) and 4 bp insertion (Sun1_plus4; SEQ ID NO: 70), and a Syne1 (Nesprin-1) mutant allele (FIG. 41A) with a 8 bp deletion (Syne1_CTdel8, or Syne1 C'TΔ8; SEQ ID NO: 78). The Sun1 mutant alleles were predicted to produce mRNA with premature stop codons resulting in a truncated Sun1 protein lacking a SUN domain (FIG. 40B). Tail tip fibroblasts were isolated from Sun1 homozygous mutant animals. Immunofluorescence staining revealed loss of Sun1 protein (FIG. 40C), suggesting that the indels generated by CRISPR caused nonsense-mediated decay of Sun1 mRNA. It is unclear whether the site of mutation, being outside the SUN domain rather than inside the SUN domain, had an effect on the expression of the mutated gene. As we were unable to obtain Sun1 mutant alleles that produced Sun1 protein lacking the SUN domain, instead obtaining essentially Sun1 null animals, we did not further characterize these mutant lines.

The Syne1 C'TΔ8 allele is predicted to produce a protein where the final 11 amino acids in the wildtype sequence (SEQ ID NO: 77) are mutated and are followed by an additional 50 amino acids encoded by an alternate reading frame (FIG. 41B; SEQ ID NO: 78). Immunoblotting performed on Syne1WT and Syne1C'TΔ8 heart and muscle tissues revealed a ~120 kDa band in WT corresponding to the striated muscle-enriched Nesprin-1α isoform of the Syne1 gene (FIG. 41C, D). In the C'TΔ8 heart and muscle tissues, the presumptive Nesprin-1a polypeptide appeared to be less abundant and of lower electrophoretic mobility than in the wildtype (FIG. 41C, D). This is consistent with the 8 bp deletion in the Syne1C'TΔ8 allele introducing a novel stop codon downstream, resulting in a protein of higher molecular weight. In addition, a ~1 MDa band likely corresponding to Nesprin-1Giant was observed in heart tissue from both Syne1WT and Syne1C'TΔ8 mice.

Figure 43:
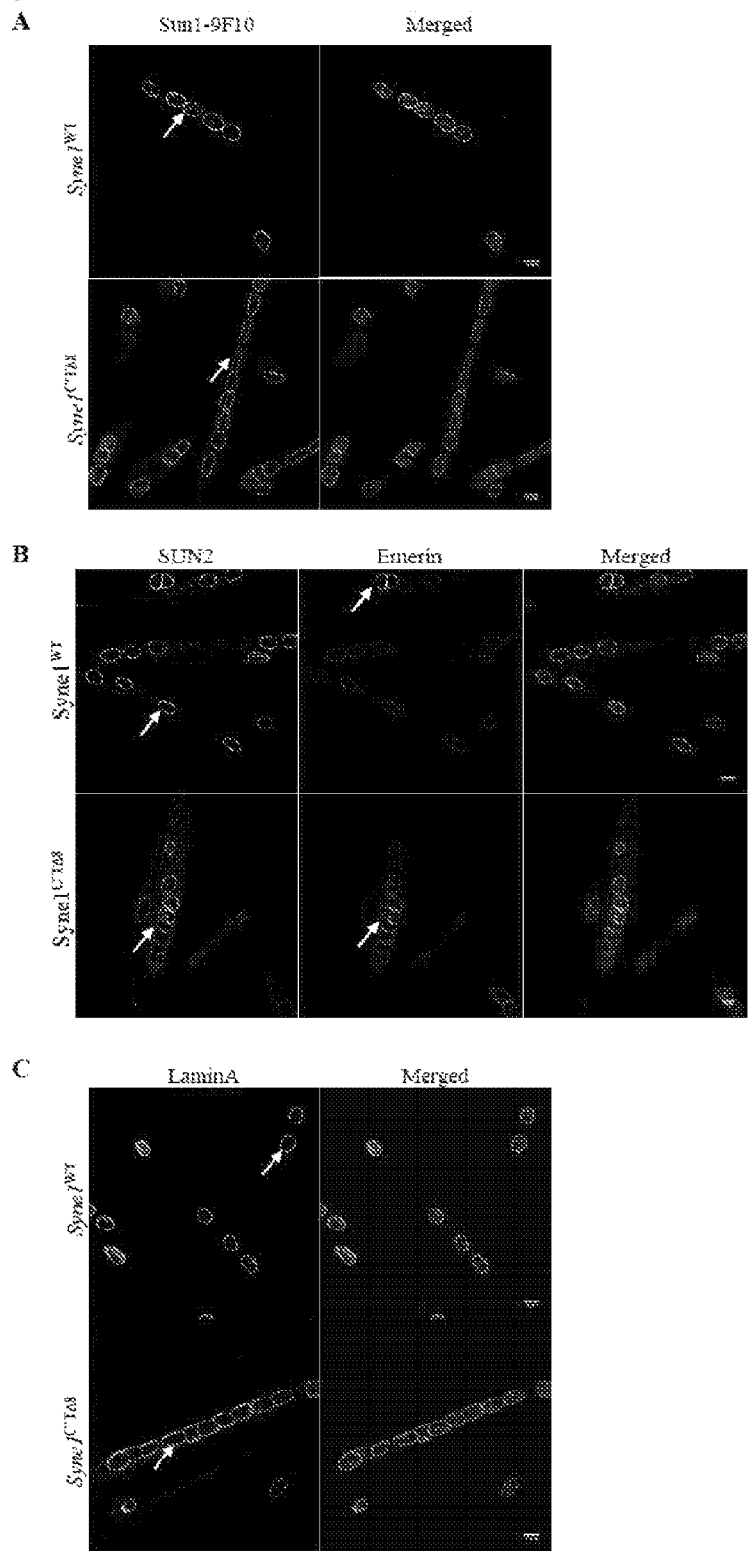
FIG. 43A-C are photomicrographs showing Syne1 mutation does not disrupt localization of certain nuclear envelope proteins. (A-C) Immunofluorescence staining of mouse primary myotubes derived from wildtype (WT) and Syne1C'TΔ8 mutant mice. Sun1 (A), Sun2 and emerin (B) and lamin A/C (C) localize normally to the nuclear envelope. Merged images show protein and DNA staining. Arrows indicate examples of normally localized nuclear envelope proteins. Scale bar=10 μm.
Figure 44:
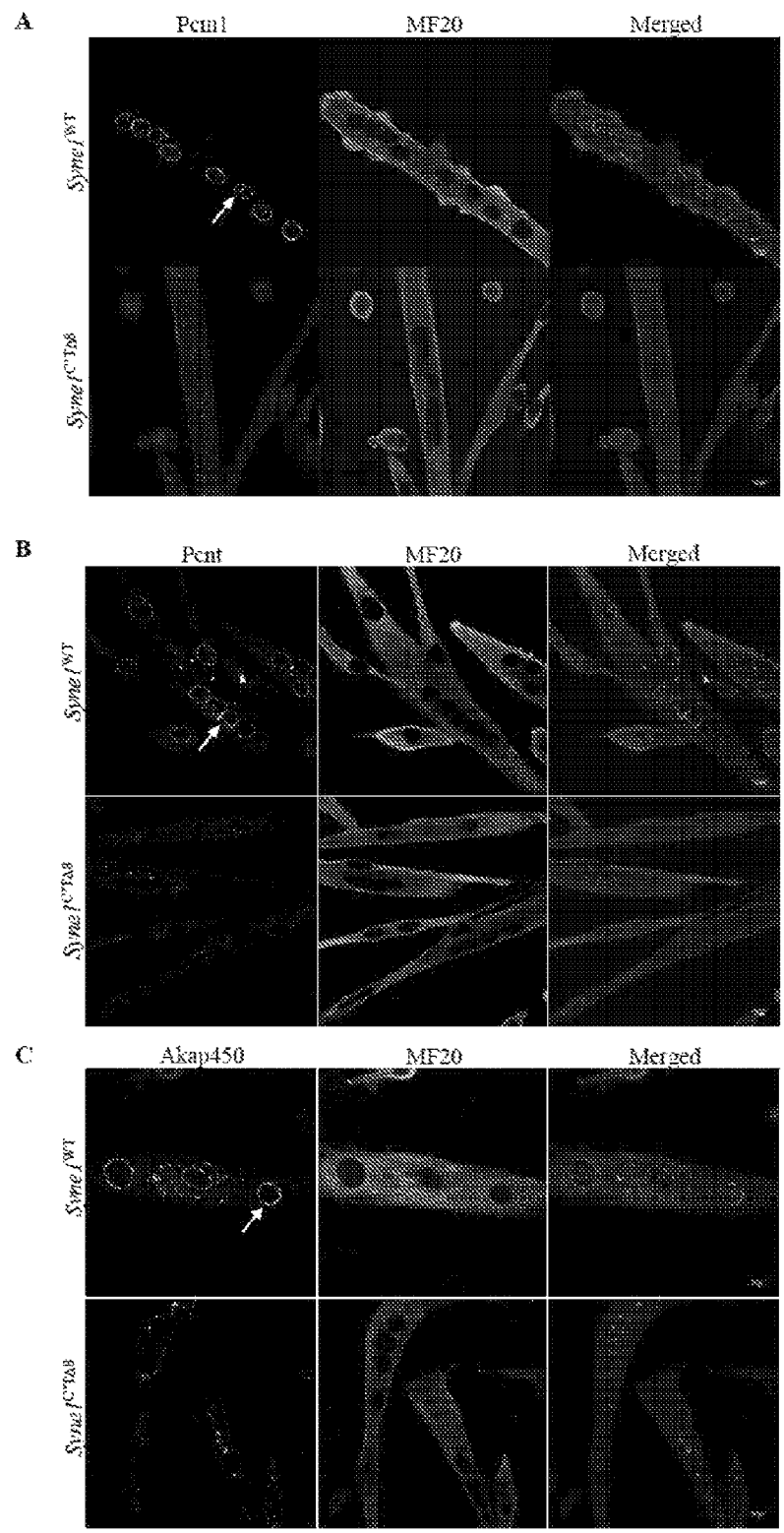
FIG. 44A-C are photomicrographs showing Syne1 mutation disrupts localization of nuclear-envelope-localized centrosomal proteins. (A-C) Immunofluorescence staining of mouse primary myotubes derived from wildtype (WT) and Syne1C'TΔ8 mutant mice. Pcm1, Pericentrin (Pcnt), and Akap450, which normally localize to the nuclear envelope in myotubes, are displaced from the nuclear envelope in Syne1C'TΔ8 mutant myotubes. MF20 is an antibody for myosin heavy chain, a myotube marker. Merged images show protein and DNA staining. Arrows indicate typical nuclear envelope staining for these centrosomal proteins. Scale bar=10 μm.

Immunofluorescence analysis of mouse adult fibroblasts (MAFs) derived from 12 week old mice revealed that Nesprin-1 was mis-localized from the nuclear envelope to the cytoplasm in the Syne1C'TΔ8 MAFs (FIG. 42A). Similarly, in myotubes, Nesp-1 redistributes to the cytoplasm in the Syne1C'TΔ8 myotubes as compared to Syne1WT (FIG. 42B). Other LINC complex and NE proteins such as SUN, SUN2, Emerin and LaminA remained localized to the NE (FIG. 43A-C). Consistent with previous reports [Gimpel at al., Curr. Biol. 27: 2999-3009.e9. (2017)], disruption of Nesprin-1 in myotubes led to mislocalization of centrosomal proteins PCM1. Pcnt and Akap450 from the myotube nuclear envelope (FIG. 44A-C). Mislocalization of Nesprin-1 from the nuclear envelope is consistent with disruption of the Nesprin-1 KASH domain, preventing Nesprin-1C'TΔ8 mutant protein from interacting with the SUN domains of Sun1 and Sun2, which would normally restrict Nesprin-1 to the nuclear envelope. As the transmembrane region is not disrupted, it is likely that Nesprin-1 is mislocalized to the endoplasmic reticulum (ER) in the C'TΔ8 mutant, as the ER and the perinuclear space form a contiguous membrane system.

Figure 45:
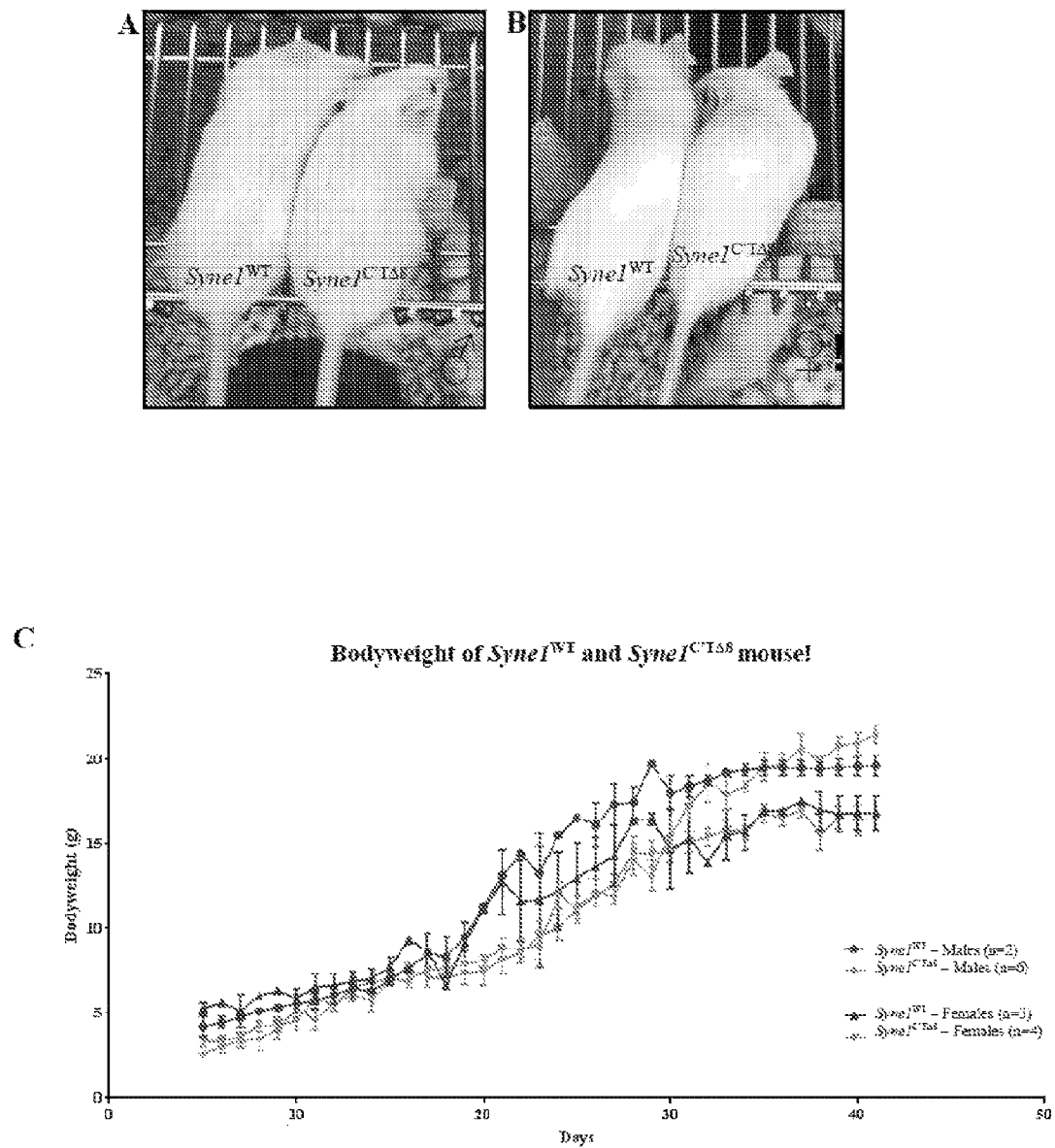
FIG. 45A-C shows Syne1 mutation does not affect mouse phenotype. (A-B) Representative images of 12-week-old male (A) and female (B) mice. (C) Bodyweight of male and female, wildtype (WT) and Syne1C'TΔ8 mutant, mice over 6 weeks.

Similar to one previously reported Nesprin-1 mouse model [Zhang et al., Development 134(5): 901-8 (2007)], and in contrast to two other models [Puckelwartz at al., Hum Mol Genet 18: 607-620 (2009); Zhang et al., Hum Mol Genet 19: 329-341 (2010)], the disrupted KASH domain of Nesprin-1 results in no overt phenotypic differences between the Syne1 wildtype (WT) and Syne1C'TΔ8 mutant (FIG. 45A-B). Both male and female homozygous mutants were fertile with no significant differences in body weight between the Syne1WT and Syne1C'TΔ8 mice (FIG. 45C). Syne1C'TΔ8 mice also did not exhibit any growth retardation or obvious muscle dystrophy, nor did they display any difficulty in movement or grooming, which can be indications of muscle deterioration.

Figure 46A:
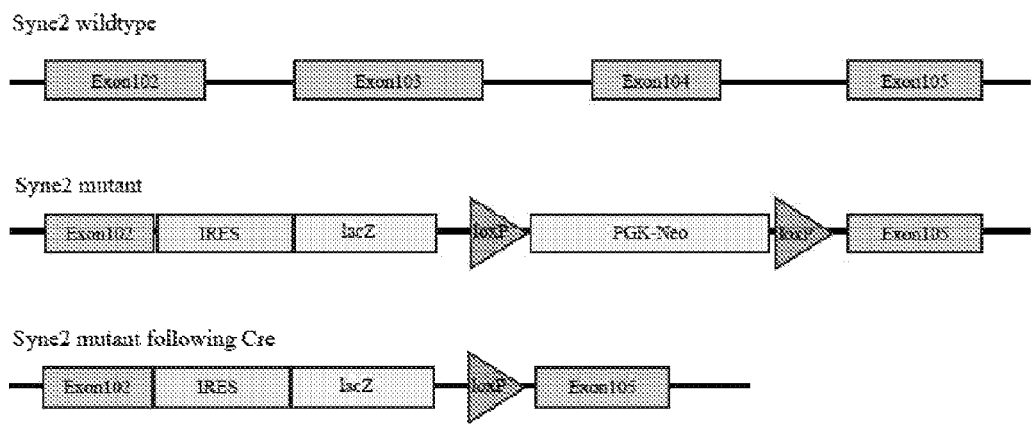
FIGS. 46A-46C shows Syne2 constructs and Syne1/Syne2 double mutant mice experience perinatal lethality.
Figure 46B:
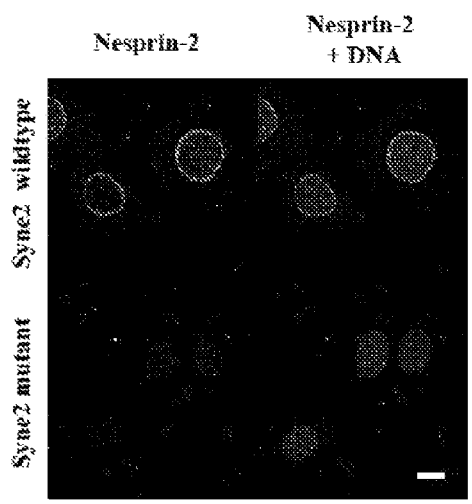
Figure 46C:
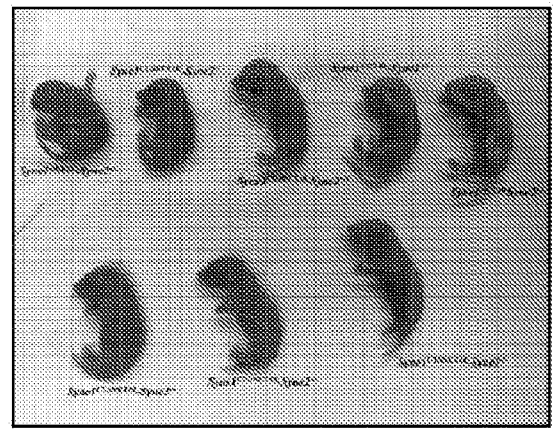

In order to probe the role of other KASH domain proteins in Lnma pathology, mice mutant for Syne2, encoding Nesprin-2, were generated by conventional gene targeting (FIG. 46A). To characterize the mutation, immunofluorescence microscopy of tail tip fibroblasts was carried out. Syne2+homozygous mutant fibroblasts expressed little to no Nesprin-2 (FIG. 46B). Consistent with previous findings [Zhang at al., Development 134(5): 901-8 (2007)], while Syne2$^{-/-}$ mice were overtly normal, with no growth retardation or infertility, Nesprin-1/2 double mutant mice (Syne1$^{C'TΔ8/C'TΔ8}$:Syne2$^{-/-}$) were perinatal lethals (FIG. 46C).

Disruption of Nesprin-1 KASH Domain Ameliorates Lmna Pathologies

Figure 24:
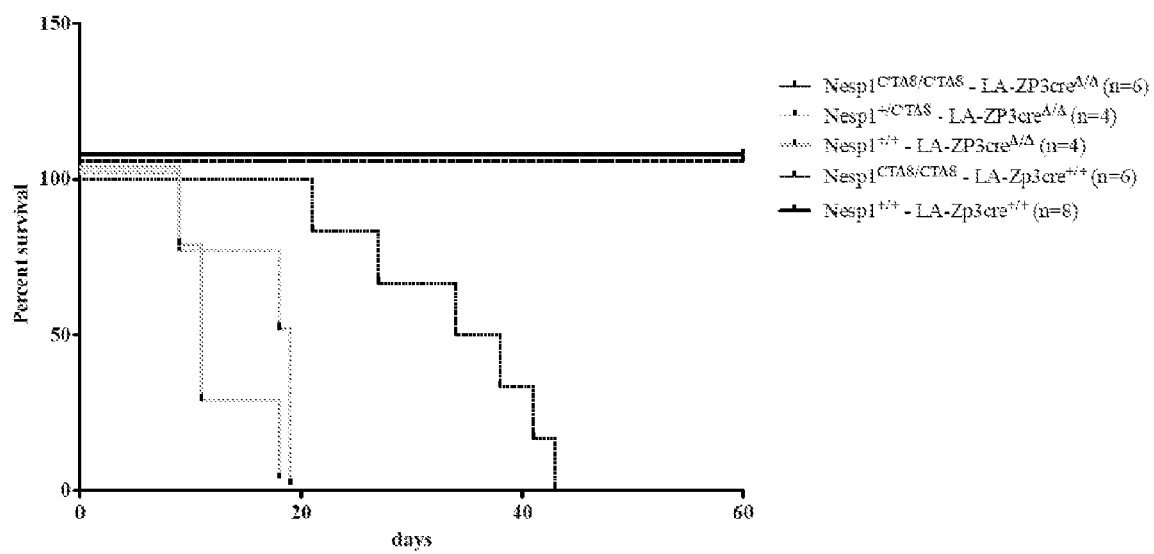
FIG. 24 is a Kaplan Meier curve showing that wild type (C57/Bl6) mice with or without a Nesprin-1 KASH-disrupting (C'TΔ8) mutation have a normal lifespan. Mice with a Lmna null/KO mutation (LA-ZP3cre$^{\Delta/\Delta}$) and wildtype (Nesp1$^{+/+}$) or heterozygous (Nesp1$^{+/C'T\Delta 8}$) for Nesp1-C'TΔ8 have a median lifespan of 15 or 18 days, which is increased to 38 days in Lmna KO/homozygous Nesp1 mutant (LA-ZP3cre$^{\Delta/\Delta}$; Nesp1$^{C'T\Delta 8/C'T\Delta 8}$) mice.
Figure 47:
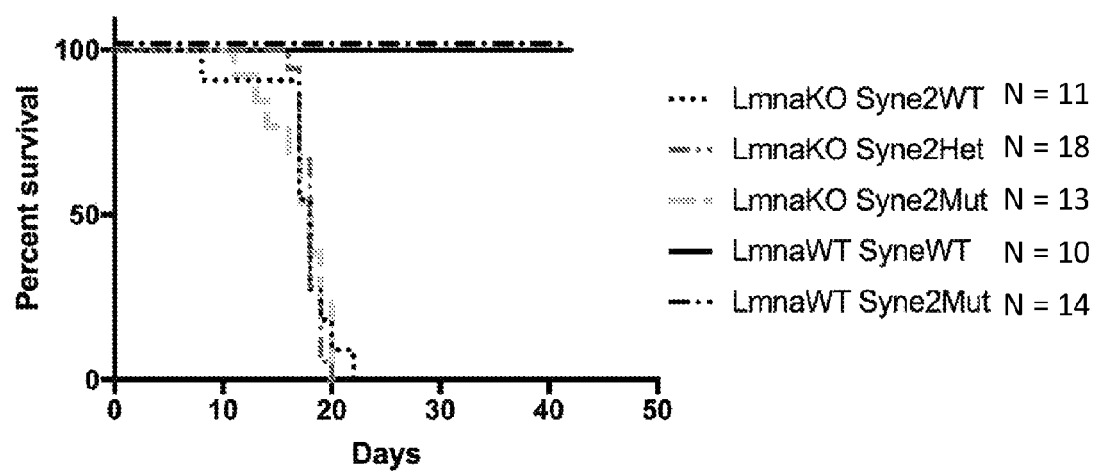
FIG. 47 is a Kaplan Meier graph showing a Syne2 mutation does not ameliorate Lmna pathology. Kaplan-Meier survival curve showing that regardless of their Syne2 mutation status (wildtype, heterozygous or mutant), Lmna$^{\Delta/\Delta}$ mice die within 3 weeks of birth.

Even though Nesprin-1 was still expressed, Nesprin-1-containing LINC complexes would not be formed in Syne1$^{C'TΔ8/C'TΔ8}$ cells and animals. Since AAV-mediated disruption of the LINC complex using dominant negative Sun1 in vivo rescues Lmna pathologies (Example 5), we reasoned that the "KASH-less" Nesprin-1 mutant allele we generated might also rescue Lmna pathology. To test this hypothesis, mice heterozygous for a Lmna null (Lmna$^{Δ/Δ}$) allele (Example 1) were intercrossed with Syne1C'TΔ8 mice to obtain Lmna$^{Δ/Δ}$:Syne1$^{C'TΔ8/C'TΔ8}$ double mutant mice. While Lmna$^{Δ/Δ}$ mice lived for 15-17 days, Lmna$^{Δ/Δ}$:Syne1$^{C'TΔ8/C'TΔ8}$ double mutant mice lived for up to 42 days (FIG. 24). Lmna null mice heterozygous for the Syne1$^{C'TΔ8}$ allele did not experience any lifespan extension. Lmna$^{Δ/Δ}$ mice on a Syne2$^{-/-}$ homozygous mutant background also did not experience lifespan extension (FIG. 47), indicating that Lmna pathology is mediated primarily by Nesprin-1/Sun1 LINC complexes.

Figure 25:
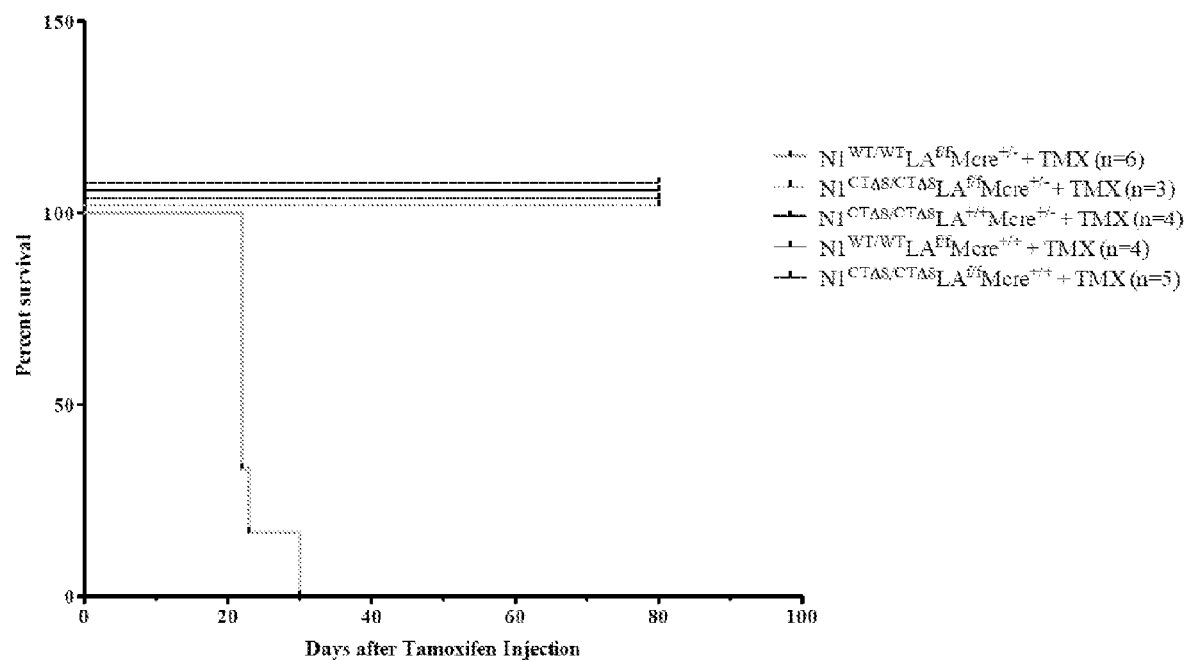
FIG. 25 is a Kaplan Meier curve showing that mice with wildtype Lmna (N1$^{CT\Delta 8/CT\Delta 8}$LA$^{+/+}$MCre$^{+/-}$), or floxed alleles of Lmna but lacking a cardiac-specific Cre driver (N1$^{CT\Delta 8/CT\Delta 8}$LA$^{f/f}$MCre$^{+/+}$ and N1$^{WT/WT}$LA$^{f/f}$MCre$^{+/+}$), live for length of the experiment (~80 days at priority filing, which extended to 120 days unchanged). Mice with a cardiomyocyte-specific deletion of Lmna (N1$^{WT/WT}$LA$^{f/f}$MCre$^{+/-}$) have a lifespan of 22-24 days following induction of the Cre/loxP-mediated deletion by tamoxifen (TMX) delivery, which is increased to the length of the experiment in mice with a cardiomyocyte-specific deletion of Lmna induced by TMX and also homozygous mutant for Nesprin-1 (N1$^{CT\Delta 8/CT\Delta 8}$LA$^{f/f}$MCre$^{+/-}$).

To examine the effect of the Syne1$^{C'TΔ8/C'TΔ8}$ allele in mice with cardiac-specific loss of Lmna, mice homozygous for a conditional Lmna$^{Flx/Flx}$ allele carrying the inducible cardiomyocyte specific Cre Tg(Myh6-cre/Esr1) (here abbreviated to mcm), in which Cre is induced by a single injection of tamoxifen (Tmx), were used as described in Examples 1-2. Cardiac-specific deletion of Lmna results in death within a month, but mice with the same deletion induced on a homozygous Syne1$^{C'TΔ8/C'TΔ8}$ background lived for at least 120 days after Tmx induction (FIG. 25; no change from day 80-120).

Example 7

Method for Screening Small Molecules that Block SUN-KASH Interactions

Figure 5A:
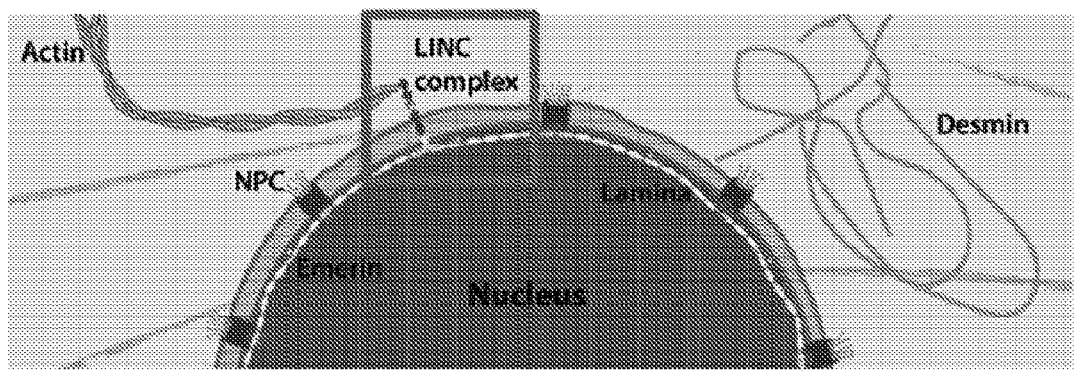
FIGS. 5A-5B show schematics of a LINC complex (FIG. 5A) and Interaction between KASH and SUN (FIG. 5B).
Figure 5B:
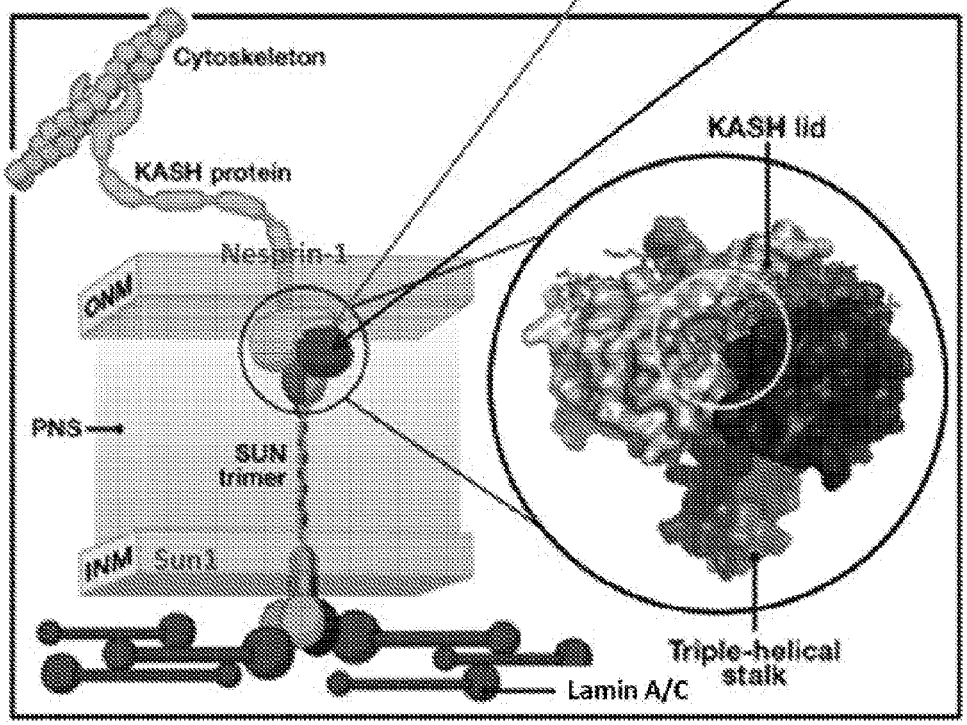
Figure 6A:
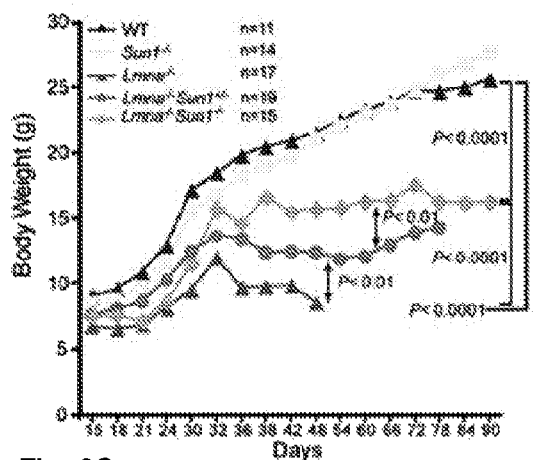
FIG. 6 shows defects in body weight and longevity in $Lmna^{-/-}$ and $Lmna\Delta9$ mice are ameliorated in homozygous Sun1 knockout $Lmna^{-/-} Sun1^{-/-}$ and $Lmna\Delta9Sun1^{-/-}$ animals. (A) Body weights are averages from mice with the indicated genotypes. The number (n) of animals used Is Indicated. (B) Kaplan-Meier graph showing Increased life span of $Lmna^{-/-}Sun1^{-/-}$ compared to $Lmna^{-/-}$ mice. Median survival of wild-type or $Sun1^{-/-}$ is >210 days in a 7 month follow up; $Lmna^{-/-}$ mice have median survival of 41 days; $Lmna^{-/-}Sun1^{+/-}$ mice have a median survival of 54 days; $Lmna^{-/-} Sun1^{-/-}$ mice have a median survival of 104 days ($p<0.01$ comparing $Lmna^{-/-}$ and $Lmna^{-/-} Sun1^{-/-}$). (C) Body weights of $Lmna\Delta9$ mice that are wild-type, heterozygous, or homozygous for Sun1 deficiency. Wild-type and $Sun1^{-/-}$ cohorts are graphed for comparison. Values are averages ± SEM from animals in each cohort. Number (n) of animals is indicated ($p<0.0001$ comparing $Lmna\Delta9Sun1^{+/+}$ and $Lmna\Delta9Sun1^{-/-}$). (D) Kaplan-Meier graph showing increased life span of $Lmna\Delta9Sun1^{-/-}$ compared to $Lmna\Delta9Sun1^{+/+}$ mice. $Lmna\Delta9Sun1^{+/-}$ mice are also graphed. ($p<0.0001$ comparing $Lmna\Delta9Sun1^{+/+}$ and $Lmna\Delta9Sun1^{-/-}$). (E) Cell proliferation of the indicated MEFs. Curves are averages±SD, representative of >3 independent isolates from embryos of the indicated genotypes. (F) Proliferation curves of MAFs (mouse adult fibroblasts) from WT. $Sun1^{-/-}$, $Lmna\Delta9Sun1^{+/+}$ and $Lmna\Delta9Sun1^{-/-}$ mice. MAFs were seeded at a density of 1000 cells per well. Growth was measured, and normalized cell indexes (averages±SD) are presented.
Figure 6B:
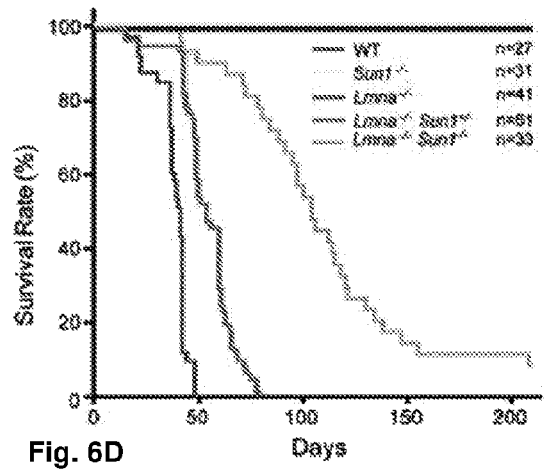
Figure 6C:
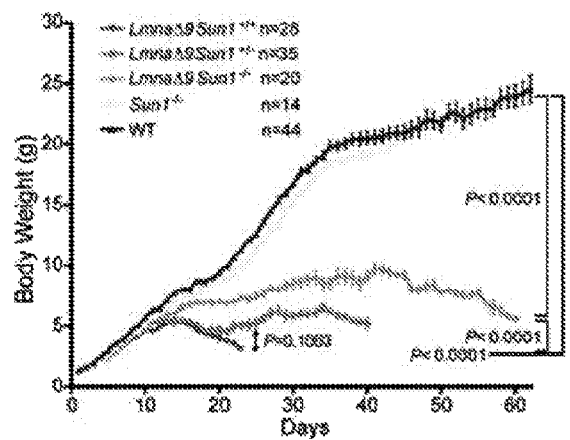
Figure 6D:
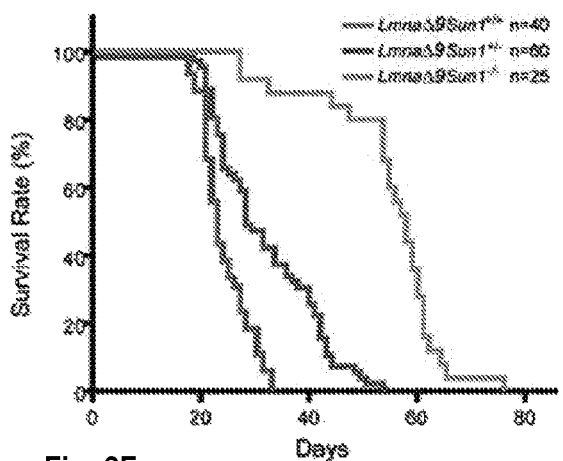
Figure 6E:
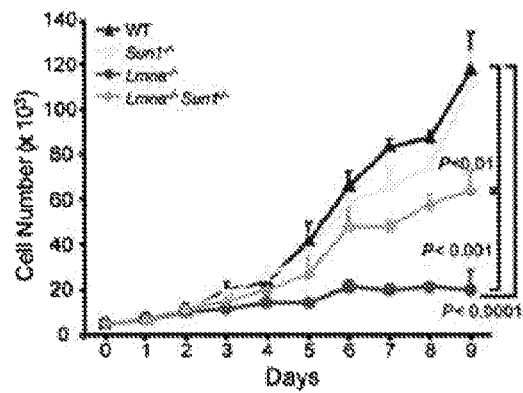
Figure 6F:
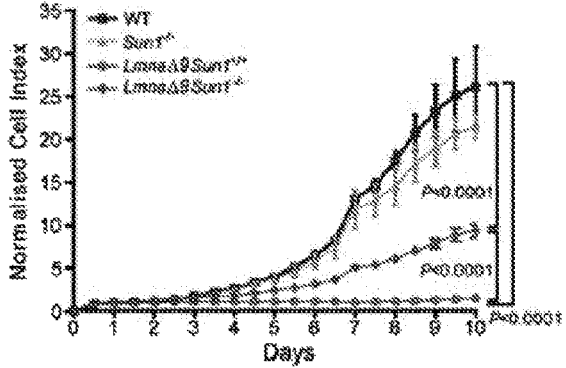
Figure 7:
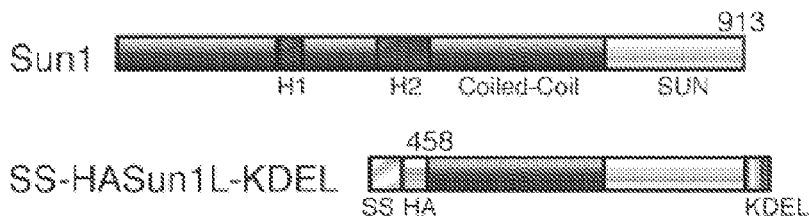
FIG. 7 shows a schematic of the features of the Sun1 protein and the components used to generate a dominant negative Sun1 protein, including a signal sequence, oiled-coil sequence, SUN domain sequence and KDEL sequence.
Figure 8:
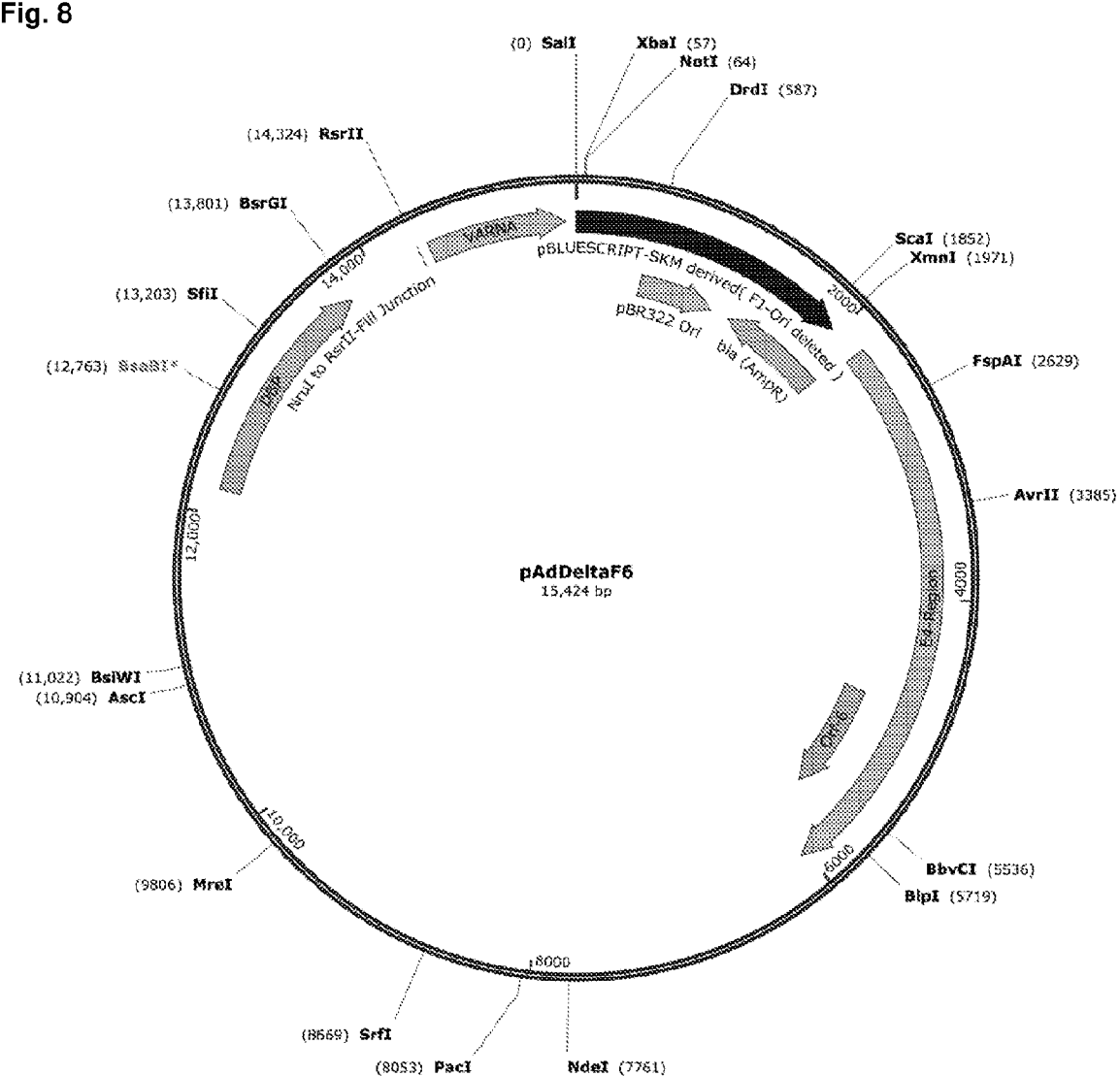
FIG. 8 shows a schematic of a plasmid (SEQ ID NO: 1) used for AAV production.
Figure 9:
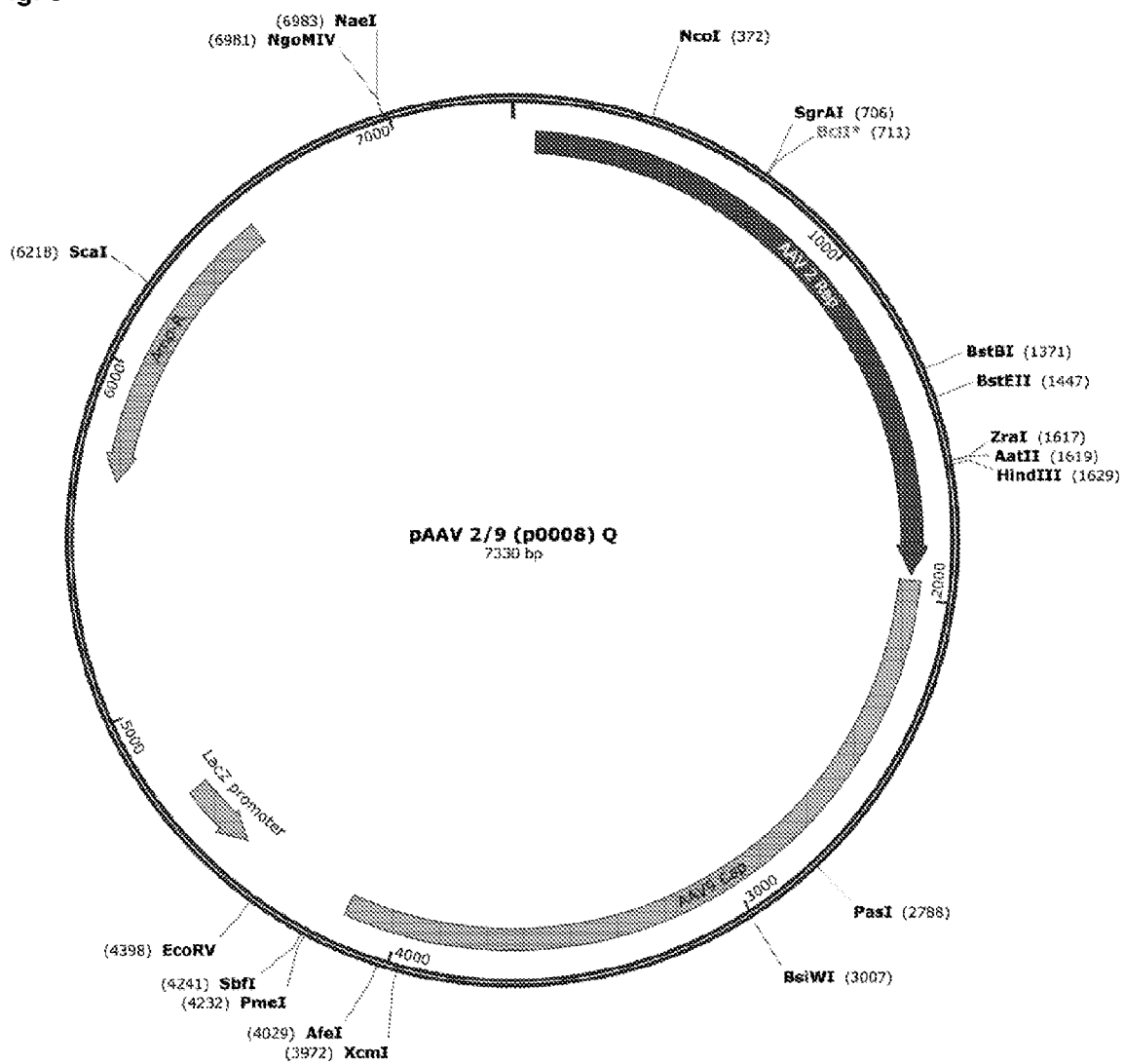
FIG. 9 shows a schematic of a plasmid (SEQ ID NO: 2) comprising sequences from AAV2 and AAV9 for AAV production.
Figure 21:
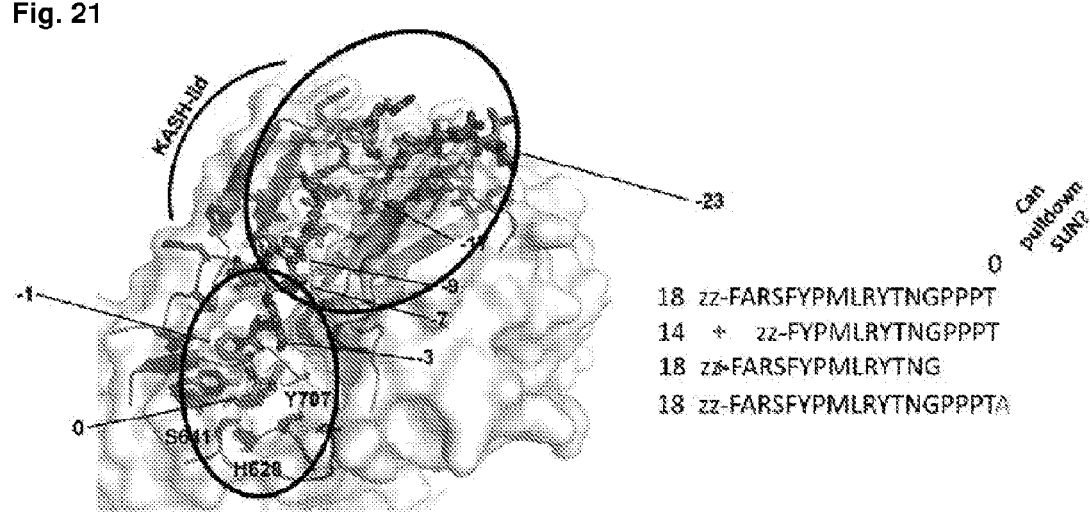
FIG. 21 shows C-terminal amino acids of the KASH domain of Nesprin-2 (KASH2). The 14 or 18 amino acid sequence from KASH2 C-terminus are able to physically interact with the SUN domain of SUN2. Loss of the last 4 amino acids from KASH2 or addition of a single alanine amino acid at the C-terminus of KASH2 is sufficient to disrupt interaction of the KASH2 domain with the SUN domain.
Figure 22:
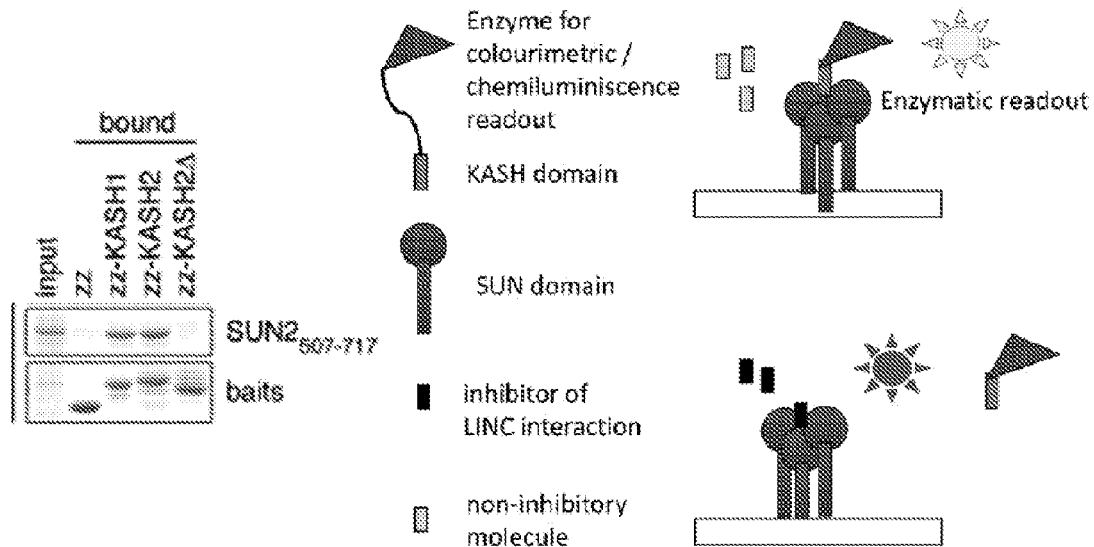
FIG. 22 shows a schematic of a screening method for detecting agents that disrupt the LINC complex.

Crystallographic studies of human SUN2 reveal that the SUN domain is assembled as a clover-like trimeric structure [Sosa et al., Cell 149(5): 1035-47 (2012)]. Trimerization is mediated by a triple-helical coiled-coil, with an estimated length of 40-45 nm. This is sufficient to bridge the perinuclear space (PNS), allowing SUN and KASH domains to directly interact [Sosa et al., Cell 149(5): 1035-47 (2012)]. The KASH binding site is formed primarily within a groove formed at the interface between adjacent SUN domains (FIG. 5B; FIG. 21 left panel). This groove accommodates part of the KASH domain, about 18 residues, in an extended conformation. However, it is the C-terminal tetrapeptide of the KASH domain, featuring three proline residues followed by a terminal aliphatic reside, Leu or Thr (for Nesp1 and Nesp2 respectively), that is crucial for the SUN-KASH interaction (FIG. 21 right panel, adapted from FIG. 1 of Sosa et al, Cell 149(5): 1035-47 (2012). The significance of this tetrapeptide is that it is situated in a well-defined pocket formed within a single SUN monomer. Modification of this peptide in any way, including the addition of a single residue (an Ala) at the C-terminus, completely eliminates the SUN-KASH association over the entire SUN-KASH contact region (Sosa et al., Cell 149(5): 1035-47 (2012) and FIG. 22 left panel). The conclusion is that while stable binding of the KASH domain requires 18-20 residues, it is the C-terminal tetrapeptide that actually initiates binding. Thus, blocking the tetrapeptide binding-pocket within the SUN monomer will abolish SUN-KASH association. We have described in this disclosure an AAV-based gene therapy strategy to break endogenous SUN-KASH interactions as a treatment for laminopathies, including dilated cardiomyopathy. Alternatively, a small molecule that blocks the SUN-KASH interaction at the SUN binding pocket would disrupt LINC complexes and similarly treat laminopathies. A variety of standard methods exist to screen for small molecule drugs in vitro.

An in vitro screen can be set up employing recombinant SUN and KASH domains or KASH peptide, for which methods of production have been previously published [Sosa at al., Cell 149(5): 1035-47 (2012)]. One such screen involves an assay technique analogous to an enzyme-linked immunosorbent assay (FIG. 22 right panel, similar to Lepourcelet et al., Cancer Cell. 5(1):91-102 (2004)). Recombinant SUN domain is immobilized on a solid surface, typically in 98-well plates, and then complexed with recombinant KASH domain linked to an enzyme that can generate a colorimetric or chemiluminescent readout. One method for enabling this linkage is to synthesize a biotinylated KASH peptide, which can then be linked with commercially available streptavidin-horseradish peroxidase (HRP) conjugate. Candidate compounds are obtained from appropriate suppliers and screened for their ability to inhibit KASH-SUN associations in vitro. Compounds that fail to inhibit the SUN-KASH interaction will result in a well in the plate where the recombinant SUN binds to the enzyme-linked KASH domain. Following wash steps and incubation with colorimetric or chemiluminescent HRP substrates, the presence of the SUN-KASH interaction is detected in standard plate readers. If the compound can inhibit SUN-KASH interaction then, following the wash step, the KASH domain is removed and there would be reduced or no enzymatic reaction in the well.

Alternatively, fluorescence anisotropy or polarization can be used to screen for small molecule inhibitors of SUN-KASH interactions in vitro [Lea, W. A., and Simeonov, A. Expert Opin Drug Discov 6: 17-32 (2011)]. This assay also employs recombinant SUN and KASH domains. The KASH domain is fluorescently labeled; for example a chemically synthesized KASH peptide could be readily functionalized with a fluorescein moiety. Fluorescence anisotropy of the interacting KASH domain interacting with SUN domain can be measured using standard equipment such as a plate reader. A small molecule inhibitor that disrupts the SUN-KASH interaction can be readily detected as the fluorescence anisotropy of the fluorescent KASH will change if it is not bound to SUN.

Figure 23:
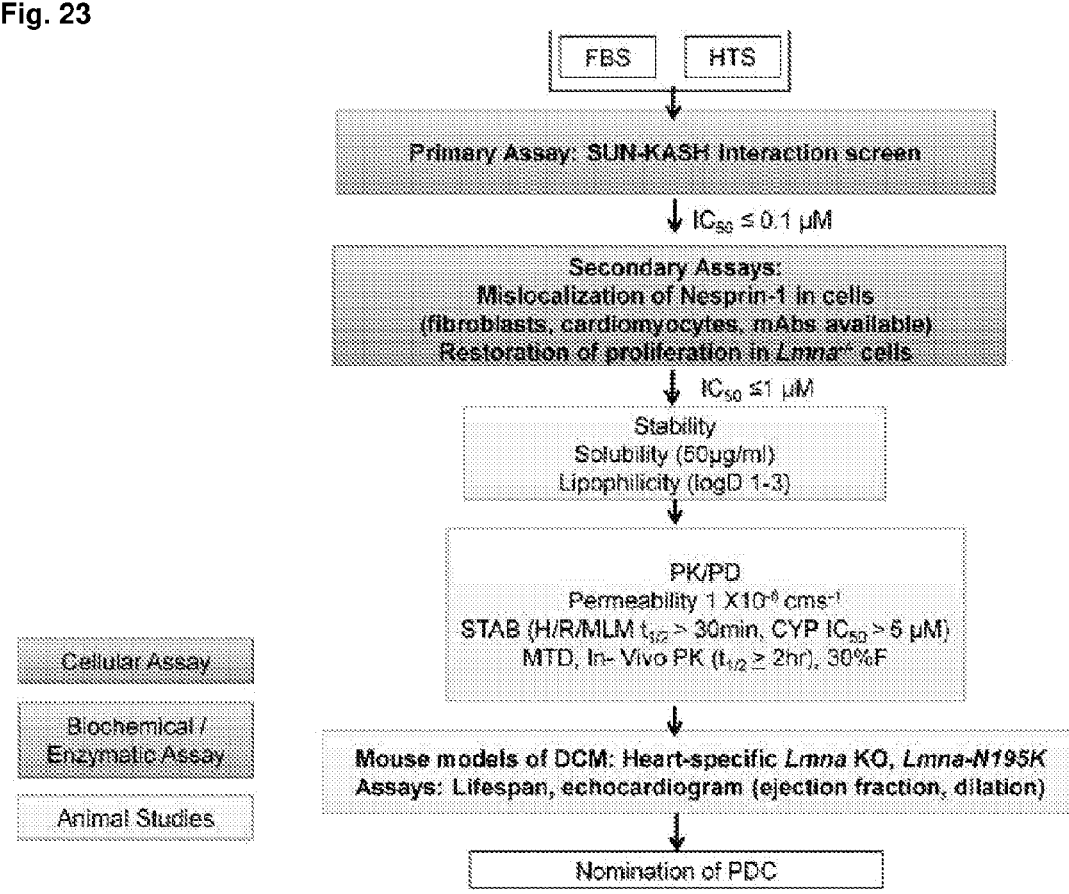
FIG. 23 shows a flowchart showing a more detailed screening method for identifying a small molecule to disrupt the LINC complex.

As is typical in drug screening campaigns, the compounds which successfully pass the in vitro primary screen will then be subjected to cell-based secondary screens (FIG. 23). In this case, immunofluorescence microscopy will be employed to identify those compounds that can dissociate LINC complexes. This is manifest as dispersal of the KASH component to the peripheral endoplasmic reticulum while the cognate SUN protein is retained in the inner nuclear membrane. This microscopy-based assay can be performed first on HeLa cells. Active compounds are then evaluated on cultured cells from disease-relevant tissue, such as cardiac cells. An additional secondary screen may include the ability of the identified compound to rescue proliferation defects in Lmna knockout cells. Following hit-to-lead optimization of the identified compound using standard methods, the compound can be tested in mouse models of laminopathies such as those described herein for Lmna dilated cardiomyopathy. Efficacy of the leads can be evaluated using lifespan of the mutant mice and echocardiograms, as described herein, to assess heart function.

DISCUSSION

DCM caused by LMNA is regarded as being aggressive, and often leads to premature death or cardiac transplantation [M. Pasotti et al., *J Am Coll Cardiol* 52: 1250-1260 (2008); M. R. Taylor et al., *J Am Coll Cardiol* 41: 771-780 (2003)]. By 60 years, 55% of LMNA mutation carriers die of cardiovascular failure or receive a heart transplant, compared with 11% of patients with idiopathic cardiomyopathy. Attempts to ameliorate DCM by fitting a pacemaker have been at best of transient benefit. Consequently it is necessary develop new therapeutic avenues to treat DCM caused by LMNA mutations.

The majority of LMNA mutations causing DCM are dominant negative missense. Treatment by conventional gene therapy to repair each mutation would be daunting and removal of the mutated allele, leaving the patient hemizygous for the remaining normal WT allele may also result in heart failure [G. Bonne et al., *Nature genetics* 21: 285-288 (1999)]. Various other routes downstream of the Lamin gene have been explored for potential therapeutic intervention, and have included mTOR inhibition with rapamycin/rapalogues [J. C. Choi et al., *Science translational medicine* 4: 144ra102 (2012); F. J. Ramos et al., *Science translational medicine* 4: 144ra103 (2012)] and inhibition of the MEK1/2 kinase pathway [W. Wu, et al., *Circulation* 123: 53-61 (2011)]. Both avenues, resulted in improved ventricular function and increased longevity (10-40%) but the extent and long-term efficacy was significantly less than that we observed with the loss of Sun1.

The molecular mechanisms underlying the varied phenotypes of the laminopathies are still not well understood, though two alternative hypotheses have been proposed to explain the tissue-specific pathologies. The first "gene regulation hypothesis" proposes that LMNA mutations/loss disrupt the equilibrium of various molecular pathways due to the mutations altering interactions with NE proteins and chromatin, which in turn alter gene expression. Evidence in support of this hypothesis comes from studies reporting changes in signalling pathways including the AKT-MTOR pathway [J. C. Choi et al., *Science translational medicine* 4: 144ra102 (2012)], WNT/β-catenin pathway [L. Hernandez et al., *Dev Cell* 19: 413-425 (2010); C. Le Dour et al., *Hum Mol Genet* 26: 333-343 (2017)], TGF-β/Smad [J. H. Van Berlo et al., *Hum Mol Genet* 14: 2839-2849 (2005); T. V. Cohen et al., *Hum Mol Genet* 22: 2852-2869 (2013)], MAP Kinase pathway [A. Brull, et al., *Front Physiol* 9: 1533 (2018)] and the ERK1/2-CTGF/CCN2 pathway [M. Chatzifrangkeskou et al., *Hum Mol Genet* 25: 2220-2233 (2016)]. While these changes have been documented, none has clearly established whether these changes are not a secondary compensatory effect of a diseased tissue. Sun1 also fits into this rubric of disrupted expression levels as Sun1 protein, but not mRNA, is upregulated in laminopathies, leading to the proposal that laminopathy phenotypes are caused by toxicity from excess Sun1 [C. Y. Chen et al., *Cell* 149: 565-577 (2012)].

Figure 32A:
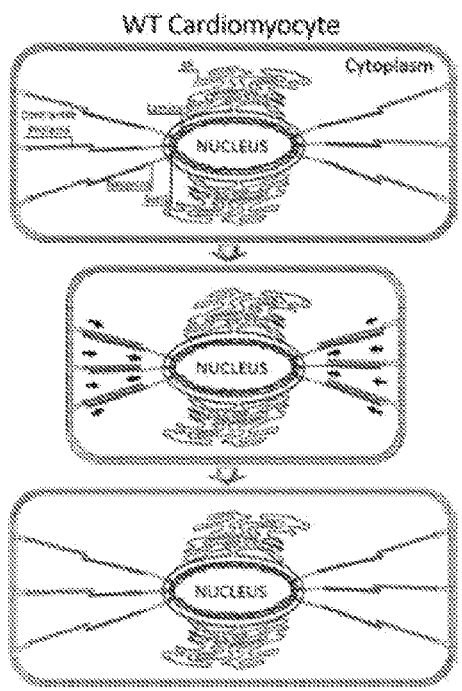
FIGS. 32A-32D shows models of how breaking the LINC by disrupting Sun1 protects cardiomyocytes from contraction induced stress (FIG. 32A) Cardiomyocyte nuclei expressing LmnaA/C, are able to withstand mechanical stress and tension forces transmitted via the LINC complex from the cytoplasm to the NE.
Figure 32B:
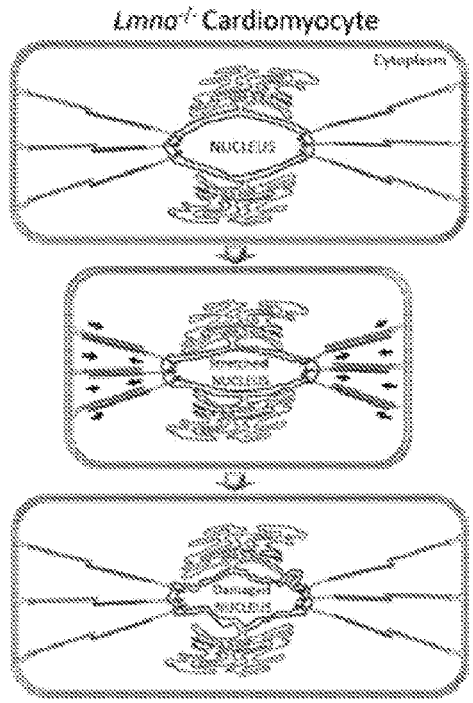
Figure 32C:
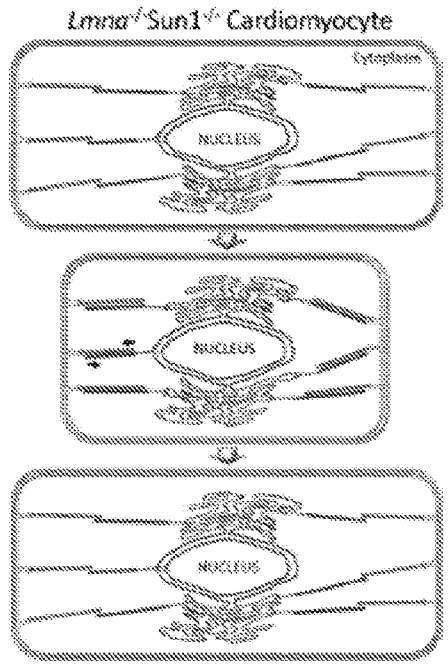

The second hypothesis suggested Lmna loss or mutation leads to Increased nuclear fragility. As a result mechanical stress and tension forces transmitted via the LINC complex from the cytoplasm to the NE causes damage to the NE [J. Lammerding et al., *J Clin Invest* 113: 370-378 (2004)]. This hypothesis is similar to that proposed for Duchenne muscular dystrophy (DMD), where loss of dystrophin increases the fragility of the muscle cell membrane and when tension-stress forces are applied during muscle contraction this results muscle cell rupture and death [D. J. Blake, et al., *Physiol Rev* 82: 291-329 (2002)]. Lmna mutant fibroblasts show nuclear deformation, defective mechanotransduction, and reduced viability when subjected to mechanical strain, together with increased nuclear rupture at low and moderate pressures when compared to WT nuclei [J. Lammerding et al., *J Clin Invest* 113: 370-378 (2004); J. Lammerding et al., *J Cell Biol* 170: 781-791 (2005); J. Lammerding et al., *J Biol Chem* 281: 25768-25780 (2006)]. In contracting mouse cardiomyocytes, mechanical stress and tension forces caused by 500-600 contractions per minute are transmitted to the NE via the LINC complex, resulting in nuclear distortion, damage and eventual death/loss as described in FIGS. 28 and 29. Presumably, such forces would cause significant damage to the fragile NE of Lmna null cardiomyocytes, resulting in CM death. If the tension-stress hypothesis is damaging to the NE, then unlinking the LINC complex, by disrupting SUN1, would reduce the tension-stress on the CM nuclei, and prevent CM cell death in the mutant CMs (FIG. 32A-C). One caveat here is that complete disruption of the LINC complex, as would be the case following overexpression of DN-Sun1, could potentially be deleterious rather than therapeutic. At the cellular level, multiple mechanical phenomena including intracellular force transmission, cell polarization and migration, were impacted following LINC complex disruption by dominant negative SUN and KASH constructs [Lombardi et al., *J Biol Chem* 286(30):26743-53 (2011)]. In animal models, Sun1/Sun2 [Lai et al., *Proc Natl Acad Sci* 106(25):10207-12 (2009)] and Nesprin-1/Nesprin-2 [Zhang et al., *Development* 134(5):901-8 (2007)] double mutant mice experience perinatal lethality and cardiac-specific disruption of the KASH domains of Nesprin-1 and Nesprin-2 using an embryonic cardiac Cre driver (Nkx2.5-Cre) results in early onset cardiomyopathy [Banerjee et al., *PLOS Genet* 10(2): e1004114 (2014)].

Figure 32D:
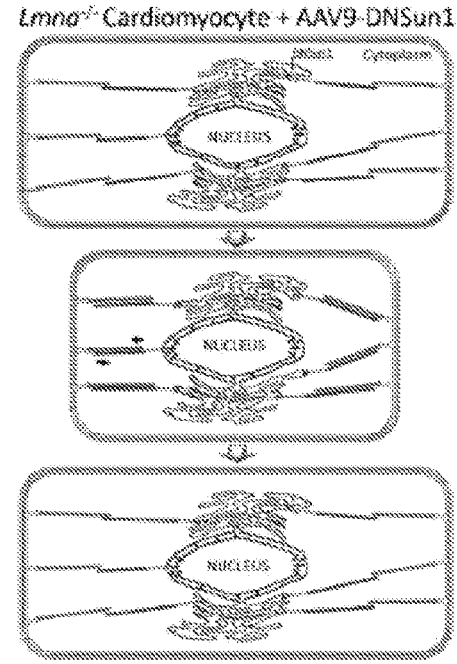

We attempted to distinguish the tension-stress hypothesis from the expression level hypothesis in cardiomyocytes, using a DN-Sun1 construct to compete with endogenous Sun1 and Sun2 proteins for KASH-domain-binding and so unlink the LINC complex without directly altering Sun1 levels (FIGS. 32D & 34). The AAV9 vector, which has a high affinity for CM, was used to deliver DN-Sun1 under the cTnT promoter to CMs [C. Zincarelli, et al., *Mol Ther* 16: 1073-1080 (2008)]. Our results showed the successful delivery of GFP to cardiomyocytes (FIG. 31C), and robust expression of both the control GFP and DN-Sun1 proteins (FIG. 31C) with the latter resulting in the dispersal of the KASH domain proteins from the cardiomyocyte nuclei (FIG. 31D). Surprisingly, not only did AAV-DN-Sun1 ameliorate the pathology in mice with depleted cardiac Lmna levels, it also had no discernible effect on the cardiac health of wildtype mice, which would be expected to also experience complete LINC complex disruption in their hearts (FIGS. 31E & G). This suggests that an intact LINC complex may be required in embryonic development, but not postnatally.

In addition, using CRISPR/Cas9 in nice, we generated a Syne1 mutant allele (C'TΔ8) that gave rise to a truncated Nesprin-1 protein with a disrupted, non-functional, KASH domain. Mice lacking Lmna globally or in the heart have a shortened lifespan, but the presence of a homozygous Syne1$^{C'T\Delta 8/C'T\Delta 8}$ mutation resulted in significant lifespan extension. Loss of Sun1 or AAV-mediated disruption of the LINC complex by dominant negative transgenes in vivo resulted in similar rescue of Lmna pathology (Example 2-5), while Sun2 and Nesprin-2 mutations did not. Taken together, these data suggest that LINC complexes comprised of Sun1 and Nesprin-1 drive the pathology in Lmna mutant cells and animals.

There have been a number of reports on the use of AAV to deliver CRISPR/Cas components in vivo for treating diseases. Our results predict that AAV-mediated CRISPR/Cas, such as CRISPR/Cas9, delivery to target the Nesprin-1 KASH domain in disease-affected tissue can be used to treat laminopathies, including dilated cardiomyopathy. For instance, cardiotropic AAVs (e.g. AAV9) can be used to deliver transgene cassette(s) containing a cardiac-specific promoter (e.g. cTnT) driving Cas endonuclease enzyme expression and an appropriate promoter (e.g. U6) driving gRNA expression to treat LMNA DCM. Since the packaging capacity of AAV is limited to 4.7 kb, a smaller Cas9 derived from *Staphylococcus aureus* (saCas9) rather than the larger, more commonly used, *Streptococcus pyogenes* Cas9 may be preferred. Alternatively, other CRISPR enzymes such as Cpf1, which is small enough for AAV packaging and has a more commonly found protospacer adjacent motif (PAM) than saCas9, could be used [Zetsche, B., et al., Cpf1 Is a Single RNA-Guided Endonuclease of a Class 2 CRISPR-Cas System. *Cell* 163, 759-771 (2015)].

Guide RNAs would target the 3' region of the Nesprin-1 gene encoding the KASH domain (Table 3). While we have targeted the region adjacent to the stop codon, in principle any gene region encoding the KASH domain could be targeted as indels generated by CRISPR would likely result in frameshift mutations that disable the KASH domain. However, as the final 4 amino acids in the KASH domain are known to be absolutely required for SUN domain interaction and hence LINC complex formation [Sosa et al., *Cell* 149(5):1035-47 (2012)], it is prudent to select gRNA in the vicinity of the stop codon as even indels that do not result in a frameshift could still mutate the relevant KASH amino acids required for the SUN-KASH interaction. Furthermore, it should be noted that because the Syne1 gene encoding Nesprin-1 is very large and has multiple splice isoforms and alternative start sites, guide RNAs targeted outside the KASH domain, while giving rise to some mutant Nesprin-1 isoforms, may not perturb expression of other isoforms of Nesprin-1 protein, including KASH-containing isoforms. This would result in formation of functional or partially functional Nesprin-1/Sun1 LINC complexes that would still be able to drive pathology in Lmna mutants. This CRISPR/Cas9 strategy likely cannot be extended to the KASH domain of Nesprin-2, since Lmna$^{\Delta/\Delta}$:Syne2$^{-/-}$ mice are phenotypically indistinguishable from Lmn$^{\Delta/\Delta}$ mice.

We did not further investigate the Sun1 mutant mice generated in this study as instead of mice with Sun1 lacking the SUN domain, we essentially obtained Sun1 null mice, which have already been well characterized. We suspect that inducing CRISPR mutation in Sun1 resulted in nonsense-mediated decay (NMD) of Sun1 transcript. Occurrence of a premature termination codon (PTC) 50-55 nucleotides upstream of a exon-exon junction is a trigger for NMD [Popp, M. W., and Maquat, L. E. *Cell* 165: 1319-1322 (2016)]. Also, PTCs occurring in the middle of a transcript are more likely to result in NMD [Eberle et al., *PLOS Biology* 6: e92 (2008); Reber et al., *MBoC* 29: 75-83 (2018)]. In the Sun1_plus4 mutant, the PTC is more than 55 nucleotides upstream of the exon-exon junction and is likely to trigger NMD. For the Sun1Δ7 mutant, the PTC is less than 50 nucleotides from the exon-exon junction. However for both mutants, since we targeted upstream of the sizeable SUN domain, the PTCs are roughly ⅔ of the way along the length of the transcript, and hence also likely to trigger NMD. In order to specifically disrupt the SUN domain in Sun1 without inducing a null mutation, we can adopt a similar strategy as for Nesprin-1—directing the guide RNA at the very 3' end of the coding region of the transcript (Table 3). Earlier work demonstrated that mutation of a tyrosine residue to phenylalanine at the C-terminus of SUN2 (Y707F) abolished KASH binding [Sosa et al., *Cell* 149(5): 1035-47 (2012)]. This critical tyrosine residue is conserved in SUN1 (Y812 in Uniprot E9PHI4) and present in the final coding exon of the SUN transcript. Selection of a gRNA 5' proximal to the codon for Y812 would produce Indel mutations that cause a frameshift mutation that would mutate Y812 and disrupt KASH binding. As the gRNA would be in the final coding exon, the likelihood of triggering NMD would be low. One can thus envision a CRISPR/Cas9-based strategy to treat laminopathies by targeting a critical residue required for KASH-binding in the SUN1 SUN domain. AAVs could be used to deliver CRISPR enzyme and gRNA targeting SUN in appropriate disease tissue, such as the heart. Incapacitation of SUN KASH binding would then ameliorate the deleterious effects of Lmna mutations.

From these results we propose that the loss of or mutations within Lmna causes instability in the CM nuclei due to loss or incorrect assembly of the nuclear lamina. This makes the nuclei susceptible to the tension/stress forces exerted via the LINC complex from the contractile sarcomeres of the CMs. In the absence of SUN1, or following mutation of Nesprin-1 KASH domain, the untethered LINC complexes exert less tensional force on the CM nuclei, enabling survival of the lamin deficient cardiomyocyte.

These results provide an opportunity to use the AAV-mediated delivery of DN-Sun, DN-KASH, or direct mutation of endogenous SUN or KASH proteins as potential therapeutics for laminopathy-related DCM in patients. The AAV system, as a therapeutic delivery route in patients is established and has been approved by the FDA for treating some diseases. It is becoming more widely used with multiple on-going clinical trials, including the introduction into patients with heart disease. However, even though tension-stress may be the primary cause for Lmna deficient CM death, disrupting SUN1 may not be effective in preventing LMNA mutation induced cell death in skeletal muscle, as Lmna$^{\Delta/\Delta}$:Sun$^{-/-}$ die at an earlier age than those mice where Lmna was specifically deleted in the CMs. Which muscle groups (or even other tissues lacking Lmna) result in the early lethality remain to be identified. However in most of the LMNA DCM patients it is heart failure that is the cause of death, and our results show that disrupting the LINC complex in CMs could be effective at preventing heart failure for an extended period.

BIBLIOGRAPHY

1. M. Ackers-Johnson et al., A Simplified, Langendorfif-Free Method for Concomitant Isolation of Viable Cardiac Myocytes and Nonmyocytes From the Adult Mouse Heart. *Circulation Research* 119: 909 (2016).
2. R. Agah et al., Gene recombination in postmitotic cells. Targeted expression of Cre recombinase provokes cardiac-restricted, site-specific rearrangement in adult ventricular muscle in vivo. *The Journal of clinical investigation* 100: 169-179 (1997).
3. S. G. Alam et al., The mammalian LINC complex regulates genome transcriptional responses to substrate rigidity. *Scientific reports* 6: 38063 (2016).
4. A. T. Bertrand et al., DeIK32-lamin A/C has abnormal location and induces incomplete tissue maturation and severe metabolic defects leading to premature death. *Hum Mol Genet* 21:1037-1048 (2012).
5. D. J. Blake, S. E. Newey, K. E. Davies, Function and genetics of dystrophin and dystrophin-related proteins in muscle. *Physiol Rev* 82: 291-329 (2002).
6. G. Bonne et al., Mutations in the gene encoding lamin A/C cause autosomal dominant Emery-Dreifuss muscular dystrophy. *Nature genetics* 21: 285-288 (1999).
7. A. Brull, B. Morales Rodriguez, G. Bonne, A. Muchir, A. T. Bertrand, The Pathogenesis and Therapies of Striated Muscle Laminopathies. *Front Physiol* 9: 1533 (2018).
8. A. Buchwalter, M. W. Hetzer, Nucleolar expansion and elevated protein translation in premature aging. *Nature communications* 8: 328 (2017).
9. B. Burke, C. L. Stewart, The nuclear lamins: flexibility in function. *Nat Rev Mol Cell Biol* 14: 13-24 (2013).
10. G. Captur et al., Lamin and the heart. *Heart* 104: 468-479 (2018).
11. M. Chatzifrangkeskou et al., ERK1/2 directly acts on CTGF/CCN2 expression to mediate myocardial fibrosis in cardiomyopathy caused by mutations in the lamin A/C gene. *Hum Mol Genet* 25: 2220-2233 (2016).
12. C. Y. Chen et al., Accumulation of the Inner nuclear envelope protein Sun1 is pathogenic in progeric and dystrophic laminopathies. *Cell* 149: 565-577 (2012).
13. Y. H. Chi et al., Requirement for Sun1 in the expression of meiotic reproductive genes and piRNA. *Development* 136: 965-973 (2009).
14. J. C. Choi et al., Temsirolimus activates autophagy and ameliorates cardiomyopathy caused by lamin A/C gene mutation. *Science translational medicine* 4: 144ra102 (2012).
15. M. Crisp et al., Coupling of the nucleus and cytoplasm: role of the LINC complex. *J Cell Biol* 172: 41-53 (2006).
16. T. V. Cohen et al., Defective skeletal muscle growth in lamin A/C-deficient mice is rescued by loss of Lap2alpha. *Hum Mol Genet* 22: 2852-2869 (2013).
17. W. N. de Vries et al., Expression of Cre recombinase in mouse oocytes: a means to study maternal effect genes. *Genesis* 26: 110-112 (2000).
18. Eberle, A. B., Stalder, L., Mathys, H., Orozco, R. Z., and Mühlemann, O. Posttranscriptional Gene Regulation by Spatial Rearrangement of the 3' Untranslated Region. *PLOS Biology* 6: e92 (2008).
19. D. Fatkin et al., Missense mutations in the rod domain of the lamin A/C gene as causes of dilated cardiomyopathy and conduction-system disease. *N Engl J Med* 341: 1715-1724 (1999).
20. Gimpel, P., et al., Nesprin-1α-Dependent Microtubule Nucleation from the Nuclear Envelope via Akap450 Is Necessary for Nuclear Positioning in Muscle Cells. *Curr. Biol.* 27: 2999-3009.e9. (2017).
21. F. Haque et al., Mammalian SUN protein interaction networks at the inner nuclear membrane and their role in laminopathy disease processes. *J Biol Chem* 285: 3487-3498 (2010).
22. L. Hernandez et al., Functional coupling between the extracellular matrix and nuclear lamina by Wnt signaling in progeria. *Dev Cell* 19: 413-425 (2010).
23. R. E. Hershberger, A. Morales, in *Gene Reviews((R))*, M. P. Adam et al., Eds. (Seattle (Wash.), 1993).
24. R. E. Hershberger, D. J. Hedges, A. Morales, Dilated cardiomyopathy: the complexity of a diverse genetic architecture. *Nat Rev Cardiol* 10: 531-547 (2013).
25. D. S. Herman et al., Truncations of titin causing dilated cardiomyopathy. *N Engl J Med* 366: 619-628 (2012).
26. H. F. Horn, LINC complex proteins in development and disease. *Current topics in developmental biology* 109: 287-321 (2014).
27. J. L. Jefferies, J. A. Towbin, Dilated cardiomyopathy. *Lancet* 375: 752-762 (2010).
28. Kim, D. I., Birendra, K. C., and Roux, K. J. (2015). Making the LINC: SUN and KASH protein Interactions. *Biol. Chem.* 396: 295-310.
29. T. J. Kirby, J. Lammerding, Emerging views of the nucleus as a cellular mechanosensor. *Nature cell biology* 20: 373-381 (2018).
30. J. Lammerding et al., Lamin A/C deficiency causes defective nuclear mechanics and mechanotransduction. *The Journal of clinical investigation* 113: 370-378 (2004).
31. J. Lammerding et al., Abnormal nuclear shape and impaired mechanotransduction in emerin-deficient cells. *J Cell Biol* 170: 781-791 (2005).
32. J. Lammerding et al., Lamins A and C but not lamin B1 regulate nuclear mechanics. *J Biol Chem* 281: 25768-25780 (2006).
33. Lea, W. A., and Simeonov, A. Fluorescence Polarization Assays in Small Molecule Screening. *Expert Opin Drug Discov* 8: 17-32 (2011).
34. C. Le Dour et al., Decreased WNT/beta-catenin signalling contributes to the pathogenesis of dilated cardiomyopathy caused by mutations in the lamin a/C gene. *Hum Mol Genet* 26: 333-343 (2017).
35. K. Lei et al., SUN1 and SUN2 play critical but partially redundant roles in anchoring nuclei in skeletal muscle cells in mice. *Proc Nat Acad Sci USA* 106: 10207-10212 (2009).
36. Lepourcelet et al., Small-molecule antagonists of the oncogenic Tcf/beta-catenin protein complex. *Cancer Cell.* 5(1): 91-102 (2004).
37. C. J. Malone, W. D. Fixsen, H. R. Horvitz, M. Han, UNC-84 localizes to the nuclear envelope and is required for nuclear migration and anchoring during *C. elegans* development. *Development* 126: 3171-3181 (1999).
38. L. C. Mounkes, S. V. Kozlov, J. N. Rottman, C. L. Stewart, Expression of an LMNA-N195K variant of A-type lamins results in cardiac conduction defects and death in mice. *Hum Mol Genet* 14: 2167-2180 (2005).

39. M. D. Muzumdar, B. Tasic, K Miyamichi, L. Li, L Luo, A global double-fluorescent Cre reporter mouse. *Genesis* 45: 593-605 (2007).
40. V. Nikolova et al., Defects in nuclear structure and function promote dilated cardiomyopathy in lamin A/C-deficient mice. *The Journal of clinical investigation* 113: 357-369 (2004).
41. M. Pasotti et al., Long-term outcome and risk stratification in dilated cardiolaminopathies. *J Am Coll Cardiol* 52: 1250-1280 (2008).
42. Popp, M. W., and Maquat, L. E. Leveraging Rules of Nonsense-Mediated mRNA Decay for Genome Engineering and Personalized Medicine. *Cell* 165:1319-1322 (2016).
43. K M. Prasad, Y. Xu, Z. Yang, S. T. Acton, B. A. French, Robust cardiomyocyte-specific gene expression following systemic injection of AAV: in vivo gene delivery follows a Poisson distribution. *Gene Ther* 18: 43-52 (2011).
44. Puckelwartz, M. J., et al., Disruption of nesprin-1 produces an Emery Dreifuss muscular dystrophy-like phenotype in mice. *Hum Mol Genet* 18: 607-620 (2009).
45. Ran F A, et al., Genome engineering using the CRISPR-Cas9 system. *Nat. Protoc* 8: 2281-2308 (2013);
46. Ran F A, at al., Double nicking by RNA-guided CRISPR Cas9 for enhanced genome editing specificity. *Cell* 154: 1380-1389 (2013)
47. F. J. Ramos et al., Rapamycin reverses elevated mTORC1 signaling in lamin A/C-deficient mice, rescues cardiac and skeletal muscle function, and extends survival. *Science translational medicine* 4: 144ra103 (2012).
48. Reber, S., et al., CRISPR-Trap: a clean approach for the generation of gene knockouts and gene replacements in human cells. *MBoC* 29:75-83 (2018).
49. T. Sieprath et al., Sustained accumulation of prelamin A and depletion of lamin A/C both cause oxidative stress and mitochondrial dysfunction but induce different cell fates. *Nucleus* 6: 230-246 (2015).
50. D. S. Sohal et al., Temporally regulated and tissue-specific gene manipulations in the adult and embryonic heart using a tamoxifen-inducible Cre protein. *Circ Res* 89: 20-25 (2001).
51. I. Solovei et al., LBR and lamin A/C sequentially tether pepheral heterochromatin and Inversely regulate differentiation. *Cell* 152: 584-598 (2013).
52. Sosa B A, Rothballer A, Kutay U, Schwartz T U, LINC complexes form by binding of three KASH peptides to domain interfaces of trimeric SUN proteins. *Cell* 149(5): 1035-47 (2012).
53. C. L. Stewart, S. Kozlov, L. G. Fong, S. G. Young, Mouse models of the laminopathies. *Exp Cell Res* 313: 2144-2156 (2007).
54. C. Stewart and B. Burke, RNAi-based therapies for cardiomyopathies, muscular dystrophies and laminopathies. WO2013/158046.
55. T. Sullivan et al., Loss of A-type lamin expression compromises nuclear envelope integrity leading to muscular dystrophy. *J Cell Biol* 147: 913-920 (1999).
56. E C. Tapley, D. A. Starr, Connecting the nucleus to the cytoskeleton by SUN-KASH bridges across the nuclear envelope. *Curr Opin Cell Biol* 25, 57-62 (2013).
57. U. Tayal, S. Prasad, S. A. Cook, Genetics and genomics of dilated cardiomyopathy and systolic heart failure. *Genome Med* 9: 20 (2017).
58. M. R. Taylor et al., Natural history of dilated cardiomyopathy due to lamin A/C gene mutations. *J Am Coll Cardiol* 41: 771-780 (2003).
59. C. Toepfer et al., Myosin regulatory light chain (RLC) phosphorylation change as a modulator of cardiac muscle contraction in disease. *J Biol Chem* 288: 13446-13454 (2013).
60. C. N. Toepfer, T. G. West, M. A. Ferenczi, Revisiting Frank-Starling: regulatory light chain phosphorylation alters the rate of force redevelopment (ktr) in a length-dependent fashion. *J Physiol* 594: 5237-5254 (2016).
61. J. H. Van Berlo et al., A-type lamins are essential for TGF-beta1 Induced PP2A to dephosphorylate transcription factors. *Hum Mol Genet* 14: 2839-2849 (2005).
62. B. van Steensel, A. S. Belmont, Lamina-Associated Domains: Links with Chromosome Architecture, Heterochromatin, and Gene Repression. *Cell* 169: 780-791 (2017).
63. J. P. van Tintelen et al., High yield of LMNA mutations in patients with dilated cardiomyopathy and/or conduction disease referred to cardiogenetics outpatient clinics. *Am Heart J* 154: 1130-1139 (2007).
64. H. Wakimoto, J. G. Seidman, R. S. Y. Foo, J. Jiang, in *Current Protocols in Molecular Biology*. (John Wiley & Sons, Inc., 2001).
65. A. S. Wang, S. V. Kozlov, C. L. Stewart, H. F. Horn, Tissue specific loss of A-type lamins in the gastrointestinal epithelium can enhance polyp size. *Differentiation* 89: 11-21 (2015).
66. H. J. Worman, C. Ostlund, Y. Wang, Diseases of the nuclear envelope. *Cold Spring Harbor perspectives in biology* 2: a000760 (2010).
67. W. Wu, A. Muchir, J. Shan, G. Bonne, H. J. Worman, Mitogen-activated protein kinase inhibitors improve heart function and prevent fibrosis in cardiomyopathy caused by mutation in lamin A/C gene. *Circulation* 123: 53-61 (2011).
68. Zetsche, B., et al., Cpf1 Is a Single RNA-Guided Endonuclease of a Class 2 CRISPR-Cas System. *Cell* 163, 759-771 (2015).
69. Zhang, J., Felder, A., Liu, Y., Guo, L. T., Lange, S., Dalton, N. D., Gu, Y., Peterson, K. L., Mizisin, A. P., Shelton, G. D., et al. (2010). Nesprin 1 is critical for nuclear positioning and anchorage. *Hum Mol Genet* 19: 329-341.
70. Zhang, X., Xu, R., Zhu, B., Yang, X., Ding, X., Duan, S., Xu, T., Zhuang, Y., and Han, M. (2007). Syne-1 and Syne-2 play crucial roles in myonuclear anchorage and motor neuron innervation. *Development* 134: 901-908.
71. C. Zincarelli, S. Soltys, G. Rengo, J. E. Rabinowitz, Analysis of AAV serotypes 1-9 mediated gene expression and tropism in mice after systemic injection. *Mol Ther* 16: 1073-1080 (2008).

The invention claimed is:

1. A method of treating a laminopathy in a subject in need thereof, wherein the laminopathy is a disease caused by a mutation in the Lamin A (LMNA) gene, the method comprising administering to the subject an effective amount of an adeno-associated virus (AAV) expression vector operably linked to a transgene; wherein the transgene comprises a nucleic acid sequence encoding a dominant negative Sun domain containing protein; wherein the AAV expression vector comprises a cardiac-or cardiomyocyte-specific promoter; wherein the AAV expression vector is administered intravascularly, wherein expression of the dominant negative Sun domain containing protein disrupts the protein-protein interactions of the Linker of Nucleoskeleton and Cyotoskeleton (LINC) complex, which uncouples the nucleus from its linkage to the cytoskeleton, resulting in treatment of the laminopathy.

2. The method according to claim 1, wherein the protein-protein interaction is between a Sad Ip UNC-84 (SUN) domain and a Klarsicht, Anc-1 and a Syne Homology (KASH) domain of the LINC complex.

3. The method according to claim 1, wherein the nucleic acid further comprises a lumenal domain of a Sun domain containing protein, an N-terminal signal sequence, a signal peptidase cleavage site, and a C-terminal targeting peptide sequence preventing secretion of the SUN domain-containing protein, wherein the lumenal domain comprises a coiled coil domain and a Sun domain.

4. The method according to claim 3, wherein the SUN domain-containing protein is SUN1 or SUN2.

5. The method according to claim 3, wherein the C-terminal targeting peptide sequence is a KDEL sequence.

6. The method according to claim 1, wherein the AAV expression vector is a cardiac or cardiomyocyte-specific expression vector.

7. The method according to claim 6, wherein in the AAV expression vector is selected from the group consisting of: AAV9, AAV1, AAV6, AAV8, AAV2i8, and AAV9.45.

8. The method according to claim 1, wherein the cardiac- or cardiomyocyte-specific promoter is selected from the group consisting of: a cardiac troponin T promoter (cTnT), a a-myosin heavy chain (a-MHC) promoter and a myosin light chain (MLC2v) promoter.

9. The method according to claim 1, wherein laminopathy is selected from the group consisting of: Acrogeria, Gottron Type; Arrhythmogenic cardiomyopathy; Arrhythmogenic right ventricular cardiomyopathy; Arthropathy syndrome, autosomal recessive; Atrial fibrillation; Atypical progeroid syndrome; Atypical Werner syndrome; Autosomal dominant spinal muscular dystrophy; Axonal neuropathy; muscular dystrophy [; cardiac disease or cardiomyopathy; Axonal neuropathy, muscular dystrophy, cardiac disease, leuconychia; Cardiac arrhythmia; Cardiac conduction defect; Cardiomyopathy with advanced atrioventricular block and arrhythmia; Charcot-Marie-Tooth disease type 2; Congenital fiber type disproportion; Congenital muscular dystrophy; Diabetes Mellitus, Non-Insulin-Dependent (NIDDM); Dilated cardiomyopathy; Distal acroosteolysis, poikiloderma and joint stiffness (DAPJ); Distal motor neuropathy; Dropped Head Syndrome; Emery-Dreifuss muscular dystrophy, autosomal dominant; Familial partial lipodystrophy (Dunnigan Type); Familial partial lipodystrophy, Kobberling; Generalized lipoatrophy syndrome; Hallerman-Streiff syndrome; Heart-hand syndrome, Slovenian Type; Hutchinson-Gilford progeria syndrome; Lamin-related rigid spine muscular dystrophy; Limb-girdle muscular dystrophy type 1B; Muscular dystrophy; Lone atrial fibrillation; Mandibuloacral dysplasia with type A lipodystrophy; Metabolic Syndrome; Muscular dystrophy and lipodystrophy; Progeroid syndrome, neonatal;-Restrictive dermopathy; Spinal muscular atrophy with cardiac involvement; Type A insulin resistance syndrome; cardiomyopathy associated with Emery-Dreifuss muscular dystrophy (autosomal dominant); cardiomyopathy associated with Emery-Dreifuss muscular dystrophy (autosomal recessive); cardiomyopathy associated with Limb-girdle muscular dystrophy type 1B; cardiomyopathy associated with congenital muscular dystrophy; and a premature aging syndrome; cardiomyopathy associated with Atypical Werner syndrome; and cardiomyopathy associated with Hutchinson-Gilford progeria syndrome.

10. The method of claim 9, wherein the cardiac disease or cardiomyopathy is selected from the group consisting of Arrhythmogenic cardiomyopathy, dilated cardiomyopathy 1 Az, and dilated cardiomyopathy with conduction system defects.

11. The method of claim 9, wherein the muscular dystrophy is selected from the group consisting of Autosomal dominant spinal muscular dystrophy; Congenital muscular dystrophy; Emery-Dreifuss muscular dystrophy, autosomal dominant; Lamin-related rigid spine muscular dystrophy; Limb-girdle muscular dystrophy type 1B; and Spinal muscular atrophy with cardiac involvement.

12. The method of claim 9, wherein the cardiac disease or cardiomyopathy is selected from the group consisting of Cardiac arrhythmia; Atrial fibrillation; Cardiac conduction defect; Lone atrial fibrillation; Sudden cardiac death; cardiomyopathy associated with Emery-Dreifuss muscular dystrophy; Cardiac conduction defect; cardiomyopathy associated with Limb-girdle muscular dystrophy type 1B; cardiomyopathy associated with congenital muscular dystrophy; cardiomyopathy associated with Atypical Werner syndrome; and cardiomyopathy associated with Hutchinson-Gilford progeria syndrome.

13. The method of claim 9, wherein the Progeroid syndrome is selected from the group consisting of Progeroid syndrome, neonatal; Acrogeria, Groton Type; Atypical progeroid syndrome; Atypical Werner syndrome; and Hutchinson-Gilford progeria syndrome.

* * * * *

SEQUENCE LISTING

<160> NUMBER OF SEQ ID NOS: 81

<210> SEQ ID NO 1
<211> LENGTH: 15424

<212> TYPE: DNA
<213> ORGANISM: Artificial Sequence
<220> FEATURE:
<223> OTHER INFORMATION: Plasmid pAdDeltaF6

<400> SEQUENCE: 1

| | | | | | |
|---|---|---|---|---|---|
| tcgacggtat | cgataagctt | gatatcgaat | tcctgcagcc | cggggggatcc | actagttcta | 60 |
| gagcggccgc | caccgcggtg | gagctccagc | ttttgttccc | tttagtgagg | gttaatttcg | 120 |
| agcttggcgt | aatcatggtc | atagctgttt | cctgtgtgaa | attgttatcc | gctcacaatt | 180 |
| ccacacaaca | tacgagccgg | aagcataaag | tgtaaagcct | ggggtgccta | atgagtgagc | 240 |
| taactcacat | taattgcgtt | gcgctcactg | cccgctttcc | agtcgggaaa | cctgtcgtgc | 300 |
| cagctgcatt | aatgaatcgg | ccaacgcgcg | gggagaggcg | gtttgcgtat | tgggcgctct | 360 |
| tccgcttcct | cgctcactga | ctcgctgcgc | tcggtcgttc | ggctgcggcg | agcggtatca | 420 |
| gctcactcaa | aggcggtaat | acggttatcc | acagaatcag | gggataacgc | aggaaagaac | 480 |
| atgtgagcaa | aaggccagca | aaaggccagg | aaccgtaaaa | aggccgcgtt | gctggcgttt | 540 |
| ttccataggc | tccgcccccc | tgacgagcat | cacaaaaatc | gacgctcaag | tcagaggtgg | 600 |
| cgaaacccga | caggactata | aagataccag | gcgtttcccc | ctggaagctc | cctcgtgcgc | 660 |
| tctcctgttc | cgaccctgcc | gcttaccgga | tacctgtccg | cctttctccc | ttcgggaagc | 720 |
| gtggcgcttt | ctcatagctc | acgctgtagg | tatctcagtt | cggtgtaggt | cgttcgctcc | 780 |
| aagctgggct | gtgtgcacga | accccccgtt | cagcccgacc | gctgcgcctt | atccggtaac | 840 |
| tatcgtcttg | agtccaaccc | ggtaagacac | gacttatcgc | cactggcagc | agccactggt | 900 |
| aacaggatta | gcagagcgag | gtatgtaggc | ggtgctacag | agttcttgaa | gtggtggcct | 960 |
| aactacggct | acactagaag | gacagtattt | ggtatctgcg | ctctgctgaa | gccagttacc | 1020 |
| ttcggaaaaa | gagttggtag | ctcttgatcc | ggcaaacaaa | ccaccgctgg | tagcggtggt | 1080 |
| ttttttgttt | gcaagcagca | gattacgcgc | agaaaaaaag | gatctcaaga | agatcctttg | 1140 |
| atcttttcta | cggggtctga | cgctcagtgg | aacgaaaact | cacgttaagg | gattttggtc | 1200 |
| atgagattat | caaaaaggat | cttcacctag | atccttttaa | attaaaaatg | aagttttaaa | 1260 |
| tcaatctaaa | gtatatatga | gtaaacttgg | tctgacagtt | accaatgctt | aatcagtgag | 1320 |
| gcacctatct | cagcgatctg | tctatttcgt | tcatccatag | ttgcctgact | ccccgtcgtg | 1380 |
| tagataacta | cgatacggga | gggcttacca | tctggcccca | gtgctgcaat | gataccgcga | 1440 |
| gacccacgct | caccggctcc | agatttatca | gcaataaacc | agccagccgg | aagggccgag | 1500 |
| cgcagaagtg | gtcctgcaac | tttatccgcc | tccatccagt | ctattaattg | ttgccgggaa | 1560 |
| gctagagtaa | gtagttcgcc | agttaatagt | ttgcgcaacg | ttgttgccat | tgctacaggc | 1620 |
| atcgtggtgt | cacgctcgtc | gtttggtatg | gcttcattca | gctccggttc | ccaacgatca | 1680 |
| aggcgagtta | catgatcccc | catgttgtgc | aaaaaagcgg | ttagctcctt | cggtcctccg | 1740 |
| atcgttgtca | gaagtaagtt | ggccgcagtg | ttatcactca | tggttatggc | agcactgcat | 1800 |
| aattctctta | ctgtcatgcc | atccgtaaga | tgcttttctg | tgactggtga | gtactcaacc | 1860 |
| aagtcattct | gagaatagtg | tatgcggcga | ccgagttgct | cttgcccggc | gtcaatacgg | 1920 |
| gataataccg | cgccacatag | cagaacttta | aaagtgctca | tcattggaaa | acgttcttcg | 1980 |
| gggcgaaaac | tctcaaggat | cttaccgctg | ttgagatcca | gttcgatgta | acccactcgt | 2040 |
| gcacccaact | gatcttcagc | atcttttact | ttcaccagcg | tttctgggtg | agcaaaaaca | 2100 |
| ggaaggcaaa | atgccgcaaa | aaagggaata | agggcgacac | ggaaatgttg | aatactcata | 2160 |

```
ctcttcctttt ttcaatatta ttgaagcatt tatcagggtt attgtctcat gagcggatac    2220
atatttgaat gtatttagaa aaataaacaa atagggttc cgcgcacatt tccccgaaaa      2280
gtgccacctg acgtctaaga aaccattatt atcatgacat taacctataa aaataggcgt     2340
atcacgaggc cctttcgtct tcaagaattc tcatgtttga cagcttatca tcgataagct     2400
ttaatgcggt agtttatcac agttaaattg ctaacgcagt caggcaccgt gtatgaaatc     2460
taacaatgcg ctcatcgtca tcctcggcac cgtcaccctg gatgctgtag gcataggctt     2520
ggttatgccg gtactgccgg gcctcttgcg ggatatcgtc cattccgaca gcatcgccag     2580
tcactatggc gtgctgctag cgctatatgc gttgatgcaa tttctatgcg cacccgttct     2640
cggagcactg tccgaccgct ttggccgccg cccagtcctg ctcgcttcgc tacttggagc     2700
cactatcgac tacgcgatca tggcgaccac accgtcctg tggatccggc gcacaccaaa      2760
aacgtcactt ttgccacatc cgtcgcttac atgtgttccg ccacacttgc aacatcacac     2820
ttccgccaca ctactacgtc acccgccccg ttcccacgcc ccgcgccacg tcacaaactc     2880 cacccctca ttatcatatt ggcttcaatc caaaataaat catcaataat ataccttatt      2940
ttggattgaa gccaatatga taatgagggg gtggagtttg tgacgtggcg cggggcgtgg     3000
gaacggggcg ggtgacgtag gttttagggc ggagtaactt gtatgtgttg ggaattgtag     3060
ttttcttaaa atgggaagtt acgtaacgtg ggaaaacgga agtgacgatt tgaggaagtt     3120
gtgggttttt tggctttcgt ttctgggcgt aggttcgcgt gcggttttct gggtgttttt     3180
tgtggacttt aaccgttacg tcatttttta gtcctatata tactcgctct gcacttggcc     3240
cttttttaca ctgtgactga ttgagctggt gccgtgtcga gtggtgtttt tttaataggt     3300 tttcttttttt actggtaagg ctgactgtta ggctgccgct gtgaagcgct gtatgttgtt     3360
ctggagcggg agggtgctat tttgcctagg caggaggggt tttcaggtgt ttatgtgttt     3420
ttctctccta ttaattttgt tatacctcct atgggggctg taatgttgtc tctacgcctg     3480
cgggtatgta ttccccgggg ctatttcggt cgcttttag cactgaccga tgaatcaacc      3540
tgatgtgttt accgagtctt acattatgac tccggacatg accgaggagc tgtcggtggt     3600 gcttttaat cacggtgacc agtttttta cggtcacgcc ggcatggccg tagtccgtct       3660
tatgcttata agggttgttt ttcctgttgt aagacaggct tctaatgttt aaatgttttt     3720
ttgttatttt attttgtgtt tatgcagaaa cccgcagaca tgtttgagag aaaaatggtg     3780 tcttttttctg tggtggttcc ggagcttacc tgcctttatc tgcatgagca tgactacgat    3840
gtgctttctt ttttgcgcga ggctttgcct gattttttga gcagcacctt gcatttata      3900 tcgccgccca tgcaacaaag cttacatcgg ggctacgctg gttagcatag ctccgagtat     3960
gcgtgtcata atcagtgtgg gttcttttgt caaggttcct ggcggggaag tggccgcgct     4020
ggtccgtgca gacctgcacg attatgttca gctggccctg cgaagggacc tacgggatcg     4080
cggtattttt gttaatgttc cgcttttgaa tcttatacag gtctgtgagg aacctgaatt     4140
tttgcaatca tgattcgctg cttgaggctg aaggtggagg gcgctctgga gcagattttt    4200
acaatggccg gacttaatat tcgggatttg cttagagata tattgagaag gtggcgagat    4260
gagaattatt tgggcatggt tgaaggtgct ggaatgttta tagaggagat tcaccctgaa    4320
gggtttagcc tttacgtcca cttggacgtg agggccgttt gccttttgga agccattgtg    4380
caacatctta caaatgccat tatctgttct ttggctgtag agtttgacca cgccaccgga    4440
ggggagcgcg ttcacttaat agatcttcat tttgaggttt tggataatct tttgaataa     4500 aaaaaaaaac atggttcttc cagctcttcc cgctcctccc gtgtgtgact cgcagaacga    4560
```

```
atgtgtaggt tggctgggtg tggcttattc tgcggtggtg gatgttatca gggcagcggc   4620
gcatgaagga gtttacatag aacccgaagc caggggcgc ctggatgctt tgagagagtg   4680
gatatactac aactactaca cagagcgatc taagcggcga gaccggagac gcagatctgt   4740
ttgtcacgcc cgcacctggt tttgcttcag gaaatatgac tacgtccggc gttccatttg   4800
gcatgacact acgaccaaca cgatctcggt tgtctcggcg cactccgtac agtagggatc   4860
gtctacctcc ttttgagaca gaaacccgcg ctaccatact ggaggatcat ccgctgctgc   4920
ccgaatgtaa cactttgaca atgcacaacg tgagttacgt gcgaggtctt ccctgcagtg   4980
tgggatttac gctgattcag gaatgggttg ttccctggga tatggttcta acgcgggagg   5040
agcttgtaat cctgaggaag tgtatgcacg tgtgcctgtg ttgtgccaac attgatatca   5100
tgacgagcat gatgatccat ggttacgagt cctgggctct ccactgtcat tgttccagtc   5160
ccggttccct gcagtgtata gccggcgggc aggttttggc cagctggttt aggatggtgg   5220
tggatggcgc catgtttaat cagaggttta tatggtaccg ggaggtggtg aattacaaca   5280
tgccaaaaga ggtaatgttt atgtccagcg tgtttatgag gggtcgccac ttaatctacc   5340
tgcgcttgtg gtatgatggc cacgtgggtt ctgtggtccc cgccatgagc tttggataca   5400
gcgccttgca ctgtgggatt ttgaacaata ttgtggtgct gtgctgcagt tactgtgctg   5460
atttaagtga gatcagggtg cgctgctgtg cccggaggac aaggcgcctt atgctgcggg   5520
cggtgcgaat catcgctgag gagaccactg ccatgttgta ttcctgcagg acggagcggc   5580
ggcggcagca gtttattcgc gcgctgctgc agcaccaccg ccctatcctg atgcacgatt   5640
atgactctac ccccatgtag gcgtggactt ctccttcgcc gcccgttaag caaccgcaag   5700
ttggacagca gcctgtggct cagcagctgg acagcgacat gaacttaagt gagctgcccg   5760
gggagtttat taatatcact gatgagcgtt tggctcgaca ggaaaccgtg tggaatataa   5820
cacctaagaa tatgtctgtt acccatgata tgatgctttt taaggccagc cggggagaaa   5880
ggactgtgta ctctgtgtgt tgggagggag gtggcaggtt gaatactagg gttctgtgag   5940
tttgattaag gtacggtgat ctgtataagc tatgtggtgg tggggctata ctactgaatg   6000
aaaaatgact tgaaattttc tgcaattgaa aaataaacac gttgaaacat aacacaaacg   6060
attctttatt cttgggcaat gtatgaaaaa gtgtaagagg atgtggcaaa tatttcatta   6120
atgtagttgt ggccagacca gtcccatgaa aatgacatag agtatgcact tggagttgtg   6180
tctcctgttt cctgtgtacc gtttagtgta atggttagtg ttacaggttt agttttgtct   6240
ccgtttaagt aaacttgact gacaatgtta cttttggcag ttttaccgtg agattttgga   6300
taagctgata ggttaggcat aaatccaaca gcgtttgtat aggctgtgcc ttcagtaaga   6360
tctccatttc taaagttcca atattctggg tccaggaagg aattgtttag tagcactcca   6420
ttttcgtcaa atcttataat aagatgagca ctttgaactg ttccagatat tggagccaaa   6480
ctgccttta cagccaaaac tgaaactgta gcaagtattt gactgccaca ttttgttaag   6540
accaaagtga gtttagcatc tttctctgca tttagtctac agttaggaga tggagctggt   6600
gtggtccaca aagttagctt atcattattt ttgtttccta ctgtaatggc acctgtgctg   6660
tcaaaactaa ggccagttcc tagtttagga accatagcct tgtttgaatc aaattctagg   6720
ccatggccaa ttttttgtttt gagggggattt tgtttggtg cattaggtga accaaattca   6780
agcccatctc ctgcattaat ggctatggct gtagcgtcaa acatcaaccc cttggcagtg   6840
cttaggttaa ccctcaagctt tttggaattg tttgaagctg taaacaagta aaggcctttg   6900
```

```
ttgtagttaa tatccaagtt gtgggctgag tttataaaaa gagggccctg tcctagtctt    6960
agatttagtt ggttttgagc atcaaacgga taactaacat caagtataag gcgtctgttt    7020
tgagaatcaa tccttagtcc tcctgctaca ttaagttgca tattgccttg tgaatcaaaa    7080
cccaaggctc cagtaacttt agtttgcaag gaagtattat taatagtcac acctggacca    7140
gttgctacgg tcaaagtgtt taggtcgtct gttacatgca aaggagcccc gtactttagt    7200
cctagttttc cattttgtgt ataaatgggc tctttcaagt caatgcccaa gctaccagtg    7260
gcagtagtta gaggggtga ggcagtgata gtaagggtac tgctatcggt ggtggtgagg    7320
gggcctgatg tttgcagggc tagcttttcct tctgacactg tgaggggtcc ttgggtggca    7380
atgctaagtt tggagtcgtg cacggttagc ggggcctgtg attgcatggt gagtgtgttg    7440
cccgcgacca ttagaggtgc ggcggcagcc acagttaggg cttctgaggt aactgtgagg    7500
ggtgcagata tttccaggtt tatgtttgac ttggtttttt tgagaggtgg gctcacagtg    7560
gttacatttt gggaggtaag gttgccggcc tcgtccagag agaggccgtt gcccattttg    7620
agcgcaagca tgccattgga ggtaactaga ggttcgggata ggcgcaaaga gagtacccca    7680
gggggactct cttgaaaccc attggggggat acaaagggag gagtaagaaa aggcacagtt    7740
ggaggaccgg tttccgtgtc atatggatac acggggttga aggtatcttc agacggtctt    7800
gcgcgcttca tctgcaacaa catgaagata gtgggtgcgg atggacagga acaggaggaa    7860
actgacattc catttagatt gtggagaaag tttgcagcca ggaggaagct gcaataccag    7920
agctgggagg agggcaagga ggtgctgctg aataaactgg acagaaattt gctaactgat    7980
tttaagtaag tgatgctttta ttattttttt ttattagtta aagggaataa gatccccggg    8040
tactctagtt aattaactag aggatcttga tgtaatccaa ggttaggaca gttgcaaatc    8100
acagtgagaa cacagggtcc cctgtcccgc tcaactagca gggggcgctg ggtaaactcc    8160
cgaatcaggc tacgggcaag ctctccctgg gcggtaagcc ggacgccgtg cgccgggccc    8220
tcgatatgat cctcgggcaa ttcaaagtag caaaactcac cggagtcgcg ggcaaagcac    8280
ttgtggcggc gacagtggac caggtgtttc aggcgcagtt gctctgcctc tccacttaac    8340
attcagtcgt agccgtccgc cgagtccttt accgcgtcaa agttaggaat aaattgatcc    8400
ggatagtggc cgggaggtcc cgagaagggg ttaaagtaga ccgatggcac aaactcctca    8460
ataaattgca gagttccaat gcctccagag cgcggctcag aggacgaggt ctgcagagtt    8520
aggattgcct gacgaggcgt gaatgaagga cggccggcgc cgccgatctg aaatgtcccg    8580
tccggacgga gaccaagcga ggagctcacc gactcgtcgt tgagctgaat acctcgccct    8640
ctgattgtca ggtgagttat accctgcccg ggcgaccgca ccctgtgacg aaagccgccc    8700
gcaagctgcg cccctgagtt agtcatctga acttcggcct gggcgtctct gggaagtacc    8760
acagtggtgg gagcgggact tcctggtac accagggcag cgggccaact acggggatta    8820
aggttattac gaggtgtggt ggtaatagcc gcctgttcca agagaattcg gtttcggtgg    8880
gcgcggattc cgttgacccg ggatatcatg tgggtcccg cgctcatgta gtttattcgg    8940
gttgagtagt cttgggcagc tccagccgca agtcccattt gtggctggta actccacatg    9000
tagggcgtgg gaattccctt gctcataatg gcgctgacga caggtgctgg cgccgggtgt    9060
ggccgctgga gatgacgtag ttttcgcgct taaatttgag aaagggcgcg aaactagtcc    9120
ttaagagtca gcgcgcagta tttactgaag agagcctccg cgtcttccag cgtgcgccga    9180
agctgatctt cgcttttgtg atacaggcag ctgcgggtga gggatcgcag agacctgttt    9240 tttatttttca gctcttgttc ttggcccctg ctctgttgaa atatagcata cagagtggga    9300
```

```
aaaatcctgt ttctaagctc gcgggtcgat acgggttcgt tgggcgccag acgcagcgct    9360
cctcctcctg ctgctgccgc cgctgtggat ttccttgggct ttgtcagagt cttgctatcc    9420
ggtcgccttt gcttctgtgt ggccgctgct gttgctgccg ctgccgctgc cgccggtgca    9480
gtatgggctg tagagatgac ggtagtaatg caggatgtta cggggggaagg ccacgccgtg    9540
atggtagaga agaaagcggc gggcgaagga gatgttgccc ccacagtctt gcaagcaagc    9600
aactatggcg ttcttgtgcc cgcgccatga gcggtagcct tggcgctgtt gttgctcttg    9660
ggctaacggc ggcggctgct tggacttacc ggccctggtt ccagtggtgt cccatctacg    9720
gttgggtcgg cgaacgggca gtgccggcgg cgcctgagga gcggaggttg tagccatgct    9780
ggaaccggtt gccgatttct ggggcgccgg cgaggggaat gcgaccgagg gtgacggtgt    9840
ttcgtctgac acctcttcga cctcggaagc ttcctcgtct aggctctccc agtcttccat    9900
catgtcctcc tcctcctcgt ccaaaacctc ctctgcctga ctgtcccagt attcctcctc    9960
gtccgtgggt ggcggcggca gctgcagctt ctttttgggt gccatcctgg gaagcaaggg   10020
cccgcggctg ctgctgatag ggctgcggcg gcgggggggat tgggttgagc tcctcgccgg   10080
actgggggtc caagtaaacc ccccgtccct ttcgtagcag aaactcttgg cgggcttttgt   10140
tgatggcttg caattggcca agaatgtggc cctgggtaat gacgcaggcg gtaagctccg   10200
catttggcgg gcgggattgg tcttcgtaga acctaatctc gtgggcgtgg tagtcctcag   10260
gtacaaattt gcgaaggtaa gccgacgtcc acagcccgg agtgagtttc aaccccggag   10320
ccgcggactt ttcgtcaggc gagggaccct gcagctcaaa ggtaccgata atttgacttt   10380
cgttaagcag ctgcgaattg caaaccaggg agcggtgcgg ggtgcatagg ttgcagcgac   10440
agtgacactc cagtagaccg tcaccgctca cgtcttccat tatgtcagag tggtaggcaa   10500
ggtagttggc tagctgcaga aggtagcagt ggccccaaag cggcggaggg cattcgcggt   10560
acttaatggg cacaaagtcg ctaggaagtg cacagcaggt ggcgggcaag attcctgagc   10620
gctctaggat aaagttccta aagttctgca acatgctttg actggtgaag tctggcagac   10680
cctgttgcag ggttttaagc aggcgttcgg ggaaaatgat gtccgccagg tgcgcggcca   10740
cggagcgctc gttgaaggcc gtccataggt ccttcaagtt ttgctttagc agtttctgca   10800
gctccttgag gttgcactcc tccaagcact gctgccaaac gcccatggcc gtctgccagg   10860
tgtagcatag aaataagtaa acgcagtcgc ggacgtagtc gcggcgcgcc tcgcccttga   10920
gcgtggaatg aagcacgttt tgcccaaggc ggttttcgtg caaaattcca aggtaggaga   10980
ccaggttgca gagctccacg ttggagatct tgcaggcctg gcgtacgtag ccctgtcgaa   11040
aggtgtagtg caatgttttcc tctagcttgc gctgcatctc cgggtcagca aagaaccgct   11100
gcatgcactc aagctccacg gtaacgagca ctgcggccat cattagtttg cgtcgctcct   11160
ccaagtcggc aggctcgcgc gtttgaagcc agcgcgctag ctgctcgtcg ccaactgcgg   11220
gtaggccctc ctctgtttgt tcttgcaaat ttgcatccct ctccagggc tgcgcacggc   11280
gcacgatcag ctcactcatg actgtgctca tgaccttggg gggtaggtta agtgccgggt   11340
aggcaaagtg ggtgacctcg atgctgcgtt ttagtacggc taggcgcgcg ttgtcaccct   11400
cgagttccac caacactcca gagtgacttt cattttcgct gttttcctgt tgcagagcgt   11460
ttgccgcgcg cttctcgtcg cgtccaagac cctcaaagat ttttggcact tcgttgagcg   11520
aggcgatatc aggtatgaca gcgccctgcc gcaaggccag ctgcttgtcc gctcggctgc   11580
ggttggcacg gcaggatagg ggtatcttgc agttttggaa aaagatgtga taggtggcaa   11640
```

```
gcacctctgg cacggcaaat acggggtaga agttgaggcg cgggttgggc tcgcatgtgc  11700
cgttttcttg gcgtttgggg ggtacgcgcg gtgagaatag gtggcgttcg taggcaaggc  11760
tgacatccgc tatggcgagg ggcacatcgc tgcgctcttg caacgcgtcg cagataatgg  11820
cgcactggcg ctgcagatgc ttcaacagca cgtcgtctcc cacatctagg tagtcgccat  11880
gcctttcgtc cccccgcccg acttgttcct cgtttgcctc tgcgttgtcc tggtcttgct  11940
ttttatcctc tgttggtact gagcggtcct cgtcgtcttc gcttacaaaa cctgggtcct  12000
gctcgataat cacttcctcc tcctcaagcg ggggtgcctc gacggggaag gtggtaggcg  12060
cgttggcggc atcggtggag gcggtggtgg cgaactcaga gggggcggtt aggctgtcct  12120
tcttctcgac tgactccatg atctttttct gcctatagga aaggaaatg gccagtcggg  12180 aagaggagca gcgcgaaacc accccgagc gcggacgcgg tgcggcgcga cgtcccccaa  12240
ccatggagga cgtgtcgtcc ccgtcccgt cgccgccgcc tccccgggcg ccccccaaaaa  12300 agcggatgag gcggcgtatc gagtccgagg acgaggaaga ctcatcacaa gacgcgctgg  12360
tgccgcgcac acccagcccg cggccatcga cctcggcggc ggatttggcc attgcgccca  12420
agaagaaaaa gaagcgccct tctcccaagc ccgagcgccc gccatcacca gaggtaatcg  12480
tggacagcga ggaagaaaga gaagatgtgg cgctacaaat ggtgggtttc agcaacccac  12540
cggtgctaat caagcatggc aaaggaggta agcgcacagt gcggcggctg aatgaagacg  12600
acccagtggc gcgtggtatg cggacgcaag aggaagagga agagcccagc gaagcggaaa  12660
gtgaaattac ggtgatgaac ccgctgagtg tgccgatcgt gtctgcgtgg gagaagggca  12720
tggaggctgc gcgcgcgctg atggacaagt accacgtgga taacgatcta aaggcgaact  12780
tcaaactact gcctgaccaa gtggaagctc tggcggccgt atgcaagacc tggctgaacg  12840
aggagcaccg cgggttgcag ctgaccttca ccagcaacaa gaccttttgtg acgatgatgg  12900 ggcgattcct gcaggcgtac ctgcagtcgt ttgcagaggt gacctacaag catcacgagc  12960
ccacgggctg cgcgttgtgg ctgcaccgct gcgctgagat cgaaggcgag cttaagtgtc  13020
tacacggaag cattatgata aataaggagc acgtgattga aatggatgtg acgagcgaaa  13080
acgggcagcg cgcgctgaag gagcagtcta gcaaggccaa gatcgtgaag aaccggtggg  13140
gccgaaatgt ggtgcagatc tccaacaccg acgcaaggtg ctgcgtgcac gacgcggcct  13200
gtccggccaa tcagtttttcc ggcaagtctt gcggcatgtt cttctctgaa ggcgcaaagg  13260
ctcaggtggc ttttaagcag atcaaggctt ttatgcaggc gctgtatcct aacgcccaga  13320
ccgggcacgg tcaccttttg atgccactac ggtgcgagtg caactcaaag cctgggcacg  13380 cgccctttt gggaaggcag ctaccaaagt tgactccgtt cgccctgagc aacgcggagg  13440
acctggacgc ggatctgatc tccgacaaga gcgtgctggc cagcgtgcac cacccggcgc  13500
tgatagtgtt ccagtgctgc aaccctgtgt atcgcaactc gcgcgcgcag ggcggaggcc  13560
ccaactgcga cttcaagata tcggcgcccg acctgctaaa cgcgttggtg atggtgcgca  13620
gcctgtggag tgaaaacttc accgagctgc gcgcgatggt tgtgcctgag tttaagtgga  13680
gcactaaaca ccagtatcgc aacgtgtccc tgccagtggc gcatagcgat gcgcggcaga  13740
acccccttga tttttaaacg gcgcagacgg caagggtggg ggtaaataat cacccgagag  13800
tgtacaaata aaagcatttg cctttattga aagtgtctct agtacattat ttttacatgt  13860
ttttcaagtg acaaaaagaa gtggcgctcc taatctgcgc actgtggctg cggaagtagg  13920
gcgagtggcg ctccaggaag ctgtagagct gttcctggtt gcgacgcagg gtgggctgta  13980
cctggggact gttgagcatg gagttgggta ccccggtaat aaggttcatg gtggggttgt  14040
```

```
gatccatggg agtttggggc cagttggcaa aggcgtggag aaacatgcag cagaatagtc   14100
cacaggcggc cgagttgggc ccctgtacgc tttgggtgga cttttccagc gttatacagc   14160
ggtcggggga agaagcaatg gcgctacggc gcaggagtga ctcgtactca aactggtaaa   14220
cctgcttgag tcgctggtca gaaaagccaa agggctcaaa gaggtagcat gtttttgagt   14280
gcgggttcca ggcaaaggcc atccagtgta cgcccccagt ctcggtccga gactcgaacc   14340
gggggtcccg cgactcaacc cttggaaaat aaccctccgg ctacagggag cgagccactt   14400
aatgctttcg ctttccagcc taaccgctta cgctgcgcgc ggccagtggc caaaaaagct   14460
agcgcagcag ccgccgcgcc tggaaggaag ccaaaaggag cactccccg ttgtctgacg   14520
tcgcacacct gggttcgaca cgcgggcggt aaccgcatgg atcacggcgg acggccggat   14580
acggggctcg aaccccggtc gtccgccatg atacccttgc gaatttatcc accagaccac   14640
ggaagagtgc ccgcttacag gctctccttt tgcacggtag agcgtcaacg attgcgcgcg   14700
cctgaccggc cagagcgtcc cgaccatgga gcacttttg ccgctgcgca acatctggaa   14760
ccgcgtccgc gactttccgc gcgcctccac caccgccgcc ggcatcacct ggatgtccag   14820
gtacatctac ggatatcatc gccttatgtt ggaagatctc gccccggag ccccggccac   14880
cctacgctgg cccctctacc gccagccgcc gccgcacttt ttggtgggat accagtacct   14940
ggtgcggact tgcaacgact acgtatttga ctcgagggct tactcgcgtc tcaggtacac   15000
cgagctctcg cagccgggtc accagaccgt taactggtcc gttatggcca actgcactta   15060
caccatcaac acgggcgcat accaccgctt tgtggacatg gatgacttcc agtctaccct   15120
cacgcaggtg cagcaggcca tattagccga gcgcgttgtc gccgacctag ccctgcttca   15180
gccgatgagg ggcttcgggg tcacacgcat gggaggaaga gggcgccacc tacgccaaa    15240
ctccgccgcc gccgcagcga tagatgcaag agatgcagga caagaggaag gagaagaaga   15300
agtgccggta gaaaggctca tgcaagacta ctacaaagac ctgcgccgat gtcaaaacga   15360
agcctggggc atggccgacc gcctgcgcat tcagcaggcc ggacccaagg acatggtgct   15420
tctg                                                                15424
```

<210> SEQ ID NO 2
<211> LENGTH: 7330
<212> TYPE: DNA
<213> ORGANISM: Artificial Sequence
<220> FEATURE:
<223> OTHER INFORMATION: Plasmid pAAV2_9

<400> SEQUENCE: 2

```
gtcgacggta tcgggggagc tcgcagggtc tccattttga agcgggaggt ttgaacgcgc     60
agccgccatg ccgggttttt acgagattgt gattaaggtc cccagcgacc ttgacgagca    120
tctgcccggc atttctgaca gctttgtgaa ctgggtggcc gagaaggaat gggagttgcc    180
gccagattct gacatggatc tgaatctgat tgagcaggca cccctgaccg tggccgagaa    240
gctgcagcgc gactttctga cggaatggcg ccgtgtgagt aaggcccgg aggctctttt    300
ctttgtgcaa tttgagaagg gagagagcta cttccacatg cacgtgctcg tggaaaccac    360
cggggtgaaa tccatggttt tgggacgttt cctgagtcag attcgcgaaa aactgattca    420
gagaatttac cgcgggatcg agccgacttt gccaaactgg ttcgcggtca caagaccag    480
aaatggcgcc ggaggcggga acaaggtggt ggatgagtgc tacatcccca attacttgct    540
ccccaaaacc cagcctgagc tccagtgggc gtggactaat atggaacagt atttaagcgc    600
```

```
ctgtttgaat ctcacggagc gtaaacggtt ggtggcgcag catctgacgc acgtgtcgca    660
gacgcaggag cagaacaaag agaatcagaa tcccaattct gatgcgccgg tgatcagatc    720
aaaaacttca gccaggtaca tggagctggt cgggtggctc gtggacaagg ggattacctc    780
ggagaagcag tggatccagg aggaccaggc ctcatacatc tccttcaatg cggcctccaa    840
ctcgcggtcc caaatcaagg ctgccttgga caatgcggga aagattatga gcctgactaa    900
aaccgccccc gactacctgg tgggccagca gcccgtggag gacatttcca gcaatcggat    960
ttataaaatt ttggaactaa acgggtacga tccccaatat gcggcttccg tctttctggg   1020
atgggccacg aaaaagttcg gcaagaggaa caccatctgg ctgtttgggc ctgcaactac   1080
cgggaagacc aacatcgcgg aggccatagc ccacactgtg cccttctacg ggtgcgtaaa   1140
ctggaccaat gagaactttc ccttcaacga ctgtgtcgac aagatggtga tctggtggga   1200 ggagggaag atgaccgcca aggtcgtgga gtcggccaaa gccattctcg aggaagcaa    1260 ggtgcgcgtg gaccagaaat gcaagtcctc ggcccagata gacccgactc ccgtgatcgt   1320
cacctccaac accaacatgt gcgccgtgat tgacgggaac tcaacgacct tcgaacacca   1380
gcagccgttg caagaccgga tgttcaaatt tgaactcacc cgccgtctgg atcatgactt   1440
tgggaaggtc accaagcagg aagtcaaaga cttttttccgg tgggcaaagg atcacgtggt   1500
tgaggtggag catgaattct acgtcaaaaa gggtggagcc aagaaaagac ccgcccccag   1560
tgacgcagat ataagtgagc ccaaacgggt gcgcgagtca gttgcgcagc catcgacgtc   1620
agacgcggaa gcttcgatca actacgcgga caggtaccaa aacaaatgtt ctcgtcacgt   1680
gggcatgaat ctgatgctgt ttccctgcag acaatgcgag agactgaatc agaattcaaa   1740
tatctgcttc actcacggtg tcaaagactg tttagagtgc tttcccgtgt cagaatctca   1800
acccgtttct gtcgtcaaaa aggcgtatca gaaactgtgc tacattcatc acatcatggg   1860
aaaggtgcca gacgcttgca ctgcttgcga cctggtcaat gtggacttgg atgactgtgt   1920
ttctgaacaa taaatgactt aaaccaggta tggctgccga tggttatctt ccagattggc   1980
tcgaggacaa ccttagtgaa ggaattcgcg agtggtgggc tttgaaacct ggagcccctc   2040
aacccaaggc aaatcaacaa catcaagaca acgctcgagg tcttgtgctt ccgggttaca   2100
aataccttgg acccggcaac ggactcgaca aggggagcc ggtcaacgca gcagacgcgg    2160
cggccctcga gcacgacaag gcctacgacc agcagctcaa ggccggagac aacccgtacc   2220
tcaagtacaa ccacgccgac gccgagttcc aggagcggct caaagaagat acgtcttttg   2280
ggggcaacct cggcgagca gtcttccagg ccaaaaagag gcttcttgaa cctcttggtc    2340
tggttgagga agcggctaag acggctcctg gaaagaagag gcctgtagag cagtctcctc   2400
aggaaccgga ctcctccgcg ggtattggca atcgggtgc acagcccgct aaaaagagac    2460
tcaatttcgg tcagactggc gacacagagt cagtcccaga ccctcaacca atcggagaac   2520
ctcccgcagc cccctcaggt gtgggatctc ttacaatggc ttcaggtggt ggcgcaccag   2580
tggcagacaa taacgaaggt gccgatggag tgggtagttc ctcgggaaat tggcattgcg   2640
attcccaatg gctgggggac agagtcatca ccaccagcac ccgaacctgg gccctgccca   2700
cctacaacaa tcacctctac aagcaaatct ccaacagcac atctggagga tcttcaaatg   2760
acaacgccta cttcggctac agcaccccct gggggtattt tgacttcaac agattccact   2820
gccacttctc accacgtgac tggcagcgac tcatcaacaa caactgggga ttccggccta   2880
agcgactcaa cttcaagctc ttcaacattc aggtcaaaga ggttacgac aacaatggag    2940 tcaagaccat cgccaataac cttaccagca cggtccaggt cttcacggac tcagactatc   3000
```

```
agctcccgta cgtgctcggg tcggctcacg agggctgcct cccgccgttc cagcggacg    3060
ttttcatgat tcctcagtac gggtatctga cgcttaatga tggaagccag gccgtgggtc    3120
gttcgtcctt ttactgcctg gaatatttcc cgtcgcaaat gctaagaacg ggtaacaact    3180
tccagttcag ctacgagttt gagaacgtac ctttccatag cagctacgct cacagccaaa    3240
gcctggaccg actaatgaat ccactcatcg accaatactt gtactatctc tcaaagacta    3300
ttaacggttc tggacagaat caacaaacgc taaaattcag tgtggccgga cccagcaaca    3360
tggctgtcca gggaagaaac tacatacctg gacccagcta ccgacaacaa cgtgtctcaa    3420
ccactgtgac tcaaaacaac aacagcgaat ttgcttggcc tggagcttct tcttgggctc    3480
tcaatggacg taatagcttg atgaatcctg gacctgctat ggccagccac aaagaaggag    3540
aggaccgttt ctttcctttg tctggatctt aattttttgg caaacaagga actgaagag    3600
acaacgtgga tgcggacaaa gtcatgataa ccaacgaaga agaaattaaa actactaacc    3660
cggtagcaac ggagtcctat ggacaagtgg ccacaaacca ccagagtgcc caagcacagg    3720
cgcagaccgg ctgggttcaa accaaggaa tacttccggg tatggtttgg caggacagag    3780
atgtgtacct gcaaggaccc atttgggcca aaattcctca cacggacggc aactttcacc    3840
cttctccgct gatgggaggg tttggaatga agcacccgcc tcctcagatc ctcatcaaaa    3900
acacacctgt acctgcggat cctccaacgg ccttcaacaa ggacaagctg aactctttca    3960
tcacccagta ttctactggc caagtcagcg tggagatcga gtgggagctg cagaaggaaa    4020
acagcaagcg ctggaacccg gagatccagt acacttccaa ctattacaag tctaataatg    4080
ttgaatttgc tgttaatact gaaggtgtat atagtgaacc ccgccccatt ggcaccagat    4140
acctgactcg taatctgtaa ttgcttgtta atcaataaac cgtttaattc gtttcagttg    4200
aactttggtc tctgcgaagg gcgaattcgt ttaaacctgc aggactagag gtcctgtatt    4260
agaggtcacg tgagtgtttt gcgacatttt gcgacaccat gtggtcacgc tgggtattta    4320
agcccgagtg agcacgcagg gtctccattt tgaagcggga ggtttgaacg cgcagccgcc    4380
aagccgaatt ctgcagatat ccatcacact ggcggccgct cgactagagc ggccgccacc    4440
gcggtggagc tccagctttt gttcccttta gtgagggtta attgcgcgct tggcgtaatc    4500
atggtcatag ctgtttcctg tgtgaaattg ttatccgctc acaattccac acaacatacg    4560
agccggaagc ataaagtgta aagcctgggg tgcctaatga gtgagctaac tcacattaat    4620
tgcgttgcgc tcactgcccg ctttccagtc gggaaacctg tcgtgccagc tgcattaatg    4680
aatcggccaa cgcgcgggga gaggcggttt gcgtattggg cgctcttccg cttcctcgct    4740
cactgactcg ctgcgctcgg tcgttcggct gcggcgagcg gtatcagctc actcaaaggc    4800
ggtaatacgg ttatccacag aatcagggga taacgcagga agaacatgt gagcaaaagg    4860
ccagcaaaag gccaggaacc gtaaaaaggc cgcgttgctg gcgttttcc ataggctccg    4920
ccccctgac gagcatcaca aaaatcgacg ctcaagtcag aggtggcgaa acccgacagg    4980
actataaaga taccaggcgt ttccccctgg aagctccctc gtgcgctctc ctgttccgac    5040
cctgccgctt accggatacc tgtccgcctt tctcccttcg ggaagcgtgg cgctttctca    5100
tagctcacgc tgtaggtatc tcagttcggt gtaggtcgtt cgctccaagc tgggctgtgt    5160
gcacgaaccc ccgttcagc ccgaccgctg cgccttatcc ggtaactatc gtcttgagtc    5220
caacccggta agacacgact tatcgccact ggcagcagcc actggtaaca ggattagcag    5280
agcgaggtat gtaggcggtg ctacagagtt cttgaagtgg tggcctaact acggctacac    5340
```

```
tagaagaaca gtatttggta tctgcgctct gctgaagcca gttaccttcg gaaaaagagt    5400
tggtagctct tgatccggca aacaaaccac cgctggtagc ggtggttttt ttgtttgcaa    5460
gcagcagatt acgcgcagaa aaaaggatc tcaagaagat cctttgatct tttctacggg    5520
gtctgacgct cagtggaacg aaaactcacg ttaagggatt ttggtcatga gattatcaaa    5580
aaggatcttc acctagatcc ttttaaatta aaaatgaagt tttaaatcaa tctaaagtat    5640
atatgagtaa acttggtctg acagttacca atgcttaatc agtgaggcac ctatctcagc    5700
gatctgtcta tttcgttcat ccatagttgc ctgactcccc gtcgtgtaga taactacgat    5760
acgggagggc ttaccatctg gccccagtgc tgcaatgata ccgcgagacc cacgctcacc    5820
ggctccagat ttatcagcaa taaaccagcc agccggaagg gccgagcgca agtggtcc    5880 tgcaacttta tccgcctcca tccagtctat taattgttgc cgggaagcta gagtaagtag    5940
ttcgccagtt aatagtttgc gcaacgttgt tgccattgct acaggcatcg tggtgtcacg    6000
ctcgtcgttt ggtatggctt cattcagctc cggttcccaa cgatcaaggc gagttacatg    6060
atcccccatg ttgtgcaaaa aagcggttag ctccttcggt cctccgatcg ttgtcagaag    6120
taagttggcc gcagtgttat cactcatggt tatggcagca ctgcataatt ctcttactgt    6180
catgccatcc gtaagatgct tttctgtgac tggtgagtac tcaaccaagt cattctgaga    6240
atagtgtatg cggcgaccga gttgctcttg cccggcgtca atacgggata ataccgcgcc    6300
acatagcaga actttaaaag tgctcatcat tggaaaacgt tcttcgggc gaaaactctc    6360 aaggatctta ccgctgttga tccagttc gatgtaaccc actcgtgcac ccaactgatc    6420
ttcagcatct tttactttca ccagcgtttc tgggtgagca aaaacaggaa ggcaaaatgc    6480
cgcaaaaaag gaataaggg cgacacggaa atgttgaata ctcatactct ccttttttca    6540
atattattga agcatttatc agggttattg tctcatgagc ggatacatat ttgaatgtat    6600
ttagaaaaat aaacaaatag gggttccgcg cacatttccc cgaaaagtgc cacctaaatt    6660
gtaagcgtta atattttgtt aaaattcgcg ttaaattttt gttaaatcag ctcatttttt    6720
aaccaatagg ccgaaatcgg caaaatccct tataaatcaa agaatagac cgagataggg    6780 ttgagtgttg ttccagtttg gaacaagagt ccactattaa agaacgtgga ctccaacgtc    6840
aaagggcgaa aaaccgtcta tcagggcgat ggcccactac gtgaaccatc accctaatca    6900
agttttttgg ggtcgaggtg ccgtaaagca ctaaatcgga acctaaagg agcccccga    6960 tttagagctt gacggggaaa gccggcgaac gtggcgagaa aggaagggaa gaaagcgaaa    7020
ggagcgggcg ctagggcgct ggcaagtgta gcggtcacgc tgcgcgtaac caccacaccc    7080
gccgcgctta atgcgccgct acagggcgcg tcccattcgc cattcaggct gcgcaactgt    7140
tgggaagggc gatcggtgcg ggcctcttcg ctattacgcc agctggcgaa agggggatgt    7200
gctgcaaggc gattaagttg ggtaacgcca gggttttccc agtcacgacg ttgtaaaacg    7260
acggccagtg agcgcgcgta atacgactca ctatagggcg aattgggtac cgggcccccc    7320
ctcgatcgag                                                          7330

<210> SEQ ID NO 3
<211> LENGTH: 5720
<212> TYPE: DNA
<213> ORGANISM: Artificial Sequence
<220> FEATURE:
<223> OTHER INFORMATION: Plasmid pENN.AAV.cTnT.PI.Sun1-dom-neg

<400> SEQUENCE: 3
ctgcgcgctc gctcgctcac tgaggccgcc cgggcaaagc ccgggcgtcg ggcgaccttt     60
```

```
ggtcgcccgg cctcagtgag cgagcgagcg cgcagagagg gagtggccaa ctccatcact    120
aggggttcct tgtagttaat gattaacccg ccatgctact tatctaccag ggtaatgggg    180
atcctctaga actatagcta gaattcgccc ttacgggccc cccctcgagg tcgggataaa    240
agcagtctgg gctttcacat gacagcatct ggggctgcgg cagagggtcg ggtccgaagc    300
gctgccttat cagcgcccca gccctggagt gtgacagctg gctggcttgt gtcagcccct    360
cgggcactca cgtatctccg tccgacgggt ttaaaatagc aaaactctga ggccacacaa    420
tagcttgggc ttatatgggc tcctgtgggg aaggggggag cacggagggg gccggggccg    480
ctgctgccaa aatagcagct cacaagtgtt gcattcctct ctgggcgccg ggcacattcc    540
tgctggctct gcccgccccg gggtgggcgc cgggggggacc ttaaagcctc tgccccccaa    600
ggagcccttc ccagacagcc gccggcaccc accgctccgt gggacgatcc ccgaagctct    660
agagctttat tgcggtagtt tatcacagtt aaattgctaa cgcagtcagt gcttctgaca    720
caacagtctc gaacttaagc tgcagaagtt ggtcgtgagg cactgggcag gtaagtatca    780
aggttacaag acaggtttaa ggagaccaat agaaactggg cttgtcgaga cagagaagac    840
tcttgcgttt ctgataggca cctattggtc ttactgacat ccactttgcc tttctctcca    900
caggtgtcca ctcccagttc aattacagct cttaaggcta gagtacttaa tacgactcac    960
tataggctag cctcgagaat tcacgcgggc cgccatgaag tgggtaacct ttatttccct   1020 tcttttttctc tttagctcgg cctattccag gggtgtgttt cgtcgagatg ggcccgctta   1080
cccttacgat gtaccggatt acgcactcga cgattccaag ggcatgcata gacctggccc   1140 tcttccccccg agcccacctc caaaggttga tcacaaggct tcccagtggc ctcaggagag   1200
tgacatgggg cagaaggtag cttctttgag tgcgcagtgc cacaaccatg atgagagact   1260
tgcagagctg acagtcctgc ttcagaaact acagatacgg gtagaccaag tggatgacgg   1320
cagggaaggg ctgtcactgt gggtcaagaa tgtggttgga cagcacctgc aggagatggg   1380
caccatagaa ccacctgatg ctaagactga cttcatgact ttccaccatg accatgaagt   1440
gcgtctctcc aacttggaag atgttcttag aaaaactgaca gaaaaatctg aggctatcca   1500
gaaggagctg gaagaaacca agctgaaagc aggcagcagg gatgaagagc agcccctcct   1560
tgaccgtgtg cagcacctag aactggaact gaacctgttg aagtcacagc tgtcagactg   1620
gcagcatctg aagaccagct gtgagcaggc tggggcccgc atccaggaga ctgtgcagct   1680
catgttctct gaggatcagc agggcggttc cctcgagtgg ctattagaga agctttcttc   1740
tcggttcgtg agcaaggatg agctgcaggt gctcttacat gaccttgagc tgaaactgct   1800
gcagaatatc acacaccaca tcaccgtgac aggacaggcc ccgacatccg aggctattgt   1860
gtctgccgtg aatcaggcag ggatttcagg aatcacagaa gcgcaagcac atatcattgt   1920
gaacaatgct ctgaagctgt actcccaaga caagacgggg atggtggact tgctctgga   1980 gtctggaggt ggcagcatcc taagcactcg gtgtctctgag acctatgaga ccaagacggc   2040
actgctgagc ctgtttgggg tcccactgtg gtacttctca cagtcacctc gagtggtgat   2100
ccagcccgac atctacccag ggaattgctg ggcgttcaaa ggttcccagg gtacctggt   2160 ggtgcggttg tccatgaaga tctacccaac cacattcacc atggaacaca ttccaaagac   2220
actatcaccc actggtaaca tctccagtgc ccccaaagac tttgcagtct atggactgga   2280
aacggagtat caagaagagg ggcagcctct gggacggttc acctatgacc aggaaggaga   2340
ctcactccag atgttccaca cactggaaag acctgaccaa gccttccaga tagtagagct   2400
```

```
ccgggtcctg tccaactggg gccaccctga gtacacttgc ctctaccggt tccgagtcca    2460
cggagagccc atccagaaag atgagttgta gtaaggtacc tctagagtcg acccgggcgg    2520
cctcgaggac ggggtgaact acgcctgagg atccgatctt tttccctctg ccaaaaatta    2580
tggggacatc atgaagcccc ttgagcatct gacttctggc taataaagga aatttatttt    2640
cattgcaata gtgtgttgga attttttgtg tctctcactc ggaagcaatt cgttgatctg    2700
aatttcgacc acccataata cccattaccc tggtagataa gtagcatggc gggttaatca    2760
ttaactacaa ggaaccccta gtgatggagt tggccactcc ctctctgcgc gctcgctcgc    2820
tcactgaggc cgggcgacca aaggtcgccc gacgcccggg cttttgcccgg gcggcctcag   2880 tgagcgagcg agcgcgcagc cttaattaac ctaattcact ggccgtcgtt ttacaacgtc    2940
gtgactggga aaaccctggc gttacccaac ttaatcgcct tgcagcacat cccccttttcg   3000 ccagctggcg taatagcgaa gaggcccgca ccgatcgccc ttcccaacag ttgcgcagcc    3060
tgaatggcga atgggacgcg ccctgtagcg gcgcattaag cgcggcgggt gtggtggtta    3120
cgcgcagcgt gaccgctaca cttgccagcg ccctagcgcc cgctccttt c gctttcttcc    3180 cttcctttct cgccacgttc gccggctttc cccgtcaagc tctaaatcgg gggctccctt    3240
tagggttccg atttagtgct ttacggcacc tcgaccccaa aaaacttgat tagggtgatg    3300
gttcacgtag tgggccatcg ccctgataga cggtttttcg ccctttgacg ttggagtcca    3360
cgttctttaa tagtggactc ttgttccaaa ctggaacaac actcaaccct atctcggtct    3420
attcttttga tttataaggg attttgccga tttcggccta ttggttaaaa aatgagctga   3480
tttaacaaaa atttaacgcg aattttaaca aaatattaac gcttacaatt taggtggcac    3540
ttttcgggga atgtgcgcgg aacccctat t tgtttatt t ttctaaatac attcaaatat    3600
gtatccgctc atgagacaat aaccctgata aatgcttcaa taatattgaa aaaggaagag    3660
tatgagtatt caacatttcc gtgtcgccct tattcccttt tttgcggcat tttgccttcc    3720
tgtttttgct cacccagaaa cgctggtgaa agtaaaagat gctgaagatc agttgggtgc    3780
acgagtgggt tacatcgaac tggatctcaa cagcggtaag atccttgaga gttttcgccc    3840
cgaagaacgt tttccaatga tgagcacttt taaagttctg ctatgtggcg cggtattatc    3900
ccgtattgac gccgggcaag agcaactcgg tcgccgcata cactattctc agaatgactt    3960
ggttgagtac tcaccagtca cagaaaagca tcttacggat ggcatgacag taagagaatt    4020
atgcagtgct gccataacca tgagtgataa cactgcggcc aacttacttc tgacaacgat    4080
cggaggaccg aaggagctaa ccgcttttt t gcacaacatg ggggatcatg taactcgcct    4140
tgatcgttgg gaaccggagc tgaatgaagc cataccaaac gacgagcgtg acaccacgat    4200
gcctgtagca atggcaacaa cgttgcgcaa actattaact ggcgaactac ttactctagc    4260
ttcccggcaa caattaatag actggatgga ggcggataaa gttgcaggac cacttctgcg    4320
ctcggccctt ccggctggct ggtttattgc tgataaatct ggagccggtg agcgtgggtc    4380
tcgcggtatc attgcagcac tggggccaga tggtaagccc tcccgtatcg tagttatcta    4440
cacgacgggg agtcaggcaa ctatggatga acgaaataga cagatcgctg agataggtgc    4500
ctcactgatt aagcattggt aactgtcaga ccaagtttac tcatatatac tttagattga    4560
tttaaaactt cattttaat t taaaaggat ctaggtgaag atcctttttg ataatctcat    4620
gaccaaaatc ccttaacgtg agttttcgtt ccactgagcg tcagacccc g tagaaaagat    4680 caaaggatct tcttgagatc cttttttct g cgcgtaatc tgctgcttgc aaacaaaaaa    4740
accaccgcta ccagcggtgg tttgtttgcc ggatcaagag ctaccaactc tttttccgaa    4800
```

```
ggtaactggc ttcagcagag cgcagatacc aaatactgtt cttctagtgt agccgtagtt    4860
aggccaccac ttcaagaact ctgtagcacc gcctacatac ctcgctctgc taatcctgtt    4920
accagtggct gctgccagtg gcgataagtc gtgtcttacc gggttggact caagacgata    4980
gttaccggat aaggcgcagc ggtcgggctg aacgggggt tcgtgcacac agcccagctt    5040
ggagcgaacg acctacaccg aactgagata cctacagcgt gagctatgag aaagcgccac    5100
gcttcccgaa gggagaaagg cggacaggta tccggtaagc ggcagggtcg aacaggaga    5160
gcgcacgagg gagcttccag ggggaaacgc ctggtatctt tatagtcctg tcgggtttcg    5220
ccacctctga cttgagcgtc gattttttgtg atgctcgtca gggggcgga gcctatggaa    5280
aaacgccagc aacgcggcct ttttacggtt cctggccttt tgctggcctt ttgctcacat    5340
gttctttcct gcgttatccc ctgattctgt ggataaccgt attaccgcct ttgagtgagc    5400
tgataccgct cgccgcagcc gaacgaccga gcgcagcgag tcagtgagcg aggaagcgga    5460
agagcgccca atacgcaaac cgcctctccc cgcgcgttgg ccgattcatt aatgcagctg    5520
gcacgacagg tttcccgact ggaaagcggg cagtgagcgc aacgcaatta atgtgagtta    5580
gctcactcat taggcacccc aggctttaca ctttatgctt ccggctcgta tgttgtgtgg    5640
aattgtgagc ggataacaat ttcacacagg aaacagctat gaccatgatt acgccagatt    5700
taattaaggc cttaattagg                                                5720

<210> SEQ ID NO 4
<211> LENGTH: 1461
<212> TYPE: DNA
<213> ORGANISM: Artificial Sequence
<220> FEATURE:
<223> OTHER INFORMATION: Humanized Sun1DN
<220> FEATURE:
<221> NAME/KEY: Start codon
<222> LOCATION: (1)..(3)
<220> FEATURE:
<221> NAME/KEY: Signal sequence
<222> LOCATION: (4)..(84)
<220> FEATURE:
<221> NAME/KEY: Sun1
<222> LOCATION: (88)..(1446)
<220> FEATURE:
<221> NAME/KEY: KDEL
<222> LOCATION: (1447)..(1458)
<220> FEATURE:
<221> NAME/KEY: Stop codon
<222> LOCATION: (1459)..(1461)

<400> SEQUENCE: 4
atgaagtggg taacctttat ttcccttctt tttctcttta gctcggccta ttccagggt      60
gtgtttcgtc gagatgggcc cgctctcgat gacccccagg acgtgtttaa acccacgact    120
tctcgcctga agcagcctct gcagggtgac agtgaggctt ttccgtggca ttggatgagt    180
ggcgtggagc agcaggtggc ctctctgtct ggacagtgcc accaccatgg tgagaatctc    240
cgagagctga ccactttgct acagaagctg caggctcggg tggaccagat ggaaggcggc    300
gctgccgggc cgtcagcttc ggtcagagac gctgtgggac agccccgag ggagactgac     360
tttatggcct ttcaccaaga acatgaagtg cgtatgtcac acttggaaga tattctggga    420
aaactgagag aaaaatctga ggccatccag aaggaactag aacagaccaa gcaaaaaaca    480
atcagtgcgg ttggtgagca gctcctgccc acagtcgagc acctccagct ggagctggat    540
cagctaaagt cagagctgtc cagctggcga cacgtgaaga ccggctgtga gacagtggat    600
gccgtacaag aaagagtgga cgtgcaagtc agagaaatgg tgaaactcct gttttccgaa    660
```

```
gatcagcaag gcggttctct ggaacagctg ctgcagaggt tctcatcaca gtttgtgagc    720
aaaggcgact tgcagacgat gctgcgagac ctgcagctgc agatcctgcg gaacgtcacc    780
caccacgttt ccgtgaccaa gcagctccca acctcagaag ccgtggtgtc tgctgtgagc    840
gaggcggggg cgtctggaat aacagaggcg caagcacgtg ccatcgtgaa cagcgccttg    900
aagctgtatt cccaagataa gaccgggatg gtggactttg ctctggaatc tggtggtggc    960
agcatcttga gtactcgctg ttctgaaact tacgaaacca aaacggcgct gatgagtctg   1020
tttgggatcc cgctgtggta cttctcgcag tccccgcgcg tggtcatcca gcctgacatt   1080
taccccggta actgctgggc atttaaaggc tcccagggggt acctggtggt gaggctctcc   1140
atgatgatcc acccagccgc cttcactctg gagcacatcc ctaagacgct gtcgccaaca   1200
ggcaacatca gcagcgcccc caaggacttc gccgtctatg gattagaaaa tgagtatcag   1260
gaagaagggc agcttctggg acagttcacg tatgatcagg atggggagtc gctccagatg   1320
ttccaggccc tgaaaagacc cgacgacaca gctttccaaa tagtgaaact tcggattttt   1380
tctaactggg gccatcctga gtatacctgt ctgtatcggt tcagagttca tggcgaacct   1440
gtcaagaaag atgagttgtg a                                             1461

<210> SEQ ID NO 5
<211> LENGTH: 1482
<212> TYPE: DNA
<213> ORGANISM: Artificial Sequence
<220> FEATURE:
<223> OTHER INFORMATION: SUN2
<220> FEATURE:
<221> NAME/KEY: Start codon
<222> LOCATION: (1)..(3)
<220> FEATURE:
<221> NAME/KEY: Signal sequence
<222> LOCATION: (4)..(84)
<220> FEATURE:
<221> NAME/KEY: Sun2
<222> LOCATION: (88)..(1467)
<220> FEATURE:
<221> NAME/KEY: KDEL
<222> LOCATION: (1468)..(1479)
<220> FEATURE:
<221> NAME/KEY: Stop codon
<222> LOCATION: (1480)..(1482)

<400> SEQUENCE: 5
atgaagtggg taacctttat ttcccttctt tttctcttta gctcggccta ttccaggggt     60
gtgtttcgtc gagatgggcc cgctctcgat gagggctggg aagccagaga ctcatcgcca    120
catttccagg ctgagcagcg tgttatgtcc cgggtacact ctctggagcg gcgtctggaa    180
gctcttgctg ctgaatttttc ctccaactgg cagaaggagg ccatgcggct ggaacgtctg    240
gagctgcggc aaggggctcc tggccaggga ggtggtggtg gcctgagcca cgaggacacc    300
ctggcgctgc tggaggggct agtgagccgc cgtgaagctg ccctgaagga ggatttccgc    360
agggaaactg ctgctcgcat ccaggaagaa ctgtctgccc tgagagcaga gcatcagcaa    420
gactcagaag acctcttcaa gaagatcgtc cgggcctccc aggagtccga ggctcgcatc    480
cagcagctga agtcagagtg gcaaaagcat acccaggagt ccttccagga gagctctgtg    540
aaggagctga ggcggctgga ggaccagctg gccggcctgc agcaggagct ggcggctctg    600
gcactgaagc agagctcggt ggcggaagaa tgggcctgc tgcccagca gatccaggcc    660 gtgcgggacg acgtggaatc tcagttcccg gcctggatca gtcagttcct tgcccgaggt    720 ggaggggggcc gcgtggggct ccttcagaga gaggagatgc aagctcagct gcgagagctg    780
```

```
gagagcaaga tcctcaccca tgtggcagag atgcagggca agtcggccag ggaagccgcg    840
gcctccctga gcctgacgct gcagaaagaa ggtgtgattg gagtgacaga ggagcaggtg    900
caccacatcg tgaagcaggc cctgcagcgc tacagtgagg accgcatcgg gctggcagac    960
tacgccctgg agtcaggagg ggccagcgtc atcagcaccc gatgttctga gacctacgag   1020
accaagacgg ccctcctcag cctcttcggc atcccctgt  ggtaccactc ccagtcaccc   1080
cgagtcatcc tccagccaga tgtgcaccca ggcaactgct gggccttcca ggggccacaa   1140
ggcttcgccg tggtccgcct ctctgcccgc atccgcccca cagccgttac cttagagcat   1200
gtgcccaagg ccttgtcacc caacagcact atctccagtg cccccaagga cttcgccatc   1260
tttgggtttg acgaagacct gcagcaggag gggacactcc ttggcaagtt cacttacgat   1320
caggacggcg agcctattca gacgtttcac tttcaggccc ctacgatggc cacgtaccag   1380
gtggtggagc tgcggatcct gactaactgg ggccaccccg agtacacctg catctaccgc   1440
ttcagagtgc atggggagcc cgcccacaaa gatgagttgt ag                      1482
```

<210> SEQ ID NO 6
<211> LENGTH: 180
<212> TYPE: DNA
<213> ORGANISM: Artificial Sequence
<220> FEATURE:
<223> OTHER INFORMATION: KASH1, derived from Nesprin-1

<400> SEQUENCE: 6

```
cgcggcttcc tgttcagagt cctccgagca gctcttcccc ttcagcttct cctgctcctc     60
ctcatcgggc ttgcctgcct tgtaccaatg tcagaggaag actacagctg tgccctctcc    120
aacaactttg cccggtcatt ccaccccatg ctcagataca cgaatggccc tcctccactc    180
```

<210> SEQ ID NO 7
<211> LENGTH: 60
<212> TYPE: PRT
<213> ORGANISM: Artificial Sequence
<220> FEATURE:
<223> OTHER INFORMATION: KASH1 amino acid sequence

<400> SEQUENCE: 7

```
Arg Gly Phe Leu Phe Arg Val Leu Arg Ala Ala Leu Pro Leu Gln Leu
1               5                   10                  15

Leu Leu Leu Leu Leu Ile Gly Leu Ala Cys Leu Val Pro Met Ser Glu
            20                  25                  30

Glu Asp Tyr Ser Cys Ala Leu Ser Asn Asn Phe Ala Arg Ser Phe His
        35                  40                  45

Pro Met Leu Arg Tyr Thr Asn Gly Pro Pro Pro Leu
    50                  55                  60
```

<210> SEQ ID NO 8
<211> LENGTH: 180
<212> TYPE: DNA
<213> ORGANISM: Artificial Sequence
<220> FEATURE:
<223> OTHER INFORMATION: KASH2, derived from Nesprin-2

<400> SEQUENCE: 8

```
cgctccttcc tctcaagggt ggtccgggca gccctacccc tgcagctgct cctcctgctg     60
ctgctgctcc tggcctgcct gctgccctcc tccgaagaag actacagctg cactcaggcc    120
aacaactttg cccggtcctt ttaccccatg ctgaggtaca ccaatgggcc acccccaca     180
```

<210> SEQ ID NO 9
<211> LENGTH: 60
<212> TYPE: PRT
<213> ORGANISM: Artificial Sequence
<220> FEATURE:
<223> OTHER INFORMATION: KASH2 amino acid sequence

<400> SEQUENCE: 9

Arg Ser Phe Leu Ser Arg Val Val Arg Ala Ala Leu Pro Leu Gln Leu
1               5                   10                  15

Leu Leu Leu Leu Leu Leu Leu Leu Ala Cys Leu Leu Pro Ser Ser Glu
                20                  25                  30

Glu Asp Tyr Ser Cys Thr Gln Ala Asn Asn Phe Ala Arg Ser Phe Tyr
            35                  40                  45

Pro Met Leu Arg Tyr Thr Asn Gly Pro Pro Pro Thr
    50                  55                  60

<210> SEQ ID NO 10
<211> LENGTH: 177
<212> TYPE: DNA
<213> ORGANISM: Artificial Sequence
<220> FEATURE:
<223> OTHER INFORMATION: KASH3, derived from Nesprin-3

<400> SEQUENCE: 10
ggctccctct tccggagggc gtgctgtgtg gcgctcccac tgcagctgct tctgctgctg      60
ttcctcctcc tgctgttcct gctcccaatc agggaagagg accgcagctg caccctggcc     120
aacaacttcg cccgctcctt cacgctcatg ctgcgctaca atggcccacc acccacc        177

<210> SEQ ID NO 11
<211> LENGTH: 59
<212> TYPE: PRT
<213> ORGANISM: Artificial Sequence
<220> FEATURE:
<223> OTHER INFORMATION: KASH3 amino acid sequence

<400> SEQUENCE: 11

Gly Ser Leu Phe Arg Arg Ala Cys Cys Val Ala Leu Pro Leu Gln Leu
1               5                   10                  15

Leu Leu Leu Leu Phe Leu Leu Leu Leu Phe Leu Leu Pro Ile Arg Glu
                20                  25                  30

Glu Asp Arg Ser Cys Thr Leu Ala Asn Asn Phe Ala Arg Ser Phe Thr
            35                  40                  45

Leu Met Leu Arg Tyr Asn Gly Pro Pro Pro Thr
    50                  55

<210> SEQ ID NO 12
<211> LENGTH: 174
<212> TYPE: DNA
<213> ORGANISM: Artificial Sequence
<220> FEATURE:
<223> OTHER INFORMATION: KASH4, derived from Nesprin-4

<400> SEQUENCE: 12
gatcctgcat ccaggcagcc tctgaccttc ctccttatcc tcttcctcct cttcctcctc      60
ctggtgggtg ccatgtttct cctgcccgcg tcaggaggcc cctgctgctc tcatgcccga     120
atacccagga caccctacct ggtgctcagc tatgtcaatg gtcttccccc agtc            174

<210> SEQ ID NO 13
<211> LENGTH: 58

```
<212> TYPE: PRT
<213> ORGANISM: Artificial Sequence
<220> FEATURE:
<223> OTHER INFORMATION: KASH4 amino acid sequence

<400> SEQUENCE: 13

Asp Pro Ala Ser Arg Gln Pro Leu Thr Phe Leu Leu Ile Leu Phe Leu
1               5                   10                  15

Leu Phe Leu Leu Leu Val Gly Ala Met Phe Leu Leu Pro Ala Ser Gly
            20                  25                  30

Gly Pro Cys Cys Ser His Ala Arg Ile Pro Arg Thr Pro Tyr Leu Val
        35                  40                  45

Leu Ser Tyr Val Asn Gly Leu Pro Pro Val
    50                  55

<210> SEQ ID NO 14
<211> LENGTH: 144
<212> TYPE: DNA
<213> ORGANISM: Artificial Sequence
<220> FEATURE:
<223> OTHER INFORMATION: KASH5, derived from CCDC155/KASH5

<400> SEQUENCE: 14
ctcagagtca ctcgacatcc actgatccca gctcctgtcc tgggcctgct gctgctgctg      60
ctgctctctg tcctgctgct tggcccgtcc ccacctccca cctggcccca cctccagctc     120
tgctacctcc agcccctcc agtg                                             144

<210> SEQ ID NO 15
<211> LENGTH: 48
<212> TYPE: PRT
<213> ORGANISM: Artificial Sequence
<220> FEATURE:
<223> OTHER INFORMATION: KASH5 amino acid sequence

<400> SEQUENCE: 15

Leu Arg Val Thr Arg His Pro Leu Ile Pro Ala Pro Val Leu Gly Leu
1               5                   10                  15

Leu Leu Leu Leu Leu Leu Ser Val Leu Leu Leu Gly Pro Ser Pro Pro
            20                  25                  30

Pro Thr Trp Pro His Leu Gln Leu Cys Tyr Leu Gln Pro Pro Pro Val
        35                  40                  45

<210> SEQ ID NO 16
<211> LENGTH: 22
<212> TYPE: DNA
<213> ORGANISM: Artificial Sequence
<220> FEATURE:
<223> OTHER INFORMATION: FLX/FLX-F1 primer

<400> SEQUENCE: 16
ccagcttaca gagcaccgag ct                                               22

<210> SEQ ID NO 17
<211> LENGTH: 22
<212> TYPE: DNA
<213> ORGANISM: Artificial Sequence
<220> FEATURE:
<223> OTHER INFORMATION: FLX/FLX-F2 primer

<400> SEQUENCE: 17
tccttgcagt ccctcttgca tc                                               22
```

```
<210> SEQ ID NO 18
<211> LENGTH: 21
<212> TYPE: DNA
<213> ORGANISM: Artificial Sequence
<220> FEATURE:
<223> OTHER INFORMATION: FLX/FLX-R1 primer

<400> SEQUENCE: 18
aggcaccatt gtcacagggt c                                        21

<210> SEQ ID NO 19
<211> LENGTH: 29
<212> TYPE: DNA
<213> ORGANISM: Artificial Sequence
<220> FEATURE:
<223> OTHER INFORMATION: Sun1-F primer

<400> SEQUENCE: 19
ggcaagtgga tctcttgtga attcttgac                                29

<210> SEQ ID NO 20
<211> LENGTH: 27
<212> TYPE: DNA
<213> ORGANISM: Artificial Sequence
<220> FEATURE:
<223> OTHER INFORMATION: Sun1-R primer

<400> SEQUENCE: 20
gtagcaccca ccttggtgag ctggtac                                  27

<210> SEQ ID NO 21
<211> LENGTH: 20
<212> TYPE: DNA
<213> ORGANISM: Artificial Sequence
<220> FEATURE:
<223> OTHER INFORMATION: Sun1-E8 primer

<400> SEQUENCE: 21
agccacataa ccacctggag                                          20

<210> SEQ ID NO 22
<211> LENGTH: 26
<212> TYPE: DNA
<213> ORGANISM: Artificial Sequence
<220> FEATURE:
<223> OTHER INFORMATION: MyHC-tF primer

<400> SEQUENCE: 22
atgacagaca gatccctcct atctcc                                   26

<210> SEQ ID NO 23
<211> LENGTH: 24
<212> TYPE: DNA
<213> ORGANISM: Artificial Sequence
<220> FEATURE:
<223> OTHER INFORMATION: MyHC-tR primer

<400> SEQUENCE: 23
ctcatcactc gttgcatcat cgac                                     24

<210> SEQ ID NO 24
<211> LENGTH: 20
<212> TYPE: DNA
<213> ORGANISM: Artificial Sequence
<220> FEATURE:
<223> OTHER INFORMATION: MyHC-F primer
```

<400> SEQUENCE: 24
caaatgttgc ttgtctggtg                                          20

<210> SEQ ID NO 25
<211> LENGTH: 20
<212> TYPE: DNA
<213> ORGANISM: Artificial Sequence
<220> FEATURE:
<223> OTHER INFORMATION: MyHC-R primer

<400> SEQUENCE: 25
gtcagtcgag tgcacagttt                                          20

<210> SEQ ID NO 26
<211> LENGTH: 20
<212> TYPE: DNA
<213> ORGANISM: Artificial Sequence
<220> FEATURE:
<223> OTHER INFORMATION: mcm-3798t primer

<400> SEQUENCE: 26
aggtggacct gatcatggag                                          20

<210> SEQ ID NO 27
<211> LENGTH: 20
<212> TYPE: DNA
<213> ORGANISM: Artificial Sequence
<220> FEATURE:
<223> OTHER INFORMATION: mcm-8346t primer

<400> SEQUENCE: 27
ataccggaga tcatgcaagc                                          20

<210> SEQ ID NO 28
<211> LENGTH: 24
<212> TYPE: DNA
<213> ORGANISM: Artificial Sequence
<220> FEATURE:
<223> OTHER INFORMATION: mcm-7338 primer

<400> SEQUENCE: 28
ctaggccaca gaattgaaag atct                                     24

<210> SEQ ID NO 29
<211> LENGTH: 25
<212> TYPE: DNA
<213> ORGANISM: Artificial Sequence
<220> FEATURE:
<223> OTHER INFORMATION: mcm-7339 primer

<400> SEQUENCE: 29
gtaggtggaa attctagcat catcc                                    25

<210> SEQ ID NO 30
<211> LENGTH: 44
<212> TYPE: DNA
<213> ORGANISM: Artificial Sequence
<220> FEATURE:
<223> OTHER INFORMATION: aav Sun1 F primer

<400> SEQUENCE: 30
cgagaattca cgcgggccgc catgaagtgg gtaacctta tttc                44

<210> SEQ ID NO 31
<211> LENGTH: 46

```
<212> TYPE: DNA
<213> ORGANISM: Artificial Sequence
<220> FEATURE:
<223> OTHER INFORMATION: aav Sun1 R primer

<400> SEQUENCE: 31
cgggtcgact ctagaggtac cttactacaa ctcatctttc tggatg          46

<210> SEQ ID NO 32
<211> LENGTH: 44
<212> TYPE: DNA
<213> ORGANISM: Artificial Sequence
<220> FEATURE:
<223> OTHER INFORMATION: aav GFP Sun R primer

<400> SEQUENCE: 32
cgggtcgact ctagaggtac ttactacaac tcatctttgg atcc            44

<210> SEQ ID NO 33
<211> LENGTH: 21
<212> TYPE: DNA
<213> ORGANISM: Artificial Sequence
<220> FEATURE:
<223> OTHER INFORMATION: Sun1 delSUN RNA guide sequence

<400> SEQUENCE: 33
gcacaatagc ctcggatgtc g                                     21

<210> SEQ ID NO 34
<211> LENGTH: 20
<212> TYPE: DNA
<213> ORGANISM: Artificial Sequence
<220> FEATURE:
<223> OTHER INFORMATION: Syne1-stop guide RNA sequence

<400> SEQUENCE: 34
ccgttggtat atctgagcat                                       20

<210> SEQ ID NO 35
<211> LENGTH: 21
<212> TYPE: DNA
<213> ORGANISM: Artificial Sequence
<220> FEATURE:
<223> OTHER INFORMATION: Tyrosinase4a guide RNA sequence

<400> SEQUENCE: 35
ggttatggcc gataggtgca t                                     21

<210> SEQ ID NO 36
<211> LENGTH: 20
<212> TYPE: DNA
<213> ORGANISM: Artificial Sequence
<220> FEATURE:
<223> OTHER INFORMATION: Common reverse primer for in vitro
      transcription

<400> SEQUENCE: 36
aaaagcaccg actcggtgcc                                       20

<210> SEQ ID NO 37
<211> LENGTH: 39
<212> TYPE: DNA
<213> ORGANISM: Artificial Sequence
<220> FEATURE:
<223> OTHER INFORMATION: Sun1delSUN gRNA-specific forward primer

<400> SEQUENCE: 37
```
ttaatacgac tcactatagc acaatagcct cggatgtcg                       39

<210> SEQ ID NO 38
<211> LENGTH: 39
<212> TYPE: DNA
<213> ORGANISM: Artificial Sequence
<220> FEATURE:
<223> OTHER INFORMATION: Syne1-stop gRNA-specific forward primer

<400> SEQUENCE: 38
ttaatacgac tcactatagc cgttggtata tctgagcat                       39

<210> SEQ ID NO 39
<211> LENGTH: 39
<212> TYPE: DNA
<213> ORGANISM: Artificial Sequence
<220> FEATURE:
<223> OTHER INFORMATION: Tyrosinase4a gRNA-specific forward primer

<400> SEQUENCE: 39
ttaatacgac tcactatagg ttatggccga taggtgcat                       39

<210> SEQ ID NO 40
<211> LENGTH: 20
<212> TYPE: DNA
<213> ORGANISM: Artificial Sequence
<220> FEATURE:
<223> OTHER INFORMATION: Syne1CT' del8 forward primer

<400> SEQUENCE: 40
tgctcctgct gctgcttatt                                            20

<210> SEQ ID NO 41
<211> LENGTH: 22
<212> TYPE: DNA
<213> ORGANISM: Artificial Sequence
<220> FEATURE:
<223> OTHER INFORMATION: Syne1CT' del8 reverse primer

<400> SEQUENCE: 41
acatggtgga gcatttgtct cc                                         22

<210> SEQ ID NO 42
<211> LENGTH: 20
<212> TYPE: DNA
<213> ORGANISM: Artificial Sequence
<220> FEATURE:
<223> OTHER INFORMATION: Sun1 CRISPR forward primer

<400> SEQUENCE: 42
tgaccttgag ctgaaactgc                                            20

<210> SEQ ID NO 43
<211> LENGTH: 20
<212> TYPE: DNA
<213> ORGANISM: Artificial Sequence
<220> FEATURE:
<223> OTHER INFORMATION: Sun1 CRISPR reverse primer

<400> SEQUENCE: 43
tcagaacact ggcacacaca                                            20

<210> SEQ ID NO 44
<211> LENGTH: 20
<212> TYPE: DNA

```
<213> ORGANISM: Artificial Sequence
<220> FEATURE:
<223> OTHER INFORMATION: Potential guide RNA sequence, SYNE1

<400> SEQUENCE: 44
tcgtgtatct gagcatgggg                                              20

<210> SEQ ID NO 45
<211> LENGTH: 20
<212> TYPE: DNA
<213> ORGANISM: Artificial Sequence
<220> FEATURE:
<223> OTHER INFORMATION: Potential guide RNA sequence, SYNE1

<400> SEQUENCE: 45
gccattcgtg tatctgagca                                              20

<210> SEQ ID NO 46
<211> LENGTH: 20
<212> TYPE: DNA
<213> ORGANISM: Artificial Sequence
<220> FEATURE:
<223> OTHER INFORMATION: Potential guide RNA sequence, SYNE1

<400> SEQUENCE: 46
tccaccccat gctcagatac                                              20

<210> SEQ ID NO 47
<211> LENGTH: 20
<212> TYPE: DNA
<213> ORGANISM: Artificial Sequence
<220> FEATURE:
<223> OTHER INFORMATION: Potential guide RNA sequence, SYNE1

<400> SEQUENCE: 47
gagcatgggg tggaatgacc                                              20

<210> SEQ ID NO 48
<211> LENGTH: 20
<212> TYPE: DNA
<213> ORGANISM: Artificial Sequence
<220> FEATURE:
<223> OTHER INFORMATION: Potential guide RNA sequence, SYNE1

<400> SEQUENCE: 48
tgagcatggg gtggaatgac                                              20

<210> SEQ ID NO 49
<211> LENGTH: 20
<212> TYPE: DNA
<213> ORGANISM: Artificial Sequence
<220> FEATURE:
<223> OTHER INFORMATION: Potential guide RNA sequence, SYNE1

<400> SEQUENCE: 49
tcgtgtatct gagcatgggg                                              20

<210> SEQ ID NO 50
<211> LENGTH: 20
<212> TYPE: DNA
<213> ORGANISM: Artificial Sequence
<220> FEATURE:
<223> OTHER INFORMATION: Potential guide RNA sequence, SYNE1

<400> SEQUENCE: 50
cattcgtgta tctgagcatg                                              20
```

```
<210> SEQ ID NO 51
<211> LENGTH: 20
<212> TYPE: DNA
<213> ORGANISM: Artificial Sequence
<220> FEATURE:
<223> OTHER INFORMATION: Potential guide RNA sequence, SYNE1

<400> SEQUENCE: 51
ccattcgtgt atctgagcat                                              20

<210> SEQ ID NO 52
<211> LENGTH: 20
<212> TYPE: DNA
<213> ORGANISM: Artificial Sequence
<220> FEATURE:
<223> OTHER INFORMATION: Potential guide RNA sequence, SYNE1

<400> SEQUENCE: 52
gccattcgtg tatctgagca                                              20

<210> SEQ ID NO 53
<211> LENGTH: 20
<212> TYPE: DNA
<213> ORGANISM: Artificial Sequence
<220> FEATURE:
<223> OTHER INFORMATION: Potential guide RNA sequence, SYNE1

<400> SEQUENCE: 53
cccatgctca gatacacgaa                                              20

<210> SEQ ID NO 54
<211> LENGTH: 20
<212> TYPE: DNA
<213> ORGANISM: Artificial Sequence
<220> FEATURE:
<223> OTHER INFORMATION: Potential guide RNA sequence, SYNE1

<400> SEQUENCE: 54
cccggtcatt ccaccccatg                                              20

<210> SEQ ID NO 55
<211> LENGTH: 20
<212> TYPE: DNA
<213> ORGANISM: Artificial Sequence
<220> FEATURE:
<223> OTHER INFORMATION: Potential guide RNA sequence, SUN1

<400> SEQUENCE: 55
tttttctaac tggggccatc                                              20

<210> SEQ ID NO 56
<211> LENGTH: 20
<212> TYPE: DNA
<213> ORGANISM: Artificial Sequence
<220> FEATURE:
<223> OTHER INFORMATION: Potential guide RNA sequence, SUN1

<400> SEQUENCE: 56
ccgatacaga caggtatact                                              20

<210> SEQ ID NO 57
<211> LENGTH: 20
<212> TYPE: DNA
<213> ORGANISM: Artificial Sequence
<220> FEATURE:
```

<223> OTHER INFORMATION: Potential guide RNA sequence, SUN1

<400> SEQUENCE: 57
aacttcggat tttttctaac        20

<210> SEQ ID NO 58
<211> LENGTH: 20
<212> TYPE: DNA
<213> ORGANISM: Artificial Sequence
<220> FEATURE:
<223> OTHER INFORMATION: Potential guide RNA sequence, SUN1

<400> SEQUENCE: 58
acttcggatt ttttctaact        20

<210> SEQ ID NO 59
<211> LENGTH: 20
<212> TYPE: DNA
<213> ORGANISM: Artificial Sequence
<220> FEATURE:
<223> OTHER INFORMATION: Potential guide RNA sequence, SUN1

<400> SEQUENCE: 59
cttcggattt tttctaactg        20

<210> SEQ ID NO 60
<211> LENGTH: 20
<212> TYPE: DNA
<213> ORGANISM: Artificial Sequence
<220> FEATURE:
<223> OTHER INFORMATION: Potential guide RNA sequence, SUN1

<400> SEQUENCE: 60
acagacaggt atactcagga        20

<210> SEQ ID NO 61
<211> LENGTH: 20
<212> TYPE: DNA
<213> ORGANISM: Artificial Sequence
<220> FEATURE:
<223> OTHER INFORMATION: Potential guide RNA sequence, SUN1

<400> SEQUENCE: 61
ctgagtatac ctgtctgtat        20

<210> SEQ ID NO 62
<211> LENGTH: 20
<212> TYPE: DNA
<213> ORGANISM: Artificial Sequence
<220> FEATURE:
<223> OTHER INFORMATION: Potential guide RNA sequence, SUN1

<400> SEQUENCE: 62
ttctaactgg ggccatcctg        20

<210> SEQ ID NO 63
<211> LENGTH: 20
<212> TYPE: DNA
<213> ORGANISM: Artificial Sequence
<220> FEATURE:
<223> OTHER INFORMATION: Potential guide RNA sequence, SUN1

<400> SEQUENCE: 63
tctaactggg gccatcctga        20

```
<210> SEQ ID NO 64
<211> LENGTH: 20
<212> TYPE: DNA
<213> ORGANISM: Artificial Sequence
<220> FEATURE:
<223> OTHER INFORMATION: Potential guide RNA sequence, SUN1

<400> SEQUENCE: 64
ctaactgggg ccatcctgag                                               20

<210> SEQ ID NO 65
<211> LENGTH: 20
<212> TYPE: DNA
<213> ORGANISM: Artificial Sequence
<220> FEATURE:
<223> OTHER INFORMATION: Potential guide RNA sequence, SUN1

<400> SEQUENCE: 65
taactggggc catcctgagt                                               20

<210> SEQ ID NO 66
<211> LENGTH: 21
<212> TYPE: DNA
<213> ORGANISM: Artificial Sequence
<220> FEATURE:
<223> OTHER INFORMATION: Cas9 mRNA and gRNA targeting SUN1 domain

<400> SEQUENCE: 66
gcacaatagc ctcggatgtc g                                             21

<210> SEQ ID NO 67
<211> LENGTH: 20
<212> TYPE: DNA
<213> ORGANISM: Artificial Sequence
<220> FEATURE:
<223> OTHER INFORMATION: Cas9 mRNA and gRNA targeting the KASH1 domain

<400> SEQUENCE: 67
ccgttggtat atctgagcat                                               20

<210> SEQ ID NO 68
<211> LENGTH: 21
<212> TYPE: DNA
<213> ORGANISM: Artificial Sequence
<220> FEATURE:
<223> OTHER INFORMATION: gRNA targeting tyrosinase

<400> SEQUENCE: 68
ggttatggcc gataggtgca t                                             21

<210> SEQ ID NO 69
<211> LENGTH: 176
<212> TYPE: DNA
<213> ORGANISM: Mus musculus

<400> SEQUENCE: 69
catgaccttg agctgaaact gctgcagaat atcacacacc acatcaccgt gacaggacag   60
gccccgacat ccgaggctat tgtgtctgcc gtgaatcagg cagggatttc aggaatcaca   120
gaagcgcaag cacatatcat tgtgaacaat gctctgaagc tgtactccca agacaa       176

<210> SEQ ID NO 70
<211> LENGTH: 180
<212> TYPE: DNA
<213> ORGANISM: Artificial Sequence
<220> FEATURE:
```

<223> OTHER INFORMATION: Sun1_plus4

<400> SEQUENCE: 70

```
catgaccttg agctgaaact gctgcagaat atcacacacc acatcaccgt gacaggacag    60
gccccgagac acatccgagg ctattgtgtc tgccgtgaat caggcaggga tttcaggaat   120
cacagaagcg caagcacata tcattgtgaa caatgctctg aagctgtact cccaagacaa   180
```

<210> SEQ ID NO 71
<211> LENGTH: 169
<212> TYPE: DNA
<213> ORGANISM: Artificial Sequence
<220> FEATURE:
<223> OTHER INFORMATION: Sun1_del7

<400> SEQUENCE: 71

```
catgaccttg agctgaaact gctgcagaat atcacacacc acatcaccgt gacaggacag    60
gccccgaggc tattgtgtct gccgtgaatc aggcagggat ttcaggaatc acagaagcgc   120
aagcacatat cattgtgaac aatgctctga agctgtactc ccaagacaa              169
```

<210> SEQ ID NO 72
<211> LENGTH: 253
<212> TYPE: PRT
<213> ORGANISM: Mus musculus

<400> SEQUENCE: 72

```
Trp Leu Leu Glu Lys Leu Ser Ser Arg Phe Val Ser Lys Asp Glu Leu
1               5                   10                  15

Gln Val Leu Leu His Asp Leu Glu Lys Leu Leu Gln Asn Ile Thr
            20                  25                  30

His His Ile Thr Val Thr Gly Gln Ala Pro Thr Ser Glu Ala Ile Val
        35                  40                  45

Ser Ala Val Asn Gln Ala Gly Ile Ser Gly Ile Thr Glu Ala Gln Ala
    50                  55                  60

His Ile Ile Val Asn Asn Ala Leu Lys Leu Tyr Ser Gln Asp Lys Thr
65                  70                  75                  80

Gly Met Val Asp Phe Ala Leu Glu Ser Gly Gly Ser Ile Leu Ser
                85                  90                  95

Thr Arg Cys Ser Glu Thr Tyr Glu Thr Lys Thr Ala Leu Leu Ser Leu
            100                 105                 110

Phe Gly Val Pro Leu Trp Tyr Phe Ser Gln Ser Pro Arg Val Val Ile
        115                 120                 125

Gln Pro Asp Ile Tyr Pro Gly Asn Cys Trp Ala Phe Lys Gly Ser Gln
    130                 135                 140

Gly Tyr Leu Val Val Arg Leu Ser Met Lys Ile Tyr Pro Thr Thr Phe
145                 150                 155                 160

Thr Met Glu His Ile Pro Lys Thr Leu Ser Pro Thr Gly Asn Ile Ser
                165                 170                 175

Ser Ala Pro Lys Asp Phe Ala Val Tyr Gly Leu Glu Thr Glu Tyr Gln
            180                 185                 190

Glu Glu Gly Gln Pro Leu Gly Arg Phe Thr Tyr Asp Gln Glu Gly Asp
        195                 200                 205

Ser Leu Gln Met Phe His Thr Leu Glu Arg Pro Asp Gln Ala Phe Gln
    210                 215                 220

Ile Val Glu Leu Arg Val Leu Ser Asn Trp Gly His Pro Glu Tyr Thr
225                 230                 235                 240
```

Cys Leu Tyr Arg Phe Arg Val His Gly Glu Pro Ile Gln
                245                 250

<210> SEQ ID NO 73
<211> LENGTH: 101
<212> TYPE: PRT
<213> ORGANISM: Artificial Sequence
<220> FEATURE:
<223> OTHER INFORMATION: Sun1_plus4 protein

<400> SEQUENCE: 73

Trp Leu Leu Glu Lys Leu Ser Ser Arg Phe Val Ser Lys Asp Glu Leu
1               5                   10                  15

Gln Val Leu Leu His Asp Leu Glu Leu Lys Leu Leu Gln Asn Ile Thr
            20                  25                  30

His His Ile Thr Val Thr Gly Gln Ala Pro Arg His Ile Arg Gly Tyr
        35                  40                  45

Cys Val Cys Arg Glu Ser Gly Arg Asp Phe Arg Asn His Arg Ser Ala
    50                  55                  60

Ser Thr Tyr His Cys Glu Gln Cys Ser Glu Ala Val Leu Pro Arg Gln
65                  70                  75                  80

Asp Gly Asp Gly Gly Leu Cys Ser Gly Val Trp Arg Trp Gln His Pro
                85                  90                  95

Lys His Ser Val Leu
            100

<210> SEQ ID NO 74
<211> LENGTH: 48
<212> TYPE: PRT
<213> ORGANISM: Artificial Sequence
<220> FEATURE:
<223> OTHER INFORMATION: Sun1_del7 protein

<400> SEQUENCE: 74

Trp Leu Leu Glu Lys Leu Ser Ser Arg Phe Val Ser Lys Asp Glu Leu
1               5                   10                  15

Gln Val Leu Leu His Asp Leu Glu Leu Lys Leu Leu Gln Asn Ile Thr
            20                  25                  30

His His Ile Thr Val Thr Gly Gln Ala Pro Arg Leu Leu Cys Leu Pro
        35                  40                  45

<210> SEQ ID NO 75
<211> LENGTH: 180
<212> TYPE: DNA
<213> ORGANISM: Mus musculus

<400> SEQUENCE: 75
tattggactc acctgccttg tacccatgtc agagaaagac tacagctgtg ccctctccaa      60
caactttgcc cgatccttcc atccgatgct cagatatacc aacggtcctc ctccactctg     120
aagcaagcag acatccccac acaagtgcag gcagtaagag gagaaggaat atcaaatggc     180

<210> SEQ ID NO 76
<211> LENGTH: 172
<212> TYPE: DNA
<213> ORGANISM: Artificial Sequence
<220> FEATURE:
<223> OTHER INFORMATION: Syne1_CTdel8

<400> SEQUENCE: 76
tattggactc acctgccttg tacccatgtc agagaaagac tacagctgtg ccctctccaa      60
caactttgcc cgatccttcc atccgatata ccaacggtcc tcctccactc tgaagcaagc 120
agacatcccc acacaagtgc aggcagtaag aggagaagga atatcaaatg gc 172

<210> SEQ ID NO 77
<211> LENGTH: 79
<212> TYPE: PRT
<213> ORGANISM: Mus musculus

<400> SEQUENCE: 77

Ser Thr Arg Asp Gly Ser Asp Ser Ser Arg Ser Asp Pro Arg Pro Glu
1               5                   10                  15

Arg Val Gly Arg Ala Phe Leu Phe Arg Ile Leu Arg Ala Ala Leu Pro
            20                  25                  30

Phe Gln Leu Leu Leu Leu Leu Leu Ile Gly Leu Thr Cys Leu Val Pro
        35                  40                  45

Met Ser Glu Lys Asp Tyr Ser Cys Ala Leu Ser Asn Asn Phe Ala Arg
    50                  55                  60

Ser Phe His Pro Met Leu Arg Tyr Thr Asn Gly Pro Pro Pro Leu
65                  70                  75

<210> SEQ ID NO 78
<211> LENGTH: 129
<212> TYPE: PRT
<213> ORGANISM: Artificial Sequence
<220> FEATURE:
<223> OTHER INFORMATION: Nesprin1_CTdel8

<400> SEQUENCE: 78

Ser Thr Arg Asp Gly Ser Asp Ser Ser Arg Ser Asp Pro Arg Pro Glu
1               5                   10                  15

Arg Val Gly Arg Ala Phe Leu Phe Arg Ile Leu Arg Ala Ala Leu Pro
            20                  25                  30

Phe Gln Leu Leu Leu Leu Leu Leu Ile Gly Leu Thr Cys Leu Val Pro
        35                  40                  45

Met Ser Glu Lys Asp Tyr Ser Cys Ala Leu Ser Asn Asn Phe Ala Arg
    50                  55                  60

Ser Phe His Pro Ile Tyr Gln Arg Ser Ser Thr Leu Lys Gln Ala
65                  70                  75                  80

Asp Ile Pro Thr Gln Val Gln Ala Val Arg Gly Glu Gly Ile Ser Asn
            85                  90                  95

Gly Arg Glu Ala Pro Lys Glu Lys Phe Asn Ile Leu Asn His Gln Gly
        100                 105                 110

Asn Ala Asn Gln Asn Asn Pro Glu Met Glu Thr Asn Ala Pro Pro Cys
    115                 120                 125

Ser

<210> SEQ ID NO 79
<211> LENGTH: 183
<212> TYPE: DNA
<213> ORGANISM: Homo sapiens

<400> SEQUENCE: 79
cgcggcttcc tgttcagagt cctccgagca gctcttcccc ttcagcttct cctgctcctc 60
ctcatcgggc ttgcctgcct tgtaccaatg tcagaggaag actacagctg tgccctctcc 120
aacaactttg cccggtcatt ccaccccatg ctcagataca cgaatggccc tcctccactc 180
tga 183

```
<210> SEQ ID NO 80
<211> LENGTH: 534
<212> TYPE: DNA
<213> ORGANISM: Homo sapiens

<400> SEQUENCE: 80
gataagaccg ggatggtgga ctttgctctg gaatctggtg gtggcagcat cttgagtact      60
cgctgttctg aaacttacga aaccaaaacg gcgctgatga gtctgtttgg gatcccgctg     120
tggtacttct cgcagtcccc gcgcgtggtc atccagcctg acatttaccc cggtaactgc     180
tgggcattta aaggctccca ggggtacctg gtggtgaggc tctccatgat gatccaccca     240
gccgccttca ctctggagca catccctaag acgctgtcgc caacaggcaa catcagcagc     300
gcccccaagg acttcgccgt ctatggatta gaaaatgagt atcaggaaga agggcagctt     360
ctgggacagt tcacgtatga tcaggatggg gagtcgctcc agatgttcca ggccctgaaa     420
agacccgacg acacagcttt ccaaatagtg gaacttcgga ttttttctaa ctggggccat     480
cctgagtata cctgtctgta tcggttcaga gttcatggcg aacctgtcaa gtga           534

<210> SEQ ID NO 81
<211> LENGTH: 117
<212> TYPE: DNA
<213> ORGANISM: Homo sapiens

<400> SEQUENCE: 81
aaaagacccg acgacacagc tttccaaata gtggaacttc ggattttttc taactggggc      60
catcctgagt atacctgtct gtatcggttc agagttcatg gcgaacctgt caagtga        117
```